(12) United States Patent
Walter et al.

(10) Patent No.: US 6,855,710 B2
(45) Date of Patent: Feb. 15, 2005

(54) SUBSTITUTED INDOLINES WITH AN INHIBITORY EFFECT ON VARIOUS KINASES AND COMPLEXES OF CDKS

(75) Inventors: Rainer Walter, Biberach (DE); Wolfgang Grell, Biberach (DE); Armin Heckel, Biberach (DE); Frank Himmelsbach, Mittelbiberach (DE); Wolfgang Eberlein, Biberach (DE); Gerald Roth, Biberach (DE); Jacobus C.A. van Meel, Moedling (AT); Norbert Redemann, Biberach (DE); Walter Spevak, Oberrohrbach (AT); Ulrike Tontsch-Grunt, Baden (AT); Thomas von Rueden, Planegg (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/666,643

(22) Filed: Sep. 19, 2003

(65) Prior Publication Data

US 2004/0058978 A1 Mar. 25, 2004

Related U.S. Application Data

(63) Continuation of application No. 09/787,974, filed as application No. PCT/EP99/07040 on Sep. 22, 1999, now abandoned.

(30) Foreign Application Priority Data

Sep. 25, 1998 (DE) .......................................... 198 44 003
Aug. 7, 1999 (DE) .......................................... 199 37 496

(51) Int. Cl.[7] .................... C07D 401/12; C07D 401/14; C07D 403/12; A61K 31/404; A61P 35/00
(52) U.S. Cl. .................... 514/228.2; 514/414; 514/418; 514/254.09; 514/235.2; 514/323; 548/486; 548/467; 544/373; 544/144; 544/58.2; 544/62; 546/201
(58) Field of Search ................ 548/486, 487; 544/373, 144, 58.2, 62; 546/201, 414, 418, 254.09, 235.2, 228.2, 323

(56) References Cited

FOREIGN PATENT DOCUMENTS

WO    WO 96/22976 A1    8/1996
WO    WO 96/40116 A1    12/1996

OTHER PUBLICATIONS

Aurich et al, {Liebigs Ann. Chem. 732, 195–198 (1970)}.*
Aurich et al. (Liebigs Ann. Chem. 732, 195–198 (1970).

* cited by examiner

*Primary Examiner*—Mark L. Berch
*Assistant Examiner*—Kahsay Habte
(74) *Attorney, Agent, or Firm*—Michael F. Morris; Mary-Ellen M. Devlin; Thomas Blankinship

(57) ABSTRACT

The present invention relates to new substituted indolinones of general formula

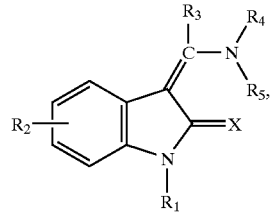

(I)

wherein
X and $R_1$ to $R_5$ are defined as in claim 1, the isomers and the salts thereof which have valuable properties.

The above compounds of general formula I wherein $R_1$ denotes a hydrogen atom, a $C_{1-3}$-alkyl group or a prodrug group have valuable pharmacological properties, particularly an inhibiting effect on various kinases, on viral cyclin and on receptor tyrosine kinases, and the other compounds of the above general formula I wherein $R_1$ does not represent a hydrogen atom, a $C_{1-3}$-alkyl group or a prodrug group are valuable intermediate products for the preparation of the abovementioned compounds.

9 Claims, No Drawings

SUBSTITUTED INDOLINES WITH AN INHIBITORY EFFECT ON VARIOUS KINASES AND COMPLEXES OF CDKS

This application is a CON of Ser. No. 09/787,974, Oct. 3, 2001, ABN which is a 371 of PCT/EP00/07040 Sep. 22, 1999.

The present invention relates to new substituted indolinones of general formula

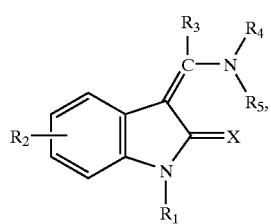

the isomers thereof, the salts thereof, particularly the physiologically acceptable salts thereof which have valuable properties.

The above compounds of general formula I wherein $R_1$ denotes a hydrogen atom, a $C_{1-3}$-alkyl group or a prodrug group have valuable pharmacological properties, particularly an inhibiting effect on various kinases, especially on complexes of CDKs (CDK1, CDK2, CDK3, CDK4, CDK6, CDK7, CDK8 and CDK9) with their specific cyclins (A, B1, B2, C, D1, D2, D3, E, F, G1, G2, H, I and K), on viral cyclin (cf. L. Mengtao in J. Virology 71(3), 1984–1991 (1997)), and on receptor tyrosine kinases such as HER2, EGFR, FGFR, IGF-1R and KDR, and the other compounds of the above general formula I wherein $R_1$ does not represent a hydrogen atom, a $C_{1-3}$-alkyl group or a prodrug group are valuable intermediate products for the preparation of the above-mentioned compounds which have useful pharmacological properties.

The present invention thus relates to the above compounds of general formula I, in which the compounds wherein $R_1$ denotes a hydrogen atom, a $C_{1-3}$-alkyl group or a prodrug group such as a $C_{1-4}$-alkoxycarbonyl or $C_{2-4}$-alkanoyl group have valuable pharmacological properties, the pharmaceutical compositions containing the pharmacologically active compounds, their use and processes for preparing them.

In the above general formula I

X denotes an oxygen or sulphur atom, $R_1$ denotes a hydrogen atom, $C_{1-3}$-alkyl or hydroxy group, $R_2$ denotes a hydrogen, fluorine, chlorine, bromine or iodine atom, a $C_{1-3}$-alkyl or nitro group, $R_3$ denotes a phenyl or naphthyl group, each of which may be mono- or disubstituted by fluorine, chlorine, bromine or iodine atoms, by $C_{1-3}$-alkyl, $C_{1-3}$-alkoxy, carboxy, cyano, trifluoromethyl, nitro, amino, $C_{1-3}$-alkylamino, di-($C_{1-3}$-alkyl)-amino, $C_{1-3}$-alkylsulphonylamino, amino-$C_{1-3}$-alkyl, 2-carboxy-phenylcarbonylaminomethyl, $C_{1-3}$-alkylamino-$C_{1-3}$-alkyl, $C_{2-4}$-alkanoylamino-$C_{1-3}$-alkyl, N—($C_{2-4}$-alkanoyl)-$C_{1-3}$-alkylamino-$C_{1-3}$-alkyl, di-($C_{1-3}$- alkyl)-amino-$C_{1-3}$-alkyl, carboxy-$C_{2-3}$-alkenyl, N-(carboxy-$C_{1-3}$-alkyl)-aminocarbonyl, N-(carboxy-$C_{1-3}$-alkyl)-N—($C_{1-3}$-alkyl)-aminocarbonyl or imidazolyl-$C_{1-3}$-alkyl groups, while the substituents may be identical or different, $R_4$ denotes a hydrogen atom or a $C_{1-3}$-alkyl group and $R_5$ denotes a phenyl or naphthyl group optionally substituted by a $C_{1-3}$-alkyl group, each of which may additionally be substituted in the aromatic moiety by a fluorine, chlorine, bromine or iodine atom, by a $C_{1-3}$-alkyl, $C_{1-3}$-alkoxy, cyano, nitro or trifluoromethyl group, by a $C_{1-3}$-alkoxy group which is substituted by a carboxy, aminocarbonyl, $C_{1-3}$-alkylaminocarbonyl or di-($C_{1-3}$-alkyl)-aminocarbonyl group or in the 2 or 3 position by an amino, $C_{1-3}$-alkylamino, di-($C_{1-3}$-alkyl)-amino, phenyl-$C_{1-3}$-alkylamino, N-(phenyl-$C_{1-3}$-alkyl)-N—($C_{1-3}$-alkyl)-amino, pyrrolidino, piperidino or hexamethyleneimino group, by a $C_{2-3}$-alkenyl group optionally substituted by a di-($C_{1-3}$-alkyl)-amino group, which may additionally be substituted in the alkenyl moiety by a chlorine or bromine atom, by a $C_{2-3}$-alkynyl group optionally substituted by a di-($C_{1-3}$-alkyl)-amino group, by a $C_{1-3}$-alkyl group which is substituted by a 3- to 7-membered cycloalkyleneimino group, by a dehydropiperidino, morpholino, thiomorpholino, 1-oxido-thiomorpholino, 1,1-dioxido-thiomorpholino, piperazino, N—($C_{1-3}$-alkyl)-piperazino, N—($C_{1-3}$-alkanoyl)-piperazino or N—($C_{1-5}$-alkoxycarbonyl)-piperazino group, whilst the above-mentioned substituents may be substituted by a $C_{1-3}$-alkyl, phenyl or phenyl-$C_{1-3}$-alkyl group and the abovementioned piperidino or hexamethyleneimino groups may additionally be substituted by a $C_{1-3}$-alkyl group or in the 3 or 4 position by a hydroxy, $C_{1-3}$-alkoxy, hydroxy-$C_{1-3}$-alkyl, carboxy, aminocarbonyl, N—($C_{1-3}$-alkyl)-aminocarbonyl or N,N-di-($C_{1-3}$-alkyl)-aminocarbonyl group, by a $C_{1-3}$-alkyl group substituted by a hydroxy, $C_{1-3}$-alkoxy, carboxy or cyano group, whilst a $C_{1-3}$-alkyl group substituted by a carboxy group may additionally be substituted in the alkyl moiety by an amino or $C_{1-5}$-alkoxycarbonylamino group, by an aminocarbonylamino, amidino or guanidino group optionally substituted by one or two $C_{1-3}$-alkyl groups, by a piperidino, hexamethyleneimino, morpholino, piperazino or N—($C_{1-3}$-alkyl)-piperazino group, by a formyl, carboxy or trifluoroacetyl group, by a carbonyl group which
  is substituted by a $C_{1-3}$-alkyl, $C_{1-3}$-alkoxy-$C_{1-3}$-alkyl, amino, $C_{1-5}$-alkylamino or di-($C_{1-3}$-alkyl)-amino group, while the abovementioned amino and $C_{1-3}$-alkylamino groups may additionally be substituted at the nitrogen atom by a carboxy-$C_{1-3}$-alkyl group or by a $C_{2-3}$-alkyl group which is substituted in the 2 or 3 position by a hydroxy, $C_{1-3}$-alkoxy, amino, $C_{1-3}$-alkylamino or di-($C_{1-3}$-alkyl)-amino group, by a pyrrolidinocarbonyl, piperidinocarbonyl, hexamethyleneiminocarbonyl, morpholinocarbonyl, piperazinocarbonyl, N—($C_{1-3}$-alkyl)-piperazinocarbonyl or N-(phenyl-$C_{1-3}$-alkyl)-piperazinocarbonyl group, by an amidosulphonyl, pyrrolidinosulphonyl, piperidinosulphonyl or hexamethyleneiminosulphonyl group, by a $C_{1-3}$-alkylamidosulphonyl or di-($C_{1-3}$-alkyl)-amidosulphonyl group, wherein an alkyl moiety may be substituted in each case by a carboxy, aminocarbonyl, N—($C_{1-3}$-alkyl)-aminocarbonyl or N,N-di-($C_{1-3}$-alkyl)-aminocarbonyl group or, in the 2 or 3 position, by a $C_{1-3}$-alkylamino or di-($C_{1-3}$-alkyl)-amino group, by an amino, $C_{1-5}$-alkylamino, $C_{3-7}$-cycloalkylamino, phenyl-$C_{1-3}$-alkylamino, phenylamino, 6-membered heteroarylamino, amino-$C_{1-3}$-alkyl, N—($C_{1-5}$-alkyl)-amino-$C_{1-3}$-alkyl, di-($C_{1-5}$-alkyl)-amino-$C_{1-3}$-alkyl, $C_{3-7}$-cycloalkylamino-$C_{1-3}$-alkyl, N—($C_{1-5}$-alkyl)-$C_{3-7}$-cycloalkylamino-$C_{1-3}$-alkyl, phenylamino-$C_{1-3}$-alkyl, N—($C_{1-3}$-alkyl)-phenylamino-$C_{1-3}$-alkyl, phenyl-$C_{1-3}$-alkylamino-$C_{1-3}$-alkyl or N—($C_{1-5}$-alkyl)-phenyl-$C_{1-3}$-alkylamino-$C_{1-3}$-alkyl group or by a 6-membered heteroarylamino-$C_{1-3}$-alkyl group optionally substituted at the nitrogen atom by a $C_{1-5}$-alkyl group, while the N-alkyl moiety of the abovementioned groups may be substituted in each case by a cyano, carboxy, aminocarbonyl, $C_{1-3}$-alkylaminocarbonyl, di-($C_{1-3}$-alkyl)-aminocarbonyl, 2-[di-($C_{1-3}$-alkyl)-amino]-ethylaminocarbonyl, 3-[di-($C_{1-3}$-alkyl)-amino]-propylaminocarbonyl, N-{2-[di-($C_{1-3}$-alkyl)-amino]-ethyl}-N—($C_{1-3}$-alkyl)-aminocarbonyl or N-{3-[di-($C_{1-3}$-alkyl)-amino]-propyl}-N—($C_{1-3}$-alkyl)-aminocarbonyl group or in the 2 or 3 position by a hydroxy, $C_{1-3}$-alkoxy, amino, $C_{1-3}$-alkylamino, di-($C_{1-3}$-alkyl)-amino, pyrrolidino, piperidino, hexamethyleneimino, morpholino, piperazino or N—($C_{1-3}$-alkyl)-piperazino group and the nitrogen atom of the abovementioned amino, N—($C_{1-5}$-alkyl)-amino, $C_{3-7}$-cycloalkylamino, phenyl-$C_{1-3}$-alkylamino, phenylamino, 6-membered heteroarylamino, amino-$C_{1-3}$-alkyl- and N—($C_{1-5}$-alkylamino)-$C_{1-3}$-alkyl groups may additionally be substituted by a $C_{1-5}$-alkoxycarbonyl group, by a formyl, trifluoroacetyl or benzoyl group, by a carboxy-$C_{1-3}$-alkyl, aminocarbonyl-$C_{1-3}$-alkyl, N—($C_{1-3}$-alkyl)-aminocarbonyl-$C_{1-3}$-alkyl or N,N-di-($C_{1-3}$-alkyl)-aminocarbonyl-$C_{1-3}$-alkyl group, by a $C_{1-5}$-alkyl group which may be substituted, except in the 1 position, by a hydroxy, $C_{1-3}$-alkoxy, amino, $C_{1-3}$-alkylamino or di-($C_{1-3}$-alkyl)-amino group, by a $C_{2-4}$-alkanoyl group which may be substituted in the alkanoyl moiety by a carboxy, hydroxy, $C_{1-3}$-alkoxy, phenyl, amino, phthalimido, $C_{1-3}$-alkylamino, di-($C_{1-3}$-alkyl)-amino, pyrrolidino, piperidino, hexamethyleneimino or morpholino group or by a piperazino group optionally substituted at the nitrogen atom by a $C_{1-3}$-alkyl or phenyl-$C_{1-3}$-alkyl group, while the alkyl moiety of the abovementioned $C_{1-3}$-alkylamino- and di-($C_{1-3}$-alkyl)-amino substituents may be substituted in the 2 or 3 position by a hydroxy, $C_{1-3}$-alkoxy, amino, $C_{1-5}$-alkoxycarbonylamino, $C_{1-3}$-alkylamino, di-($C_{1-3}$-alkyl)-amino, phenyl, pyrrolidino, piperidino, hexamethyleneimino or morpholino group, by a $C_{1-5}$-alkylsulphonyl group in which the alkyl moiety may be substituted except in the 1 position by a di-($C_{1-3}$-alkyl)-amino, pyrrolidino, piperidino, hexamethyleneimino or morpholino group, by a phenyl-($C_{1-3}$)-alkylsulphonyl or phenylsulphonyl group optionally substituted in the phenyl moiety by a fluorine, chlorine or bromine atom or by a $C_{1-3}$-alkyl or $C_{1-3}$-alkoxy group, while additionally any carboxy, amino or imino group present may be substituted by a group which can be cleaved in vivo.

By a group which can be cleaved in vivo from an imino or amino group is meant, for example, a hydroxy group, an acyl group such as the benzoyl or pyridinoyl group or a $C_{1-16}$-alkanoyl group such as the formyl, acetyl, propionyl, butanoyl, pentanoyl or hexanoyl group, an allyloxycarbonyl group, a $C_{1-16}$-alkoxycarbonyl group such as the methoxycarbonyl, ethoxycarbonyl, propoxycarbonyl, isopropoxycarbonyl, butoxycarbonyl, tert.butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl or hexadecyloxycarbonyl group, a phenyl-$C_{1-6}$-alkoxycarbonyl group such as the benzyloxycarbonyl, phenylethoxycarbonyl or phenylpropoxycarbonyl group, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl or $R_aCO$—O—($R_bCR_c$)—O—CO group wherein $R_a$ denotes a $C_{1-8}$-alkyl, $C_{5-7}$-cycloalkyl, phenyl or phenyl-$C_{1-3}$-alkyl group, $R_b$ denotes a hydrogen atom, a $C_{1-3}$-alkyl, $C_{5-7}$-cycloalkyl or phenyl group and $R_c$ denotes a hydrogen atom, a $C_{1-3}$-alkyl or $R_aCO$—O—($R_bCR_c$)—O group wherein $R_a$ to $R_c$ are as hereinbefore defined, and additionally for an amino group is meant the phthalimido group, while the abovementioned ester groups may also be used as a group which can be converted into a carboxy group in vivo.

Also included are the compounds of general formula I of the German application no. 198 44 000.3 on which priority is based, in which X denotes an oxygen or sulphur atom, $R_1$ denotes a hydrogen atom or a $C_{1-3}$-alkyl group, $R_2$ denotes a hydrogen, fluorine, chlorine, bromine or iodine atom, a $C_{1-3}$-alkyl or nitro group, $R_3$ denotes a phenyl or naphthyl group, each of which may be mono or disubstituted by fluorine, chlorine or bromine atoms, by $C_{1-3}$-alkyl, $C_{1-3}$-alkoxy, cyano, trifluoromethyl, nitro, amino, $C_{1-3}$-alkylamino, di-($C_{1-3}$-alkyl)-amino, $C_{1-3}$-alkylsulphonylamino, amino-$C_{1-3}$-alkyl, $C_{1-3}$-alkylamino-$C_{1-3}$-alkyl, $C_{2-4}$-alkanoyl-amino-$C_{1-3}$-alkyl, N—($C_{2-4}$-alkanoyl)-$C_{1-3}$-alkylamino-$C_{1-3}$-alkyl or di-($C_{1-3}$-alkyl)-amino-$C_{1-3}$-alkyl groups, while the substituents may be identical or different, $R_4$ denotes a hydrogen atom or a $C_{1-3}$-alkyl group and $R_5$ denotes a phenyl or naphthyl group optionally substituted by a $C_{1-3}$-alkyl group, each of which may additionally be substituted in the aromatic moiety by a fluorine, chlorine, bromine or iodine atom, by a $C_{1-3}$-alkyl, $C_{1-3}$-alkoxy, cyano, nitro or trifluoromethyl group, by a $C_{1-3}$-alkyl group optionally substituted by a $C_{1-3}$-alkyl, phenyl or phenyl-$C_{1-3}$-alkyl group piperidino, hexamethyleneimino, morpholino, piperazino group, while the abovementioned piperidino or hexamethyleneimino groups may additionally be substituted in the 3 or 4 position by a hydroxy, $C_{1-3}$-alkoxy or carboxy group, by a $C_{1-3}$-alkyl group optionally substituted by a hydroxy, $C_{1-3}$-alkoxy, carboxy or cyano group, by a aminocarbonylamino, amidino or guanidino group optionally substituted by one or two $C_{1-3}$-alkyl groups, by a piperidino, hexamethyleneimino, morpholino, piperazino or N—($C_{1-3}$-alkyl)-piperazino group, by a formyl, carboxy or trifluoroacetyl group, by a carbonyl group which is substituted by a $C_{1-3}$-alkyl, $C_{1-3}$-alkoxy-$C_{1-3}$-alkyl, amino, $C_{1-5}$-alkylamino or di-($C_{1-3}$-alkyl)-amino group, while the above-mentioned amino- and $C_{1-3}$-alkylamino groups may additionally be substituted at the nitrogen atom by a carboxy-$C_{1-3}$-alkyl, amino-$C_{1-3}$-alkyl, $C_{1-3}$-alkylamino-$C_{1-3}$-alkyl or di-($C_{1-3}$-alkyl)-amino-$C_{1-3}$-alkyl group, by a piperidinocarbonyl, hexamethyleneiminocarbonyl, morpholinocarbonyl, piperazinocarbonyl, N—($C_{1-3}$-alkyl)-piperazinocarbonyl or N-(phenyl-$C_{1-3}$-alkyl)-piperazinocarbonyl group, by an amino, $C_{1-5}$-alkylamino, amino-$C_{1-3}$-alkyl, N—($C_{1-3}$-alkylamino)-$C_{1-3}$-alkyl or di-($C_{1-5}$-alkylamino)-$C_{1-3}$-alkyl group, while the alkyl moiety of the above-mentioned $C_{1-3}$-alkylamino moieties may be substituted by a cyano, carboxy, aminocarbonyl, $C_{1-3}$-alkylaminocarbonyl, di-($C_{1-3}$-alkyl)-aminocarbonyl, 2-[di-($C_{1-3}$-alkyl)-amino]-ethylaminocarbonyl or 3-[di-($C_{1-3}$-alkyl)-amino]-propylaminocarbonyl group or in the 2 or 3 position may be substituted by a hydroxy, $C_{1-3}$-alkoxy, di-($C_{1-3}$-alkyl)-amino, piperidino, hexamethyleneimino, morpholino, piperazino or N—($C_{1-3}$-alkyl)-piperazino group and the nitrogen atom of the abovementioned amino, $C_{1-3}$-alkylamino, amino-$C_{1-3}$-alkyl or N—($C_{1-5}$-alkylamino)-$C_{1-3}$-alkyl moieties may additionally be substituted
  by a $C_{1-5}$-alkoxycarbonyl group,
  by a formyl or trifluoroacetyl group,
  by a $C_{1-5}$-alkyl group which may be substituted, except in the 1 position, by a hydroxy, $C_{1-3}$-alkoxy, amino, $C_{1-3}$-alkylamino or di-($C_{1-3}$-alkyl)-amino group,
  by a $C_{2-4}$-alkanoyl group which may be substituted in the alkanoyl moiety by a carboxy, hydroxy, $C_{1-3}$-alkoxy, amino, $C_{2-4}$-alkanoylamino, $C_{1-5}$-alkoxycarbonylamino, $C_{1-3}$-alkylamino, di-($C_{1-3}$-alkyl)-amino, piperidino, hexamethyleneimino or morpholino group or by a piperazino group optionally substituted at the nitrogen atom by a $C_{1-3}$-alkyl or phenyl-$C_{1-3}$-alkyl group,
  by a $C_{1-3}$-alkylsulphonyl, amidosulphonyl, $C_{1-3}$-alkylamidosulphonyl or di-($C_{1-3}$-alkyl)-amidosulphonyl group,
  by a phenyl-($C_{1-3}$)-alkylsulphonyl or phenylsulphonyl group optionally substituted in the phenyl moiety by a fluorine, chlorine or bromine atom or by a $C_{1-3}$-alkyl or $C_{1-3}$-alkoxy group, while additionally any carboxy, amino or imino group present may be substituted by a group which can be cleaved in vivo, the isomers and the salts thereof.

Preferred compounds of general formula I are those wherein

X denotes an oxygen or sulphur atom, $R_1$ denotes a hydrogen atom, a $C_{1-3}$-alkyl, hydroxy, $C_{1-4}$-alkoxycarbonyl or $C_{2-4}$-alkanoyl group, $R_2$ denotes a hydrogen, fluorine, chlorine, bromine or iodine atom, a $C_{1-3}$-alkyl or nitro group, $R_3$ denotes a phenyl or naphthyl group, each of which may be mono- or disubstituted by fluorine, chlorine, bromine or iodine atoms, by $C_{1-3}$-alkyl, imidazolylmethyl, 2-carboxyethenyl, 2-($C_{1-3}$-alkoxycarbonyl)-ethenyl, $C_{1-3}$-alkoxy, cyano, carboxy, $C_{1-3}$-alkoxycarbonyl, trifluoromethyl, nitro, amino, phthalimidomethyl, 2-carboxy-phenylcarbonylaminomethyl, $C_{1-3}$-alkylamino, di-($C_{1-3}$-alkyl)-amino, $C_{1-3}$-alkylsulphonylamino, amino-$C_{1-3}$-alkyl, $C_{1-3}$-alkylamino-$C_{1-3}$-alkyl, $C_{2-4}$-alkanoylamino-$C_{1-3}$-alkyl, N—($C_{2-4}$-alkanoyl)-$C_{1-3}$-alkylamino-$C_{1-3}$-alkyl, di-($C_{1-3}$-alkyl)-amino-$C_{1-3}$-alkyl, carboxy-$C_{1-3}$-alkylaminocarbonyl or $C_{1-3}$-alkoxycarbonyl-$C_{1-3}$-alkylaminocarbonyl groups, while the substituents may be identical or different, $R_4$ denotes a hydrogen atom or a $C_{1-3}$-alkyl group and $R_5$ denotes a phenyl or naphthyl group optionally substituted by a $C_{1-3}$-alkyl group, each of which may additionally be substituted in the aromatic moiety by a fluorine, chlorine, bromine or iodine atom, by a $C_{1-3}$-alkyl, $C_{1-3}$-alkoxy, cyano, nitro or trifluoromethyl group, while the abovementioned alkyl group may simultaneously be substituted by a carboxy or $C_{1-3}$-alkoxycarbonyl group and an amino or $C_{1-4}$-alkoxycarbonylamino group, a $C_{1-3}$-alkyl group which is substituted by a 4- to 7-membered cycloalkyleneimino group, by a dehydropiperidino, morpholino, thiomorpholino, 1-oxido-thiomorpholino, 1,1-dioxido-thiomorpholino, piperazino or N—($C_{1-4}$-alkoxycarbonyl)-piperazino group, while the abovementioned piperidino, hexamethyleneimino, morpholino, thiomorpholino, 1-oxido-thiomorpholino, 1,1-dioxido-thiomorpholino- and piperazino groups may be substituted by a $C_{1-3}$-alkyl, phenyl or phenyl-$C_{1-3}$-alkyl group and the abovementioned piperidino groups may additionally be substituted by a $C_{1-3}$-alkyl group or in the 3 or 4 position by a hydroxy, $C_{1-3}$-alkoxy, hydroxy-$C_{1-3}$-alkyl, carboxy, aminocarbonyl, N—($C_{1-3}$-alkyl)-aminocarbonyl or N,N-di-($C_{1-3}$-alkyl)-aminocarbonyl group, by a $C_{1-3}$-alkyl group optionally substituted by a hydroxy, $C_{1-3}$-alkoxy, carboxy, $C_{1-3}$-alkoxycarbonyl or cyano group, by an aminocarbonylamino, amidino or guanidino group optionally substituted by one or two $C_{1-3}$-alkyl groups, by a piperidino, hexamethyleneimino, morpholino, piperazino or N—($C_{1-3}$-alkyl)-piperazino group, by a formyl, carboxy, $C_{1-3}$-alkoxycarbonyl or trifluoroacetyl group, by a carbonyl group which
  is substituted by a $C_{1-3}$-alkyl, $C_{1-3}$-alkoxy-$C_{1-3}$-alkyl, amino, $C_{1-5}$-alkylamino or di-($C_{1-3}$-alkyl)-amino group, while the abovementioned amino- and $C_{1-3}$-alkylamino groups may additionally be substituted at the nitrogen atom by a carboxy-$C_{1-3}$-alkyl or $C_{1-3}$-alkoxycarbonyl-$C_{1-3}$-alkyl group or by a $C_{2-3}$-alkyl group which may be substituted in the 2 or 3 position by a hydroxy, $C_{1-3}$-alkoxy, amino, $C_{1-3}$-alkylamino or di-($C_{1-3}$-alkyl)-amino group, by a pyrrolidinocarbonyl, pyrrolidinosulphonyl, piperidinocarbonyl, hexamethyleneiminocarbonyl, morpholinocarbonyl, piperazinocarbonyl, N—($C_{1-3}$-alkyl)-piperazinocarbonyl or N-(phenyl-$C_{1-3}$-alkyl)-piperazinocarbonyl group, by an amidosulphonyl, $C_{1-3}$-alkylamidosulphonyl or di-($C_{1-3}$-alkyl)-amidosulphonyl group, wherein an alkyl moiety may be substituted by a carboxy, $C_{1-3}$-alkoxycarbonyl, aminocarbonyl, $C_{1-3}$-alkylaminocarbonyl or di-($C_{1-3}$-alkyl)-aminocarbonyl group or in the 2 or 3 position may be substituted by an amino, $C_{1-3}$-alkylamino or di-($C_{1-3}$-alkyl)-amino group, by an amino, $C_{1-5}$-alkylamino, amino-$C_{1-3}$-alkyl, N—($C_{1-3}$-alkyl)-amino-$C_{1-3}$-alkyl, N-(2-hydroxyethyl)-amino-$C_{1-3}$-alkyl, N-(3-hydroxypropyl)-amino-$C_{1-3}$-alkyl, di-($C_{1-5}$-alkyl)-amino-$C_{1-3}$-alkyl, N—($C_{3-7}$-cycloalkyl)-amino-$C_{1-3}$-alkyl, N—($C_{3-7}$-cycloalkyl)-N—($C_{1-3}$-alkyl)-amino-$C_{1-3}$-alkyl or N-(phenyl-$C_{1-3}$-alkyl)-amino-$C_{1-3}$-alkyl group, while the N-alkyl moiety of the abovementioned groups may be substituted by a cyano, carboxy, $C_{1-3}$-alkylcarbonyl, aminocarbonyl, $C_{1-3}$-alkylaminocarbonyl, di-($C_{1-3}$-alkyl)-aminocarbonyl, 2-[di-($C_{1-3}$-alkyl)-amino]-ethylaminocarbonyl, 3-[di-($C_{1-3}$-alkyl)-amino]-propylaminocarbonyl, N-{2-[di-($C_{1-3}$-alkyl)-amino]-ethyl}-N—($C_{1-3}$-alkyl)-aminocarbonyl or N-{3-[di-($C_{1-3}$-alkyl)-amino]-propyl}-N—($C_{1-3}$-alkyl)-aminocarbonyl group or may be substituted in the 2 or 3 position by a hydroxy, $C_{1-3}$-alkoxy, amino, $C_{1-3}$-alkylamino, di-($C_{1-3}$-alkyl)-amino or morpholino group, while the nitrogen atom of the abovementioned amino, $C_{1-5}$-alkylamino, amino-$C_{1-3}$-alkyl or N—($C_{1-3}$-alkylamino)-$C_{1-3}$-alkyl moieties may additionally be substituted by a $C_{1-5}$-alkoxycarbonyl group, by a formyl, trifluoroacetyl or benzoyl group, by a $C_{1-5}$-alkyl group which may be substituted, except in the 1 position, by a hydroxy, $C_{1-3}$-alkoxy, amino, $C_{1-3}$-alkylamino or di-($C_{1-3}$)-alkylamino group, by a $C_{2-4}$-alkanoyl group which may be substituted in the alkanoyl moiety by a hydroxy, $C_{1-3}$-alkoxy, amino, $C_{2-4}$-alkanoylamino, $C_{1-5}$-alkoxycarbonylamino, phthalimido, $C_{1-3}$-alkylamino, di-($C_{1-3}$-alkyl)-amino, N—($C_{1-3}$-alkyl)-phenylamino, pyrrolidino, piperidino or morpholino group or by a piperazino group optionally substituted at the nitrogen atom by a $C_{1-3}$-alkyl or phenyl-$C_{1-3}$-alkyl group, while the N-alkyl moiety of the abovementioned groups may be substituted in the 2 or 3 position by a methoxy, di-($C_{1-3}$-alkyl)-amino or morpholino group, by a $C_{1-5}$-alkylsulphonyl group in which the alkyl moiety may be substituted, except in the 1 position, by a di-($C_{1-3}$-alkyl)-amino, pyrrolidino, piperidino, hexamethyleneimino or morpholino group, by a pyridinyl or pyrimidinyl group, by a phenyl, phenyl-($C_{1-3}$)-alkylsulphonyl or phenylsulphonyl group optionally substituted in the phenyl moiety by a $C_{1-3}$-alkyl group, by a $C_{1-3}$-alkoxy group which is substituted by a carboxy, $C_{1-3}$-alkoxycarbonyl, aminocarbonyl, $C_{1-3}$-alkylaminocarbonyl or di-($C_{1-3}$-alkyl)-aminocarbonyl group or is substituted in the 2 or 3 position by an amino, $C_{1-3}$-alkylamino, di-($C_{1-3}$-alkyl)-amino, N—($C_{1-3}$-alkyl)-N-(phenyl-$C_{1-3}$-alkyl)-amino, piperidino or hexamethyleneimino group, by a prop-1-enyl, 2-chloro-prop-1-enyl or prop-1-ynyl group which is substituted in the 3 position by a di-($C_{1-3}$-alkyl)-amino group, the isomers and the salts thereof.

Particularly preferred compounds of general formula I are those wherein

X denotes an oxygen atom, $R_1$ denotes a hydrogen atom, a $C_{1-3}$-alkyl, $C_{1-4}$-alkoxycarbonyl or $C_{2-4}$-alkanoyl group, $R_2$ denotes a hydrogen, fluorine, chlorine, bromine or iodine atom, a $C_{1-3}$-alkyl or nitro group, $R_3$ denotes a phenyl group which may be mono- or disubstituted by fluorine, chlorine, bromine or iodine atoms, by $C_{1-3}$-alkyl, trifluoromethyl, imidazolylmethyl, 2-carboxyethenyl, 2-$C_{1-3}$-alkoxycarbonyl-ethenyl, $C_{1-3}$-alkoxy, cyano, carboxy, $C_{1-3}$-alkoxycarbonyl, nitro, amino, phthalimidomethyl, 2-carboxybenzoylaminomethyl, $C_{1-3}$-alkylamino, di-($C_{1-3}$-alkyl)-amino, $C_{1-3}$-alkylsulphonylamino, amino-$C_{1-3}$-alkyl, $C_{1-3}$-alkylamino-$C_{1-3}$-alkyl, $C_{2-4}$-alkanoylamino-$C_{1-3}$-alkyl, N—($C_{2-4}$-alkanoyl)-$C_{1-3}$-alkylamino-$C_{1-3}$-alkyl, di-($C_{1-3}$-alkyl)-amino-$C_{1-3}$-alkyl, carboxy-$C_{1-3}$-alkylaminocarbonyl or $C_{1-3}$-alkoxycarbonyl-$C_{1-3}$-alkylaminocarbonyl groups, while the substituents may be identical or different, $R_4$ denotes a hydrogen atom or a $C_{1-3}$-alkyl group and $R_5$ denotes a phenyl or naphthyl group optionally substituted by a $C_{1-3}$-alkyl group, each of which may additionally be substituted in the aromatic moiety by a fluorine, chlorine, bromine or iodine atom, by a $C_{1-3}$-alkoxy, cyano, nitro or trifluoromethyl group, a $C_{1-3}$-alkyl group which is substituted by a 4- to 7-membered cycloalkyleneimino group, by a dehydropiperidino, morpholino, thiomorpholino, 1-oxido-thiomorpholino, 1,1-dioxido-thiomorpholino, piperazino or N—($C_{1-4}$-alkoxycarbonyl)-piperazino group, while the abovementioned piperidino, hexamethyleneimino, morpholino and piperazino groups may be substituted by a $C_{1-3}$-alkyl, phenyl or phenyl-$C_{1-3}$-alkyl group and the abovementioned piperidino groups may additionally be substituted by a $C_{1-3}$-alkyl group or may be substituted in the 3 or 4 position by a hydroxy, $C_{1-3}$-alkoxy, hydroxy-$C_{1-3}$-alkyl, carboxy, aminocarbonyl, N—($C_{1-3}$-alkyl)-aminocarbonyl or N,N-di-($C_{1-3}$-alkyl)-aminocarbonyl group, by a $C_{1-3}$-alkyl group optionally substituted by a hydroxy, $C_{1-3}$-alkoxy, carboxy, $C_{1-3}$-alkoxycarbonyl or cyano group, by an aminocarbonylamino, amidino or guanidino group optionally substituted by one or two $C_{1-3}$-alkyl groups, by a piperidino, hexamethyleneimino, morpholino, piperazino or N—($C_{1-3}$-alkyl)-piperazino group, by a formyl, carboxy, $C_{1-3}$-alkoxycarbonyl or trifluoroacetyl group, by a carbonyl group which is substituted by a $C_{1-3}$-alkyl, $C_{1-3}$-alkoxy-$C_{1-3}$-alkyl, amino, $C_{1-5}$-alkylamino or di-($C_{1-3}$-alkyl)-amino group, while the abovementioned amino and $C_{1-3}$-alkylamino groups may additionally be substituted at the nitrogen atom by a carboxy-$C_{1-3}$-alkyl, $C_{1-3}$-alkoxycarbonyl-$C_{1-3}$-alkyl or $C_{1-3}$-alkoxycarbonyl-$C_{1-3}$-alkyl group or by a $C_{2-3}$-alkyl group which may be substituted in the 2 or 3 position by a hydroxy, $C_{1-3}$-alkoxy, amino, $C_{1-3}$-alkylamino or di-($C_{1-3}$-alkyl)-amino group, by a pyrrolidinocarbonyl, pyrrolidinosulphonyl, piperidinocarbonyl or hexamethyleneiminocarbonyl group, by an amidosulphonyl, $C_{1-3}$-alkylamidosulphonyl or di-($C_{1-3}$-alkyl)-amidosulphonyl group, wherein an alkyl moiety may be substituted by a carboxy, $C_{1-3}$-alkoxycarbonyl or dimethylaminocarbonyl group or in the 2 or 3 position by a dimethylamino group, by a straight-chain $C_{1-2}$-alkyl group which is terminally substituted by an amino, benzylamino, pyridylamino or pyrimidylamino group, by a $C_{1-4}$-alkylamino group in which the alkyl moiety may be substituted in position 2, 3 or 4 by a hydroxy or methoxy group, or by a $C_{1-2}$-alkylamino group substituted in the $C_{1-2}$-alkyl moiety by a carboxy, $C_{1-3}$-alkoxycarbonyl or di-($C_{1-3}$-alkyl)-aminocarbonyl group, while in the abovementioned groups any hydrogen atom present at the amino nitrogen atom may additionally be replaced by a $C_{3-6}$-cycloalkyl group, by a $C_{1-4}$-alkyl group in which the alkyl moiety may be substituted in position 2, 3 or 4 by a hydroxy group, by a $C_{1-2}$- alkylcarbonyl group optionally substituted by a methoxy, carboxy, $C_{1-3}$-alkoxycarbonyl, amino, methylamino, dimethylamino, acetylamino, $C_{1-5}$-alkoxycarbonylamino, N-methyl-$C_{1-5}$-alkoxycarbonylamino or morpholinocarbonylamino group, by a $C_{1-5}$-alkoxycarbonyl, $C_{1-4}$-alkylsulphonyl, phenylsulphonyl or tolylsulphonyl group, by a 3-dimethylaminopropyl or 3-dimethylamino-prop-1-enyl group, by an ethyl group which is substituted in the 1 position by an amino or $C_{1-5}$-alkoxycarbonylamino group, by an ethyl group which is substituted in the 2 position by an amino or $C_{1-5}$-alkoxycarbonylamino group and by a carboxy or $C_{1-3}$-alkoxycarbonyl group, by an amino or $C_{1-3}$-alkylamino group in which the alkyl moiety may be substituted by a cyano, carboxy, $C_{1-3}$-alkoxycarbonyl, aminocarbonyl, methylaminocarbonyl or dimethylaminocarbonyl group or may be substituted in the 2 or 3 position by an amino, methylamino, dimethylamino, acetylamino, N-methyl-acetylamino or morpholino group, by an N—($C_{1-3}$-alkyl)-aminocarbonyl or N—($C_{1-3}$-alkyl)-methylaminocarbonyl group optionally substituted in the 2 or 3 position of the $C_{1-3}$-alkyl moiety by a dimethylamino group, while any hydrogen atom present at the amino nitrogen atom in the abovementioned groups may additionally be replaced by a formyl, trifluoroacetyl, benzoyl, $C_{1-4}$-alkoxycarbonyl or $C_{1-4}$-alkylaminocarbonyl group, by a $C_{2-4}$-alkanoyl group which may be terminally substituted by an amino, acetylamino, $C_{1-4}$-alkoxycarbonylamino, pyrrolidino, piperidino, morpholino, piperazino, 4-methylpiperazino, 4-benzylpiperazino or phthalimido group or by a $C_{1-3}$-alkylamino, N-acetyl-$C_{1-3}$-alkyl-amino or di-($C_{1-3}$-alkyl)-amino group, while in the abovementioned $C_{1-3}$-alkylamino, N-acetyl-$C_{1-3}$-alkyl-amino- and di-($C_{1-3}$-alkyl)-amino groups any $C_{1-3}$-alkyl moiety may additionally be substituted by a phenyl group or in the 2 or 3 position by a methoxy, dimethylamino or morpholino group, by a $C_{1-4}$-alkylsulphonyl group in which the alkyl moiety may additionally be substituted in the 2 or 3 position by a dimethylamino, piperidino or morpholino group, by a phenylsulphonyl or toluenesulphonyl group, by a $C_{1-3}$-alkoxy group which is substituted by a carboxy, $C_{1-3}$-alkoxycarbonyl, aminocarbonyl, methylaminocarbonyl or dimethylaminocarbonyl group or is substituted in the 2 or 3 position by an amino, methylamino, dimethylamino, N-methyl-benzylamino, piperidino or hexamethyleneimino group, by a $C_{1-3}$-alkylaminocarbonyl or di-($C_{1-3}$-alkyl)-aminocarbonyl group wherein a $C_{1-3}$-alkyl moiety may be substituted in the 2 or 3 position by a methoxy or dimethylamino group, the isomers and the salts thereof.

Most particularly preferred compounds of general formula I are those wherein

X denotes an oxygen atom $R_1$ denotes a hydrogen atom, $R_2$ denotes a hydrogen, chlorine or bromine atom, a methyl or nitro group, $R_3$ denotes a phenyl group which may be substituted by a fluorine, chlorine or bromine atom, by a methyl, methoxy, aminomethyl, acetylaminomethyl, carboxy, methoxycarbonyl or imidazolylmethyl group, $R_4$ denotes a hydrogen atom, $R_5$ denotes a phenyl group which may be substituted by a fluorine, chlorine or bromine atom, by a methyl, methoxy, nitro, cyano or trifluoromethyl group, by a methyl or ethyl group, each of which is substituted by a carboxy, $C_{1-3}$-alkoxycarbonyl, cyano, azetidin-1-yl, pyrrolidino, piperidino, 4-phenylpiperidino, 3,6-dihydro-2H-pyridin-1-yl, hexamethyleneimino, morpholino, thiomorpholino, 1-oxido-thiomorpholino, piperazino, 4-methylpiperazino or 4-acetylpiperazino group, while the abovementioned piperidino groups may additionally be substituted by one or two methyl groups or may be substituted in the 3 or 4 position by a hydroxy, methoxy, carboxy, hydroxymethyl, $C_{1-3}$-alkoxycarbonyl, aminocarbonyl, methylaminocarbonyl or dimethylaminocarbonyl group, by a straight-chain $C_{1-2}$-alkyl group which may be terminally substituted by an amino or benzylamino group, by a $C_{1-4}$-alkylamino group in which the alkyl moiety in positions 2, 3 or 4 is substituted by a hydroxy or methoxy group, by a $C_{1-2}$-alkylamino group substituted in the $C_{1-2}$-alkyl moiety by a carboxy, $C_{1-3}$-alkoxycarbonyl or dimethylaminocarbonyl group, while in the abovementioned groups a hydrogen atom present at the amino nitrogen may additionally be replaced by a $C_{3-6}$-cycloalkyl group, by a $C_{1-4}$-alkyl group in which the alkyl moiety may be substituted in positions 2, 3 or 4 by a hydroxy group, or by a $C_{1-2}$-alkylcarbonyl group optionally substituted by an amino, methylamino or dimethylamino group, by a 3-dimethylamino-prop-1-enyl group, by an ethyl group which is substituted in the 1-position by an amino or $C_{1-4}$-alkoxycarbonylamino group, by an amino or $C_{1-3}$-alkylamino group in which the alkyl moiety may be terminally substituted by a carboxy, aminocarbonyl, methylaminocarbonyl or dimethylaminocarbonyl group or in the 2 or 3 position by an amino, methylamino, dimethylamino, acetylamino, N-acetyl-methylamino or morpholino group or by an N—($C_{1-3}$-alkyl)-aminocarbonyl or N—($C_{1-3}$-alkyl)-methylaminocarbonyl group optionally substituted in the 2 or 3 position by a dimethylamino group, while a hydrogen atom present at the amino nitrogen in the abovementioned groups may additionally be substituted by a formyl or benzoyl group, by a $C_{2-4}$-alkanoyl group which may be terminally substituted by an amino, acetylamino, pyrrolidino, piperidino, morpholino, piperazino or 4-methylpiperazino group or by a $C_{1-3}$-alkylamino, N-acetyl-$C_{1-3}$-alkylamino or di-($C_{1-3}$-alkyl)-amino group, while in the abovementioned $C_{1-3}$-alkylamino, N-acetyl-$C_{1-3}$-alkylamino or di-($C_{1-3}$-alkyl)-amino groups a $C_{1-3}$-alkyl moiety may additionally be substituted in the 2 or 3 position by a methoxy, dimethylamino or morpholino group, by a $C_{1-4}$-alkylsulphonyl group which may be substituted in the 2 or 3 position by a dimethylamino group, by a pyrrolidinosulphonyl group, an aminosulphonyl, $C_{1-3}$-alkylaminosulphonyl or di-($C_{1-3}$-alkyl)-aminosulphonyl group, wherein in each case a $C_{1-3}$-alkyl moiety may be substituted by a carboxy, $C_{1-3}$- alkoxycarbonyl, aminocarbonyl, methylaminocarbonyl or dimethylaminocarbonyl group or, except in the 1 position, by a dimethylamino group, by a $C_{2-3}$-alkoxy group which is substituted in the 2 or 3 position by a dimethylamino or piperidino group, by an aminocarbonyl, $C_{1-3}$-alkylaminocarbonyl or di-($C_{1-3}$-alkyl)-aminocarbonyl group, wherein in each case the $C_{1-3}$-alkyl moieties may be substituted by a methoxy or dimethylamino group, except in the 1 positions, particularly those compounds of the above general formula I wherein X and $R_2$ to $R_4$ are as hereinbefore defined,
$R_1$ denotes a hydrogen atom and
$R_5$ denotes a phenyl group which may be substituted
by a methyl or ethyl group, each of which is substituted by an azetidin-1-yl, pyrrolidino, piperidino, hexamethyleneimino, morpholino, 1-oxido-thiomorpholino, piperazino, 4-methylpiperazino or 4-acetylpiperazino group, while the abovementioned piperidino groups may additionally be substituted by one or two methyl groups or in the 4 position may be substituted by a hydroxy, methoxy, hydroxymethyl, aminocarbonyl, methylaminocarbonyl or dimethylaminocarbonyl group, by a straight-chain $C_{1-2}$-alkyl group which is terminally substituted by an amino group or by a $C_{1-3}$-alkylamino group, while the alkyl moiety of the $C_{1-3}$-alkylamino group may be substituted in positions 2 or 3 by a hydroxy or methoxy group and in the abovementioned groups the hydrogen atom present at the amino nitrogen may additionally be replaced
by a $C_{3-6}$-cycloalkyl group, by a $C_{1-3}$-alkyl group in which the alkyl moiety in positions 2 or 3 may be substituted by a hydroxy group, or by a $C_{1-2}$-alkylcarbonyl group substituted by an amino, methylamino or dimethylamino group, by an ethyl group substituted in the 1 position by an amino group, by an amino or $C_{1-3}$-alkylamino group in which the alkyl moiety may be terminally substituted by a carboxy, aminocarbonyl, methylaminocarbonyl, dimethylaminocarbonyl, N-(2-dimethylamino-ethyl)-aminocarbonyl or N-(2-dimethylamino-ethyl)-N-methyl-aminocarbonyl group or may be substituted in the 2 or 3 position by an amino, methylamino, dimethylamino, acetylamino, N-acetyl-methylamino or morpholino group, while the hydrogen atom present at the amino nitrogen of the abovementioned groups may additionally be replaced
by a $C_{2-4}$-alkanoyl group which may be terminally substituted by an amino, acetylamino, pyrrolidino, piperidino, morpholino, piperazino or 4-methylpiperazino group or by a $C_{1-3}$-alkylamino, N-acetyl-$C_{1-3}$-alkylamino or di-($C_{1-3}$-alkyl)-amino group, while in the abovementioned $C_{1-3}$-alkylamino, N-acetyl-$C_{1-3}$-alkylamino or di-($C_{1-3}$-alkyl)-amino groups a $C_{1-3}$-alkyl moiety may additionally be substituted in the 2 or 3 position by a methoxy, dimethylamino or morpholino group, by a $C_{1-4}$-alkylsulphonyl group which may be substituted in the 2 or 3 position by a dimethylamino group, by a pyrrolidinosulphonyl group, an aminosulphonyl, $C_{1-3}$-alkylaminosulphonyl or di-($C_{1-3}$-alkyl)-aminosulphonyl group, wherein in each case a $C_{1-3}$-alkyl moiety may be substituted by a carboxy, methoxycarbonyl, aminocarbonyl, methylaminocarbonyl or dimethylaminocarbonyl group or, except in the 1 position, by a dimethylamino group, by a $C_{1-3}$-alkoxy group substituted in the 2 or 3 position by a dimethylamino or piperidino group, by an aminocarbonyl, $C_{1-3}$-alkylaminocarbonyl or di-($C_{1-3}$-alkyl)-aminocarbonyl group, wherein in each case a $C_{1-3}$-alkyl moiety may be substituted by a methoxy or dimethylamino group, except in the 1 position, the isomers and the salts thereof.

The following are mentioned as examples of particularly preferred compounds of general formula I:

(a) (Z)-3-[1-(4-dimethylaminomethyl-phenylamino)-1-phenyl-methylidene]-5-nitro-2-indolinone,
(b) (Z)-3-[1-(4-piperidinomethyl-phenylamino)-1-phenyl-methylidene]-5-nitro-2-indolinone,
(c) (Z)-3-{1-[4-(2-morpholinoethyl)-phenylamino]-1-phenyl-methylidene}-5-nitro-2-indolinone,
(d) (Z)-3-{1-[4-(2-dimethylamino-ethyl)-phenylamino]-1-phenyl-methylidene}-5-nitro-2-indolinone and
(e) (Z)-3-{1-[4-(N-(2-dimethylamino-ethyl)-N-methylsulphonyl-amino)-phenylamino]-1-phenyl-methylidene}-2-indolinone and the salts thereof.

According to the invention, the new compounds may be obtained, for example, by the following methods known in principle from the literature:

a. Reaction of a Compound of General Formula

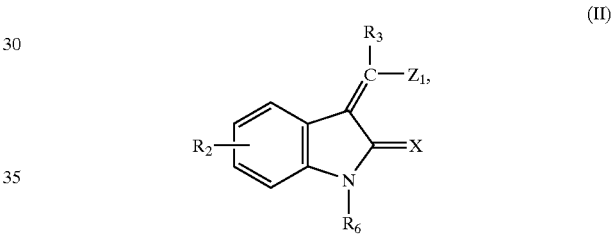

(II)

wherein
X, $R_2$ and $R_3$ are as hereinbefore defined,
$R_6$ denotes a hydrogen atom, a protecting group for the nitrogen atom of the lactam group or a bond to a solid phase and
$Z_1$ denotes a halogen atom, a hydroxy, alkoxy or aralkoxy group, e.g. a chlorine or bromine atom, a methoxy, ethoxy or benzyloxy group, with an amine of general formula

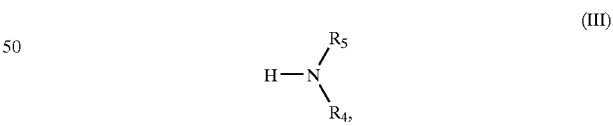

(III)

wherein
$R_4$ and $R_5$ are as hereinbefore defined,
and if necessary subsequently cleaving any protecting group used for the nitrogen atom of the lactam group or cleaving from a solid phase.

A protecting group for the nitrogen atom of the lactam group might be for example an acetyl, benzoyl, ethoxycarbonyl, tert.butyloxycarbonyl or benzyloxycarbonyl group and the solid phase might be a Rink resin such as a p-benzyloxybenzyl alcohol resin, whilst the bond may conveniently be formed via an intermediate member such as a 2,5-dimethoxy-4-hydroxy-benzyl derivative.

The reaction is conveniently carried out in a solvent such as dimethylformamide, toluene, acetonitrile, tetrahydrofuran, dimethylsulphoxide, methylene chloride or mixtures thereof, optionally in the presence of an inert base such as triethylamine, N-ethyl-diisopropylamine or sodium hydrogen carbonate at temperatures between 20 and 175° C., whilst any protecting group used can be cleaved simultaneously by transamidation.

If $Z_1$ in a compound of general formula II denotes a halogen atom, the reaction is preferably carried out in the presence of an inert base at temperatures between 20 and 120° C.

If $Z_1$ in a compound of general formula II denotes a hydroxy, alkoxy or aralkoxy group, the reaction is preferably carried out at temperatures between 20 and 200° C.

If any protecting group used subsequently has to be cleaved, this is conveniently carried out either hydrolytically in an aqueous or alcoholic solvent, e.g. in methanol/water, ethanol/water, isopropanol/water, tetrahydrofuran/water, dioxane/water, dimethylformamide/water, methanol or ethanol in the presence of an alkali metal base such as lithium hydroxide, sodium hydroxide or potassium hydroxide at temperatures between 0 and 100° C., preferably at temperatures between 10 and 50° C., or advantageously by transamidation with a primary or secondary organic base such as methylamine, butylamine, dimethylamine or piperidine in a solvent such as methanol, ethanol, dimethylformamide and mixtures thereof or in an excess of the amine used at temperatures between 0 and 100° C., preferably at temperatures between 10 and 50° C.

Any solid phase used is preferably cleaved using trifluoroacetic acid and water in the presence of a dialkylsulphide such as dimethylsulphide at temperatures between 0 and 35° C., preferably at ambient temperature.

b. In order to prepare a compound of general formula I which contains an aminomethyl group and wherein X denotes an oxygen atom:
Reduction of a Compound of General Formula

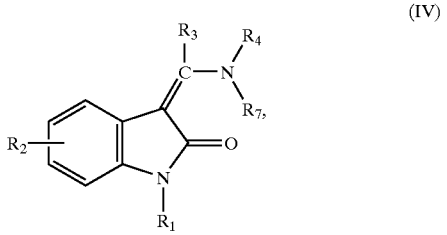

(IV)

wherein $R_1$ to $R_4$ are as hereinbefore defined and $R_7$ has the meanings given for $R_5$ hereinbefore, with the proviso that that $R_5$ contains a cyano group.

The reduction is preferably carried out by catalytic hydrogenation with hydrogen in the presence of a catalyst such as palladium/charcoal or platinum in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, but preferably 3 to 5 bar.

c. In order to prepare a compound of general formula I wherein $R_1$ denotes a hydrogen atom and X denotes an oxygen atom:
Reduction of a Compound of General Formula

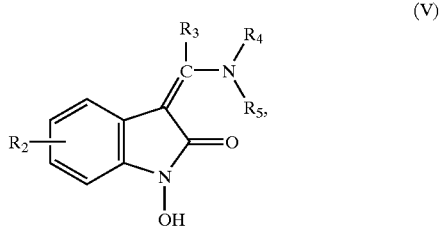

(V)

wherein $R_2$ to $R_5$ are as hereinbefore defined.

The reduction is preferably carried out by catalytic hydrogenation with hydrogen in the presence of a catalyst such as palladium/charcoal or platinum in a solvent such as methanol, ethanol, ethyl acetate, dimethylformamide, dimethylformamide/acetone or glacial acetic acid, at temperatures between 0 and 50° C., but preferably at ambient temperature, and at a hydrogen pressure of 1 to 7 bar, but preferably 3 to 5 bar.

If according to the invention a compound of general formula I is obtained which contains an alkoxycarbonyl group, this can be converted by hydrolysis into a corresponding carboxy compound, or if a compound of general formula I is obtained which contains an amino or alkylamino group, this may be converted by alkylation or reductive alkylation into a corresponding alkylamino or dialkylamino compound, or if a compound of general formula I is obtained which contains an amino or alkylamino group, this may be converted by acylation into a corresponding acyl compound, or if a compound of general formula I is obtained which contains a carboxy group, this may be converted by esterification or amidation into a corresponding ester or aminocarbonyl compound, or if a compound of general formula I is obtained wherein $R_3$ denotes a phenyl group which contains a chlorine, bromine or iodine atom, this may be converted into a corresponding alkenylated compound by reaction with an alkenyl compound, or if a compound of general formula I is obtained wherein $R_3$ denotes a phenyl group which contains a chlorine, bromine or iodine atom, this may be converted into a corresponding alkynylated compound by reaction with an alkynyl compound.

The subsequent hydrolysis is preferably carried out in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide at temperatures between 0 and 100° C., preferably at temperatures between 10 and 50° C.

The subsequent reductive alkylation is preferably carried out in a suitable solvent such as methanol, methanol/water, methanol/water/ammonia, ethanol, ether, tetrahydrofuran, dioxane or dimethylformamide optionally with the addition of an acid such as hydrochloric acid in the presence of catalytically activated hydrogen, e.g. hydrogen in the presence of Raney nickel, platinum or palladium/charcoal, or in the presence of a metal hydride such as sodium borohydride, sodium cyanoborohydride, lithium borohydride or lithium aluminium hydride at temperatures between 0 and 100° C., preferably at temperatures between 20 and 80° C.

The subsequent alkylation is carried out with an alkylating agent such as an alkyl halide or dialkyl sulphate such as methyl iodide, dimethylsulphate or propyl bromide preferably in a solvent such as methanol, ethanol, methylene chloride, tetrahydrofuran, toluene, dioxane, dimethylsulphoxide or dimethylformamide optionally in the presence of an inorganic or a tertiary organic base such as triethylamine, N-ethyl-diisopropylamine or dimethylaminopyridine, preferably at temperatures between 20° C. and the boiling temperature of the solvent used.

The subsequent acylation is preferably carried out in a solvent such as methylene chloride, diethyl ether, tetrahydrofuran, toluene, dioxane, acetonitrile, dimethylsulphoxide or dimethylformamide, optionally in the presence of an inorganic or a tertiary organic base, preferably at temperatures between 20° C. and the boiling temperature of the solvent used. The acylation with a corresponding acid is preferably carried out in the presence of a dehydrating agent, e.g. in the presence of isobutyl chloroformate, tetraethyl orthocarbonate, trimethyl orthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexyl-carbodiimide/N-hydroxysuccinimide, N,N'-dicyclohexylcarbodiimide/1-hydroxy-benztriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylamino-pyridine, N-methyl-morpholine or triethylamine, conveniently at temperatures between 0 and 150° C., preferably at temperatures between 0 and 100° C., and the acylation with a corresponding reactive compound such as an anhydride, ester, imidazolide or halide thereof is optionally carried out in the presence of a tertiary organic base such as triethylamine, N-ethyl-diisopropylamine or N-methylmorpholine at temperatures between 0 and 150° C., preferably at temperatures between 50 and 100° C.

The subsequent esterification or amidation is expediently carried out by reacting a corresponding reactive carboxylic acid derivative with a corresponding alcohol or amine as described hereinbefore.

The subsequent alkenylation is preferably carried out in a solvent such as dimethylformamide, dimethylacetamide or acetonitrile in the presence of a palladium catalyst such as bis-(triphenylphosphine)-palladium-dichloride and preferably in the presence of a suitable base such as, for example, triethylamine, tributylamine, N-ethyl-diisopropylamine or sodium acetate at temperatures between 20 and 120° C. (cf. R. F. Heck, Org. Reactions 27, 345–390 (1982).

The subsequent alkynylation is preferably carried out in a solvent such as benzene, toluene, dimethylformamide or chloroform in the presence of a palladium catalyst such as tetrakis-triphenylphosphine-palladium and copper-(I)-iodide, preferably in the presence of a suitable base such as triethylamine, at temperatures between 20 and 100° C. (cf. also N. A. Bumagin et al. Synthesis 1984, 728–729; K. Sonogashira et al. Tetrahedron Lett. 1975, 4467).

Alkenyl-substituted arylamines are prepared under the conditions of palladium-catalysed coupling. To do this, aryl halide and the alkenyl compound are reacted with a catalytic amount of a palladium catalyst such as bis-(triphenylphosphine)-palladium-dichloride in a solvent such as DMF, dimethylacetamide or acetonitrile in the presence of an inert base such as, for example, triethylamine, tributylamine, N-ethyl-diisopropylamine or sodium acetate at temperatures between 20 and 120° C.

In the reactions described hereinbefore, any reactive groups present such as carboxy, amino, alkylamino or imino groups may be protected during the reaction by conventional protecting groups which are cleaved again after the reaction.

For example, a protecting group for a carboxyl group may be a trimethylsilyl, methyl, ethyl, tert.butyl, benzyl or tetrahydropyranyl group and a protecting group for an amino, alkylamino or imino group may be an acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, tetrahydrofuran/water or dioxane/water, in the presence of a acid such as trifluoroacetic acid, hydrochloric acid or sulphuric acid or in the presence of an alkali metal base such as lithium hydroxide, sodium hydroxide or potassium hydroxide, at temperatures between 0 and 100° C., preferably at temperatures between 10 and 50° C.

However, a benzyl, methoxybenzyl or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid or glacial acetic acid at temperatures between 0 and 50° C., but preferably at ambient temperature, and at a hydrogen pressure of 1 to 7 bar, but preferably 3 to 5 bar.

A methoxybenzyl group may also be cleaved in the presence of an oxidising agent such as cerium(IV) ammonium nitrate in a solvent such as methylene chloride, acetonitrile or acetonitrile/water at temperatures of between 0 and 50° C., but preferably at ambient temperature.

A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid, optionally using a solvent such as methylene chloride, dioxan, ethyl acetate or ether.

A phthalyl group is preferably cleaved in the presence of hydrazine or a primary amine such as methylamine, ethylamine or n-butylamine in a solvent such as methanol, ethanol, isopropanol, toluene/water or dioxan at temperatures between 20 and 50° C.

Moreover, chiral compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid, dibenzoyltartaric acid, di-o-tolyltartaric acid, malic acid, mandelic acid, camphorsulphonic acid, glutamic acid, N-acetylglutamic acid, aspartic acid, N-acetylaspartic acid or quinic acid. An optically active alcohol may be for example (+)- or (−)-menthol and an optically active acyl group in amides, for example, may be a (+)- or (−)-menthyloxycarbonyl group.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid, maleic acid or methanesulphonic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

The compounds of general formulae I to VIII used as starting materials are known from the literature in some cases or may be obtained by methods known from the literature or are described in the Examples.

As already mentioned, the new compounds of general formula I wherein $R_1$ denotes a hydrogen atom or a prodrug group have valuable pharmacological properties, particularly inhibitory effects on various kinases, especially on complexes of CDK's (CDK1, CDK2, CDK3, CDK4, CDK5, CDK6, CDK7, CDK8 and CDK9) with their specific cyclins (A, B1, B2, C, D1, D2, D3, E, F, G1, G2, H, I and K), on viral cyclin (cf. L. Mengtao in J. Virology 71(3), 1984–1991 (1997)) and on receptor-tyrosine kinases such as HER2, EGFR, FGFR, IGF-1 R and KDR, on the proliferation of cultivated human tumour cells and after oral administration on the growth of tumours in nude mice which have been infected with human tumour cells.

The biological properties of the compounds listed in Table 1 were tested as follows:

Test 1

Inhibition of Cyclin/CDK Enzyme, In Vitro Activity

High Five™ insect cells (BTI-TN-5B1-4) which had been infected with a high titre of recombinant baculovirus were used to produce active human cyclin/CDK holoenzymes. By using a baculovirus vector which contained two promoters (polyhedrin enhancer promoter, P10 enhancer promoter), GST-tagged cyclins (e.g. cyclin D1 or cyclin D3) with the corresponding $His_6$-tagged CDK subunit (e.g. for CDK4 or CDK6) were expressed in the same cell. The active holoenzyme was isolated by affinity chromatography on glutathione sepharose. Recombinant GST-tagged pRB (aa 379–928) was produced in *E. coli* and purified by affinity chromatography on glutathione sepharose.

The substrates used for the kinase assays depended on the specific kinases. Histone H1 (Sigma) was used as the substrate for cyclin E/CDK2, cyclin A/CDK2, cyclin B/CDK1 and for v-cyclin/CDK6. GST-tagged pRB (aa 379–928) was used as substrate for cyclin D1/CDK4, cyclin D3/CDK4, cyclin D1/CDK6 and for cyclin D3/CDK6.

Lysates of the insect cells infected with recombinant baculovirus or recombinant kinases (obtained from the lysates by purification) were incubated together with radio-labelled ATP in the presence of a suitable substrate with various concentrations of the inhibitor in a 1% DMSO solution (dimethyl sulphoxide) for 45 minutes at 30° C. The substrate proteins with associated radioactivity were precipitated with 5% TCA (trichloroacetic acid) in water-repellent PVDF multi-well microtitre plates (Millipore) or with 0.5% phosphoric acid solution on Whatman P81 filters. After the addition of scintillation liquid the radioactivity was measured in a Wallace 1450 Microbeta Liquid Scintillation Counter. For each concentration of the substance double measurements were carried out; $IC_{50}$ values were calculated for the enzyme inhibition.

Test 2

Inhibition of the Proliferation of Cultivated Human Tumour Cells

Cells of the Leimyosarcoma tumour cell line SK-UT-1B (obtained from the American Type Culture Collection (ATCC)) were cultivated in Minimum Essential Medium with non-essential amino acids (Gibco), supplemented with sodium pyruvate (1 mmol), glutamine (2 mmol) and 10% foetal calf serum (Gibco) and harvested during the log-growth phase. Then the SK-UT-1B cells were added to Cytostar® multi-well plates (Amersham) at a density of 4000 cells per well and incubated overnight in an incubator. Various concentrations of the compounds (dissolved in DMSO; final concentration: <1%) were added to the cells. After 48 hours' incubation $^{14}C$-thymidine (Amersham) was added to each well and incubation was continued for a further 24 hours. The quantity of $^{14}C$-thymidine incorporated into the tumour cells in the presence of the inhibitor and representing the number of cells in the S phase was measured in a Wallace 1450 Microbeta Liquid Scintillation Counter. $IC_{50}$ values for the inhibition of proliferation (=inhibition of incorporated $^{14}C$-thymidine) were calculated, correcting for the background radiation. All the measurements were done twice.

Test 3

In Vivo Effects on Tumour-bearing Nude Mice $10^6$ cells [SK-UT-1B, or non-small cell lung tumour NCI-H460 (obtained from ATCC)] in a volume of 0.1 ml were injected subcutaneously into male and/or female nude mice (NMRI nu/nu; 25–35 g; N=10–20); alternatively, small fragments of SK-UT-1B or NCI-H460 cell clumps were implanted subcutaneously. One to three weeks after the injection or implantation a kinase inhibitor was administered daily by oral route for a period of 2 to 4 weeks (by oesophageal tube). The size of the tumour was measured three times a week using a digital sliding gauge. The effect of a kinase inhibitor on the tumour growth was determined as a percentage inhibition compared with a control group treated with placebo.

The Table which follows contains the results obtained in in vitro test 2:

| Compound (Example no.) | Inhibition of SKUT-1B-proliferation IC$_{50}$ [µM] |
|---|---|
| 117 | 0.34 |
| 170 | 0.22 |
| 133 | 0.48 |
| 134 | 0.56 |
| 188 | 0.15 |

In view of their biological properties, the new compounds of general formula I, their isomers and physiologically acceptable salts are suitable for the treatment of diseases characterised by excessive or abnormal cell proliferation.

Such diseases include (with no claim to completeness): viral infections (e.g. HIV and Kaposi's sarcoma); inflammation and autoimmune diseases (e.g. colitis, arthritis, Alzheimer's disease, glomerulonephritis and wound healing); bacterial, fungal and/or parasitic infections; leukaemias, lymphoma and solid tumours; skin diseases (e.g. psoriasis); bone diseases; cardiovascular diseases (e.g. restenosis and hypertrophy). They are also useful for protecting proliferating cells (e.g. hair, intestinal, blood and progenitor cells) against DNA damage caused by radiation, UV treatment and/or cytostatic treatment.

The new compounds may be used for the short-term or long-term treatment of the abovementioned diseases, optionally in conjunction with other 'state of the art' compounds such as other cytostatics.

The dosage required to achieve such an effect is appropriately 0.1 to 30 mg/kg, preferably 0.3 to 10 mg/kg by intravenous route, and 0.1 to 100 mg/kg, preferably 0.3 to 30 mg/kg by oral route, in each case administered 1 to 4 times a day. For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The Examples which follow are intended to illustrate the invention:

Abbreviations Used:
CDI=N,N'-carbonyldiimidazole
DMF=dimethylformamide
HOBt=1-hydroxy-1H-benzotriazole
TBTU=O-(benzotriazol-1-yl)-N,N,N',N'-bis(tetramethylene)-uronium hexafluorophosphate
THF=Tetrahydrofuran

EXAMPLE 1

(Z)-3-(1-Anilino-1-phenyl-methylidene)-2-indolinone a) 1-acetyl-2-indolinone 13.3 g (0.1 mol) of 2-indolinone and 30 ml of acetic anhydride are stirred for 3 hours at 170° C. After cooling, 150 ml of ice water are added, the crystalline product is suction filtered, washed with water and dried.
Yield: 16.6 g (95% of theory),
Melting point: 129–130° C.

b) 1-acetyl-3-(1-ethoxy-1-phenyl-methylidene)-2-indolinone 35.0 g (0.2 mol) of 1-acetyl-2-indolinone are dissolved in 300 ml of acetic anhydride and after the addition of 135 g (0.6 mol) of triethyl orthobenzoate the mixture is refluxed for 22 hours. The solvent is distilled off and the residue diluted with petroleum ether. After 18 hours' standing at ambient temperature, the crystalline precipitate is suction filtered, washed and dried.
Yield: 41.2 g (67% of theory).

c) (Z)-3-(1-Anilino-1-phenyl-methylidene)-2-indolinone 450 mg (1.5 mmol) of 1-acetyl-3-(1-ethoxy-1-phenyl-methylidene)-2-indolinone and 0.41 ml of (4.5 mmol) of aniline are stirred in 7 ml of DMF for 90 minutes at 120° C. After cooling to ambient temperature 7 ml of methanol and 3 ml of 1N sodium hydroxide solution are added. The mixture is stirred for 20 minutes, then diluted with water, the crystalline reaction product is suction filtered and dried.
Yield: 49% of theory,
Melting point: 325° C.
$C_{21}H_{16}N_2O$ (312.37).
Mass spectrum: M$^+$=312.

EXAMPLE 2

(Z)-3-[1-(4-methoxy-phenylamino)-1-phenyl-methylidene]-2-indolinone a) 1-acetyl-3-(1-hydroxy-1-phenyl-methylidene)-2-indolinone 880 mg (5 mmol) of 1-acetyl-2-indolinone and 610 mg (5 mmol) of benzoic acid are dissolved in 15 ml of DMF and after the addition of 1.8 g (5.5 mmol) of TBTU, 840 mg (5.5 mmol) of HOBt and 3.2 g (25 mmol) of N-ethyl-N,N-diisopropyl-amine are stirred for 16 hours at ambient temperature. The solution is stirred into dilute hydrochloric acid, the precipitate is suction filtered and dried at 60° C.
Yield: 1.1 g (80% of theory),
Melting point: 126–129° C.

b) 1-acetyl-3-(1-chloro-1-phenyl-methylidene)-2-indolinone 5.6 g (20 mmol) of 1-acetyl-3-(1-hydroxy-1-phenyl-methylidene)-2-indolinone are suspended in 45 ml of toluene and while cooling with ice combined with 4.2 g (20 mmol) of phosphorus pentachloride and then stirred for 18 hours at ambient temperature. The precipitate formed after cooling with ice is suction filtered and dried.
Yield: 5.3 g (89% of theory).

c) (Z)-3-[1-(4-methoxy-phenylamino)-1-phenyl-methylidene]-2-indolinone 0.18 g (1.5 mmol) of 4-methoxyaniline and 0.2 g (0.28 mmol) of triethylamine are dissolved in 5 ml of dichloromethane and at 5° C. combined with a solution of 0.45 g (1.5 mmol) of 1-acetyl-3-(1-chloro-1-phenyl-methylidene)-2-indolinone in 10 ml of dichloromethane and then stirred for 3 hours at ambient temperature. After removal of the solvent in vacuo the residue is taken up in ethyl acetate/water. The organic phase is washed with water, dried and the solvent is eliminated in vacuo. Then the mixture is dissolved in 15 ml of methanol, combined with 3 ml of 1N sodium hydroxide solution, stirred for 3 hours at ambient temperature and diluted with water and ethyl acetate. The organic phase is dried and concentrated by evaporation. The residue is heated in ethyl acetate, cooled, then suction filtered and dried.
Yield: 100 mg (20% of theory),
Melting point: 267–270° C.

$C_{22}H_{18}N_2O_2$ (342.40).

Mass spectrum: $M^+=342$.

Calc.: C, 77.17; H, 5.30; N, 8.18. Found: 76.43; 5.39; 8.06.

EXAMPLE 3

(Z)-3-[1-(3-methoxy-phenylamino)-1-phenyl-methylidene]-2-indolinone

Prepared analogously to Example 2 from 1-acetyl-3-(1-chloro-1-phenyl-methylidene)-2-indolinone and 3-methoxyaniline in THF and subsequent treatment with sodium hydroxide solution.

Yield: 69% of theory,

Melting point: 218–221° C.

$C_{22}H_{18}N_2O_2$ (342.40).

Mass spectrum: $M^+=342$.

Calc.: C, 77.17; H, 5.30; N, 8.18. Found: 76.74; 5.30; 7.74.

EXAMPLE 4

(Z)-3-[1-(2-methoxy-phenylamino)-1-phenyl-methylidene]-2-indolinone

Prepared analogously to Example 1 from 1-acetyl-3-(1-ethoxy-1-phenyl-methylidene)-2-indolinone and 2-methoxyaniline in DMF and subsequent treatment with sodium hydroxide solution in methanol.

Yield: 44% of theory,

Melting point: 237° C.

$C_{22}H_{18}N_2O_2$ (342.40).

Mass spectrum: $M^+=342$.

$R_f$ value: 0.47 (silica gel; petroleum ether/ethyl acetate=4:6).

$C_{22}H_{18}N_2O_2 \times H_2O$ (360.42).

Calc.: C, 73.32; H, 5.59; N, 7.77. Found: 73.51; 5.61; 7.66.

EXAMPLE 5

(Z)-3-[1-(3-methoxymethyl-phenylamino)-1-phenyl-methylidene]-2-indolinone

Prepared analogously to Example 2 from 1-acetyl-3-(1-chloro-1-phenyl-methylidene)-2-indolinone and 3-methoxymethyl-aniline-hydrochloride in THF and subsequent treatment with sodium hydroxide solution in methanol.

Yield: 28% of theory,

Melting point: 182–184° C.

$C_{23}H_{20}N_2O_2$ (356.43).

Mass spectrum: $M^+=356$.

Calc.: C, 77.51; H, 5.66; N, 7.86. Found: 77.12; 5.91; 7.74.

EXAMPLE 6

(Z)-3-[1-(3-methyl-phenylamino)-1-phenyl-methylidene]-2-indolinone

Prepared analogously to Example 2 from 1-acetyl-3-(1-chloro-1-phenyl-methylidene)-2-indolinone and m-toluidine in dichloromethane and subsequent treatment with sodium hydroxide solution in methanol.

Yield: 3% of theory,

Melting point: 218–220° C.

$C_{22}H_{18}N_2O$ (326.40).

Mass spectrum: $M^+=326$.

EXAMPLE 7

(Z)-3-[1-(2-methoxycarbonyl-phenylamino)-1-phenyl-methylidene]-2-indolinone

Prepared analogously to Example 1 from 1-acetyl-3-(1-ethoxy-1-phenyl-methylidene)-2-indolinone and methyl anthranilate in DMF and subsequent brief treatment with sodium hydroxide solution in methanol.

Yield: 12% of theory,

Melting point: 241–244° C.

$C_{23}H_{18}N_2O_3$ (370.41).

Mass spectrum: $M^+=370$.

Calc.: C, 74.58; H, 4.90; N, 7.56. Found: 73.87; 4.85; 7.44.

EXAMPLE 8

(Z)-3-[1-(2-carboxy-phenylamino)-1-phenyl-methylidene]-2-indolinone 176 mg (0.48 mmol) of (Z)-3-[1-(2-methoxycarbonyl-phenylamino)-1-phenyl-methylidene]-2-indolinone are dissolved in 15 ml of methanol and 2 ml of dioxane and after the addition of 1.4 ml of 1N sodium hydroxide solution stirred for two hours at 80° C. Then the mixture is neutralised 1.4 ml of 1N hydrochloric acid while being cooled, the product precipitated is suction filtered, washed with water and dried.

Yield: 100 mg (59% of theory),

Melting point: 227–230° C.

$C_{22}H_{16}N_2O_3$ (356.38).

Mass spectrum: $M^+=356$.

$R_f$ value: 0.30 (silica gel; dichloromethane/methanol/glacial acetic acid=19:1:0.1).

EXAMPLE 9

(Z)-3-[1-(3-carboxy-phenylamino)-1-phenyl-methylidene]-2-indolinone a) 1-benzoyl-3-(1-hydroxy-1-phenyl-methylidene)-2-indolinone 26.6 g (0.2 mol) of 2-indolinone and 53.8 g (0.44 mol) of 4-dimethylamino-pyridine are dissolved in 400 ml of DMF and after the addition of 30.9 g (0.22 mol) of benzoylchloride in 100 ml of DMF stirred for 45 minutes at 45° C. The solution is poured onto 3 l of water and 100 ml of conc. hydrochloric acid, the precipitate formed is suction filtered, recrystallised from glacial acetic acid and dried.

Yield: 11.8 g (17% of theory),

Melting point: 185–187° C.

b) 1-benzoyl-3-(1-chloro-1-phenyl-methylidene)-2-indolinone

Prepared analogously to Example 2b from 1-benzoyl-3-(1-hydroxy-1-phenyl-methylidene)-2-indolinone and phosphorus pentachloride in toluene.

Yield: 99% of theory,

Melting point: 170–176° C.

c) (Z)-3-[1-(3-carboxy-phenylamino)-1-phenyl-methylidene]-2-indolinone

Prepared analogously to Example 2c from 1-benzoyl-3-(1-chloro-1-phenyl-methylidene)-2-indolinone and ethyl 3-aminobenzoate and subsequent total saponification with sodium hydroxide solution in methanol.

Yield: 60% of theory,
$C_{22}H_{16}N_2O_3$ (356.38).
Mass spectrum: $M^+=356$.
$R_f$ value: 0.33 (silica gel; petroleum ether/ethyl acetate= 3:2).

EXAMPLE 10

(Z)-3-{1-[3-(aminocarbonyl)phenylamino]-1-phenyl-methylidene}-2-indolinone

Prepared analogously to Example 9 from 1-benzoyl-3-(1-chloro-1-phenyl-methylidene)-2-indolinone and 3-aminobenzoic acid amide in THF and subsequent treatment with sodium hydroxide solution in methanol.
Yield: 76% of theory,
Melting point: 258–263° C.
$C_{22}H_{17}N_3O_2$ (355.40).
Mass spectrum: $M^+=355$.

EXAMPLE 11

(Z)-3-[1-(3-ethoxycarbonylmethyl-phenylamino)-1-phenyl-methylidene]-2-indolinone a) 3-(1-ethoxy-1-phenyl-methylidene)-2-indolinone 6.15 g (20 mmol) of 1-acetyl-3-(1-ethoxy-1-phenyl-methylidene)-2-indolinone are suspended in a little ethanol. 10 ml of 4N sodium hydroxide solution are added and the mixture is stirred for 1.5 hours at ambient temperature. After the addition of 100 ml of water the precipitate is suction filtered, washed with water and a little ether and dried at 80° C.
Yield 2.8 g (56% of theory),
Melting point: 168–169° C.

b) (Z)-3-[1-(3-ethoxycarbonylmethyl-phenylamino)-1-phenyl-methylidene]-2-indolinone Prepared analogously to Example 1c from 3-(1-ethoxy-1-phenyl-methylidene)-2-indolinone and ethyl 3-aminophenylacetate in DMF.
Yield: 71% of theory,
Melting point: 178–181° C.
$C_{25}H_{22}N_2O_3$ (398.47).
Mass spectrum: $M^+=398$.
$R_f$ value: 0.52 (silica gel; dichloromethane/methanol= 24:1).
Calc.: C, 75.36; H, 5.56; N, 7.03. Found: 75.23; 5.69; 6.95.

EXAMPLE 12

(Z)-3-[1-(3-carboxymethyl-phenylamino)-1-phenyl-methylidene]-2-indolinone

Prepared analogously to Example 8 by saponification of (Z)-3-[1-(3-ethoxycarbonylmethyl-phenylamino)-1-phenyl-methylidene]-2-indolinone in sodium hydroxide solution.
Yield: 90% of theory,
Melting point: 268–270° C.
$C_{23}H_{18}N_2O_3$ (370.41).
Mass spectrum: $M^+=370$.
$R_f$ value: 0.21 (silica gel; dichloromethane/methanol= 19:1).
Calc.: C, 74.58; H, 4.90; N, 7.56. Found: 74.54; 4.94; 7.59.

EXAMPLE 13

(Z)-3-[1-(4-ethoxycarbonyl-phenylamino)-1-phenyl-methylidene]-2-indolinone

Prepared analogously to Example 2 from 1-acetyl-3-(1-chloro-1-phenyl-methylidene)-2-indolinone and ethyl 4-aminobenzoate in dichloromethane and subsequent treatment with sodium hydroxide solution in methanol.
Yield: 19% of theory,
Melting point: 227–228° C.
$C_{24}H_{20}N_2O_3$ (384.44).
Mass spectrum: $M^+=384$.
Calc.: C, 74.98; H, 5.24; N, 7.29. Found: 74.37; 5.08; 7.02.

EXAMPLE 14

(Z)-3-[1-(3-ethoxycarbonyl-phenylamino)-1-phenyl-methylidene]-2-indolinone

Prepared analogously to Example 9c and 8 from 1-benzoyl-3-(1-chloro-1-phenyl-methylidene)-2-indolinone and ethyl 3-aminobenzoate in THF and subsequent treatment with sodium hydroxide solution in methanol.
Yield: 45% of theory,
Melting point: 194–195° C.
$C_{24}H_{20}N_2O_3$ (384.44).
Mass spectrum: $M^+=384$.
Calc.: C, 74.98; H, 5.24; N, 7.29. Found: 74.01; 5.28; 6.96.

EXAMPLE 15

(Z)-3-[1-(4-ethoxycarbonylmethyl-phenylamino)-1-phenyl-me-thylidene]-2-indolinone Prepared analogously to Example 1 from 1-acetyl-3-(1-ethoxy-1-phenyl-methylidene)-2-indolinone and ethyl 4-aminophenylacetate in DMF and subsequent treatment with piperidine.
Yield: 64% of theory,
Melting point: 167–168° C.
$C_{25}H_{22}N_2O_3$ (398.47).
Mass spectrum: $M^+=398$.
Calc.: C, 75.36; H, 5.56; N, 7.03. Found: 75.41; 5.63; 7.10.

EXAMPLE 16

(Z)-3-[1-(4-carboxymethyl-phenylamino)-1-phenyl-methylidene]-2-indolinone

Prepared analogously to Example 8 from (Z)-3-[1-(4-ethoxycarbonylmethyl-phenylamino)-1-phenyl-methylidene]-2-indolinone and sodium hydroxide solution in ethanol.
Yield: 81% of theory,
Melting point: 214–216° C.
$C_{23}H_{18}N_2O_3$ (370.41).
Mass spectrum: $M^+=370$.
Calc.: C, 74.58; H, 4.90; N, 7.56. Found: 74.82; 4.78; 7.74.

EXAMPLE 17

(Z)-3-[1-(4-carboxy-phenylamino)-1-phenyl-methylidene]-2-indolinone

Prepared analogously to Example 8 from (Z)-3-[1-(4-ethoxycarbonyl-phenylamino]-1-phenyl-methylidene]-2-indolinone and sodium hydroxide solution in ethanol.

Yield: 96% of theory,
Melting point: 312–316° C.
$C_{22}H_{16}N_2O_3$ (356.38).
Mass spectrum: $M^+$=356.
Calc.: C, 74.15; H, 4.53; N, 7.86. Found: 73.23; 4.48; 7.61.

EXAMPLE 18

(Z)-3-[1-(4-dimethylaminocarbonyl-phenylamino)-1-phenyl-me-thylidene]-2-indolinone 285 mg (0.8 mmol) of (Z)-3-[1-(4-carboxyphenylamino)-1-phenyl-methylidene]-2-indolinone and 330 mg (4 mmol) of dimethylamine-hydrochloride are dissolved in 8 ml of DMF and after the addition of 385 mg (1.2 mmol) of TBTU, 184 mg (1.2 mmol) of HOBt and 1.03 g (8 mmol) of N-ethyl-N,N-diisopropylamine, the mixture is stirred for 14 hours at ambient temperature. The solution is diluted with water, the product precipitated is suction filtered, washed with water and ethanol and dried.

Yield: 270 mg (88% of theory),
Melting point: 240–243° C.
$C_{24}H_{21}N_3O_2$ (383.45).
Mass spectrum: $M^+$=383.
Calc.: C, 75.18; H, 5.52; N, 10.96. Found: 75.19; 5.60; 10.94.

EXAMPLE 19

(Z)-3-[1-(4-methylaminocarbonyl-phenylamino)-1-phenyl-me-thylidene]-2-indolinone Prepared analogously to Example 18 from (Z)-3-[1-(4-carboxyphenylamino)-1-phenyl-methylidene]-2-indolinone, methylamine-hydrochloride, TBTU, HOBt and N-ethyl-N,N-diisopropylamine in DMF.

Yield: 68% of theory,
Melting point: 290–293° C.
$C_{23}H_{19}N_3O_2$ (369.43).
Mass spectrum: $M^+$=369.
Calc.: C, 74.78; H, 5.19; N, 11.37. Found: 75.58; 5.19; 11.22.

EXAMPLE 20

(Z)-3-[1-(4-aminocarbonyl-phenylamino)-1-phenyl-methylidene]-2-indolinone 356 mg (1 mmol) of (Z)-3-[1-(4-carboxyphenylamino)-1-phenyl-methylidene]-2-indolinone are dissolved in 10 ml of DMF and combined with 194 mg (1 mmol) of CDI. The mixture is stirred for 2 hours at ambient temperature, 2 ml of methanolic ammonia solution are added, then stirring is continued for 16 hours at ambient temperature. Then water is added, the precipitate is removed by suction filtering, washed with water and a little ether and dried at 80° C.

Yield: 270 mg (76% of theory),
Melting point: 321–323° C.
$C_{22}H_{17}N_3O_2$ (355.40).
Mass spectrum: $M^+$=355.
Calc.: C, 74.35; H, 4.82; N, 11.82. Found: 74.04; 4.93; 11.27.

EXAMPLE 21

(Z)-3-[1-(3-methylaminocarbonyl-phenylamino)-1-phenyl-methylidene]-2-indolinone

Prepared analogously to Example 18 from (Z)-3-[1-(3-carboxyphenylamino)-1-phenyl-methylidene]-2-indolinone, methylamine-hydrochloride, TBTU, HOBt and triethylamine in DMF.

Yield: 41% of theory,
Melting point: 250–252° C.
$C_{23}H_{19}N_3O_2$ (369.43).
Mass spectrum: $M^+$=369.

EXAMPLE 22

(Z)-3-[1-(3-dimethylaminocarbonyl-phenylamino)-1-phenyl-methylidene]-2-indolinone Prepared analogously to Example 21 from (Z)-3-[1-(3-carboxyphenylamino)-1-phenyl-methylidene]-2-indolinone, dimethylamine-hydrochloride, TBTU, HOBt and triethylamine in DMF.

Yield: 87% of theory,
Melting point: 261–263° C.
$C_{24}H_{21}N_3O_2$ (383.45).
Mass spectrum: $M^+$=383.
$R_f$ value: 0.51 (silica gel; ethyl acetate).
Calc.: C, 75.18; H, 5.52; N, 10.96. Found: 75.05; 5.58; 10.93.

EXAMPLE 23

(Z)-3-[1-(3-ethoxycarbonylmethylaminocarbonyl-phenylamino)-1-phenyl-methylidene]-2-indolinone Prepared analogously to Example 21 from (Z)-3-[1-(3-carboxyphenylamino)-1-phenyl-methylidene]-2-indolinone, glycine ethyl ester, TBTU, HOBt and triethylamine in DMF.

Yield: 91% of theory,
Melting point: 233–235° C.
$C_{26}H_{23}N_3O_4$ (441.49).
Mass spectrum: $M^+$=441.
$R_f$ value: 0.55 (silica gel; ethyl acetate).
Calc.: C, 70.73; H, 5.25; N, 9.52. Found: 70.69; 5.33; 9.52.

EXAMPLE 24

(Z)-3-[1-(3-carboxymetylaminocarbonyl-phenylamino)-1-phenyl-methylidene]-2-indolinone Prepared analogously to Example 8 from (Z)-3-[1-(3-ethoxycarbonylmethylaminocarbonyl-phenylamino)-1-phenyl-methylidene]-2-indolinone and sodium hydroxide solution in ethanol.

Yield: 81% of theory,
Melting point: 248–250° C.
$C_{24}H_{19}N_3O_4$ (413.44).
Mass spectrum: $(M-H)^-$=412.

EXAMPLE 25

(Z)-3-{1-[3-(N-ethoxycarbonylmethyl-N-methyl-aminocarbonyl)-phenylamino]-1-phenyl-methylidene}-2-indolinone Prepared analogously to Example 21 from (Z)-3-[1-(3-carboxyphenylamino)-1-phenyl-methylidene]-2-indolinone, sarcosine ethyl ester, TBTU, HOBt and triethylamine in DMF.

Yield: 91% of theory,
Melting point: 148–150° C.

$C_{27}H_{25}N_3O_4$ (455.52).

Mass spectrum: $M^+=455$.

Calc.: C, 71.19; H, 5.53; N, 9.22. Found: 70.75; 5.63; 9.38.

EXAMPLE 26

(Z)-3-{1-[3-(N-carboxymethyl-N-methyl-aminocarbonyl)-phenyl-amino]-1-phenyl-methylidene}-2-indolinone Prepared analogously to Example 8 from (Z)-3-{1-[3-(N-ethoxycarbonylmethyl-N-methylaminocarbonyl)-phenylamino]-1-phenyl-methylidene}-2-indolinone and sodium hydroxide solution in ethanol.

Yield: 89% of theory,

Melting point: 218–220° C.

$C_{25}H_{21}N_3O_4$ (427.46).

Mass spectrum: $(M-H)^-=426$.

EXAMPLE 27

(Z)-3-{1-[(3-(2-dimethylaminoethyl-aminocarbonyl)-phenylamino]-1-phenyl-methylidene}-2-indolinone Prepared analogously to Example 21 from (Z)-3-[1-(3-carboxyphenylamino)-1-phenyl-methylidene]-2-indolinone, N,N-dimethylethylene-diamine, TBTU, HOBt and triethylamine in DMF.

Yield: 66% of theory,

Melting point: 203–205° C.

$C_{26}H_{26}N_4O_2$ (426.52).

Mass spectrum: $M^+=426$.

$R_f$ value: 0.17 (silica gel; ethyl acetate/methanol=6:4).

Calc.: C, 73.22; H, 6.14; N, 13.14. Found: 72.42; 6.29; 12.85.

EXAMPLE 28

(Z)-3-[1-(4-tert.butoxycarbonylamino-phenylamino)-1-phenyl-methylidene]-2-indolinone Prepared analogously to Example 1 from 1-acetyl-3-(1-ethoxy-1-phenyl-methylidene)-2-indolinone and 4-tert.butoxycarbonylamino-aniline in DMF and subsequent treatment with sodium hydroxide solution in methanol.

Yield: 64% of theory,

Melting point: 244–246° C.

$C_{26}H_{25}N_3O_3$ (427.51).

Mass spectrum: $M^+=427$.

Calc.: C, 73.05; H, 5.86; N, 9.83. Found: 72.80; 5.84; 9.92.

EXAMPLE 29

(Z)-3-[1-(4-formylamino-phenylamino)-1-phenyl-methylidene]-2-indolinone a) (Z)-3-[1-(4-aminophenylamino)-1-phenyl-methylidene]-2-indolinone 1.7 g (4 mmol) of (Z)-3-[1-(4-tert.butoxycarbonylamino-phenylamino)-1-phenyl-methylidene]-2-indolinone are suspended in 15 ml of dichloromethane and after the addition of 35 ml of ethyl acetate/hydrogen chloride for 18 hours at ambient temperature and stirred for 2 hours at 40° C. After cooling the mixture is diluted with ether and the precipitate is suction filtered. The residue is divided between sodium chloride solution and methylene chloride, the organic extracts are dried and concentrated by evaporation.

Yield: 1.0 g (77% of theory,

Melting point: 299–300° C.

b) (Z)-3-[1-(4-formylamino-phenylamino)-1-phenyl-methylidene]-2-indolinone 200 mg (0.6 mmol) of (Z)-3-[1-(4-aminophenylamino)-1-phenyl-methylidene]-2-indolinone and 5 ml of ethyl formate are stirred in 2.5 ml of DMF for 60 hours at 90° C. After removal of the solvent in vacuo ethyl acetate is added and the mixture is again concentrated by evaporation. The residue is stirred with ether, suction filtered and dried.

Yield: 73% of theory.

Melting point: 268–269° C.

$C_{22}H_{17}N_3O_2$ (355.40).

Mass spectrum: $M^+=355$.

EXAMPLE 30

(Z)-3-[1-(3-formylamino-phenylamino)-1-phenyl-methylidene]-2-indolinone

Prepared analogously to Example 29 from (Z)-3-[1-(3-aminophenylamino)-1-phenyl-methylidene]-2-indolinone and ethyl formate in DMF.

Yield: 80% of theory,

Melting point: 231° C.

$C_{22}H_{17}N_3O_2$ (355.40).

Mass spectrum: $M^+=355$.

$C_{22}H_{17}N_3O_2 \times H_2O$ (373.41).

Calc.: C, 70.76; H, 5.13; N, 11.25. Found: 70.66; 4.77; 11.03.

EXAMPLE 31

(Z)-3-[1-(4-acetylamino-phenylamino]-1-phenyl-methylidene]-2-indolinone 196 mg (0.6 mmol) of (Z)-3-[1-(4-aminophenylamino)-1-phenyl-methylidene]-2-indolinone are dissolved in 5 ml of glacial acetic acid and after the addition of 0.1 g (1 mmol) of acetic anhydride stirred for 3 hours at ambient temperature. Then 15 ml of water are added, the product precipitated is suction filtered, washed with water and dried.

Yield: 210 mg (95% of theory),

Melting point: 236–238° C.

$C_{23}H_{19}N_3O_2$ (369.43).

Mass spectrum: $M^+=369$.

Calc.: C, 74.78; H, 5.18; N, 11.37. Found: 74.32; 5.28; 11.15.

EXAMPLE 32

(Z)-3-[1-(3-acetylamino-phenylamino)-1-phenyl-methylidene]-2-indolinone

Prepared analogously to Example 31 from (Z)-3-[1-(3-aminophenylamino)-1-phenyl-methylidene]-2-indolinone and acetic anhydride in glacial acetic acid.

Yield: 89% of theory,

Melting point: 285–288° C.

$C_{23}H_{19}N_3O_2$ (369.43).

Mass spectrum: $M^+=369$.

Calc.: C, 74.78; H, 5.18; N, 11.37. Found: 74.53; 5.37; 11.37.

EXAMPLE 33

(Z)-3-[1-(3-trifluoroacetylamino-phenylamino)-1-phenyl-methylidene]-2-indolinone Prepared analogously to Example 31 from (Z)-3-[1-(3-aminophenylamino)-1-phenyl-methylidene]-2-indolinone and trifluoroacetic anhydride in trifluoroacetic acid.

Yield: 79% of theory,
Melting point: 273–276° C.
$C_{23}H_{16}F_3N_3O_2$ (423.40).
Mass spectrum: $M^+$=423.
Calc.: C, 65.25; H, 3.81; N, 9.92. Found: 65.48; 3.85; 9.96.

EXAMPLE 34

(Z)-3-[1-(4-tert.butoxycarbonylaminomethylcarbonylamino-phenylamino)-1-phenyl-methylidene]-2-indolinone Prepared analogously to Example 18 from (Z)-3-[1-(4-aminophenylamino)-1-phenyl-methylidene]-2-indolinone, N-tert.butoxycarbonyl-glycine, TBTU, HOBt and N-methylmorpholine in DMF.

Yield: 31% of theory,
Melting point: 243–244° C. (decomposition).
$C_{28}H_{28}N_4O_4$ (484.56).
Mass spectrum: $M^+$=484.
Calc.: C, 69.41; H, 5.82; N, 11.56. Found: 68.52; 5.73; 11.30.

EXAMPLE 35

(Z)-3-[1-(4-aminomethylcarbonylamino-phenylamino)-1-phenyl-methylidene]-2-indolinone-hydrochloride Prepared analogously to Example 29a from (Z)-3-[1-(4-tert.butoxycarbonylaminomethylcarbonylamino-phenylamino)-1-phenyl-methylidene]-2-indolinone and ethyl acetate/hydrogen chloride in dichloromethane.

Yield: 73% of theory,
Melting point: 289–290° C.
$C_{23}H_{20}N_4O_2$ (384.44).
Mass spectrum: $M^+$=384.
$C_{23}H_{20}N_4O_2 \times HCl \times H_2O$.

EXAMPLE 36

(Z)-3-{1-[3-(N-trifluoroacetyl-N-methyl-amino)-phenylamino]-1-phenyl-methylidene}-2-indolinone 636 mg (1.5 mmol) of (Z)-3-[1-(3-trifluoroacetylamino-phenylamino)-1-phenyl-methylidene]-2-indolinone are dissolved in 20 ml of acetone and after the addition of 423 mg (3 mmol) of potassium carbonate and 0.25 g (3 mmol) of methyl iodide stirred for 18 hours at ambient temperature. The reaction solution is freed from the solvent in vacuo after the insoluble matter has been filtered off. The residue is divided between dichloromethane/water, the organic phase is dried and concentrated by evaporation. The residue is triturated with ether, suction filtered and dried.

Yield: 550 mg (85% of theory),
Melting point: 224–227° C.
$C_{24}H_{18}F_3N_3O_2$ (437.43).

Mass spectrum: $M^+$=437.
Calc.: C, 65.90; H, 4.15; N, 9.61. Found: 65.96; 4.22; 9.59.

EXAMPLE 37

(Z)-3-[1-(3-methylamino-phenylamino)-1-phenyl-methylidene]-2-indolinone

Prepared analogously to Example 8 from (Z)-3-{1-[3-(N-trifluoroacetyl-N-methyl-amino)-phenylamino]-1-phenyl-methylidene}-2-indolinone and sodium hydroxide solution in methanol.

Yield: 91% of theory,
Melting point: 247–248° C.
$C_{22}H_{19}N_3O$ (341.42).
Mass spectrum: $M^+$=341.
Calc.: C, 77.40; H, 5.61; N, 12.31. Found: 76.65; 5.60; 12.09.

EXAMPLE 38

(Z)-3-{1-[3-(N-acetyl-N-methylamino)-phenylamino]-1-phenyl-methylidene}-2-indolinone Prepared analogously to Example 31 from (Z)-3-[1-(3-methylamino-phenylamino)-1-phenyl-methylidene]-2-indolinone and acetic anhydride in glacial acetic acid.

Yield: 73% of theory,
Melting point: 237–239° C.
$C_{24}H_{21}N_3O_2$ (383.45).
Mass spectrum: $M^+$=383.
Calc.: C, 75.18; H, 5.52; N, 10.96. Found: 74.51; 5.51; 10.80.

EXAMPLE 39

(Z)-3-[1-(4-propionylamino-phenylamino)-1-phenyl-methylidene]-2-indolinone a) 3-(1-ethoxy-1-phenyl-methylidene)-2-indolinone 4.0 g (13.2 mmol) of 1-acetyl-3-(1-ethoxy-1-phenyl-methylidene)-2-indolinone are suspended in 50 ml of ethanol and after the addition of 10 ml of 4N sodium hydroxide solution stirred for 90 minutes at ambient temperature. The solution is diluted with 150 ml of water, the crystalline product is suction filtered, washed and dried.

Yield: 2.8 g (80% of theory),
Melting point: 168–169° C.

b) N-propionyl-4-nitroaniline 6.9 g (50 mmol) of nitroaniline are suspended in 50 ml of propionic acid and combined with 9.1 g (50 mmol) of propionic acid anhydride. The mixture is heated for 90 minutes to 50° C. and then stirred for 16 hours at ambient temperature. Then 200 ml of water are added. The precipitate is suction filtered, washed and dried.

Yield: 9.4 g (97% of theory),
Melting point: 192–195° C.

c) 4-propionylamino-aniline 250 mg (2 mmol) of N-propionyl-4-nitroaniline are dissolved in 200 ml of methanol and combined with 0.6 g of 10% palladium/charcoal. The product is hydrogenated in a hydrogen atmosphere at 2 bar for 30 minutes. Then the catalyst is filtered off and the solvent is eliminated in vacuo.

Yield: 4.5 g (91% of theory),
Melting point: 82–84° C.
$C_9H_{12}N_2O$ (164.21).
Calc.: C, 65.83; H, 7.37; N, 17.06. Found: 65.99; 7.36; 17.02.

c) (Z)-3-[1-(4-propionylamino-phenylamino)-1-phenyl-methylidene]-2-indolinone 265 mg (1 mmol) of 3-(1-ethoxy-1-phenyl-methylidene)-2-indolinone are dissolved in 5 ml of DMF and after the addition of 300 mg (1.8 mmol) of 4-propionylamino-aniline stirred for 8 hours at 150° C. After cooling, it is diluted with water, the crystalline product is suction filtered, washed and dried.

Yield: 280 mg (68% of theory),
Melting point: 255–256° C.
$C_{24}H_{21}N_3O_2$ (383.45).
Mass spectrum: $M^+$=383.
$C_{24}H_{21}N_3O_2 \times H_2O$ (401.47).
Calc.: C, 71.80; H, 5.77; N, 10.47. Found: 71.62; 5.61; 10.50.

EXAMPLE 40

(Z)-3-[1-(4-methoxymethylcarbonylamino-phenylamino)-1-phenyl-methylidene]-2-indolinone Prepared analogously to Examples 1 and 39 from 1-acetyl-3-(1-ethoxy-1-phenyl-methylidene)-2-indolinone and 4-methoxymethylcarbonylamino-aniline in DMF and subsequent treatment with sodium hydroxide solution in methanol.

Yield: 80% of theory,
Melting point: 238–240° C.
$C_{24}H_{21}N_3O_3$ (399.45).
Mass spectrum: $M^+$=399.
Calc.: C, 72.17; H, 5.30; N, 10.52. Found: 71.92; 5.33; 10.44.

EXAMPLE 41

(Z)-3-[1-(4-dimethylaminomethylcarbonylamino-phenylamino)-1-phenyl-methylidene]-2-indolinone Prepared analogously to Example 1 from 1-acetyl-3-(1-ethoxy-1-phenyl-methylidene)-2-indolinone and 4-dimethylaminomethyl-carbonylamino-aniline in DMF and subsequent treatment with sodium hydroxide solution in methanol.

Yield: 68% of theory,
Melting point: 234–236° C.
$C_{25}H_{24}N_4O_2$ (412.50).
Mass spectrum: $M^+$=412.
$R_f$ value: 0.28 (silica gel; ethyl acetate/methanol=19:1).
Calc.: C, 72.29; H, 5.86; N, 13.58. Found: 72.35; 5.83; 13.37.

EXAMPLE 42

(Z)-3-[1-(4-Diethylaminomethylcarbonylamino-phenylamino)-1-phenyl-methylidene]-2-indolinone-hydrochloride Prepared analogously to Example 1 from 1-acetyl-3-(1-ethoxy-1-phenyl-methylidene)-2-indolinone and 4-diethylaminomethyl-carbonylamino-aniline in DMF and subsequent treatment with sodium hydroxide solution in methanol.

Yield: 80% of theory,
Melting point: 267–269° C.
$C_{27}H_{28}N_4O_2$ (440.55).
Mass spectrum: $M^+$=440.

$R_f$ value: 0.32 (silica gel; dichloromethane/methanol=19:1).
$C_{27}H_{28}N_4O_2 \times HCl \times 1.5H_2O$ (504.03).
Calc.: C, 64.34; H, 6.40; N, 11.12. Found: 64.72; 6.69; 11.16.

EXAMPLE 43

(Z)-3-[1-(4-morpholinomethylcarbonylamino-phenylamino)-1-phenyl-methylidene]-2-indolinone a) N-morpholinomethylcarbonyl-4-nitroaniline 2.6 g (30 mmol) of morpholine and 4.2 g (30 mmol) of potassium carbonate are suspended in 120 ml of acetone. 5.3 g (20 mmol) of N-bromoacetyl-4-nitro-aniline, dissolved in 80 ml of acetone, are added dropwise over a period of 20 minutes and then stirred for 2 hours at ambient temperature. The precipitate is filtered off and the solvent is eliminated in vacuo. The residue is suspended with water. The precipitate is suction filtered and dried in a drying cupboard.

Yield: 5.0 g (94% of theory),
Melting point: 148–149° C.

b) 4-morpholinomethylcarbonylamino-aniline

Prepared analogously to Example 39c by catalytic hydrogenation from N-morpholinomethylcarbonyl-4-nitroaniline.

Yield: 92% of theory,
Melting point: 106–107° C.
$C_{12}H_{17}N_3O_2$ (235.29).
Calc.: C, 61.26; H, 7.28; N, 17.86. Found: 60.91; 7.28; 17.60.

c) (Z)-3-[1-(4-morpholinomethylcarbonylamino-phenylamino)-1-phenyl-methylidene]-2-indolinone Prepared analogously to Example 1 from 1-acetyl-3-(1-ethoxy-1-phenyl-methylidene)-2-indolinone and 4-morpholinomethyl-carbonylamino-aniline in DMF and subsequent treatment with sodium hydroxide solution in methanol.

Yield: 97% of theory,
Melting point: 246–248° C.
$C_{27}H_{26}N_4O_3$ (454.53).
Mass spectrum: $M^+$=454.
$R_f$ value: 0.35 (silica gel; ethyl acetate).
$C_{27}H_{26}N_4O_3 \times 0.5H_2O$ (463.54).
Calc.: C, 69.96; H, 5.87; N, 12.09. Found: 70.36; 5.90; 12.08.

EXAMPLE 44

(Z)-3-{1-[4-(4-methylpiperazinomethylcarbonylamino-phenylamino]-1-phenyl-methylidene}-2-indolinone Prepared analogously to Example 43 from 1-acetyl-3-(1-ethoxy-1-phenyl-methylidene)-2-indolinone and 4-(4-methyl-piperazinomethylcarbonylamino)-aniline in DMF and subsequent treatment with sodium hydroxide solution in methanol.

Yield: 86% of theory,
Melting point: 282–284° C.
$C_{28}H_{29}N_5O_2$ (467.58).
Mass spectrum: $M^+$=467.
$R_f$ value: 0.32 (silica gel; dichloromethane/methanol=9:1).
$C_{28}H_{29}N_5O_2 \times 0.5H_2O$ (476.58).
Calc.: C, 70.57; H, 6.34; N, 14.70. Found: 70.88; 6.29; 14.54.

EXAMPLE 45

(Z)-3-[1-(4-ethylaminocarbonylamino-phenylamino)-1-phenyl-methylidene]-2-indolinone 196 mg (0.6 mmol) of (Z)-3-[1-(4-aminophenylamino)-1-phenyl-methylidene]-2-indolinone are suspended in 10 ml of THF and after the addition of 70 mg (0.1 mmol) of ethyl isocyanate stirred for 140 hours at ambient temperature. The product precipitated is suction filtered, washed with ether and dried.

Yield: 200 mg (84% of theory),
Melting point: 264–265° C.
$C_{24}H_{22}N_4O_2$ (398.47).
Mass spectrum: M$^+$=398.
Calc.: C, 72.34; H, 5.57; N, 14.06. Found: 71.70; 5.83; 13.49.

EXAMPLE 46

(Z)-3-[1-(4-butylaminocarbonylamino-phenylamino)-1-phenyl-methylidene]-2-indolinone Prepared analogously to Example 45 from (Z)-3-[1-(4-aminophenylamino)-1-phenyl-methylidene]-2-indolinone and butyl isocyanate in THF.

Yield: 72% of theory,
Melting point: 216–217° C.
$C_{26}H_{26}N_4O_2$ (426.52).
Mass spectrum: M$^+$=426.
Calc.: C, 73.22; H, 6.14; N, 13.14. Found: 72.74; 5.94; 12.67.

EXAMPLE 47

(Z)-3-{1-[4-(N-acetyl-N-methyl-amino)-phenylamino]-1-phenyl-methylidene}-2-indolinone Prepared analogously to Example 1 from 1-acetyl-3-(1-ethoxy-1-phenyl-methylidene)-2-indolinone and 4-(N-acetyl-N-methyl-amino)-aniline in DMF and subsequent treatment with sodium hydroxide solution in methanol.

Yield: 50% of theory,
Melting point: 287–288° C.
$C_{24}H_{21}N_3O_2$ (383.45).
Mass spectrum: M$^+$=383.
Calc.: C, 75.18; H, 5.52; N, 10.96. Found: 75.18; 5.62; 10.89.

EXAMPLE 48

(Z)-3-{1-[4-(N-dimethylaminomethylcarbonyl-N-methyl-amino)-phenylamino]-1-phenyl-methylidene}-2-indolinone-hydrochloride Prepared analogously to Example 43 from 1-acetyl-3-(1-ethoxy-1-phenyl-methylidene)-2-indolinone and 4-(N-dimethylaminomethylcarbonyl-N-methyl-amino)-aniline in DMF and subsequent treatment with sodium hydroxide solution in methanol.

Yield: 30% of theory,
Melting point: 290–292° C.
$C_{26}H_{26}N_4O_2$ (426.52).
Mass spectrum: M$^+$=426.
$C_{26}H_{26}N_4O_2 \times HCl \times 2H_2O$ (499.00).
Calc.: C, 62.58; H, 6.26; N, 11.23; Cl, 7.10. Found: 62.68; 6.07; 11.19; 7.88.

EXAMPLE 49

(Z)-3-{1-[4-(N-Diethylaminomethylcarbonyl-N-methyl-amino)-phenylamino]-1-phenyl-methylidene}-2-indolinone Prepared analogously to Example 43 from 1-acetyl-3-(1-ethoxy-1-phenyl-methylidene)-2-indolinone and 4-(N-diethylaminomethylcarbonyl-N-methyl-amino)-aniline in DMF and subsequent treatment with sodium hydroxide solution in methanol.

Yield: 64% of theory,
Melting point: 242–247° C.
$C_{28}H_{30}N_4O_2$ (454.58).
Mass spectrum: M$^+$=454.
$R_f$ value: 0.56 (silica gel; dichloromethane/methanol/NH$_4$OH=9:1:0.1).
$C_{28}H_{30}N_4O_2 \times 0.5H_2O$ (454.57).
Calc.: C, 72.55; H, 6.74; N, 12.09. Found: 72.70; 6.41; 12.11.

EXAMPLE 50

(Z)-3-{1-[4-(N-piperidinomethylcarbonyl-N-methyl-amino)-phenylamino]-1-phenyl-methylidene}-2-indolinone Prepared analogously to Example 43 from 1-acetyl-3-(1-ethoxy-1-phenyl-methylidene)-2-indolinone and 4-(N-piperidinomethylcarbonyl-N-methyl-amino)-aniline in DMF and subsequent treatment with sodium hydroxide solution in methanol.

Yield: 43% of theory,
Melting point: 230–235° C. (decomposition).
$C_{29}H_{30}N_4O_2$ (466.59).
Mass spectrum: M$^+$=466.
$R_f$ value: 0.54 (silica gel; dichloromethane/methanol/NH$_4$OH=9:1:0.1).
$C_{29}H_{30}N_4O_2 \times 1.5H_2O$ (493.61).
Calc.: C, 70.57; H, 6.74; N, 11.35. Found: 70.57; 6.32; 11.28.

EXAMPLE 51

(Z)-3-{1-[4-(N-morpholinomethylcarbonyl-N-methyl-amino)-phenylamino-1-phenyl-methylidene}-2-indolinone Prepared analogously to Example 43 from 1-acetyl-3-(1-ethoxy-1-phenyl-methylidene)-2-indolinone and 4-(N-morpholinomethylcarbonyl-N-methyl-amino)-aniline in DMF and subsequent treatment with sodium hydroxide solution in methanol.

Yield: 99% of theory,
Melting point: 263–265° C.
$C_{28}H_{28}N_4O_3$ (468.56).
Mass spectrum: M$^+$=468.
Calc.: C, 71.78; H, 6.02; N, 11.96. Found: 70.75; 6.05; 11.90.

EXAMPLE 52

(Z)-3-{1-[4-(N-(4-methylpiperazinomethylcarbonyl)-N-methyl-amino-phenylamino]-1-phenyl-methylidene}-2-indolinone Prepared analogously to Example 43 from 1-acetyl-3-(1-ethoxy-1-phenyl-methylidene)-2-indolinone and 4-[N-(4-methylpiperazinomethylcarbonyl)-N-methyl-amino]-aniline in DMF and subsequent treatment with sodium hydroxide solution in methanol.

Yield: 73% of theory,
Melting point: 277–278° C.

$C_{29}H_{31}N_5O_2$ (481.60).

Mass spectrum: $M^+=481$.

$R_f$ value: 0.37 (silica gel; dichloromethane/methanol/ $NH_4OH=9:1:0.1$)

EXAMPLE 53

(Z)-3-{1-[4-(N-(4-benzylpiperazinomethylcarbonyl)-N-methyl-amino)-phenylamino]-1-phenyl-methylidene}-2-indolinone Prepared analogously to Example 43 from 1-acetyl-3-(1-ethoxy-1-phenyl-methylidene)-2-indolinone and 4-[N-(4-benzylpiperazinomethylcarbonyl)-N-methylamino]-aniline in DMF and subsequent treatment with sodium hydroxide solution in methanol.

Yield: 55% of theory,

Melting point: 157–158° C.

$C_{35}H_{35}N_5O_2$ (557.70).

Mass spectrum: $M^+=557$.

$R_f$ value: 0.62 (silica gel; dichloromethane/methanol/ $NH_4OH=9:1:0.1$).

$C_{35}H_{35}N_5O_2 \times H_2O$ (575.72).

Calc.: C, 73.02; H, 6.48; N, 12.16. Found: 73.10; 6.46; 12.13.

EXAMPLE 54

(Z)-3-{1-[4-(N-piperazinomethylcarbonyl-N-methyl-amino)-phenylamino]-1-phenyl-methylidene}-2-indolinone-dihydrochloride 390 mg (0.7 mmol) of (Z)-3-{1-[4-(N—(N-benzylpiperazinomethylcarbonyl)-N-methylamino)-phenylamino]-1-phenyl-methylidene}-2-indolinone are dissolved in 20 ml of dichloromethane and after the addition of 0.2 g (1.4 mmol) of 1-chloroethyl chloroformate heated for 30 minutes at ambient temperature and refluxed for 60 minutes. The solvent is concentrated by evaporation, the residue is combined with 10 ml of methanol and refluxed for 90 minutes. After 18 hours stirring at ambient temperature, the product is suction filtered, washed with methanol and dried.

Yield: 200 mg (51% of theory),

Melting point: 255–258° C. (decomposition).

$C_{28}H_{29}N_5O_2$ (467.58).

Mass spectrum: $M^+=467$.

$C_{28}H_{29}N_5O_2 \times 2HCl \times H_2O$ (558.52).

Calc.: C, 60.22; H, 5.96; N, 12.54; Cl, 12.70. Found: 60.06; 5.91; 12.53; 12.75.

EXAMPLE 55

(Z)-3-[1-(4-aminomethyl-phenylamino)-1-phenyl-methylidene]-2-indolinone a) (Z)-3-[1-(4-cyanophenylamino)-1-phenyl-methylidene]-2-indolinone Prepared analogously to Example 1 from 1-acetyl-3-(1-ethoxy-1-phenyl-methylidene)-2-indolinone and 4-aminobenzonitrile in DMF and subsequent treatment with sodium hydroxide solution.

Yield: 44% of theory,

Melting point: 293–295° C.

$C_{22}H_{15}N_3O$ (337.38).

Calc.: C, 78.32; H, 4.48; N, 12.45. Found: 77.75; 4.68; 12.50.

b) (Z)-3-[1-(4-aminomethyl-phenylamino)-1-phenyl-methylidene]-2-indolinone 900 mg (2.7 mmol) of (Z)-3-[1-(4-cyanophenylamino)-1-phenyl-methylidene]-2-indolinone are hydrogenated in 200 ml of methanolic ammonia for 7 hours over 1.4 g of Raney nickel at a hydrogen pressure of 3 bar. The catalyst is filtered off, the solution is concentrated by evaporation and the residue is divided between water/dichloromethane. The organic phase is dried, concentrated by evaporation, triturated with ether, suction filtered and dried.

Yield: 780 mg (83% of theory),

Melting point: 236–237° C.

$C_{22}H_{19}N_3O$ (341.42).

Mass spectrum: $M^+=341$.

$C_{22}H_{19}N_3O \times 0.5H_2O$ (350.42).

Calc.: C, 75.41; H, 5.75; N, 11.99. Found: 75.08; 5.62; 11.81.

EXAMPLE 56

(Z)-3-[1-(4-acetylaminomethyl-phenylamino)-1-phenyl-methylidene]-2-indolinone

Prepared analogously to Example 31 from (Z)-3-[1-(4-aminomethyl-phenylamino)-1-phenyl-methylidene]-2-indolinone, glacial acetic acid and acetic anhydride.

Yield: 135 mg (88% of theory),

Melting point: 207–210° C.

$C_{24}H_{21}N_3O_2$ (383.45).

Mass spectrum: $M^+=383$.

Calc.: C, 75.18; H, 5.52; N, 10.96. Found: 74.79; 5.46; 10.77.

EXAMPLE 57

(Z)-3-[1-(4-tert.butoxycarbonylaminomethylcarbonylaminomethyl-phenylamino)-1-phenyl-methylidene}-2-indolinone Prepared analogously to Example 18 from (Z)-3-{1-[4-(aminomethyl)phenylamino]-1-phenyl-methylidene}-2-indolinone, N-tert.butoxycarbonyl-glycine, TBTU, HOBt and N-ethyl-N,N-diisopropylamine in DMF.

Yield: 85% of theory,

Melting point: 218–220° C.

$C_{29}H_{30}N_4O_4$ (498.59).

Mass spectrum: $M^+=498$.

Calc.: C, 69.86; H, 6.06; N, 11.24. Found: 69.40; 6.20; 11.18.

EXAMPLE 58

(Z)-3-[1-(4-aminomethylcarbonylaminomethyl-phenylamino)-1-phenyl-methylidene]-2-indolinone-hydrochloride Prepared analogously to Example 29a from (Z)-3-[1-(4-tert.butoxycarbonylaminomethylcarbonylaminomethyl-phenylamino)-1-phenyl-methylidene]-2-indolinone and ethyl acetate/hydrogen chloride in dichloromethane.

Yield: 88% of theory,

Melting point: 190–195° C.

$C_{24}H_{22}N_4O_2$ (398.47).

Mass spectrum: $M^+=398$.

$C_{24}H_{22}N_4O_2 \times HCl \times H_2O$ (452.95).

Calc.: C, 63.64; H, 5.56; N, 12.37. Found: 64.11; 5.55; 12.19.

EXAMPLE 59

(Z)-3-[1-(4-morpholinomethyl-phenylamino)-1-phenyl-methyli-den]-2-indolinone

Prepared analogously to Example 1 from 1-acetyl-3-(1-ethoxy-1-phenyl-methylidene)-2-indolinone and 4-morpholinomethyl-aniline in DMF and subsequent treatment with sodium hydroxide solution in methanol.

Yield: 66% of theory,
Melting point: 267–268° C.
$C_{26}H_{25}N_3O_2$ (411.51).
Mass spectrum: $M^+$=411.
$R_f$ value: 0.58 (silica gel; ethyl acetate/petroleum ether= 9:1).
Calc.: C, 75.89; H, 6.12; N, 10.21. Found: 75.18; 6.09; 10.14.

EXAMPLE 60

(Z)-3-[1-(4-acetylphenylamino)-1-phenyl-methylidene]-2-indolinone

Prepared analogously to Example 1 from 1-acetyl-3-(1-ethoxy-1-phenyl-methylidene)-2-indolinone and 4-aminoacetophenone in DMF and subsequent treatment with sodium hydroxide solution in methanol.

Yield: 20% of theory,
Melting point: 207–209° C.
$C_{23}H_{18}N_2O_2$ (354.41).
Mass spectrum: $M^+$=354.
$R_f$ value: 0.24 (silica gel; dichloromethane/methanol= 19:1).

EXAMPLE 61

3-{1-[N-(4-cyanophenyl)-N-methyl-amino]-1-phenyl-methylidene}-2-indolinone

Prepared analogously to Example 2 from 1-acetyl-3-(1-chloro-1-phenyl-methylidene)-2-indolinone and 4-methylamino-benzonitrile in THF and subsequent treatment with sodium hydroxide solution in methanol.

Yield: 6% of theory,
Melting point: 239° C.
$C_{23}H_{17}N_3O$ (351.82).
Mass spectrum: $M^+$=351.

EXAMPLE 62

(Z)-3-{1-[N-(4-amidinophenyl)-amino]-1-phenyl-methylidene}-2-indolinone-hydroacetate 1.0 g (2.8 mmol) of (Z)-1-benzoyl-3-[1-(4-cyanophenylamino]-1-phenyl-methylidene]-2-indolinone are dissolved in 20 ml of saturated methanolic hydrochloric acid and stirred for 18 hours at ambient temperature. The solvent is distilled off, the residue is dissolved in 20 ml of absolute methanol and adjusted to pH 8 with conc. ammonia. The precipitate is suction filtered, suspended in methanol and refluxed for 2 hours with 0.4 g of ammonium acetate. The product is suction filtered, washed with methanol and dried.

Yield: 340 mg (34% of theory),
Melting point: >260° C. (decomposition).
$C_{22}H_{18}N_4O$ (354.41).
Mass spectrum: $(M+H)^+$=355.
$R_f$ value: 0.44 (Reversed phase P8; water/acetonitrile= 1:1+1% trifluoroacetic acid).

EXAMPLE 63

(Z)-3-[1-(3-cyanophenylamino-1-phenyl-methylidene]-2-indolinone

Prepared analogously to Example 9 from 1-benzoyl-3-(1-chloro-1-phenyl-methylidene]-2-indolinone and 3-aminobenzonitrile in THF and subsequent treatment with sodium hydroxide solution in methanol.

Yield: 70% of theory,
Melting point: 262–272° C.
$C_{22}H_{15}N_3O$ (337.38).
Mass spectrum: $M^+$=337.

EXAMPLE 64

(Z)-3-[1-(3-amidinophenylamino)-1-phenyl-methylidene]-2-indolinone

Prepared analogously to Example 62 from (Z)-3-[1-(3-cyanophenylamino)-1-phenyl-methylidene]-2-indolinone and methanolic hydrochloric acid in methanol and ammonium acetate.

Yield: 26% of theory,
Melting point: 235–237° C.
$C_{22}H_{18}N_4O$ (354.41).
Mass spectrum: $M^+$=354.

EXAMPLE 65

(Z)-3-{1-[3-(N-methylcarbamimidoyl)-phenylamino]-1-phenyl-methylidene}-2-indolinone Prepared analogously to Example 62 from (Z)-3-[1-(3-cyanophenylamino)-1-phenyl-methylidene]-2-indolinone, methanolic hydrochloric acid and methylamine in methanol.

Yield: 7% of theory,
Melting point: 248–250° C.
$C_{23}H_{20}N_4O$ (368.44).
Mass spectrum: $(M+H)^+$=369.
$R_f$ value: 0.23 (Reversed phase P8; methanol/5% saline solution=6:4).

EXAMPLE 66

(Z)-3-{1-[3-(N,N-dimethylcarbamimidoyl)-phenylamino)-1-phenyl-methylidene}-2-indolinone Prepared analogously to Example 62 from (Z)-3-[1-(3-cyanophenylamino)-1-phenyl-methylidene]-2-indolinone, methanolic hydrochloric acid and dimethylamine in methanol.

Yield: 30% of theory,
Melting point: 238–242° C.
$C_{24}H_{22}N_4O$ (382.47).
Mass spectrum: $(M+H)^+$=383.
$R_f$ value: 0.27 (Reversed phase P8; methanol/5% saline solution=6:4).

EXAMPLE 67

(Z)-3-[1-(3-tert.butoxycarbonylaminomethyl-phenylamino)-1-phenyl-methylidene]-2-indolinone Prepared analogously to Example 9 from 1-benzoyl-3-(1-chloro-1-phenyl-methylidene)-2-indolinone and 3-tert.butoxycarbonylaminomethyl-aniline in triethylamine.

Yield: 7% of theory,
Melting point: 190–195° C.
C$_{27}$H$_{27}$N$_3$O$_3$ (441.53).
Mass spectrum: M$^+$=441.
R$_f$ value: 0.35 (silica gel; ethyl acetate/petroleum ether= 1:1).

EXAMPLE 68

(Z)-3-[1-(3-aminomethyl-phenylamino)-1-phenyl-methylidene]-2-indolinone

Prepared analogously to Example 57 from (Z)-3-[1-(3-tert.butoxycarbonylaminomethyl-phenylamino)-1-phenyl-methylidene]-2-indolinone and trifluoroacetic acid in dichloromethane.
Yield: 60% of theory,
Melting point: 175–185° C.
C$_{22}$H$_{19}$N$_3$O (341.42).
Mass spectrum: M$^+$=341.
R$_f$ value: 0.44 (silica gel; ethyl acetate/methanol/NH$_4$OH=4:1:0.5).

EXAMPLE 69

(Z)-3-[1-(3-aminophenylamino)-1-phenyl-methylidene]-2-indolinone 3.5 g (0.01 mol) of (Z)-3-[1-(3-nitrophenylamino)-1-phenyl-methylidene}-2-indolinone are dissolved in 200 ml of THF and after the addition of 0.5 g of palladium/charcoal hydrogenated with hydrogen. Then the catalyst is filtered off and concentrated by evaporation.
Yield: 3.4 g (99% of theory),
Melting point: 267–268° C.
C$_{21}$H$_{17}$N$_3$O (327.39).
Mass spectrum: M$^+$=327.

EXAMPLE 70

(Z)-3-{1-[N-(4-amino)-phenylamino]-1-phenyl-methylidene}-2-indolinone

Prepared analogously to Example 69 from (Z)-3-[1-(4-nitrophenylamino)-1-phenyl-methylidene]-2-indolinone and palladium/charcoal with hydrogen in THF.
Yield: 77% of theory,
Melting point: >290° C.
C$_{21}$H$_{17}$N$_3$O (327.39).
Mass spectrum: M$^+$=327.
R$_f$ value: 0.51 (silica gel; dichloroethane/ethyl acetate/glacial acetic acid=80:17:3).

EXAMPLE 71

(Z)-3-[1-(3-guanidinophenylamino)-1-phenyl-methylidene]-2-indolinone 2.0 g (6.1 mmol) of (Z)-3-[1-(3-aminophenylamino)-1-phenyl-methylidene]-2-indolinone and 1.0 g (23.7 mmol) of cyanamide are dissolved in 100 ml of ethanol and 10 ml of ethereal hydrochloric acid and heated for 24 hours in a glass bomb at 80° C. The solvent is distilled off. Chromatography of the residue on silica gel (ethyl acetate/methanol/glacial acetic acid/water=17:3:5:5) yields the product.
Yield: 300 mg (13% of theory),
C$_{22}$H$_{19}$N$_5$O (369.43).
Mass spectrum: (M+H)$^+$=370.

EXAMPLE 72

(Z)-3-[1-(4-guanidinophenylamino)-1-phenyl-methylidene]-2-in-dolinone

Prepared analogously to Example 71 from (Z)-3-[1-(4-aminophenylamino)-1-phenyl-methylidene]-2-indolinone and cyanamide in dioxane/hydrogen chloride.
Yield: 27% of theory,
C$_{22}$H$_{19}$N$_5$O (369.43).
Mass spectrum: (M+H)$^+$=370.
R$_f$ value: 0.27 (silica gel; methanol/water/glacial acetic acid=17:3:0.55).

EXAMPLE 73

(Z)-1-methyl-3-[1-(3-cyanophenylamino)-1-phenyl-methylidene]-2-indolinone a) 1-methyl-3-(1-hydroxy-1-phenyl-methylidene)-2-indolinone 4.15 g (41 mmol) of diisopropylamine are placed in 50 ml of THF, cooled to −70° C. and combined with a solution of 14.4 ml of (36 mmol) of n-butyl lithium solution (2.5 mol in toluene) and stirred for 10 minutes. Then a solution of 5.0 g (34 mmol) of 1-methyl-2-indolinone in 30 ml of THF is added dropwise and stirred for 45 minutes at −70° C. Then 5.8 g (0.041 mol) of benzoylchloride are added dropwise. The reaction solution is left to heat up slowly within 14 hours. It is then poured onto sodium chloride solution and extracted with ethyl acetate. The combined organic extracts are dried and concentrated by evaporation. The residue is chromatographed on silica gel (dichloromethane/methanol/ammonia=200:8:1).
Yield: 7.1 g (84% of theory),
Melting point: 145–147° C.

b) (Z)-1-methyl-3-[1-(3-cyanophenylamino)-1-phenyl-methylidene]-2-indolinone

Prepared analogously to Example 2 from 1-methyl-3-(1-hydroxy-1-phenyl-methylidene)-2-indolinone, phosphorus pentachloride and 3-aminobenzonitrile.
Yield: 15% of theory,
Melting point: 158–160° C.
C$_{23}$H$_{17}$N$_3$O (351.41).
Mass spectrum: M$^+$=351.
R$_f$ value: 0.42 (silica gel; dichloromethane/ethyl acetate= 100:3).
Calc.: C, 78.61; H, 4.88; N, 11.96. Found: 78.15; 4.89; 11.91.

EXAMPLE 74

(Z)-3-[1-(4-dimethylaminomethylcarbonylaminomethyl-phenylamino)-1-phenyl-methylidene}-2-indolinone a) isocyanatomethyl-polystyrene resin 18.2 g (31.5 mmol) of aminomethyl-polystyrene resin are allowed to swell in 200 ml of toluene for 45 minutes at ambient temperature. At 5° C. 16.6 ml (0.31 mol) of phosgene solution (20% in toluene) are added. Then the reaction solution is left for 100 minutes in an ultrasound bath at 20° C. and then refluxed for 4 hours. After 18 hours' standing at ambient temperature the mixture is suction filtered, washed with dichloromethane and ethyl acetate and dried.
Yield: 18.3 g (100% of theory).

b) 1-polystyrylmethylaminocarbonyl-2-indolinone 13.3 g (0.1 mol) of 2-indolinone and 12.1 g (20.5 mmol) of isocyanatomethyl-polystyrene resin are refluxed in 400 ml of toluene for 12 hours. Then the mixture is cooled, washed with toluene, methylene chloride and methanol and dried.

Yield: 13.4 g (100% of theory).

c) 3-(1-ethoxy-1-phenyl-methylidene)-1-polystyrylmethylamino-carbonyl-2-indolinone 13.4 g (20.5 mmol) of 1-polystyrylmethylaminocarbonyl-2-indolinone and 33.4 g (0.15 mol) of triethyl orthobenzoate are refluxed in 200 ml of acetic anhydride for 22 hours. Then the mixture is cooled, washed with ethyl acetate, methylene chloride and methanol and dried.

Yield: 14.3 g (100% of theory).

d) 3-[1-(4-tert.butoxycarbonylaminomethyl-phenylamino)-1-phenyl-methylidene]-1-polystyrylmethylaminocarbonyl-2-indolinone 710 mg (1 mmol) of 3-(1-ethoxy-1-phenyl-methylidene)-1-polystyrylmethylaminocarbonyl-2-indolinone are suspended in 15 ml of DMF and after the addition of 1.1 g (5 mmol) of 4-tert.butoxycarbonylamino-aniline heated to 120° C. for 11 hours. After 14 hours at ambient temperature the mixture is suction filtered, washed with dichloromethane and methanol and dried.

Yield: 770 mg (100% of theory).

e) 3-[1-(4-aminomethyl-phenylamino)-1-phenyl-methylidene]-1-polystyrylmethylaminocarbonyl-2-indolinone 770 mg (1 mmol) of (3-[1-(4-tert.butoxycarbonyl-aminomethyl-phenylamino)-1-phenyl-methylidene]-1-polystyrylmethylaminocarbonyl-2-indolinone are sonicated in 10 ml of dichloromethane and 5 ml of trifluoroacetic acid for 2 hours in an ultrasound bath. The mixture is then suction filtered, washed with dichloromethane and methanol and dried.

Yield: 720 mg (100% of theory), f) 3-[1-(4-(dimethylaminomethylcarbonylaminomethyl-phenylami-no)-1-phenyl-methylidene]-1-polystyrylmethyl-aminocarbonyl-2-indolinone 680 mg (1.0 mmol) of 3-[1-(4-aminomethyl-phenylamino)-1-phenyl-methylidene]-1-polystyrylmethyl-aminocarbonyl-2-indolinone, 1.6 g (5 mmol) of TBTU, 770 mg (5 mmol) of HOBt, 2.6 g (20 mmol) of N-ethyl-N,N-diisopropylamine and 515 mg (5 mmol) of dimethylglycine are sonicated for 6 hours in 20 ml of dimethylformamide in an ultrasound bath at 35° C. The mixture is then suction filtered, washed with dichloromethane and methanol and dried.

Yield: 570 mg (100% of theory), g) (Z)-3-[1-(4-dimethylaminomethylcarbonylaminomethyl-phenylamino)-1-phenyl-methylidene]-2-indolinone 560 mg (0.95 mmol) of 3-[1-(4-(dimethylamino-methylcarbonylaminomethyl-phenylamino)-1-phenyl-methylidene]-1-polystyrylmethylaminocarbonyl-2-indolinone are heated to 90° C. in 20 ml of dioxane and 5 ml of 1N sodium hydroxide solution for 7 hours. The mixture is then filtered and concentrated by evaporation. The residue is divided between dichloromethane/water, the organic phase is dried and evaporated to dryness. The crude product is triturated with ethyl acetate and ether, suction filtered and dried.

Yield: 27 mg (7% of theory),

Melting point: 200–205° C.

$C_{26}H_{26}N_4O_2$ (426.52).

Mass spectrum: $M^+=426$.

$R_f$ value: 0.60 (silica gel; dichloromethane/methanol=9:1).

EXAMPLE 75

(Z)-3-{1-[4-(2-carboxy-ethylcarbonylaminomethyl)-phenylamino]-1-phenyl-methylidene}-2-indolinone Prepared analogously to Example 74 from (Z)-3-{1-[4-(2-carboxy-ethylcarbonylaminomethyl)-phenylamino]-1-phenyl-methylidene}-1-polystyrylmethylaminocarbonyl-2-indolinone and sodium hydroxide solution in dioxane.

Yield: 5% of theory, $C_{26}H_{23}N_3O_4$ (441.49).

Mass spectrum: $(M-H)^-=440$.

EXAMPLE 76

(Z)-3-[1-(4-methoxymethylcarbonylaminomethyl-phenylamino)-1-phenyl-methylidene]-2-indolinone Prepared analogously to Example 74 from (Z)-3-[1-(4-methoxymethylcarbonylaminomethyl-phenylamino)-1-phenyl-methylidene]-1-polystyrylmethylaminocarbonyl-2-indolinone and sodium hydroxide solution in dioxane.

Yield: 6% of theory,

Melting point: 178–180° C.

$C_{25}H_{23}N_3O_3$ (413.48).

Mass spectrum: $M^+=413$.

EXAMPLE 77

(Z)-3-[1-(4-chlorophenylamino)-1-phenyl-methylidene]-5-nitro-2-indolinone a) 1-acetyl-5-nitro-2-indolinone 17.5 g (0.10 mol) of 1-acetyl-2-indolinone are dissolved in 100 ml of conc. sulphuric acid and at −10° C. 8.8 g (0.11 mol) of ammonium nitrate are added batchwise and stirred for 15 minutes. The reaction is poured onto ice water, suction filtered and washed with water. The residue is distributed in ethyl acetate/water, the combined organic extracts are dried and concentrated by evaporation.

Yield: 20.5 g (93% of theory),

Melting point: 154–156° C.

b) 1-acetyl-3-(1-methoxy-1-phenyl-methylidene)-5-nitro-2-indo-linone 30.0 g (0.137 mol) of 1-acetyl-5-nitro-2-indolinone are dissolved in 200 ml of acetic anhydride and after the addition of 50.0 g (0.274 mol) of trimethyl orthobenzoate stirred for 3 hours at 100° C. After cooling it is evaporated down to half the quantity, diluted with ether/petroleum ether, the precipitate is suction filtered and dried.

Yield: 40.9 g (88% of theory), $R_f$ value: 0.61 (silica gel; dichloromethane/petroleum ether/ethyl acetate=4:5:1).

c) (Z)-3-[1-(4-chlorophenylamino)-1-phenyl-methylidene]-5-nitro-2-indolinone 0.5 g (1.5 mmol) of 1-acetyl-3-(1-methoxy-1-phenyl-methylidene)-5-nitro-2-indolinone are dissolved in 20 ml of dichloromethane and after the addition of 0.57 g (4.5 mmol) of 4-chloroaniline stirred for 72 hours at ambient temperature. Then 3 ml of methanolic ammonia are added and stirred for 48 hours. After removal of the solvent in vacuo the residue is triturated with ether, suction filtered and dried.

Yield: 150 mg (26% of theory), $C_{21}H_{14}ClN_3O_3$ (391.82).

Mass spectrum: $M^+=393/391$.

$R_f$ value: 0.68 (silica gel; dichloromethane/methanol=9:1).

EXAMPLE 78

(Z)-3-[1-(4-methoxyphenylamino)-1-phenyl-methylidene]-5-nitro-2-indolinone

Prepared analogously to Example 77 from 1-acetyl-3-(1-methoxy-1-phenyl-methylidene)-5-nitro-2-indolinone and 4-methoxyaniline in dichloromethane and methanolic ammonia.

Yield: 87% of theory, $C_{22}H_{17}N_3O_4$ (387.40).

Mass spectrum: $M^+$=387.

$R_f$ value: 0.66 (silica gel; dichloromethane/methanol=9:1).

EXAMPLE 79

(Z)-3-[1-(4-trifluoromethyl-phenylamino)-1-phenyl-methylidene]-5-nitro-2-indolinone Prepared analogously to Example 77 from 1-acetyl-3-(1-methoxy-1-phenyl-methylidene)-5-nitro-2-indolinone and trifluoromethylanisidine in dichloromethane and subsequent treatment with methanolic ammonia.

Yield: 62% of theory, $C_{22}H_{14}F_3N_3O_3$ (425.37).

Mass spectrum: $M^+$=425.

$R_f$ value: 0.23 (silica gel; dichloromethane).

EXAMPLE 80

(Z)-3-[1-(4-morpholinophenylamino)-1-phenyl-methylidene]-5-nitro-2-indolinone

Prepared analogously to Example 77 from 1-acetyl-3-(1-methoxy-1-phenyl-methylidene)-5-nitro-2-indolinone and 4-morpholinoaniline in dichloromethane and subsequent treatment with methanolic ammonia.

Yield: 68% of theory,

Melting point: >300° C.

$C_{25}H_{22}N_4O_4$ (442.48).

Mass spectrum: $M^+$=442.

$R_f$ value: 0.56 (silica gel; ethyl acetate/cyclohexane/methanol=1:1:0.2).

EXAMPLE 81

(Z)-3-[1-(4-nitrophenylamino)-1-phenyl-methylidene]-5-nitro-2-indolinone

Prepared analogously to Example 77 from 1-acetyl-3-(1-methoxy-1-phenyl-methylidene)-5-nitro-2-indolinone and 4-nitroaniline in DMF and subsequent treatment with methanolic ammonia.

Yield: 38% of theory, $C_{21}H_{14}N_4O_5$ (402.37).

Mass spectrum: $M^+$=402.

$R_f$ value: 0.65 (silica gel; dichloromethane/methanol 9:1).

EXAMPLE 82

(Z)-3-[1-(4-Bromphenylamino)-1-phenyl-methylidene]-5-nitro-2-indolinone a) 1-acetyl-3-(1-ethoxy-1-phenyl-methylidene)-5-nitro-2-indolinone 5.07 g (23 mmol) of 5-nitro-2-indolinone are stirred for 2.5 hours at 100° C. together with 15.5 g (69 mmol) of triethyl orthobenzoate in 50 ml of acetic anhydride. After cooling, 100 ml of ether/petroleum ether (1:1) are added. The precipitate formed is suction filtered, washed with ether/petroleum ether (1:1) and dried.

Yield: 6.6 g (81% of theory),

Melting point: 233–234° C.

(b)(Z)-3-[1-(4-Bromophenylamino)-1-phenyl-methylidene]-5-nitro-2-indolinone

Prepared analogously to Example 77 from 1-acetyl-3-(1-ethoxy-1-phenyl-methylidene)-5-nitro-2-indolinone and 4-bromoaniline in DMF with heating and subsequent treatment with piperidine.

Yield: 92% of theory,

Melting point: 300–305° C.

$C_{21}H_{14}BrN_3O_3$ (436.27).

Mass spectrum: $M^+$=437/435.

$R_f$ value: 0.33 (silica gel; dichloromethane/methanol=20:1).

Calc.: C, 57.82; H, 3.23; N, 9.63; Br, 18.32. Found: 57.81; 3.20; 9.65; 18.22.

EXAMPLE 83

(Z)-3-[1-(4-cyanophenylamino)-1-phenyl-methylidene]-5-nitro-2-indolinone

Prepared analogously to Example 77 from 1-benzoyl-3-(1-methoxy-1-phenyl-methylidene)-5-nitro-2-indolinone and 4-aminobenzonitrile in DMF and subsequent treatment with methanolic ammonia.

Yield: 33% of theory, $C_{22}H_{14}N_4O_3$ (382.38).

Mass spectrum: $M^+$=382.

$R_f$ value: 0.58 (silica gel; dichloromethane/methanol=9:1).

EXAMPLE 84

(Z)-3-[1-(4-amidinophenylamino)-1-phenyl-methylidene]-5-nitro-2-indolinone-hydrochloride Prepared analogously to Example 77 from 1-acetyl-3-(1-methoxy-1-phenyl-methylidene)-5-nitro-2-indolinone and 4-aminobenzamidine in DMF.

Yield: 20% of theory, $C_{22}H_{17}N_5O_3$ (399.41).

Mass spectrum: $(M+H)^+$=400.

$R_f$ value: 0.07 (silica gel; dichloromethane/methanol=9:1).

EXAMPLE 85

(Z)-3-[1-(3-cyanophenylamino)-1-phenyl-methylidene]-5-nitro-2-indolinone 2 g (5.2 mmol) of 1-benzoyl-3-(1-hydroxy-1-phenyl-methylidene)-5-nitro-2-indolinone and 1.8 g (16 mmol) of 3-aminobenzonitrile are stirred in DMF for 70 hours at ambient temperature. Then the reaction solution is extracted with ether, the organic phase is washed with water and dried over sodium sulphate. After removal of the solvent in vacuo the residue is chromatographed on silica gel (dichloromethane/methanol=50:1).

Yield: 580 mg (23% of theory), $C_{22}H_{14}N_4O_3$ (382.38).

Mass spectrum: M$^+$=382.

R$_f$ value: 0.32 (silica gel; dichloromethane/methanol= 50:1).

EXAMPLE 86

(Z)-3-[1-(3-amidinophenylamino)-1-phenyl-methylidene]-5-nitro-2-indolinone-hydrochloride Prepared analogously to Example 77 from 1-acetyl-3-(1-methoxy-1-phenyl-methylidene)-5-nitro-2-indolinone and 3-aminobenzamidine in DMF.

Yield: 22% of theory,

C$_{22}$H$_{17}$N$_5$O$_3$ (399.41).

Mass spectrum: (M+H)$^+$=400.

R$_f$ value: 0.17 (silica gel; dichloromethane/methanol= 4:1).

EXAMPLE 87

(Z)-3-[1-(4-methoxycarbonyl-phenylamino)-1-phenyl-methylidene]-5-nitro-2-indolinone Prepared analogously to Example 77 from 1-acetyl-3-(1-methoxy-1-phenyl-methylidene)-5-nitro-2-indolinone and methyl 4-aminobenzoate in dichloromethane and subsequent treatment with methanolic ammonia.

Yield: 10% of theory,

C$_{23}$H$_{17}$N$_3$O$_5$ (415.41).

Mass spectrum: M$^+$=415.

R$_f$ value: 0.23 (silica gel; dichloromethane/methanol= 50:1).

EXAMPLE 88

(Z)-3-[1-(4-carboxy-phenylamino)-1-phenyl-methylidene]-5-nitro-2-indolinone

Prepared analogously to Example 8 from (Z)-3-[1-(4-methoxycarbonyl-phenylamino)-1-phenyl-methylidene]-5-nitro-2-indolinone and sodium hydroxide solution in methanol.

Yield: 88% of theory,

C$_{22}$H$_{15}$N$_3$O$_5$ (401.38).

Mass spectrum: M$^+$=401.

R$_f$ value: 0.52 (silica gel; dichloromethane/methanol= 9:1).

EXAMPLE 89

(Z)-3-[1-(3-acetylamino-phenylamino)-1-phenyl-methylidene]-5-nitro-2-indolinone a) 3-(1-ethoxy-1-phenyl-methylidene)-5-nitro-2-indolinone 17.6 g (50 mmol) of 1-acetyl-3-(1-ethoxy-1-phenyl-methylidene)-5-nitro-2-indolinone are suspended in 200 ml of dichloromethane and 150 ml of ethanol. 75 ml of 1N sodium hydroxide solution are added at 0° C. and the mixture is then stirred for another 30 minutes at ambient temperature. The reaction solution is evaporated down by half and 200 ml of water are then added. The product precipitated is suction filtered, washed with water, isopropanol and ether and dried.

Yield: 13.3 g (86% of theory),

Melting point: 239–240° C.

b) (Z)-3-[1-(3-acetylamino-phenylamino)-1-phenyl-methylidene]-5-nitro-2-indolinone Prepared analogously to Example 82 from 3-(1-ethoxy-1-phenyl-methylidene)-5-nitro-2-indolinone and 3-acetylamino-aniline in DMF.

Yield: 72% of theory,

Melting point: 318–320° C. (decomposition).

C$_{23}$H$_{18}$N$_4$O$_4$ (414.42).

Mass spectrum: M$^+$=414.

Calc.: C, 66.66; H, 4.38; N, 13.52. Found: 66.42; 4.46; 13.45.

EXAMPLE 90

(Z)-3-[1-(4-tert.butoxycarbonylamino-phenylamino)-1-phenyl-methylidene]-5-nitro-2-indolinone Prepared analogously to Example 82 from 1-acetyl-3-(1-methoxy-1-phenyl-methylidene)-5-nitro-2-indolinone and 4-tert.butoxycarbonylamino-aniline in DMF and subsequent treatment with sodium hydroxide solution in methanol.

Yield: 56% of theory,

Melting point: 235–237° C. (decomposition).

C$_{26}$H$_{24}$N$_4$O$_5$ (472.51).

Mass spectrum: M$^+$=472.

Calc.: C, 66.09; H, 5.12; N, 11.86. Found: 66.35; 5.19; 11.80.

EXAMPLE 91

(Z)-3-[1-(4-aminophenylamino)-1-phenyl-methylidene]-5-nitro-2-indolinone

Prepared analogously to Example 29a from (Z)-3-[1-(4-tert.butoxycarbonylamino-phenylamino)-1-phenyl-methylidene]-5-nitro-2-indolinone and ethyl acetate/hydrogen chloride in dichloromethane.

Yield: 74% of theory,

Melting point: 269° C.

C$_{21}$H$_{16}$N$_4$O$_3$ (372.39).

Mass spectrum: M$^+$=372.

Calc.: C, 67.73; H, 14.33; N, 15.05. Found: 67.70; 4.48; 14.83.

EXAMPLE 92

(Z)-3-[1-(4-formylamino-phenylamino)-1-phenyl-methylidene]-5-nitro-2-indolinone

Prepared analogously to Example 29b from (Z)-3-[1-(4-aminophenylamino)-1-phenyl-methylidene}-5-nitro-2-indolinone and ethyl formate in DMF.

Yield: 89% of theory,

Melting point: 355–356° C. (decomposition).

C$_{22}$H$_{16}$N$_4$O$_4$ (400.40).

Mass spectrum: M$^+$=400.

Calc.: C, 66.00; H, 4.03; N, 13.99. Found: 65.59; 4.13; 13.85.

EXAMPLE 93

(Z)-3-[1-(4-acetylamino-phenylamino)-1-phenyl-methylidene]-5-nitro-2-indolinone

Prepared analogously to Example 31 from (Z)-3-[1-(4-aminophenylamino)-1-phenyl-methylidene]-5-nitro-2-indolinone and acetic anhydride in glacial acetic acid.

Yield: 93% of theory,

Melting point: 328–330° C.

C$_{23}$H$_{18}$N$_4$O$_4$ (414.42).

Mass spectrum: $M^+$=414.

$C_{23}H_{18}N_4O_4 \times H_2O$ (432.44).

Calc.: C, 63.88; H, 4.66; N, 12.96. Found: 64.09; 4.68; 12.34.

EXAMPLE 94

(Z)-3-[1-(4-dimethylaminomethylcarbonylamino-phenylamino)-1-phenyl-methylidene]-5-nitro-2-indolinone Prepared analogously to Example 82 from 1-acetyl-3-(1-ethoxy-1-phenyl-methylidene)-5-nitro-2-indolinone and 4-dimethylaminomethylcarbonylamino-aniline in DMF and subsequent treatment with sodium hydroxide solution in methanol.

Yield: 63% of theory,

Melting point: 254–257° C.

$C_{25}H_{23}N_5O_4$ (457.49).

Mass spectrum: $M^+$=457.

Calc.: C, 65.64; H, 5.07; N, 15.31. Found: 65.20; 5.16; 14.99.

EXAMPLE 95

(Z)-3-[1-(4-diethylaminomethylcarbonylamino-phenylamino)-1-phenyl-methylidene]-5-nitro-2-indolinone-hydrochloride Prepared analogously to Example 82 from 1-acetyl-3-(1-ethoxy-1-phenyl-methylidene)-5-nitro-2-indolinone and 4-diethylaminomethylcarbonylamino-aniline in DMF and subsequent treatment with sodium hydroxide solution in methanol.

Yield: 54% of theory,

Melting point: 287–288.

$C_{27}H_{27}N_5O_4$ (485.55).

Mass spectrum: $M^+$=485.

EXAMPLE 96

(Z)-3-[1-(4-morpholinomethylcarbonylamino-phenylamino)-1-phenyl-methylidene]-5-nitro-2-indolinone Prepared analogously to Example 82 from 1-acetyl-3-(1-ethoxy-1-phenyl-methylidene)-5-nitro-2-indolinone and 4-morpholinomethylcarbonylamino-aniline in DMF and subsequent treatment with sodium hydroxide solution in methanol.

Yield: 88% of theory,

Melting point: 265–267° C.

$C_{27}H_{25}N_5O_5$ (499.53).

Mass spectrum: $M^+$=499.

$C_{27}H_{25}N_5O_5 \times H_2O$ (517.55).

Calc.: C, 62.60; H, 5.26; N, 13.53. Found: 62.68; 5.15; 13.57.

EXAMPLE 97

(Z)-3-{1-[4-(4-methylpiperazinomethylcarbonylamino)-phenylamino]-1-phenyl-methylidene}-5-nitro-2-indolinone Prepared analogously to Example 82 from 1-acetyl-3-(1-ethoxy-1-phenyl-methylidene)-5-nitro-2-indolinone and 4-(4-methylpiperazinomethylcarbonylamino)-aniline in DMF and subsequent treatment with sodium hydroxide solution in methanol.

Yield: 74% of theory,

Melting point: 232–233° C.

$C_{28}H_{28}N_6O_4$ (512.57).

Mass spectrum: $M^+$=512.

EXAMPLE 98

(Z)-3-{1-[4-(N-acetyl-N-methyl-amino)-phenylamino]-1-phenyl-methylidene}-5-nitro-2-indolinone Prepared analogously to Example 82 from 1-acetyl-3-(1-ethoxy-1-phenyl-methylidene)-5-nitro-2-indolinone and 4-(N-acetyl-N-methyl-amino)-aniline in DMF and subsequent treatment with sodium hydroxide solution in methanol.

Yield: 82% of theory,

Melting point: 305–307° C.

$C_{24}H_{20}N_4O_4$ (428.45).

Mass spectrum: $M^+$=428.

Calc.: C, 67.28; H, 4.71; N, 13.08. Found: 67.05; 4.76; 12.94.

EXAMPLE 99

(Z)-3-{1-[4-(N-dimethylaminomethylcarbonyl-N-methyl-amino)-1-phenylamino]-1-phenyl-methylidene}-5-nitro-2-indolinone Prepared analogously to Example 82 from 1-acetyl-3-(1-ethoxy-1-phenyl-methylidene)-5-nitro-2-indolinone and 4-(N-dimethylaminomethylcarbonyl-N-methyl-amino)-aniline in DMF and subsequent treatment with sodium hydroxide solution in methanol.

Yield: 91% of theory,

Melting point: 295–297° C.

$C_{26}H_{25}N_5O_4$ (471.52).

Mass spectrum: $M^+$=471.

$C_{26}H_{25}N_5O_4 \times 0.5H_2O$ (480.5).

Calc.: C, 64.99; H, 5.45; N, 14.57. Found: 64.49; 5.51; 14.45.

EXAMPLE 100

(Z)-3-{1[4-(N-diethylaminomethylcarbonyl-N-methyl-amino)-1-phenylamino]-1-phenyl-methylidene}-5-nitro-2-indolinone Prepared analogously to Example 82 from 1-acetyl-3-(1-ethoxy-1-phenyl-methylidene)-5-nitro-2-indolinone and 4-(N-diethylaminomethylcarbonyl-N-methyl-amino)-aniline in DMF and subsequent treatment with sodium hydroxide solution in methanol.

Yield: 40% of theory,

Melting point: 225° C.

$C_{28}H_{29}N_5O_4$ (499.57).

Mass spectrum: $M^+$=499.

Calc.: C, 67.37; H, 5.85; N, 14.02. Found: 66.99; 5.88; 13.98.

EXAMPLE 101

(Z)-3-{1-[4-(N-piperidinomethylcarbonyl-N-methyl-amino)-1-phenylamino]-1-phenyl-methylidene}-5-nitro-2-indolinone Prepared analogously to Example 82 from 1-acetyl-3-(1-ethoxy-1-phenyl-methylidene)-5-nitro-2-indolinone and 4-(N-piperidinomethylcarbonyl-N-methyl-amino)-aniline in DMF and subsequent treatment with sodium hydroxide solution in methanol.

Yield: 80% of theory,

Melting point: 267–269° C.

$C_{29}H_{29}N_5O_4$ (511.59).

Mass spectrum: $M^+$=511.

$R_f$ value: 0.55 (silica gel; dichloromethane/methanol/NH$_4$OH=9:1:0.1).

Calc.: C, 68.09; H, 5.71; N, 13.69. Found: 67.29; 5.58; 13.50.

EXAMPLE 102

(Z)-3-{1-[4-(N-morpholinomethylcarbonyl-N-methyl-amino)-phenylamino]-1-phenyl-methylidene}-5-nitro-2-indolinone Prepared analogously to Example 82 from 1-acetyl-3-(1-ethoxy-1-phenyl-methylidene)-5-nitro-2-indolinone and 4-(N-morpholinomethylcarbonyl-N-methyl-amino)-aniline in DMF and subsequent treatment with sodium hydroxide solution in methanol.

Yield: 58% of theory,

Melting point: 293–295° C.

$C_{28}H_{27}N_5O_5$ (513.56).

Mass spectrum: $M^+$=513.

Calc.: C, 64.49; H, 5.30; N, 13.64. Found: 64.54; 5.25; 13.50.

EXAMPLE 103

(Z)-3-{-[4-(N—(N-methylpiperazinomethylcarbonyl)-N-methyl-amino)-phenylamino]-1-phenyl-methylidene}-5-nitro-2-indolinone Prepared analogously to Example 82 from 1-acetyl-3-(1-ethoxy-1-phenyl-methylidene)-5-nitro-2-indolinone and 4-[N—(N-methylpiperazinomethylcarbonyl)-N-methyl-amino]-aniline in DMF and subsequent treatment with sodium hydroxide solution in methanol.

Yield: 76% of theory,

Melting point: 239–241° C.

$C_{29}H_{30}N_6O_4$ (526.60).

Mass spectrum: $M^+$=526.

$R_f$ value: 0.36 (silica gel; dichloromethane/methanol/NH$_4$OH 9:1:0.1).

$C_{29}H_{30}N_6O_4 \times H_2O$ (544.61).

Calc.: C, 63.96; H, 5.92; N, 15.43. Found: 63.81; 5.95; 15.35.

EXAMPLE 104

(Z)-3-{1-[4-(N-(4-benzylpiperazinomethylcarbonyl)-N-methyl-amino)-phenylamino]-1-phenyl-methylidene}-5-nitro-2-indolinone Prepared analogously to Example 82 from 1-acetyl-3-(1-ethoxy-1-phenyl-methylidene)-5-nitro-2-indolinone and 4-[N-(4-benzylpiperazinomethylcarbonyl)-N-methyl-amino)-aniline in DMF and subsequent treatment with sodium hydroxide solution in methanol.

Yield: 78% of theory,

Melting point: 201–203° C.

$C_{35}H_{34}N_6O_4$ (602.70).

Mass spectrum: $M^+$=602.

$R_f$ value: 0.6 (silica gel; dichloromethane/methanol/NH$_4$OH=9:1:0.1).

$C_{35}H_{34}N_6O_4 \times 0.5H_2O$ (611.70).

Calc.: C, 69.75; H, 5.69; N, 13.94. Found: 68.73; 5.69; 13.52.

EXAMPLE 105

(Z)-3-{1-[4-(N-piperazinomethylcarbonyl-N-methyl-amino)phenylamino]-1-phenyl-methylidene}-5-nitro-2-indolinone-dihydrochloride Prepared analogously to Example 54 from (Z)-3-{1-[4-(N-(4-benzylpiperazinomethylcarbonyl)-N-methyl-amino)-phenylamino]-1-phenyl-methylidene}-5-nitro-2-indolinone and 1-chloroethyl chloroformate in dichloromethane.

Yield: 68% of theory,

Melting point: 246–248° C.

$C_{28}H_{28}N_6O_4$ (512.57).

Mass spectrum: $M^+$=512.

$C_{28}H_{28}N_6O_4 \times 2HCl$ (585.50).

Calc.: C, 57.44; H, 5.16; N, 14.35. Found: 57.00; 4.87; 14.09.

EXAMPLE 106

(Z)-3-[1-(3-dimethylaminomethylcarbonylaminomethyl-phenylamino)-1-phenyl-methylidene]-5-nitro-2-indolinone Prepared analogously to Example 82 from 1-acetyl-3-(1-ethoxy-1-phenyl-methylidene)-5-nitro-2-indolinone and 3-dimethylaminomethylcarbonylaminomethyl-aniline in DMF and subsequent treatment with sodium hydroxide solution in methanol.

Yield: 64% of theory,

Melting point: 171–173° C.

$C_{26}H_{25}N_5O_4$ (471.52).

Mass spectrum: $M^+$=471.

Calc.: C, 66.23; H, 5.34; N, 14.85. Found: 65.97; 5.18; 14.79.

EXAMPLE 107

(Z)-3-[1-(3-dimethylaminomethyl-phenylamino)-1-phenyl-methylidene]-5-nitro-2-indolinone Prepared analogously to Example 82 from 1-acetyl-3-(1-ethoxy-1-phenyl-methylidene)-5-nitro-2-indolinone and 3-dimethylaminomethyl-aniline in DMF and subsequent treatment with sodium hydroxide solution in methanol.

Yield: 85% of theory,

Melting point: 214–217° C.

$C_{24}H_{22}N_4O_3$ (414.47).

Mass spectrum: $M^+$=414.

$R_f$ value: 0.48 (silica gel; dichloromethane/methanol/NH$_4$OH=9:1:0.1).

Calc.: C, 69.55; H, 5.35; N, 13.52. Found: 69.55; 5.45; 13.38.

EXAMPLE 108

(Z)-3-[1-(3-piperidinomethyl-phenylamino)-1-phenyl-methylidene]-5-nitro-2-indolinone Prepared analogously to Example 82 from 1-acetyl-3-(1-ethoxy-1-phenyl-methylidene)-5-nitro-2-indolinone and 3-piperidinomethyl-aniline in DMF and subsequent treatment with sodium hydroxide solution in methanol.

Yield: 95% of theory,
Melting point: 214–215° C.
$C_{27}H_{26}N_4O_3$ (454.53).
Mass spectrum: $M^+$=454.
Calc.: C, 71.35; H, 5.77; N, 12.33. Found: 70.85; 5.79; 12.28.

EXAMPLE 109

(Z)-3-[1-(3-morpholinomethyl-phenylamino)-1-phenyl-methyli-den]-5-nitro-2-indolinone Prepared analogously to Example 82 from 1-acetyl-3-(1-ethoxy-1-phenyl-methylidene)-5-nitro-2-indolinone and 3-morpholinomethyl-aniline in DMF and subsequent treatment with sodium hydroxide solution in methanol.

Yield: 88% of theory,
Melting point: 272–275° C.
$C_{26}H_{24}N_4O_4$ (456.51).
Mass spectrum: $M^+$=456.
Calc.: C, 68.41; H, 5.30; N, 12.27. Found: 68.05; 5.21; 12.23.

EXAMPLE 110

(Z)-3-{1-[3-(4-methylpiperazinomethyl)-phenylamino]-1-phenyl-methylidene}-5-nitro-2-indolinone Prepared analogously to Example 82 from 1-acetyl-3-(1-ethoxy-1-phenyl-methylidene)-5-nitro-2-indolinone and 3-(4-methylpiperazinomethyl)-aniline in DMF and subsequent treatment with sodium hydroxide solution in methanol.

Yield: 92% of theory,
Melting point: 256–258° C.
$C_{27}H_{27}N_5O_3$ (469.55).
Mass spectrum: $M^+$=469.
$R_f$ value: 0.59 (silica gel; dichloromethane/methanol/$NH_4OH$=9:1:0.1).
Calc.: C, 69.07; H, 5.80; N, 14.92. Found: 68.86; 5.78; 14.96.

EXAMPLE 111

(Z)-3-[1-(3-ethoxycarbonylmethylaminomethyl-phenylamino)-1-phenyl-methylidene]-5-nitro-2-indolinone Prepared analogously to Example 89 from 3-(1-ethoxy-1-phenyl-methylidene)-5-nitro-2-indolinone and 3-ethoxycarbonylmethylaminomethyl-aniline in DMF.

Yield: 38% of theory,
Melting point: 130–133° C.
$C_{26}H_{24}N_4O_5$ (472.51).
Mass spectrum: $M^+$=472.
Calc.: C, 66.09; H, 5.12; N, 11.86. Found: 66.46; 5.32; 11.80.

EXAMPLE 112

(Z)-3-{1-[3-(2-ethoxycarbonyl-ethylaminomethyl)-phenylamino]-1-phenyl-methylidene}-5-nitro-2-indolinone Prepared analogously to Example 89 from 3-(1-ethoxy-1-phenyl-methylidene)-5-nitro-2-indolinone and 3-(2-ethoxycarbonyl-ethylaminomethyl)-aniline in DMF.

Yield: 70% of theory,
Melting point: 142–145° C.
$C_{27}H_{26}N_4O_5$ (486.53).
Mass spectrum: $M^+$=486.
Calc.: C, 66.66; H, 5.39; N, 11.52. Found: 66.44; 5.49; 11.43.

EXAMPLE 113

(Z)-3-[1-(4-tert.butoxycarbonylaminomethyl-phenylamino)-1-phenyl-methylidene]-5-nitro-2-indolinone Prepared analogously to Example 82 from 1-acetyl-3-(1-ethoxy-1-phenyl-methylidene)-5-nitro-2-indolinone and 4-tert.butoxycarbonylaminomethyl-aniline in DMF and subsequent treatment with sodium hydroxide solution in methanol.

Yield: 89% of theory,
Melting point: 234–236° C. (decomposition).
$C_{27}H_{26}N_4O_5$ (486.53).
Mass spectrum: $M^+$=486.
Calc.: C, 66.66; H, 5.39; N, 11.52. Found: 66.98; 5.44; 11.42.

EXAMPLE 114

(Z)-3-[1-(4-aminomethyl-phenylamino]-1-phenyl-methylidene]-5-nitro-2-indolinone-hydrochloride Prepared analogously to Example 29a from (Z)-3-[1-(4-tert.butoxycarbonylaminomethyl-phenylamino)-1-phenyl-methylidene]-5-nitro-2-indolinone and ethyl acetate/hydrogen chloride.

Yield: 86% of theory,
Melting point: >370° C.
$C_{22}H_{18}N_4O_3$ (386.41).
Mass spectrum: $M^+$=386.
$C_{22}H_{18}N_4O_3 \times HCl \times H_2O$ (440.89).
Calc.: C, 59.93; H, 4.80; N, 12.71. Found: 60.81; 4.66; 12.80.

EXAMPLE 115

(Z)-3-[1-(4-aminomethylcarbonylaminomethyl-phenylamino]-1-phenyl-methylidene}-5-nitro-2-indolinone-hydrochloride Prepared analogously to Example 29a from (Z)-3-[1-(4-tert.butoxycarbonylaminomethylcarbonylaminomethyl-phenylamino)-1-phenyl-methylidene]-5-nitro-2-indolinone and ethyl acetate/hydrogen chloride.

Yield: 76% of theory,
Melting point: 225–228° C.
$C_{24}H_{21}N_5O_4$ (443.47).
Mass spectrum: $M^+$=443.
$C_{24}H_{21}N_5O_4 \times HCl \times 1.5H_2O$ (506.95).
Calc.: C, 56.86; H, 4.97; N, 13.81. Found: 56.71; 4.91; 13.57.

EXAMPLE 116

(Z)-3-[1-(4-methylaminomethylcarbonylaminomethyl-phenylamino]-1-phenyl-methylidene}-5-nitro-2-indolinone-hydrochloride Prepared analogously to Example 29a from (Z)-3-{1-[4-(N-tert.butoxycarbonyl-N-methylamino)methylcarbonylaminomethyl-phenylamino]-1-phenyl-methylidene}-5-nitro-2-indolinone and ethyl acetate/hydrogen chloride.

Yield: 76% of theory,
Melting point: 195–198° C.
$C_{25}H_{23}N_5O_4$ (457.49).
Mass spectrum: $M^+$=457.
$C_{25}H_{23}N_5O_4 \times HCl \times H_2O$ (511.97).
Calc.: C, 58.65; H, 5.12; N, 13.68. Found: 58.19; 4.96; 13.49.

EXAMPLE 117

(Z)-3-[1-(4-dimethylaminomethyl-phenylamino)-1-phenyl-methylidene]-5-nitro-2-indolinone Prepared analogously to Example 82 from 1-acetyl-3-(1-ethoxy-1-phenyl-methylidene)-5-nitro-2-indolinone and 4-dimethylaminomethyl-aniline in DMF and subsequent treatment with sodium hydroxide solution in methanol.

Yield: 73% of theory,
Melting point: 264–265° C.
$C_{24}H_{22}N_4O_3$ (414.47).
Mass spectrum: $M^+$=414.
Calc.: C, 69.55; H, 5.35; N, 13.52. Found: 69.29; 5.31; 13.33.

EXAMPLE 118

(Z)-3-[1-(4-morpholinomethyl-phenylamino)-1-phenyl-methylidene]-5-nitro-2-indolinone Prepared analogously to Example 82 from 1-acetyl-3-(1-ethoxy-1-phenyl-methylidene)-5-nitro-2-indolinone and 4-morpholinomethyl-aniline in DMF and subsequent treatment with sodium hydroxide solution in methanol.

Yield: 57% of theory,
Melting point: 273° C.
$C_{26}H_{24}N_4O_4$ (456.51).
Mass spectrum: $M^+$=456.
$R_f$ value: 0.43 (silica gel; ethyl acetate/methanol=9:1).
$C_{26}H_{24}N_4O_4 \times H_2O$ (474.52).
Calc.: C, 65.81; H, 5.52; N, 11.81. Found: 65.24; 5.44; 11.62.

EXAMPLE 119

(Z)-3-[1-(4-hexamethyleneiminomethyl-phenylamino)-1-phenyl-methylidene]-5-nitro-2-indolinone Prepared analogously to Example 89 from 3-(1-ethoxy-1-phenyl-methylidene)-5-nitro-2-indolinone and 4-hexamethyleneiminomethyl-aniline in DMF.

Yield: 64% of theory,
Melting point: 220° C.
$C_{28}H_{28}N_4O_3$ (468.56).
Mass spectrum: $M^+$=468.
$R_f$ value: 0.25 (silica gel; ethyl acetate/methanol=8:2).
Calc.: C, 71.78; H, 6.02; N, 11.96. Found: 71.57; 6.12; 11.71.

EXAMPLE 120

(Z)-3-{1-[4-(N-tert.butoxycarbonyl-N-methyl-aminomethyl)-phenylamino]-1-phenyl-methylidene}-5-nitro-2-indolinone Prepared analogously to Example 89 from 3-(1-ethoxy-1-phenyl-methylidene)-5-nitro-2-indolinone and 4-(N-tert.butoxycarbonyl-N-methyl-amino)methyl-aniline in DMF.

Yield: 60% of theory,
Melting point: 235.
$C_{28}H_{28}N_4O_5$ (500.56).
Mass spectrum: $M^+$=500.
$R_f$ value: 0.50 (silica gel; dichloromethane/ethyl acetate=7:3).
Calc.: C, 67.19; H, 5.64; N, 11.19. Found: 66.95; 5.68; 11.00.

EXAMPLE 121

(Z)-3-[1-(4-methylaminomethyl-phenylamino)-1-phenyl-methyliden]-5-nitro-2-indolinone-hydrochloride Prepared analogously to Example 29a from (Z)-3-{1-[4-(N-tert.butoxycarbonyl-N-methylamino)methyl-phenylamino]-1-phenyl-methylidene}-5-nitro-2-indolinone and ethyl acetate/hydrogen chloride.

Yield: 99% of theory,
Melting point: 351° C.
$C_{23}H_{20}N_4O_3$ (400.44).
Mass spectrum: $M^+$=400.
$R_f$ value: 0.36 (silica gel; dichloromethane/methanol/$NH_4OH$=9:1:0.1).
$C_{23}H_{20}N_4O_3 \times HCl$ (436.91).
Calc.: C, 63.23; H, 4.84; N, 12.82. Found: 62.37; 4.78; 12.47.

EXAMPLE 122

(Z)-3-{1-[4-(N-acetyl-N-methyl-aminomethyl)-phenylamino]-1-phenyl-methylidene}-5-nitro-2-indolinone Prepared analogously to Example 31 from (Z)-3-[1-(4-methylaminomethyl-phenylamino)-1-phenyl-methylidene]-5-nitro-2-indolinone and acetic anhydride in glacial acetic acid.

Yield: 79% of theory,
Melting point: 307° C.
$C_{25}H_{22}N_4O_4$ (442.48).
Mass spectrum: $M^+$=442.
$R_f$ value: 0.46 (silica gel; dichloromethane/methanol=9:1).

EXAMPLE 123

(Z,S)-3-{1-[4-(1-tert.butoxycarbonylamino-ethyl)-phenylamino]-1-phenyl-methylidene}-5-nitro-2-indolinone Prepared analogously to Example 89 from 3-(1-ethoxy-1-phenyl-methylidene)-5-nitro-2-indolinone and (S)-4-(1-tert.butoxycarbonylamino-ethyl)-aniline in DMF.

Yield: 66% of theory,
Melting point: 247–249° C. (decomposition).
$C_{28}H_{28}N_4O_5$ (500.56).
Mass spectrum: $M^+$=500.
Calc.: C, 67.19; H, 5.64; N, 11.19. Found: 67.23; 5.56; 11.28.

EXAMPLE 124

(Z,S)-3-{1-[4-(1-aminoethyl)-phenylamino]-1-phenyl-methyliden}-5-nitro-2-indolinone-hydrochloride Prepared analogously to Example 29a from (Z,S)-3-{1-[4-(1-tert.butoxycarbonylamino-ethyl)-phenylamino]-1- phenyl-methylidene}-5-nitro-2-indolinone and ethyl acetate/hydrogen chloride.

Yield: 88% of theory,
Melting point: 230–235° C.
$C_{23}H_{20}N_4O_3$ (400.44).
Mass spectrum: $M^+$=400.
$C_{23}H_{20}N_4O_3 \times HCl \times H_2O$ (454.92).
Calc.: C, 60.73; H, 5.10; N, 12.32. Found: 60.50; 5.09; 12.26.

EXAMPLE 125

(Z,R)-3-{1-[4-(1-tert.butoxycarbonylamino-ethyl)-phenylamino]-1-phenyl-methylidene}-5-nitro-2-indolinone Prepared analogously to Example 89 from 3-(1-ethoxy-1-phenyl-methylidene)-5-nitro-2-indolinone and (R)-4-(1-tert.butoxycarbonylamino-ethyl)-aniline in DMF.

Yield: 88% of theory,
Melting point: 247–249° C.
$C_{28}H_{28}N_4O_5$ (500.56).
Mass spectrum: $M^+$=500.
Calc.: C, 67.19; H, 5.64; N, 11.19. Found: 67.38; 5.69; 11.25.

EXAMPLE 126

(Z,R)-3-{1-[4-(1-aminoethyl)-phenylamino]-1-phenyl-methylidene}-5-nitro-2-indolinone-hydrochloride Prepared analogously to Example 29a from (Z,R)-3-{1-[4-(1-tert.butoxycarbonylamino-ethyl)-phenylamino]-1-phenyl-methylidene}-5-nitro-2-indolinone and ethyl acetate/hydrogen chloride.

Yield: 91% of theory,
Melting point: 230–235° C.
$C_{23}H_{20}N_4O_3$ (400.44).
Mass spectrum: $M^+$=400.
$C_{23}H_{20}N_4O_3 \times HCl \times H_2O$ (454.92).
Calc.: C, 60.73; H, 5.10; N, 12.32. Found: 60.87; 5.12; 12.35.

EXAMPLE 127

(Z)-3-{1-[4-(2-tert.butoxycarbonylamino-ethyl)-phenylamino]-1-phenyl-methylidene}-5-nitro-2-indolinone Prepared analogously to Example 82 from 1-acetyl-3-(1-ethoxy-1-phenyl-methylidene)-5-nitro-2-indolinone and 4-(1-tert.butoxycarbonylamino-ethyl)-aniline in DMF and subsequent treatment with sodium hydroxide solution in methanol.

Yield: 92% of theory,
Melting point: 213–214° C.
$C_{28}H_{28}N_4O_5$ (500.56).
Mass spectrum: $M^+$=500.
Calc.: C, 67.19; H, 5.64; N, 11.19. Found: 66.46; 5.79; 11.02.

EXAMPLE 128

(Z)-3-{1-[4-(2-aminoethyl)-phenylamino]-1-phenyl-methylidene}-5-nitro-2-indolinone-hydrochloride Prepared analogously to Example 29a from (Z)-3-{1-[4-(2-tert.butoxycarbonylamino-ethyl)-phenylamino]-1-phenyl-methylidene}-5-nitro-2-indolinone and ethyl acetate/hydrogen chloride.

Yield: 90% of theory,
Melting point: 335–340° C. (decomposition).
$C_{23}H_{20}N_4O_3$ (400.44).
Mass spectrum: $M^+$=400.
$C_{23}H_{20}N_4O_3 \times HCl$ (436.91).
Calc.: C, 61.95; H, 4.97; N, 12.56. Found: 61.68; 5.00; 12.50.

EXAMPLE 129

(Z)-3-{1-[4-(2-acetylamino-ethyl)-phenylamino]-1-phenyl-methylidene}-5-nitro-2-indolinone Prepared analogously to Example 31 from (Z)-3-{1-[4-(2-aminoethyl)-phenylamino]-1-phenyl-methylidene}-5-nitro-2-indolinone and acetic anhydride in glacial acetic acid.

Yield: 88% of theory,
Melting point: 306–307° C.
$C_{25}H_{22}N_4O_4$ (442.48).
Mass spectrum: $M^+$=442.
$C_{25}H_{22}N_4O_4 \times 0.5H_2O$ (451.48).
Calc.: C, 66.51; H, 5.13; N, 12.41. Found: 66.71; 5.00; 12.23.

EXAMPLE 130

(Z)-3-{1-[4-(2-diethylamino-ethyl)-phenylamino]-1-phenyl-methylidene}-5-nitro-2-indolinone Prepared analogously to Example 82 from 1-acetyl-3-(1-ethoxy-1-phenyl-methylidene)-5-nitro-2-indolinone and 4-(2-diethylamino-ethyl)-aniline in DMF and subsequent treatment with sodium hydroxide solution in methanol.

Yield: 75% of theory,
Melting point: 167–168° C.
$C_{27}H_{28}N_4O_3$ (456.55).
Mass spectrum: $(M+H)^+$=457.
Calc.: C, 71.03; H, 6.18; N, 12.27. Found: 70.83; 6.10; 12.14.

EXAMPLE 131

(Z)-3-{1-[4-(2-(N-(2-hydroxyethyl)-N-ethyl-amino)-ethyl)-phenylamino]-1-phenyl-methylidene}-5-nitro-2-indolinone Prepared analogously to Example 89 from 3-(1-ethoxy-1-phenyl-methylidene)-5-nitro-2-indolinone and {4-[2-(N-(2-hydroxyethyl)-N-ethyl-amino)-ethyl]-phenylamino}-aniline in DMF.

Yield: 68% of theory,
Melting point: 165–166° C.
$C_{27}H_{28}N_4O_4$ (472.55).
Mass spectrum: $M^+$=472.
$R_f$ value: 0.42 (silica gel; dichloromethane/methanol/$NH_4OH$=9:1:0.1).
Calc.: C, 68.63; H, 5.97; N, 11.86. Found: 68.63; 5.99; 11.74.

EXAMPLE 132

(Z)-3-{1-[4-(2-piperidinoethyl)-phenylamino]-1-phenyl-methylidene}-5-nitro-2-indolinone Prepared analogously to Example 82 from 1-acetyl-3-(1-ethoxy-1-phenyl-methylidene)-5-nitro-2-indolinone and 4-(2-piperidinoethyl)-aniline in DMF and subsequent treatment with sodium hydroxide solution in methanol.

Yield: 68% of theory,

Melting point: 236–237° C.

$C_{28}H_{28}N_4O_3$ (468.56).

Mass spectrum: $M^+$=468.

$R_f$ value: 0.62 (silica gel; dichloromethane/methanol/$NH_4OH$=4:1:0.2).

$C_{28}H_{28}N_4O_3 \times 0.5H_2O$ (477.56).

Calc.: C, 70.42; H, 6.12; N, 11.73. Found: 70.97; 6.08; 11.70.

EXAMPLE 133

(Z)-3-{1-[4-(2-morpholinoethyl)-phenylamino]-1-phenyl-methylidene}-5-nitro-2-indolinone Prepared analogously to Example 82 from 1-acetyl-3-(1-ethoxy-1-phenyl-methylidene)-5-nitro-2-indolinone and 4-(2-morpholinoethyl)-aniline in DMF and subsequent treatment with sodium hydroxide solution in methanol.

Yield: 87% of theory,

Melting point: 304–306° C.

$C_{27}H_{26}N_4O_4$ (470.53).

Mass spectrum: $M^+$=470.

$R_f$ value: 0.3 (silica gel; dichloromethane/methanol=19:1).

Calc.: C, 68.92; H, 5.57; N, 11.91. Found: 68.68; 5.55; 11.90.

EXAMPLE 134

(Z)-3-{1-[4-(2-dimethylamino-ethyl)-phenylamino]-1-phenyl-methylidene}-5-nitro-2-indolinone Prepared analogously to Example 82 from 1-acetyl-3-(1-ethoxy-1-phenyl-methylidene)-5-nitro-2-indolinone and 4-(2-dimethylamino-ethyl)-aniline in DMF and subsequent treatment with sodium hydroxide solution in methanol.

Yield: 77% of theory,

Melting point: 238–240° C.

$C_{25}H_{24}N_4O_3$ (428.50).

Mass spectrum: $M^+$=428.

$R_f$ value: 0.4 (silica gel; dichloromethane/methanol=9:1).

Calc.: C, 70.08; H, 5.65; N, 13.08. Found: 69.87; 5.64; 12.99.

EXAMPLE 135

(Z)-3-{1-[4-(2-(4-methylpiperazino)-ethyl)-phenylamino]-1-phenyl-methylidene}-5-nitro-2-indolinone Prepared analogously to Example 82 from 1-acetyl-3-(1-ethoxy-1-phenyl-methylidene)-5-nitro-2-indolinone and 4-[2-(N-methylpiperazino)-ethyl]-aniline in DMF and subsequent treatment with sodium hydroxide solution in methanol.

Yield: 90% of theory,

Melting point: 238–240° C.

$C_{28}H_{29}N_5O_3$ (483.58).

Mass spectrum: $(M+H)^+$=484.

$R_f$ value: 0.44 (silica gel; dichloromethane/methanol=9:1).

$C_{28}H_{29}N_5O_3 \times 0.5H_2O$ (492.58).

Calc.: C, 68.27; H, 6.14; N, 14.22. Found: 67.87; 6.15; 14.14.

EXAMPLE 136

(Z)-3-[1-(3-tert.butoxycarbonylaminomethylcarbonylaminomethyl-phenylamino)-1-phenyl-methylidene]-5-nitro-2-indolinone Prepared analogously to Example 82 from 1-acetyl-3-(1-ethoxy-1-phenyl-methylidene)-5-nitro-2-indolinone and 3-tert.butoxycarbonylaminomethylcarbonylaminomethyl-aniline in DMF and subsequent treatment with sodium hydroxide solution in methanol.

Yield: 78% of theory,

Melting point: 228° C.

$C_{29}H_{29}N_5O_6$ (543.58).

Mass spectrum: $M^+$=543.

Calc.: C, 64.08; H, 5.38; N, 12.88. Found: 63.72; 5.45; 12.73.

EXAMPLE 137

(Z)-3-[1-(3-aminomethylcarbonylaminomethyl-phenylamino)-1-phenyl-methylidene]-5-nitro-2-indolinone-hydrochloride Prepared analogously to Example 29a from (Z)-3-[1-(3-tert.butoxycarbonylaminomethylcarbonylaminomethyl-phenylamino)-1-phenyl-methylidene]-5-nitro-2-indolinone and ethyl acetate/hydrogen chloride.

Yield: 99% of theory,

Melting point: 309° C.

$C_{24}H_{21}N_5O_4$ (443.47).

Mass spectrum: $M^+$=443.

$C_{24}H_{21}N_5O_4 \times HCl \times 0.5H_2O$ (488.94).

Calc.: C, 58.96; H, 4.74; N, 14.32. Found: 58.40; 4.74; 14.01.

EXAMPLE 138

(Z)-3-[1-(3-acetylaminomethyl-phenylamino)-1-phenyl-methylidene]-5-nitro-2-indolinone Prepared analogously to Example 89 from 3-(1-ethoxy-1-phenyl-methylidene)-5-nitro-2-indolinone and 3-acetylaminomethyl-aniline in DMF.

Yield: 57% of theory,

Melting point: 238° C.

$C_{24}H_{20}N_4O_4$ (428.45).

Mass spectrum: $M^+$=428.

$C_{24}H_{20}N_4O_4 \times 0.5H_2O$ (437.46).

Calc.: C, 65.90; H, 4.84; N, 12.81. Found: 66.29; 4.80; 12.76.

EXAMPLE 139

(Z)-3-{1-[4-(N-aminomethylcarbonyl-N-methyl-amino)-phenyl-amino]-1-phenyl-methylidene}-5-nitro-2-indolinone a) (Z)-3-{1-[4-(N-phthalimidomethylcarbonyl-N-methyl-amino)-phenylamino]-1-phenyl-methylidene}-5-nitro-2-indolinone Prepared analogously to Example 89 from 3-(1-ethoxy-1-phenyl-methylidene)-5-nitro-2-indolinone and 4-(N-phthalimidomethylcarbonyl-N-methyl-amino)-aniline in DMF.

Yield: 99% of theory,
Melting point: 303–305° C.
$C_{32}H_{23}N_5O_6$ (573.57).
Mass spectrum: $M^+$=573.
$C_{32}H_{23}N_5O_6 \times H_2O$ (591.59).
Calc.: C, 64.97; H, 4.26; N, 11.84. Found: 64.74; 4.41; 11.59.

b) (Z)-3-{1-[4-(N-aminomethylcarbonyl-N-methyl-amino) phenylamino]-1-phenyl-methylidene}-5-nitro-2-indolinone 287 mg (0.5 mmol) of (Z)-3-{1-[4-(N-phthalimidomethylcarbonyl-N-methylamino)phenylamino]-1-phenyl-methylidene}-5-nitro-2-indolinone are suspended in 20 ml of ethanol and 20 ml of dichloromethane and after the addition of 0.3 ml of 80% hydrazine hydrate solution stirred for 18 hours at 50° C. The mixture is then cooled to ambient temperature, the insoluble matter is suction filtered and the mother liquor is concentrated by evaporation. The residue is chromatographed on silica gel (dichloromethane/methanol/ammonia=92:8:0.8) and the product is again triturated with methanol, suction filtered and dried.

Yield: 220 mg (99% of theory),
Melting point: 255–256° C.
$C_{24}H_{21}N_5O_4$ (443.47).
Mass spectrum: $M^+$=443.
Calc.: C, 65.00; H, 4.77; N, 15.79. Found: 64.73; 4.91; 15.66.

EXAMPLE 140

(Z)-3-{1-[4-(N-acetylaminomethylcarbonyl-N-methyl-amino)phenylamino]-1-phenyl-methylidene}-5-nitro-2-indolinone Prepared analogously to Example 31 from (Z)-3-{1-[4-(N-aminomethylcarbonyl-N-methyl-amino)-phenylamino]-1-phenyl-methylidene}-5-nitro-2-indolinone and acetic anhydride in glacial acetic acid.

Yield: 83% of theory,
Melting point: 277–278° C.
C26H23N5O5 (485.50).
Mass spectrum: $M^+$=485.
$R_f$ value: 0.6 (silica gel; ethyl acetate/methanol/$NH_4OH$=8:2:0.1).
$C_{26}H_{23}N_4O_5 \times H_2O$ (503.52).
Calc.: C, 62.02; H, 5.00; N, 13.91. Found: 61.77; 5.01; 13.79.

EXAMPLE 141

(Z)-3-[1-(4-morpholinomethylcarbonylaminomethyl-phenylamino)-1-phenyl-methylidene]-5-nitro-2-indolinone Prepared analogously to Example 74 from (Z)-1-polystyrylmethylaminocarbonyl-3-{1-[4-(morpholino-methylcarbonyl-aminomethyl)-phenylamino]-1-phenyl-methylidene}-5-nitro-2-indolinone and sodium hydroxide solution in dioxane.

Yield: 33% of theory,
Melting point: 290–295° C.
$C_{28}H_{27}N_5O_5$ (513.56).
Mass spectrum: $M^+$=513.
Calc.: C, 65.49; H, 5.30; N, 13.64. Found: 65.09; 5.32; 13.46.

EXAMPLE 142

(Z)-3-[1-(4-dimethylaminomethylcarbonylaminomethyl-phenylamino)-1-phenyl-methylidene]-5-nitro-2-indolinone Prepared analogously to Example 74 from (Z)-1-polystyrylmethylaminocarbonyl-3-{1-[4-(dimethylamino-methylcarbonyl-aminomethyl)phenylamino]-1-phenyl-methylidene}-5-nitro-2-indolinone and sodium hydroxide solution in dioxane.

Yield: 32% of theory,
Melting point: 272–273° C.
$C_{26}H_{25}N_5O_4$ (471.52).
Mass spectrum: $M^+$=471.
$R_f$ value: 0.55 (silica gel; dichloromethane/methanol/$NH_4OH$=9:1:0.1).
Calc.: C, 66.23; H, 5.34; N, 14.85. Found: 66.10; 5.35; 14.70.

EXAMPLE 143

(Z)-3-[1-(4-acetylaminomethyl-phenylamino)-1-phenyl-methylidene]-5-nitro-2-indolinone Prepared analogously to Example 74 from (Z)-1-polystyrylmethylamino-carbonyl-3-[1-(4-acetylamino-methyl-phenylamino)-1-phenyl-methylidene]-5-nitro-2-indolinone and sodium hydroxide solution in dioxane.

Yield: 37% of theory,
Melting point: 345–346° C.
$C_{24}H_{20}N_4O_4$ (428.45).
Mass spectrum: $M^+$=428.
Calc.: C, 67.94; H, 4.79; N, 12.73. Found: 66.46; 4.87; 12.80.

EXAMPLE 144

(Z)-3-[1-(4-tert.butoxycarbonylaminomethylcarbonylaminomethyl-phenylamino)-1-phenyl-methylidene]-5-nitro-2-indolinone Prepared analogously to Example 74 from (Z)-1-polystyrylmethylaminocarbonyl-3-{1-[4-(tert.butoxy-carbonylaminomethylcarbonylaminomethyl)-phenylamino]-1-phenyl-methylidene}-5-nitro-2-indolinone and sodium hydroxide solution in dioxane.

Yield: 24% of theory,
Melting point: 219–221° C. (decomposition).
$C_{29}H_{29}N_5O_6$ (543.58).
Mass spectrum: $M^+$=543.
$C_{29}H_{29}N_5O_6 \times 0.5H_2O$ (552.59).
Calc.: C, 63.03; H, 5.47; N, 12.67. Found: 63.20; 5.35; 12.61.

EXAMPLE 145

(Z)-3-{1-[4-((N-tert.butoxycarbonyl-N-methyl-amino)-methylcarbonylaminomethyl)-phenylamino]-1-phenyl-methylidene}-5-nitro-2-indolinone Prepared analogously to Example 74 from (Z)-1-polystyrylmethylaminocarbonyl-3-{1-[4-((N-tert.butoxycarbonyl-N-methyl-amino)-methylcarbonyl-aminomethyl)-phenylamino]-1-phenyl-methylidene}-5-nitro-2-indolinone and sodium hydroxide solution in dioxane.

Yield: 31% of theory,
Melting point: 225–227° C. (decomposition).
$C_{30}H_{31}N_5O_6$ (557.61).
Mass spectrum: $M^+$=557.
$C_{30}H_{31}N_5O_6 \times 0.5H_2O$ (566.62).
Calc.: C, 63.59; H, 5.69; N, 12.36. Found: 63.75; 5.31; 12.22.

EXAMPLE 146

(Z)-3-[1-(4-tert.butoxycarbonylaminomethyl-phenylamino)-1-(4-phthalimidomethyl-phenyl)-methylidene]-1-acetyl-5-nitro-2-indolinone a) tert.butyl 4-phthalimidomethyl-benzoate b)

18.5 g (0.1 mol) of phthalimide-potassium are suspended in 80 ml of DMF and combined with 22.5 g (0.09 mol) of tert.butyl 4-bromomethyl-benzoate. The reaction solution is stirred for 16 hours at ambient temperature and then stirred into 40 ml of water, extracted with ethyl acetate and chromatographed on silica gel (toluene).

Yield: 17.9 g (60% of theory),
Melting point: 144–145° C.
$C_{20}H_{19}NO_4 \times 0.25H_2O$ (341.88).
Calc.: C, 70.26; H, 5.75; N, 4.10. Found: 70.10; 5.73; 4.11.

b) 4-phthalimidomethyl-benzoic acid 337 mg (1.0 mmol) of tert.butyl 4-phthalimidomethyl-benzoate are stirred in 3 ml of trifluoroacetic acid for 45 minutes at ambient temperature. Then the solvent is eliminated in vacuo.

Yield: 96% of theory,
Melting point: 260–262° C.
$C_{16}H_{11}NO_4$ (281.3).
Mass spectrum: $M^+$=281.

c) 3-[1-hydroxy-1-(4-phthalimidomethyl-phenyl)-methylidene]-1-acetyl-5-nitro-2-indolinone Prepared analogously to Example 2a from 1-acetyl-5-nitro-2-indolinone and 4-phthalimidomethyl-benzoic acid, TBTU, HOBt and N-ethyl-N,N-diisopropyl-amine in DMF.

Yield: 75% of theory,
Melting point: 246–248° C. (decomposition).
$R_f$ value: 0.55 (silica gel; dichloromethane/methanol=10:1).

d) 3-[1-chloro-1-(4-phthalimidomethyl-phenyl)-methylidene]-1-acetyl-5-nitro-2-indolinone Prepared analogously to Example 2b from 3-[1-hydroxy-1-(4-phthalimidomethyl-phenyl)-methylidene]-1-acetyl-5-nitro-2-indolinone and phosphorus pentachloride in toluene.

Yield: 65% of theory,
Melting point: 234–236° C. (decomposition).
$C_{26}H_{16}ClN_3O_6$ (501.9).
Calc.: C, 62.22; H, 3.21; N, 8.37; Cl, 7.06. Found: 62.25; 3.31; 8.27; 7.20.

e) (Z)-3-[1-(4-tert.butoxycarbonylaminomethyl-phenylamino)-1-(4-phthalimidomethyl-phenyl)-methylidene]-1-acetyl-5-nitro-2-indolinone Prepared analogously to Example 2c from 3-[1-chloro-1-(4-phthalimidomethyl-phenyl)-methylidene]-1-acetyl-5-nitro-2-indolinone, 4-tert.butoxycarbonylaminomethyl-aniline and triethylamine in dichloromethane.

Yield: 47% of theory,
Melting point: 125° C. (decomposition).
$C_{38}H_{33}N_5O_8$ (687.71).
Mass spectrum: $M^+$=687.

EXAMPLE 147

(Z)-3-{1-[4-tert.butoxycarbonylaminomethyl-phenylamino]-1-[4-(2-carboxyphenyl)-carbonylaminomethyl-phenyl]-methylidene}-5-nitro-2-indolinone Prepared analogously to Example 1 from (Z)-3-[1-(4-tert.butyloxycarbonylaminomethyl-phenylamino)-1-(4-phthalimidomethyl-phenyl)-methylidene]-1-acetyl-5-nitro-2-indolinone and sodium hydroxide solution in methanol.

Yield: 88% of theory,
Melting point: 138° C. (decomposition).
$C_{36}H_{33}N_5O_8$ (663.69).
Mass spectrum: $(M+H)^+$=664 $R_f$ value: 0.31 (silica gel; dichloromethane/methanol=10:1)

EXAMPLE 148

(Z)-3-[1-(4-tert.butoxycarbonylaminomethyl-phenylamino)-1-(4-aminomethyl-phenyl)-methylidene]-5-nitro-2-indolinone Prepared analogously to Example 139b from (Z)-3-[1-(4-tert.butoxycarbonylaminomethyl-phenylamino)-1-(4-phthalimidomethyl-phenyl)-methylidene]-1-acetyl-5-nitro-2-indolinone and hydrazine hydrate solution in ethanol.

Yield: 42% of theory,
Melting point: 220–223° C.
$C_{28}H_{29}N_5O_5$ (515.57).
Mass spectrum: $M^+$=515.
$R_f$ value: 0.61 (silica gel; dichloromethane/methanol=9:1).

EXAMPLE 149

(Z)-3-[1-(4-aminomethyl-phenylamino]-1-(4-aminomethyl-phenyl)-methylidene]-5-nitro-2-indolinone-dihydrotrifluoroacetate Prepared analogously to Example 29a from (Z)-3-[1-(4-tert.butoxycarbonylaminomethyl-phenylamino)-1-(4-aminomethyl-phenyl)-methylidene]-5-nitro-2-indolinone and trifluoroacetic acid in dichloromethane.

Yield: 54% of theory,
Melting point: 265° C.
$C_{23}H_{21}N_5O_3$ (415.46).
Mass spectrum: $M^+$=415.
$R_f$ value: 0.50 (Reversed phase P8; methanol/5% saline solution=6:4).
$C_{23}H_{21}N_5O_3 \times 2C_2HF_3O_2 \times 2H_2O$ (679.53).
Calc.: C, 47.72; H, 4.00; N, 10.30. Found: 47.69; 3.96; 10.39.

EXAMPLE 150

(Z)-3-[1-(4-tert.butoxycarbonylaminomethyl-phenylamino)-1-(4-acetylaminomethyl-phenyl)-methylidene]-5-nitro-2-indolinone Prepared analogously to Example 31 from (Z)-3-[1-(4-tert.butoxycarbonylaminomethyl-phenylamino)-1-(4-aminomethyl-phenyl)-methylidene]-5-nitro-2-indolinone and acetic anhydride in dioxane.

Yield: 61% of theory,
Melting point: 234° C. (decomposition).
$C_{30}H_{31}N_5O_6$ (557.61).
Mass spectrum: $M^+$=557.
$R_f$ value: 0.60 (silica gel; dichloromethane/methanol=20:1).
$C_{30}H_{31}N_5O_6 \times 0.25H_2O$ (562.12).
Calc.: C, 64.07; H, 5.70; N, 12.46. Found: 64.01; 5.70; 12.13.

EXAMPLE 151

(Z)-3-[1-(4-aminomethyl-phenylamino)-1-(4-acetylaminomethyl-phenyl)-methylidene]-5-nitro-2-indolinone-dihydrotrifluoroacetate Prepared analogously to Example 29a from (Z)-3-[1-(4-tert.butoxycarbonylaminomethyl-phenylamino)-1-(4- acetylaminomethyl-phenyl)-methylidene]-5-nitro-2-indolinone and trifluoroacetic acid in dichloromethane.

Yield: 92% of theory,

Melting point: 239–241° C. (decomposition).

$C_{25}H_{23}N_5O_4$ (457.49).

Mass spectrum: $M^+$=457.

$C_{25}H_{23}N_5O_4 \times 2C_2HF_3O_2 \times 0.5H_2O$ (694.55).

Calc.: C, 50.80; H, 3.67; N, 10.21. Found: 50.14; 3.77; 10.08.

EXAMPLE 152

(Z)-3-[1-(4-acetylaminomethyl-phenylamino)-1-(4-acetylamino-methyl-phenyl)-methylidene]-5-nitro-2-indolinone-hydrotrifluoroacetate Prepared analogously to Example 31 from (Z)-3-[1-(4-aminomethyl-phenylamino)-1-(4-acetylaminomethyl-phenyl)-methylidene]-5-nitro-2-indolinone and acetic anhydride in dioxane.

Yield: 99% of theory,

Melting point: 126° C. (decomposition).

$C_{27}H_{25}N_5O_5$ (499.53).

Mass spectrum: $M^+$=499.

$R_f$ value: 0.42 (silica gel; dichloromethane/methanol/$NH_4OH$=10:1:0.1).

EXAMPLE 153

(Z)-3-[1-phenylamino-1-(4-phthalimidomethyl-phenyl)-methylidene]-5-nitro-2-indolinone Prepared analogously to Example 146 from 1-acetyl-3-[1-chloro-1-(4-phthalimidomethyl-phenyl)-methylidene]-5-nitro-2-indolinone, aniline, N-ethyl-N,N-diisopropyl-amine and DMF.

Yield: 18% of theory,

Melting point: 334–336° C. (decomposition).

$C_{30}H_{20}N_4O_5$ (516.52).

Mass spectrum: $M^+$=516.

$R_f$ value: 0.30 (silica gel; toluene/acetone=4:1).

EXAMPLE 154

(Z)-3-[1-phenylamino-1-(4-aminomethyl-phenyl)-methylidene]-5-nitro-2-indolinone

Prepared analogously to Example 140 from (Z)-3-[1-phenylamino-1-(4-phthalimidomethyl-phenyl)-methylidene]-5-nitro-2-indolinone and hydrazine hydrate solution in ethanol.

Yield: 66% of theory,

Melting point: 332° C. (decomposition).

$C_{22}H_{18}N_4O_3$ (386.41).

Mass spectrum: $(M+H)^+$=387.

$R_f$ value: 0.38 (silica gel; dichloromethane/methanol/$NH_4OH$=10:1:0.1).

EXAMPLE 155

(Z)-3-{1-[4-(2-tert.butoxycarbonylamino-ethyl)-phenylamino]-1-(4-aminomethyl-phenyl)-methylidene}-5-nitro-2-indolinone Prepared analogously to Example 140 from (Z)-3-{1-[4-(2-tert.butoxycarbonylamino-ethyl)-phenylamino]-1-(4-phthalimidomethyl-phenyl)-methylidene}-1-acetyl-5-nitro-2-indolinone and hydrazine hydrate solution in ethanol.

Yield: 65% of theory,

Melting point: 215–217° C. (decomposition).

$C_{29}H_{31}N_5O_5$ (529.60).

Mass spectrum: $M^+$=529.

$R_f$ value: 0.33 (silica gel; dichloromethane/methanol=10:1).

$C_{29}H_{31}N_5O_5 \times H_2O \times C_8H_6N_2O_2$ (628.70).

Calc.: C, 63.05; H, 5.77; N, 13.37. Found: 63.16; 5.73; 13.50.

EXAMPLE 156

(Z)-3-{1-[4-(2-aminoethyl)-phenylamino]-1-(4-aminomethyl-phenyl)-methylidene}-5-nitro-2-indolinone-dihydrotrifluoroacetate Prepared analogously to Example 29a from (Z)-3-{1-[4-(2-tert.butoxycarbonylamino-ethyl)-phenylamino]-1-(4-aminomethyl-phenyl)-methylidene}-5-nitro-2-indolinone and trifluoroacetic acid in dichloromethane.

Yield: 96% of theory,

Melting point: 230–232° C. (decomposition).

$C_{24}H_{23}N_5O_3$ (429.48).

Mass spectrum: 429.

$R_f$ value: 0.27 (silica gel; dichloromethane/methanol/$NH_4OH$=4:1:0.1).

$C_{24}H_{23}N_5O_3 \times 2C_2HF_3O_2$ (657.53).

Calc.: C, 51.14; H, 3.83; N, 10.65. Found: 51.53; 4.05; 11.05.

EXAMPLE 157

(Z)-3-{1-[4-(2-tert.butoxycarbonylamino-ethyl)-phenylamino]-1-(4-acetylaminomethyl-phenyl)-methylidene}-5-nitro-2-indolinone Prepared analogously to Example 31 from (Z)-3-{1-[4-(2-tert.butoxycarbonylamino-ethyl)-phenylamino]-1-(4-aminomethyl-phenyl)-methylidene}-5-nitro-2-indolinone and acetic anhydride in dioxane.

Yield: 53% of theory,

Melting point: 94° C. (decomposition).

$C_{31}H_{33}N_5O_6$ (571.64).

Mass spectrum: $(M-H)^-$=570.

$R_f$ value: 0.52 (silica gel; dichloromethane/methanol=25:1).

$C_{31}H_{33}N_5O_6 \times H_2O$ (589.65).

EXAMPLE 158

(Z)-3-{1-[4-(2-aminoethyl)-phenylamino]-1-(4-acetylaminomethyl-phenyl)-methylidene}-5-nitro-2-indolinone-dihydrotrifluoroacetate Prepared analogously to Example 29a from (Z)-3-{1-[4-(2-tert.butoxycarbonylamino-ethyl)-phenylamino]-1-(4-acetylaminomethyl-phenyl)-methylidene}-5-nitro-2-indolinone and trifluoroacetic acid in dichloromethane.

Yield: 67% of theory,

Melting point: 229° C. (decomposition).

$C_{26}H_{25}N_5O_4$ (471.52).

Mass spectrum: 471.

$R_f$ value: 0.33 (silica gel; dichloromethane/methanol/ $NH_4OH$=4:1:0.1).

$C_{26}H_{25}N_5O_4 \times C_2HF_3O_2 \times 0.5H_2O$ (594.55).

Calc.: C, 56.56; H, 4.58; N, 11.78. Found: 56.33; 4.54; 11.62.

EXAMPLE 159

(Z)-3-[1-(4-diethylaminomethyl-phenylamino)-1-phenyl-methylidene]-5-nitro-2-indolinone 846 mg (2.0 mmol) of (Z)-[1-(4-aminomethyl-phenylamino)-1-phenyl-methylidene]-5-nitro-2-indolinone-hydrochloride are suspended in 20 ml of methanol and combined with 0.1 ml (2.5 mmol) of acetaldehyde. After 15 minutes stirring at ambient temperature 157 mg (2.5 mmol) of sodium cyanoborohydride are added. The mixture is stirred for 16 hours at ambient temperature and then another 0.1 ml of (2.5 mmol) of acetaldehyde and 157 mg (2.5 mmol) of sodium cyanoborohydride are added. After 22 hours stirring at ambient temperature the reaction mixture is concentrated by evaporation and the residue taken up in water/dichloromethane. Extraction with dichloromethane and chromatography on silica gel (dichloromethane/methanol/$NH_4OH$=93:7:0.7) yield the product.

Yield: 340 mg (38% of theory),

Melting point: 173–174° C.

$C_{26}H_{26}N_4O_3$ (442.52).

Mass spectrum: $M^+$=442.

$R_f$ value: 0.4 (silica gel; dichloromethane/methanol/ $NH_4OH$=9:1:0.1).

Calc.: C, 70.57; H, 5.92; N, 12.66. Found: 70.27; 5.90; 12.57.

EXAMPLE 160

(Z)-3-[1-(4-ethylaminomethyl-phenylamino)-1-phenyl-methylidene]-5-nitro-2-indolinone Prepared analogously to Example 159 from (Z)-3-[1-(4-aminomethyl-phenylamino)-1-phenyl-methylidene]-5-nitro-2-indolinone-hydrochloride, acetaldehyde and sodium cyanoborohydride in methanol.

Yield: 17% of theory,

Melting point: 220–223° C.

$C_{24}H_{22}N_4O_3$ (414.47).

Mass spectrum: $M^+$=414.

$R_f$ value: 0.2 (silica gel; ethyl acetate/methanol/$NH_4OH$=8:2:0.1).

$C_{24}H_{22}N_4O_3 \times 0.5H_2O$ (423.47).

Calc.: C, 68.07; H, 5.47; N, 13.23. Found: 68.55; 5.41; 13.15.

EXAMPLE 161

(Z)-3-[1-(4-Dipropylaminomethyl-phenylamino)-1-phenyl-methylidene]-5-nitro-2-indolinone Prepared analogously to Example 159 from (Z)-3-[1-(4-aminomethyl-phenylamino)-1-phenyl-methylidene]-5-nitro-2-indolinone-hydrochloride, propionaldehyde and sodium cyanoborohydride in methanol.

Yield: 29% of theory,

Melting point: 160–162° C.

$C_{28}H_{30}N_4O_3$ (470.57).

Mass spectrum: $M^+$=470.

$R_f$ value: 0.6 (silica gel; dichloromethane/methanol/ $NH_4OH$=9:1:0.1).

$C_{28}H_{30}N_4O_3 \times 0.5H_2O$ (479.58).

Calc.: C, 70.13; H, 6.52; N, 11.68. Found: 69.80; 6.61; 11.65.

EXAMPLE 162

(Z)-3-[1-(4-propylaminomethyl-phenylamino)-1-phenyl-methylidene]-5-nitro-2-indolinone Prepared analogously to Example 159 from (Z)-3-[1-(4-aminomethyl-phenylamino)-1-phenyl-methylidene]-5-nitro-2-indolinone-hydrochloride, propionaldehyde and sodium cyanoborohydride in methanol.

Yield: 12% of theory,

Melting point: 201–202° C.

$C_{25}H_{24}N_4O_3$ (428.50).

Mass spectrum: $M^+$=428.

$R_f$ value: 0.4 (silica gel; dichloromethane/methanol/ $NH_4OH$=9:1:0.1).

$C_{25}H_{24}N_4O_3 \times 0.5H_2O$ (437.50).

Calc.: C, 68.63; H, 5.76; N, 12.81. Found: 68.81; 5.87; 12.83.

EXAMPLE 163

(Z)-3-[1-(4-Diisobutylaminomethyl-phenylamino)-1-phenyl-methylidene]-5-nitro-2-indolinone Prepared analogously to Example 159 from (Z)-3-[1-(4-aminomethyl-phenylamino)-1-phenyl-methylidene]-5-nitro-2-indolinone-hydrochloride, isobutyraldehyde and sodium cyanoborohydride in methanol.

Yield: 3% of theory,

Melting point: 204–207° C.

$C_{30}H_{34}N_4O_3$ (498.63).

Mass spectrum: $M^+$=498.

$R_f$ value: 0.95 (silica gel; ethyl acetate/methanol/ $NH_4OH$=8:2:0.1).

EXAMPLE 164

(Z)-3-[1-(4-isobutylaminomethyl-phenylamino)-1-phenyl-methylidene]-5-nitro-2-indolinone Prepared analogously to Example 159 from (Z)-3-[1-(4-aminomethyl-phenylamino)-1-phenyl-methylidene]-5-nitro-2-indolinone-hydrochloride, isobutyraldehyde and sodium cyanoborohydride in methanol.

Yield: 44% of theory,

Melting point: 208° C.

$C_{26}H_{26}N_4O_3$ (442.52).

Mass spectrum: $M^+$=442.

$R_f$ value: 0.4 (silica gel; ethyl acetate/methanol/$NH_4OH$=8:2:0.1).

Calc.: C, 70.57; H, 5.92; N, 12.66. Found: 70.03; 6.00; 12.42.

EXAMPLE 165

(Z)-3-[1-(4-Dibutylaminomethyl-phenylamino)-1-phenyl-methylidene]-5-nitro-2-indolinone Prepared analogously to Example 159 from (Z)-3-[1-(4-aminomethyl-phenylamino)-1-phenyl-methylidene]-5- nitro-2-indolinone-hydrochloride, butyraldehyde and sodium cyanoborohydride in methanol.
Yield: 12% of theory,
Melting point: 175° C.
$C_{30}H_{34}N_4O_3$ (498.63).
Mass spectrum: $M^+$=498.
Calc.: C, 72.26; H, 6.87; N, 11.24. Found: 71.79; 6.91; 11.35.

EXAMPLE 166

(Z)-3-[1-(4-butylaminomethyl-phenylamino)-1-phenyl-methylidene]-5-nitro-2-indolinone Prepared analogously to Example 159 from (Z)-3-[1-(4-aminomethyl-phenylamino)-1-phenyl-methylidene]-5-nitro-2-indolinone-hydrochloride, butyraldehyde and sodium cyanoborohydride in methanol.
Yield: 14% of theory,
Melting point: 183° C.
$C_{26}H_{26}N_4O_3$ (442.52).
Mass spectrum: $M^+$=442.
Calc.: C, 70.57; H, 5.97; N, 12.66. Found: 70.33; 6.04; 12.44.

EXAMPLE 167

(Z)-3-[1-(4-methylsulphonylaminomethyl-phenylamino)-1-phenyl-methylidene]-5-nitro-2-indolinone Prepared analogously to Example 74 from (Z)-3-[1-(4-methylsulphonylaminomethyl-phenylamino)-1-phenyl-methylidene]-5-nitro-1-polystyrylmethylaminocarbonyl-2-indolinone and sodium hydroxide solution in dioxane.
Yield: 16% of theory,
Melting point: 294–296° C.
$C_{23}H_{20}N_4O_5S$ (464.50).
Mass spectrum: $M^+$=464.
$C_{23}H_{20}N_4O_5S \times H_2O$ (482.52).
Calc.: C, 57.25; H, 4.60; N, 11.61. Found: 57.56; 4.67; 11.70.

EXAMPLE 168

(Z)-3-{1-[4-(4-hydroxypiperidinomethyl)-phenylamino]-1-phenyl-methylidene}-5-nitro-2-indolinone Prepared analogously to Example 89 from 3-(1-ethoxy-1-phenyl-methylidene)-5-nitro-2-indolinone and 4-(4-hydroxypiperidinomethyl)-aniline in DMF.
Yield: 43% of theory,
Melting point: 155° C.
$C_{27}H_{26}N_4O_4$ (470.53).
Mass spectrum: $M^+$=470.
$R_f$ value: 0.45 (silica gel; ethyl acetate/methanol/$NH_4OH$=19:1:0.1).
$C_{27}H_{26}N_4O_4 \times 0.5H_2O$ (479.54).
Calc.: C, 67.63; H, 5.67; N, 11.68. Found: C 67.63; H, 5.63; N, 11.59.

EXAMPLE 169

(Z)-3-{1-[4-(4-methylpiperidinomethyl)-phenylamino]-1-phenyl-methylidene}-5-nitro-2-indolinone Prepared analogously to Example 89 from 3-(1-ethoxy-1-phenyl-methylidene)-5-nitro-2-indolinone and 4-(4-methylpiperidinomethyl)-aniline in DMF.
Yield: 92% of theory,
Melting point: 161° C.
$C_{28}H_{28}N_4O_3$ (468.56).
Mass spectrum: $M^+$=468.
$R_f$ value: 0.3 (silica gel; ethyl acetate/methanol=9:1).
$C_{28}H_{28}N_4O_3 \times 0.5H_2O$ (477.57).
Calc.: C, 70.42; H, 6.12; N, 11.73. Found: 70.58; 6.25; 11.68.

EXAMPLE 170

(Z)-3-[1-(4-piperidinomethyl-phenylamino)-1-phenyl-methylidene]-5-nitro-2-indolinone Prepared analogously to Example 89 from 3-(1-ethoxy-1-phenyl-methylidene)-5-nitro-2-indolinone and 4-piperidinomethyl-aniline in DMF.
Yield: 77% of theory,
Melting point: 242–243° C.
$C_{27}H_{26}N_4O_3$ (454.53).
Mass spectrum: $M^+$=454.
$R_f$ value: 0.3 (silica gel; dichloromethane/methanol/$NH_4OH$=9:1:0.1).
Calc.: C, 71.35; H, 5.77; N, 12.33. Found: 71.40; 6.00; 12.37.

EXAMPLE 171

(Z)-3-{1-[4-(4-methoxypiperidinomethyl)-phenylamino]-1-phenyl-methylidene}-5-nitro-2-indolinone Prepared analogously to Example 89 from 3-(1-ethoxy-1-phenyl-methylidene)-5-nitro-2-indolinone and 4-(4-methoxypiperidinomethyl)-aniline in DMF.
Yield: 48% of theory,
Melting point: 204–206° C.
$C_{28}H_{28}N_4O_4$ (484.56).
Mass spectrum: $M^+$=484.
$R_f$ value: 0.5 (silica gel; dichloromethane/methanol/$NH_4OH$=9:1:0.1).
Calc.: C, 69.41; H, 5.82; N, 11.56. Found: 69.11; 5.83; 11.47.

EXAMPLE 172

(Z)-3-{1-[4-(4-phenylmethyl-piperidinomethyl)-phenylamino]-1-phenyl-methylidene}-5-nitro-2-indolinone Prepared analogously to Example 89 from 3-(1-ethoxy-1-phenyl-methylidene)-5-nitro-2-indolinone and 4-(4-phenylmethyl-piperidino)methyl-aniline in DMF.
Yield: 48% of theory,
Melting point: 252° C.
$C_{34}H_{32}N_4O_3$ (544.66).
Mass spectrum: $M^+$=544.
Calc.: C, 74.98; H, 5.92; N, 10.29. Found: 74.52; 5.81; 10.23.

EXAMPLE 173

(Z)-3-{1-[4-(4-hydroxy-4-phenyl-piperidinomethyl)-phenylamino-1-phenyl-methylidene}-5-nitro-2-indolinone Prepared analogously to Example 89 from 3-(1-ethoxy-1-phenyl-methylidene)-5-nitro-2-indolinone and 4-(4-hydroxy-4-phenyl-piperidinomethyl)-aniline in DMF.
Yield: 68% of theory,
Melting point: 191–194° C.

$C_{33}H_{30}N_4O_4$ (546.63).

Mass spectrum: $M^+=546$.

$R_f$ value: 0.4 (silica gel; ethyl acetate/methanol/NH$_4$OH= 95:5:0.5).

Calc.: C, 72.51; H, 5.53; N, 10.25. Found: 72.04; 5.50; 10.30.

EXAMPLE 174

(Z)-3-{1-[4-(2-methoxyethylaminomethyl)-phenylamino]-1-phenyl-methylidene}-5-nitro-2-indolinone Prepared analogously to Example 89 from 3-(1-ethoxy-1-phenyl-methylidene)-5-nitro-2-indolinone and 4-(2-methoxyethylaminomethyl)-aniline in DMF.

Yield: 76% of theory,

Melting point: 184–185° C.

$C_{25}H_{24}N_4O_4$ (444.49).

Mass spectrum: $(M+H)^+=445$.

$R_f$ value: 0.3 (silica gel; ethyl acetate/methanol/NH$_4$OH= 8:2:0.1).

Calc.: C, 67.56; H, 5.44; N, 12.60. Found: 67.10; 5.68; 12.31.

EXAMPLE 175

(Z)-3-{1-[4-(4-ethylpiperidinomethyl)-phenylamino]-1-phenyl-methylidene}-5-nitro-2-indolinone Prepared analogously to Example 89 from 3-(1-ethoxy-1-phenyl-methylidene)-5-nitro-2-indolinone and 4-(4-ethylpiperidinomethyl)-aniline in DMF.

Yield: 37% of theory,

Melting point: 225–227° C.

$C_{29}H_{30}N_4O_3$ (482.59).

Mass spectrum: $[M+H]^+=483$.

$R_f$ value: 0.5 (silica gel; ethyl acetate/methanol/NH$_4$OH= 95:5:0.5).

$C_{29}H_{30}N_4O_3 \times 0.5H_2O$ (491.60).

Calc.: C, 70.86; H, 6.36; N, 11.40. Found: 71.09; 6.45; 11.32.

EXAMPLE 176

(Z)-3-{1-[4-(4-ethoxycarbonyl-piperidinomethyl)-phenylamino]-1-phenyl-methylidene}-5-nitro-2-indolinone Prepared analogously to Example 89 from 3-(1-ethoxy-1-phenyl-methylidene)-5-nitro-2-indolinone and 4-(4-ethoxycarbonyl-piperidinomethyl)-aniline in DMF.

Yield: 63% of theory,

Melting point: 194° C.

$C_{30}H_{30}N_4O_5$ (526.60).

Mass spectrum: $M^+=526$.

Calc.: C, 68.43; H, 5.74; N, 10.64. Found: 68.19; 5.86; 10.49.

EXAMPLE 177

(Z)-3-{1-[4-(4-carboxypiperidinomethyl)-phenylamino]-1-phenyl-methylidene}-5-nitro-2-indolinone Prepared analogously to Example 8 by saponification of (Z)-3-{1-[4-(4-ethoxycarbonylpiperidinomethyl)-phenylamino]-1-phenyl-methylidene}-5-nitro-2-indolinone with sodium hydroxide solution in ethanol.

Yield: 80% of theory,

Melting point: 207° C.

$C_{28}H_{26}N_4O_5$ (498.54).

Mass spectrum: $M^+=498$.

$C_{28}H_{26}N_4O_5 \times 0.5H_2O$ (507.55).

Calc.: C, 66.26; H, 5.36; N, 11.04. Found: 66.14; 5.38; 11.03.

EXAMPLE 178

(Z)-3-{1-[4-(2-ethoxycarbonylmethylamino-ethyl)-phenylamino]-1-phenyl-methylidene}-5-nitro-2-indolinone Prepared analogously to Examples 43 and 89 from 3-(1-ethoxy-1-phenyl-methylidene)-5-nitro-2-indolinone and 4-(2-ethoxycarbonylmethylamino-ethyl)-aniline in DMF.

Yield: 57% of theory,

Melting point: 139–140° C.

$C_{27}H_{26}N_4O_5$ (486.53).

Mass spectrum: $M^+=486$.

$R_f$ value: 0.5 (silica gel; ethyl acetate/methanol=9:1).

Calc.: C, 66.66; H, 5.39; N, 11.52. Found: 66.74; 5.10; 11.55.

EXAMPLE 179

(Z)-3-[1-(4-cyanomethyl-phenylamino)-1-phenyl-methylidene]-5-nitro-2-indolinone

Prepared analogously to Example 82 from 1-acetyl-3-(1-ethoxy-1-phenyl-methylidene)-5-nitro-2-indolinone, (4-aminophenyl)-acetonitrile in DMF and subsequent treatment with piperidine.

Yield: 97% of theory,

Melting point: 329° C.

$R_f$ value: 0.3 (silica gel; dichloromethane/methanol= 25:1).

$C_{23}H_{16}N_4O_3 \times 0.3H_2O$ (401.81).

Calc.: C, 68.75; H, 4.16; N, 13.94. Found: 68.84; 4.13; 14.12.

EXAMPLE 180

(Z)-3-[1-(4-methoxycarbonylmethyl-phenylamino)-1-phenyl-methylidene]-5-nitro-2-indolinone Prepared by reaction analogously to Example 62 from (Z)-3-[1-(4-cyanomethyl-phenylamino)-1-phenyl-methylidene]-5-nitro-2-indolinone with methanolic hydrochloric acid and 1,2-ethylenediamine.

Yield: 43% of theory,

Melting point: 238–240° C.

$C_{24}H_{19}N_3O_5$ (429.44).

Mass spectrum: $(M+Na)^+=452$.

$R_f$ value: 0.8 (silica gel; dichloromethane/methanol/NH$_4$OH=4:1:0.1).

EXAMPLE 181

(Z)-3-[1-(4-phenylsulphonylaminomethyl-phenylamino)-1-phenyl-methylidene]-2-indolinone Prepared analogously to Example 74 from (Z)-3-[1-(4-phenylsulphonylaminomethyl-phenylamino)-1-phenylmethylidene]-1-polystyrylmethylaminocarbonyl-2-indolinone and sodium hydroxide solution in dioxane.
Yield: 3% of theory,
$C_{28}H_{23}N_3O_3S$ (481.58).
Mass spectrum: $M^+$=481.

EXAMPLE 182

(Z)-3-[1-(4-methylsulphonylaminomethyl-phenylamino)-1-phenyl-methylidene]-2-indolinone Prepared analogously to Example 74 from (Z)-3-[1-(4-methylsulphonylaminomethyl-phenylamino)-1-phenyl-methylidene]-1-polystyrylmethylaminocarbonyl-2-indolinone and sodium hydroxide solution in dioxane.
Yield: 8% of theory,
$C_{23}H_{21}N_3O_3S$ (419.51).
Mass spectrum: $M^+$=419.

EXAMPLE 183

(Z)-3-[1-(3-methylsulphonylamino-phenylamino)-1-phenyl-methylidene]-2-indolinone Prepared analogously to Example 1 from 1-acetyl-3-(1-ethoxy-1-phenyl-methylidene)-2-indolinone and 3-methylsulphonylamino-aniline in DMF and subsequent treatment with sodium hydroxide solution in methanol.
Yield: 62% of theory,
Melting point: 275° C.
$C_{22}H_{19}N_3O_3S$ (405.48).
Mass spectrum: $M^+$=405.
Calc.: C, 65.18; H, 4.72; N, 10.36. Found: 65.02; 4.95; 9.95.

EXAMPLE 184

(Z)-3-{1-[3-(N-methyl-N-methylsulphonyl-amino)-phenylamino]-1-phenyl-methylidene}-2-indolinone Prepared analogously to Example 36 from (Z)-3-[1-(3-methylsulphonylamino-phenylamino)-1-phenyl-methylidene]-2-indolinone, methyliodide and potassium carbonate in acetone.
Yield: 96% of theory,
Melting point: 261° C.
$C_{23}H_{21}N_3O_3S$ (419.51).
Mass spectrum: $M^+$=419.

EXAMPLE 185

(Z)-3-[1-(4-methylsulphonylamino-phenylamino)-1-phenyl-methylidene]-2-indolinone Prepared analogously to Example 1 from 1-acetyl-3-(1-ethoxy-1-phenyl-methylidene)-2-indolinone and 4-methylsulphonylamino-aniline in DMF and subsequent treatment with sodium hydroxide solution in methanol.
Yield: 4% of theory,
Melting point: 299–301° C.
$C_{22}H_{19}N_3O_3S$ (405.48).
Mass spectrum: $M^+$=405.
$R_f$ value: 0.27 (silica gel; dichloromethane/ethyl acetate=7:3).

EXAMPLE 186

(Z)-3-{1-[4-(N-methyl-N-methylsulphonyl-amino)-phenylamino]-1-phenyl-methylidene}-2-indolinone Prepared analogously to Example 1 from 1-acetyl-3-(1-ethoxy-1-phenyl-methylidene)-2-indolinone and 4-(N-methyl-N-methylsulphonyl-amino)-aniline in DMF and subsequent treatment with sodium hydroxide solution in methanol.
Yield: 35% of theory,
Melting point: 269° C.
$C_{26}H_{28}N_4O_3S$ (476.60).
Mass spectrum: $M^+$=419.
$C_{23}H_{21}N_3O_3S \times 0.3H_2O$ (424.91).
Calc.: C, 65.02; H, 5.12; N, 9.89. Found: 65.15; 5.07; 9.84.

EXAMPLE 187

(Z)-3-{1-[4-(N-cyanomethyl-N-methylsulphonyl-amino)-phenyl-amino]-1-phenyl-methylidene}-2-indolinone a) N-cyanomethyl-N-methylsulphonyl-4-nitroaniline 3.24 g (15 mmol) of N-methylsulphonyl-4-nitroaniline are dissolved in 25 ml of DMSO and a total of 2.0 g (18 mmol) of potassium tert.butoxide are added batchwise. After 1 hour stirring at ambient temperature 2.7 g (23 mmol) of bromoacetonitrile are added dropwise. After 3 hours stirring at ambient temperature the mixture is poured onto ice water and extracted with ethyl acetate. The organic phase is washed with water and the solvent is eliminated in vacuo. The residue thus obtained is recrystallised from ethanol.
Yield: 2.3 g (60% of theory),
Melting point: 116–118° C.

b) 4-(N-cyanomethyl-N-methylsulphonyl-amino)-aniline

Prepared analogously to Example 39c by catalytic hydrogenation of N-cyanomethyl-N-methylsulphonyl-4-nitroaniline in DMF.
Yield: 62% of theory,
Melting point: 152–154° C.

c) (Z)-3-{1-[4-(N-cyanomethyl-N-methylsulphonyl-amino)-phenylamino]-1-phenyl-methylidene}-2-indolinone Prepared analogously to Example 11 from 3-(1-ethoxy-1-phenyl-methylidene)-2-indolinone and 4-(N-cyanomethyl-N-methylsulphonyl-amino)-aniline in DMF.
Yield: 74% of theory,
Melting point: 266–268° C.
$C_{24}H_{20}N_4O_3S$ (444.52).
Mass spectrum: $M^+$=444.
Calc.: C, 64.85; H, 4.53; N, 12.60. Found: 64.82; 4.25; 12.43.

EXAMPLE 188

(Z)-3-{1-[4-(N-(2-dimethylamino-ethyl)-N-methylsulphonyl-amino)-phenylamino-1-phenyl-methylidene}-2-indolinone Prepared analogously to Example 1 and 187 from 1-acetyl-3-(1-ethoxy-1-phenyl-methylidene)-2-indolinone and 4-[N-(2-dimethyamino-ethyl)-N-methylsulphonyl-amino]-aniline in DMF and subsequent treatment with sodium hydroxide solution in methanol.
Yield: 42% of theory,
Melting point: 234–235° C.
$C_{26}H_{28}N_4O_3S$ (476.60).
Mass spectrum: $M^+$=476.
Calc.: C, 65.52; H, 5.92; N, 11.76. Found: 65.43; 5.96; 11.78.

EXAMPLE 189

(Z)-3-{1-[4-(N-(2-morpholinoethyl)-N-methylsulphonyl-amino)-phenylamino]-1-phenyl-methylidene}-2-indolinone Prepared analogously to Examples 1 and 187 from 1-acetyl-3-(1-ethoxy-1-phenyl-methylidene)-2-indolinone and 4-[N-(2-morpholinoethyl)-N-methylsulphonyl-amino]-aniline in DMF and subsequent treatment with piperidine in methanol.

Yield: 60% of theory,
Melting point: 249–250° C.
$C_{28}H_{30}N_4O_4S$ (518.64).
Mass spectrum: $M^+$=518.
$C_{28}H_{30}N_4O_4S \times 0.5H_2O$ (527.65).
Calc.: C, 63.74; H, 5.92; N, 10.62. Found: 63.89; 5.82; 10.55.

EXAMPLE 190

(Z)-3-{1-[4-(N-carboxymethyl-N-methylsulphonyl-amino)-phenylamino-1-phenyl-methylidene}-2-indolinone Prepared analogously to Examples 1 and 187 from 1-acetyl-3-(1-ethoxy-1-phenyl-methylidene)-2-indolinone and 4-(N-ethoxycarbonylmethyl-N-methylsulphonyl-amino)-aniline in DMF and subsequent treatment with sodium hydroxide solution in methanol.

Yield: 60% of theory,
Melting point: 247–250° C.
$C_{24}H_{21}N_3O_5S$ (463.52).
Mass spectrum: $M^+$=463.
Calc.: C, 62.19; H, 14.57; N, 9.07. Found: 62.13; 4.64; 8.98.

EXAMPLE 191

(Z)-3-{1-[4-(N-aminocarbonylmethyl-N-methylsulphonyl-amino)-phenylamino]-1-phenyl-methylidene}-2-indolinone Prepared analogously to Example 18 from (Z)-3-{1-[4-(N-carboxymethyl-N-methylsulphonyl-amino)-phenylamino]-1-phenyl-methylidene}-2-indolinone, N-hydroxysuccinimide-ammonium salt, TBTU and triethylamine in DMF.

Yield: 48% of theory,
Melting point: 276–278° C.
$C_{24}H_{22}N_4O_4S$ (462.53).
Mass spectrum: $M^+$=462.
$R_f$ value: 0.5 (silica gel; dichloromethane/methanol=9:1).
$C_{24}H_{22}N_4O_4S \times 0.5H_2O$ (471.54).
Calc.: C, 61.13; H, 4.92; N, 11.88. Found: 61.26; 4.93; 11.47.

EXAMPLE 192

(Z)-3-{1-[4-(N-methylaminocarbonylmethyl-N-methylsulphonyl-amino)-phenylamino]-1-phenyl-methylidene}-2-indolinone Prepared analogously to Example 18 from (Z)-3-{1-[4-(N-carboxymethyl-N-methylsulphonyl-amino)-phenylamino]-1-phenyl-methylidene}-2-indolinone, methylammonium chloride, HOBt, TBTU and N-ethyl-N,N-diisopropylamine in DMF.

Yield: 77% of theory,
Melting point: 268–270° C.
$C_{25}H_{24}N_4O_4S$ (476.56).
Mass spectrum: $M^+$=476.
Calc.: C, 63.01; H, 5.08; N, 11.76. Found: 62.83; 5.12; 11.60.

EXAMPLE 193

(Z)-3-{1-[4-(N-dimethylaminocarbonylmethyl-N-methylsulphonylamino)-phenylamino]-1-phenyl-methylidene}-2-indolinone Prepared analogously to Example 18 from (Z)-3-{1-[4-(N-carboxymethyl-N-methylsulphonylamino)-phenylamino]-1-phenyl-methylidene}-2-indolinone, dimethylammonium chloride, HOBt, TBTU and N-ethyl-N,N-diisopropylamine in DMF.

Yield: 85% of theory,
Melting point: 260–262° C.
$C_{26}H_{26}N_4O_4S$ (490.59).
Mass spectrum: $M^+$=490.
Calc.: C, 63.66; H, 5.34; N, 11.42. Found: 63.52; 5.34; 11.37.

EXAMPLE 194

(Z)-3-{1-[4-(N-(2-dimethylamino-ethylaminocarbonylmethyl)-N-methylsulphonyl-amino)-phenylamino]-1-phenyl-methylidene}-2-indolinone Prepared analogously to Example 18 from (Z)-3-{1-[4-(N-carboxymethyl-N-methylsulphonyl-amino)-phenylamino]-1-phenyl-methylidene}-2-indolinone, 2-dimethylamino-ethylamine, HOBt, TBTU and N-ethyl-N, N-diisopropylamine in DMF.

Yield: 88% of theory,
Melting point: 214–216° C.
$C_{28}H_{31}N_5O_4S$ (533.65).
Mass spectrum: $M^+$=533.
Calc.: C, 63.02; H, 5.85; N, 13.12. Found: 62.85; 5.89; 12.96.

EXAMPLE 195

(Z)-3-{1-[4-(N-(3-ethoxycarbonyl-propyl)-N-methylsulphonyl-amino)-phenylamino]-1-phenyl-methylidene}-2-indolinone Prepared analogously to Example 187 from 3-(1-ethoxy-1-phenyl-methylidene)-2-indolinone and 4-[N-(3-ethoxycarbonyl-propyl)-N-methyl-sulphonylamino]-aniline in DMF.

Yield: 60% of theory,
Melting point: 265–268° C.
$C_{28}H_{29}N_3O_5S$ (519.62).
Mass spectrum: $M^+$=519.
Calc.: C, 64.72; H, 5.63; N, 8.09. Found: 64.82; 5.68; 8.01.

EXAMPLE 196

(Z)-3-[(4-methylsulphonylamino-phenylamino)-1-phenyl-methylidene]-5-nitro-2-indolinone Prepared analogously to Example 82 from 1-acetyl-3-(1-ethoxy-1-phenyl-methylidene)-5-nitro-2-indolinone and 4-methylsulphonylamino-aniline in DMF and subsequent treatment with sodium hydroxide solution in methanol.

Yield: 74% of theory,
Melting point: 344–346° C.
$C_{22}H_{18}N_4O_5S$ (450.48).

Mass spectrum: M$^+$=450.

Calc.: C, 58.66; H, 4.03; N, 12.44. Found: 58.22; 4.18; 12.44.

EXAMPLE 197

(Z)-3-{1-[4-(N-methyl-N-methylsulphonyl-amino)-phenylamino]-1-phenyl-methylidene}-5-nitro-2-indolinone Prepared analogously to Example 82 from 1-acetyl-3-(1-ethoxy-1-phenyl-methylidene)-5-nitro-2-indolinone and 4-(N-methyl-N-methyl-sulphonylamino)-aniline in DMF and subsequent treatment with sodium hydroxide solution in methanol.

Yield: 91% of theory,

Melting point: 306–308° C.

$C_{23}H_{20}N_4O_5S$ (464.50).

Mass spectrum: M$^+$=464.

Calc.: C, 59.47; H, 4.34; N, 12.06. Found: 59.45; 4.52; 12.10.

EXAMPLE 198

(Z)-3-{-[4-(N-ethoxycarbonylmethyl-N-methylsulphonyl-amino)-phenylamino]-1-phenyl-methylidene}-5-nitro-2-indolinone Prepared analogously to Examples 89 and 187 from 3-(1-ethoxy-1-phenyl-methylidene)-5-nitro-2-indolinone and 4-(N-ethoxycarbonylmethyl-N-methylsulphonyl-amino)-aniline in DMF.

Yield: 86% of theory,

Melting point: 236–238° C.

$C_{26}H_{24}N_4O_7S$ (536.57).

Mass spectrum: M$^+$=536.

Calc.: C, 58.20; H, 4.51; N, 10.44. Found: 58.16; 4.69; 10.45.

EXAMPLE 199

(Z)-3-{1-[4-(N-carboxymethyl-N-methylsulphonyl-amino)-phenyl-amino]-1-phenyl-methylidene}-5-nitro-2-indolinone Prepared analogously to Example 8 by saponification of (Z)-3-{1-[4-(N-ethoxycarbonylmethyl-N-methylsulphonyl-amino)-phenylamino]-1-phenyl-methylidene}-5-nitro-2-indolinone with sodium hydroxide solution in dioxane.

Yield: 89% of theory,

Melting point: 180–183° C.

$C_{24}H_{20}N_4O_7S$ (508.51).

Mass spectrum: M$^+$=508.

$C_{24}H_{20}N_4O_7S \times 0.5C_4H_8O_2$ (552.56).

Calc.: C, 56.52; H, 4.38; N, 10.14. Found: 56.52; 4.56; 9.96.

EXAMPLE 200

(Z)-3-{1-[4-(N-methylaminocarbonylmethyl-N-methylsulphonyl-amino-phenylamino]-1-phenyl-methylidene}-5-nitro-2-indolinone Prepared analogously to Example 18 from (Z)-3-{1-[4-(N-carboxymethyl-N-methylsulphonyl-amino)-phenylamino]-1-phenyl-methylidene}-5-nitro-2-indolinone, methylammonium chloride, HOBt, TBTU and N-ethyl-diisopropylamine in DMF.

Yield: 47% of theory.

Melting point: 267–268° C.

$C_{25}H_{23}N_5O_6S$ (521.56).

Mass spectrum: M$^+$=521.

Calc.: C, 57.57; H, 4.44; N, 13.43. Found: 57.44; 4.69; 13.02.

EXAMPLE 201

(Z)-3-{1-[4-(N-dimethylaminocarbonylmethyl-N-methylsulphonyl-amino)-phenylamino]-1-phenyl-methylidene}-5-nitro-2-indolinone Prepared analogously to Example 18 from (Z)-3-{1-[4-(N-carboxymethyl-N-methylsulphonyl-amino)-phenylamino]-1-phenyl-methylidene}-5-nitro-2-indolinone, dimethylammonium chloride, HOBt, TBTU and N-ethyl-N,N-diisopropylamine in DMF.

Yield: 80% of theory,

Melting point: 277–280° C.

$C_{26}H_{25}N_5O_6S$ (535.58).

Mass spectrum: (M+H)$^+$=536.

EXAMPLE 202

(Z)-3-{1-[4-(N-(2-dimethylamino-ethyl)-N-methylsulphonyl-amino)-phenylamino]-1-phenyl-methylidene}-5-nitro-2-indolinone Prepared analogously to Examples 1 and 187 from 1-acetyl-3-(1-ethoxy-1-phenyl-methylidene)-5-nitro-2-indolinone and 4-[N-(2-dimethylamino-ethyl)-N-methylsulphonyl-amino]-aniline in DMF and subsequent treatment with sodium hydroxide solution in methanol.

Yield: 86% of theory,

Melting point: 276–277° C.

$C_{26}H_{27}N_5O_5S$ (521.60).

Mass spectrum: M$^+$=521.

Calc.: C, 59.87; H, 5.22; N, 13.43. Found: 60.03; 5.19; 13.39.

EXAMPLE 203

(Z)-3-{1-[4-(N-(2-morpholinoethyl)-N-methylsulphonyl-amino)-phenylamino]-1-phenyl-methylidene}-5-nitro-2-indolinone Prepared analogously to Examples 1 and 187 from 1-acetyl-3-(1-ethoxy-1-phenyl-methylidene)-5-nitro-2-indolinone and 4-[N-(2-morpholinoethyl)-N-methylsulphonyl-amino]-aniline in DMF and subsequent treatment with piperidine in methanol.

Yield: 62% of theory,

Melting point: 255–257° C.

$C_{28}H_{29}N_5O_6S$ (563.64).

Mass spectrum: M$^+$=563.

Calc.: C, 59.67; H, 5.19; N, 12.43. Found: 59.20; 5.30; 12.18.

EXAMPLE 204

(Z)-3-{1-[4-(N-dimethylaminocarbonylmethyl-N-ethylsulphonyl-amino-phenylamino]-1-phenyl-methylidene}-2-indolinone Prepared analogously to Examples 1 and 187 from (Z)-1-acetyl-3-[1-(4-ethylsulphonylamino-phenylamino)-1- phenyl-methylidene]-2-indolinone, bromoacetic acid-N,N-dimethylamide and potassium tert.butoxide in DMSO and subsequent treatment with sodium hydroxide solution in methanol.

Yield: 30% of theory,
Melting point: 206–208° C.
$C_{27}H_{28}N_4O_4S$ (504.61).
Mass spectrum: M$^+$=504.
$C_{27}H_{28}N_4O_4S \times 0.5H_2O$ (513.62).
Calc.: C, 63.14; H, 5.69; N, 10.91. Found: 63.25; 5.62; 10.93.

EXAMPLE 205

(Z)-3-{1-[4-(N-dimethylaminocarbonylmethyl-N-phenylsulphonyl-amino)-phenylamino]-1-phenyl-methylidene}-2-indolinone Prepared analogously to Examples 1 and 187 from (Z)-1-acetyl-3-[1-(4-phenylsulphonylamino-phenylamino)-1-phenyl-methylidene]-2-indolinone, bromoacetic acid-N,N-dimethylamide and potassium tert.butoxide in DMSO and subsequent treatment with sodium hydroxide solution in methanol.

Yield: 36% of theory,
Melting point: 255–258° C.
$C_{31}H_{28}N_4O_4S$ (552.66).
Mass spectrum: M$^+$=552.

EXAMPLE 206

(Z)-3-{1-[4-(N-dimethylaminocarbonylmethyl-N-(p-tolylsulphonyl)-amino)-phenylamino]-1-phenyl-methylidene}-2-indolinone Prepared analogously to Examples 1 and 187 from (Z)-1-acetyl-3-{1-[4-(p-tolylsulphonylamino)-phenylamino]-1-phenyl-methylidene}-2-indolinone, bromoacetic acid-N,N-dimethylamide and potassium tert.butoxide in DMSO and subsequent treatment with sodium hydroxide solution in methanol.

Yield: 40% of theory,
Melting point: 223–226° C.
$C_{32}H_{30}N_4O_4S$ (566.68).
Mass spectrum: M$^+$=566.
$C_{32}H_{30}N_4O_4S \times 0.5H_2O$ (575.68).
Calc.: C, 66.76; H, 5.43; N, 9.73. Found: 66.54; 5.49; 9.81.

EXAMPLE 207

(Z)-3-{1-[4-(N-dimethylaminocarbonylmethyl-N-benzylsulphonyl-amino)-phenylamino]-1-phenyl-methylidene}-2-indolinone Prepared analogously to Examples 1 and 187 from (Z)-1-acetyl-3-[1-(4-benzylsulphonylamino-phenylamino)-1-phenyl-methylidene]-2-indolinone, bromoacetic acid-N,N-dimethylamide and potassium tert.butoxide in DMSO and subsequent treatment with sodium hydroxide solution in methanol.

Yield: 77% of theory,
Melting point: 133–135° C.
$C_{32}H_{30}N_4O_4S$ (566.68).
Mass spectrum: M$^+$=566.
$C_{32}H_{30}N_4O_4S \times H_2O$ (584.69).
Calc.: C, 65.74; H, 5.52; N, 9.58. Found: 65.62; 5.59; 9.53.

EXAMPLE 208

(Z)-3-{1-[4-(N-dimethylaminocarbonylmethyl-N-ethylsulphonyl-amino-phenylamino]-1-phenyl-methylidene}-5-nitro-2-indolinone Prepared analogously to Examples 82 and 187 from (Z)-1-acetyl-3-[1-(4-ethylsulphonylamino-phenylamino)-1-phenyl-methylidene]-5-nitro-2-indolinone, bromoacetic acid-N,N-dimethylamide and potassium tert.butoxide in DMSO and subsequent treatment with sodium hydroxide solution in methanol.

Yield: 27% of theory,
Melting point: 145–148° C.
$C_{27}H_{27}N_5O_6S$ (549.61).
Mass spectrum: M$^+$=549.
$R_f$ value: 0.42 (silica gel; dichloromethane/methanol=19:1).
Calc.: C, 59.01; H, 4.95; N, 12.74. Found: 59.20; 4.96; 12.26.

EXAMPLE 209

(Z)-3-{1-[4-(N-dimethylaminocarbonylmethyl-N-phenylsulphonyl-amino)-phenylamino]-1-phenyl-methylidene}-5-nitro-2-indolinone Prepared analogously to Examples 82 and 187 from (Z)-1-acetyl-3-[1-(4-phenylsulphonylamino-phenylamino)-1-phenyl-methylidene]-5-nitro-2-indolinone, bromoacetic acid-N,N-dimethylamide and potassium tert.butoxide in DMSO and subsequent treatment with sodium hydroxide solution in methanol.

Yield: 13% of theory,
Melting point: 160–162° C.
$C_{31}H_{27}N_5O_6S$ (597.65).
Mass spectrum: M$^+$=597.

EXAMPLE 210

(Z)-3-{1-[4-(N-dimethylaminocarbonylmethyl-N-(p-tolylsulphonyl)-amino)-phenylamino]-1-phenyl-methylidene}-5-nitro-2-indolinone Prepared analogously to Examples 82 and 187 from (Z)-1-acetyl-3-{1-[4-(p-tolylsulphonylamino)-phenylamino]-1-phenyl-methylidene}-5-nitro-2-indolinone, bromoacetic acid-N,N-dimethylamide and potassium tert.butoxide in DMSO and subsequent treatment with sodium hydroxide solution in methanol.

Yield: 40% of theory,
Melting point: 198–200° C.
$C_{32}H_{29}N_5O_6S$ (611.68).
Mass spectrum: M$^+$=611.
$C_{32}H_{29}N_5O_6S \times H_2O$ (629.69).
Calc.: C, 61.04; H, 4.96; N, 11.12. Found: 59.92; 4.53; 10.87.

EXAMPLE 211

(Z)-3-[1-(4-dimethylaminomethyl-phenylamino)-1-(p-tolyl)-methylidene]-2-indolinone Prepared analogously to Example 2 from 1-acetyl-3-[1-chloro-1-(p-tolyl)-methylidene)-2-indolinone and 4-dimethylaminomethyl-aniline in DMF and subsequent treatment with sodium hydroxide solution in methanol.

Yield: 27% of theory,
Melting point: 208–209° C.
$C_{25}H_{25}N_3O$ (383.50).
Mass spectrum: $M^+$=383.
$R_f$ value: 0.35 (silica gel; ethyl acetate/methanol/$NH_4OH$=8:2:0.1).
$C_{25}H_{25}N_3O \times 0.3H_2O$ (388.89).
Calc.: C, 77.21; H, 6.63; N, 10.80. Found: 77.45; 6.39; 10.70.

EXAMPLE 212

(Z)-3-[1-(4-dimethylaminomethyl-phenylamino)-1-(p-tolyl)-methylidene]-5-nitro-2-indolinone Prepared analogously to Example 2 from 1-acetyl-3-[1-chloro-1-(p-tolyl)-methylidene)-5-nitro-2-indolinone and 4-dimethylaminomethyl-aniline in DMF and subsequent treatment with sodium hydroxide solution in methanol.

Yield: 84% of theory,
Melting point: 274–276° C.
$C_{25}H_{24}N_4O_3$ (428.49).
Mass spectrum: $(M+H)^+$=429; $(M-H)^-$=427; $M^+$=428.
$R_f$ value: 0.5 (silica gel; dichloromethane/methanol/$NH_4OH$=9:1:0.1).
Calc.: C, 70.08; H, 5.65; N, 13.07. Found: 70.17; 5.50; 12.86.

EXAMPLE 213

(Z)-3-[1-(4-dimethylaminomethyl-phenylamino)-1-(m-tolyl)-methylidene]-2-indolinone Prepared analogously to Example 2 from 1-acetyl-3-[1-chloro-1-(m-tolyl)-methylidene)-2-indolinone and 4-dimethylaminomethyl-aniline in DMF and subsequent treatment with sodium hydroxide solution in methanol.

Yield: 36% of theory,
Melting point: 224–226° C.
$C_{25}H_{25}N_3O$ (383.50).
Mass spectrum: $M^+$=383.
$R_f$ value: 0.25 (silica gel; ethyl acetate/methanol/$NH_4OH$=8:2:0.1).
Calc.: C, 77.30; H, 6.57; N, 10.96. Found: 77.27; 6.74; 10.74.

EXAMPLE 214

(Z)-3-[1-(4-dimethylaminomethyl-phenylamino)-1-(m-tolyl)-methylidene]-5-nitro-2-indolinone Prepared analogously to Example 2 from 1-acetyl-3-[1-chloro-1-(m-tolyl)-methylidene)-5-nitro-2-indolinone and 4-dimethylaminomethyl-aniline in DMF and subsequent treatment with sodium hydroxide solution in methanol.

Yield: 20% of theory,
Melting point: 210° C.
$C_{25}H_{24}N_4O_3$ (428.49).
Mass spectrum: $M^+$=428.
Calc.: C, 70.08; H, 5.65; N, 13.08. Found: 69.63; 5.94; 12.89.

EXAMPLE 215

(Z)-3-[1-(4-dimethylaminomethyl-phenylamino)-1-(4-methoxyphenyl)-methylidene]-2-indolinone Prepared analogously to Example 2 from 1-acetyl-3-[1-chloro-1-(4-methoxyphenyl)-methylidene)-2-indolinone and 4-dimethylaminomethyl-aniline in DMF and subsequent treatment with sodium hydroxide solution in methanol.

Yield: 46% of theory,
Melting point: 206–207° C.
$C_{25}H_{25}N_3O_2$ (399.50).
Mass spectrum: $M^+$=399.
$R_f$ value: 0.3 (silica gel; ethyl acetate/methanol/$NH_4OH$=8:2:0.1).
$C_{25}H_{25}N_3O_2 \times 0.5H_2O$ (408.50).
Calc.: C, 73.51; H, 6.42; N, 10.29. Found: 73.81; 6.58; 10.15.

EXAMPLE 216

(Z)-3-[1-(4-dimethylaminomethyl-phenylamino)-1-(4-methoxyphenyl)-methylidene]-5-nitro-2-indolinone Prepared analogously to Example 2 from 1-acetyl-3-[1-chloro-1-(4-methoxyphenyl)-methylidene)-5-nitro-2-indolinone and 4-dimethylaminomethyl-aniline in DMF and subsequent treatment with sodium hydroxide solution in methanol.

Yield: 76% of theory,
Melting point: 259–262° C.
$C_{25}H_{24}N_4O_4$ (444.49).
Mass spectrum: $M^+$=444.
$R_f$ value: 0.6 (silica gel; dichloromethane/methanol=9:1).
Calc.: C, 67.56; H, 5.44; N, 12.60. Found: 67.49; 5.48; 12.39.

EXAMPLE 217

(Z)-3-[1-(4-dimethylaminomethyl-phenylamino)-1-(3-methoxyphenyl)-methylidene]-2-indolinone Prepared analogously to Example 2 from 1-acetyl-3-[1-chloro-1-(3-methoxyphenyl)-methylidene)-2-indolinone and 4-dimethylaminomethyl-aniline in DMF and subsequent treatment with sodium hydroxide solution in methanol.

Yield: 49% of theory,
Melting point: 193–194° C.
$C_{25}H_{25}N_3O_2$ (399.50).
Mass spectrum: $M^+$=399.
$R_f$ value: 0.3 (silica gel; ethyl acetate/methanol/$NH_4OH$ 8:2:0.1).
Calc.: C, 75.16; H, 6.31; N, 10.52. Found: 75.16; 6.32; 10.59.

EXAMPLE 218

(Z)-3-[1-(4-dimethylaminomethyl-phenylamino)-1-(3-methoxyphenyl)-methylidene]-5-nitro-2-indolinone Prepared analogously to Example 2 from 1-acetyl-3-[1-chloro-1-(3-methoxyphenyl)-methylidene)-5-nitro-2-indolinone and 4-dimethylaminomethyl-aniline in DMF and subsequent treatment with sodium hydroxide solution in methanol.

Yield: 38% of theory,
Melting point: 206–208° C.
$C_{25}H_{24}N_4O_4$ (444.49).
Mass spectrum: $M^+$=444.

$R_f$ value: 0.5 (silica gel; dichloromethane/methanol/ $NH_4OH$=9:1:0.1).

Calc.: C, 67.56; H, 5.44; N, 12.60. Found: 67.12; 5.38; 12.33.

EXAMPLE 219

(Z)-3-[1-(4-dimethylaminomethyl-phenylamino)-1-(4-nitrophenyl)-methylidene]-2-indolinone Prepared analogously to Example 2 from 1-acetyl-3-[1-chloro-1-(4-nitrophenyl)-methylidene)-2-indolinone and 4-dimethylaminomethyl-aniline in DMF and subsequent treatment with sodium hydroxide solution in methanol.

Yield: 39% of theory,
Melting point: 235° C.
$C_{24}H_{22}N_4O_3$ (414.47).
Mass spectrum: $M^+$=414.
$R_f$ value: 0.5 (silica gel; dichloromethane/methanol/ $NH_4OH$=9:1:0.1).
Calc.: C, 69.55; H, 5.35; N, 13.52. Found: 69.52; 5.58; 13.42.

EXAMPLE 220

(Z)-3-[1-(4-dimethylaminomethyl-phenylamino)-1-(4-nitrophenyl)-methylidene]-5-nitro-2-indolinone Prepared analogously to Example 2 from 1-acetyl-3-[1-chloro-1-(4-nitrophenyl)-methylidene)-5-nitro-2-indolinone and 4-dimethylaminomethyl-aniline in DMF and subsequent treatment with sodium hydroxide solution in methanol.

Yield: 22% of theory,
Melting point: 233° C.
$C_{24}H_{21}N_5O_5$ (459.47).
Mass spectrum: $M^+$=459.
Calc.: C, 62.74; H, 4.61; N, 15.24. Found: 62.60; 4.91; 15.33.

EXAMPLE 221

(Z)-3-[1-(4-dimethylaminomethyl-phenylamino)-1-(4-chlorophenyl)-methylidene]-2-indolinone Prepared analogously to Example 2 from 1-acetyl-3-[1-chloro-1-(4-chlorophenyl)-methylidene)-2-indolinone and 4-dimethylaminomethyl-aniline in DMF and subsequent treatment with sodium hydroxide solution in methanol.

Yield: 46% of theory,
Melting point: 213° C.
$C_{24}H_{22}ClN_3O$ (403.92).
Mass spectrum: $M^+$=405/403.
$R_f$ value: 0.4 (silica gel; ethyl acetate/methanol/$NH_4OH$=8:2:0.1).
$C_{24}H_{22}ClN_3O \times 0.5H_2O$ (412.92).
Calc.: C, 69.81; H, 5.61; N, 10.18. Found: 70.06; 5.87; 10.13.

EXAMPLE 222

(Z)-3-[1-(4-dimethylaminomethyl-phenylamino)-1-(4-chlorophenyl)-methylidene]-5-nitro-2-indolinone Prepared analogously to Example 2 from 1-acetyl-3-[1-chloro-1-(4-chlorophenyl)-methylidene)-5-nitro-2-indolinone and 4-dimethylaminomethyl-aniline in DMF and subsequent treatment with sodium hydroxide solution in methanol.

Yield: 36% of theory,
Melting point: 311° C.
$C_{24}H_{21}ClN_4O_3$ (448.91).
Mass spectrum: $M^+$=450/448.
$R_f$ value: 0.85 (silica gel; dichloromethane/methanol=8:2).
Calc.: C, 64.21; H, 4.71; N, 12.48. Found: 64.13; 4.73; 12.20.

EXAMPLE 223

(Z)-3-[1-(4-dimethylaminomethyl-phenylamino)-1-(3-chlorophenyl)-methylidene]-2-indolinone Prepared analogously to Example 2 from 1-acetyl-3-[1-chloro-1-(3-chlorophenyl)-methylidene)-2-indolinone and 4-dimethylaminomethyl-aniline in DMF and subsequent treatment with sodium hydroxide solution in methanol.

Yield: 14% of theory,
Melting point: 197–198° C.
$C_{24}H_{22}ClN_3O$ (403.92).
Mass spectrum: $M^+$=405/403.
$C_{24}H_{22}ClN_3O \times 0.5H_2O$ (412.92).
Calc.: C, 69.81; H, 5.61; N, 10.18. Found: 69.74; 5.63; 10.07.

EXAMPLE 224

(Z)-3-[1-(4-dimethylaminomethyl-phenylamino)-1-(3-chlorophenyl)-methylidene]-5-nitro-2-indolinone Prepared analogously to Example 2 from 1-acetyl-3-[1-chloro-1-(3-chlorophenyl)-methylidene)-5-nitro-2-indolinone and 4-dimethylaminomethyl-aniline in DMF and subsequent treatment with sodium hydroxide solution in methanol.

Yield: 20% of theory,
Melting point: 274° C.
$C_{24}H_{21}ClN_4O_3$ (448.91).
Mass spectrum: $M^+$=450/448.
$C_{24}H_{21}ClN_4O_3 \times 0.5H_2O$ (457.92).
Calc.: C, 62.95; H, 4.84; N, 12.24. Found: 62.97; 4.81; 12.29.

EXAMPLE 225

(Z)-3-{1-[4-(2-tert.butoxycarbonylamino-2-methoxycarbonyl-ethyl)-phenylamino]-1-phenyl-methylidene}-5-nitro-2-indolinone Prepared analogously to Example 89.
Melting point: 139° C.
$C_{30}H_{30}N_4O_7$ (558.60).
Mass spectrum: $M^+$=558.
Calc.: C, 64.51; H, 5.41; N, 10.03. Found: 64.02; 5.56; 9.98.

EXAMPLE 226

(Z)-3-{1-[4-(2-tert.butoxycarbonylamino-2-carboxy-ethyl)-phenylamino]-1-phenyl-methylidene}-5-nitro-2-indolinone Prepared analogously to Example 8.
Melting point: 235° C. (decomposition).

$C_{29}H_{28}N_4O_7$ (544.57).

Mass spectrum: $M^+=544$.

$C_{29}H_{28}N_4O_7 \times H_2O$ (562.59).

Calc.: C, 61.01; H, 5.37; N, 9.96. Found: 62.45; 5.40; 10.06.

EXAMPLE 227

(Z)-3-{1-[4-(2-amino-2-methoxycarbonyl-ethyl)-phenylamino]-1-phenyl-methylidene}-5-nitro-2-indolinone-hydrochloride Prepared analogously to Example 29a.

Melting point: 215° C. (decomposition).

$C_{25}H_{22}N_4O_5$ (458.48).

Mass spectrum: $M^+=458$.

$C_{25}H_{22}N_4O_5 \times HCl \times H_2O$ (521.96).

Calc: C, 57.53; H, 5.02; N, 10.73. Found: 57.54; 5.13; 10.59.

EXAMPLE 228

(Z)-3-{1-[4-(2-amino-2-carboxy-ethyl)-phenylamino]-1-phenyl-methylidene}-5-nitro-2-indolinone-hydrochloride Prepared analogously to Example 29a.

Melting point: 225° C. (decomposition).

$C_{24}H_{20}N_4O_5$ (444.45).

Mass spectrum: $[M-CO_2]^+=400$.

$C_{24}H_{20}N_4O_5 \times HCl \times 2H_2O$ (516.94).

Calc: C, 55.76; H, 4.87; N, 10.84. Found: 55.81; 5.15; 10.82.

EXAMPLE 229

(Z)-3-[1-(4-thiomorpholinomethyl-phenylamino)-1-phenyl-methylidene]-5-nitro-2-indolinone Prepared analogously to Example 89.

Melting point: 276–277° C.

$C_{26}H_{24}N_4O_3S$ (472.57).

Mass spectrum: $M^+=472$.

Calc.: C, 66.08; H, 5.12; N, 11.86. Found: 65.89; 5.24; 11.84.

EXAMPLE 230

(Z)-3-{1-[4-((1-oxothiomorpholino)-methyl)-phenylamino]-1-phenyl-methylidene}-5-nitro-2-indolinone a) 4-(4-nitrophenylmethyl)-thiomorpholine-1-oxide 11.7 g (58 mmol) of m-chloroperbenzoic acid are added to a solution of 11.5 g (48 mmol) of 4-(4-nitrophenylmethyl)-thiomorpholine in 100 ml of dichloromethane at ambient temperature. The reaction solution is stirred for 4 hours at ambient temperature and then washed with 1N sodium hydroxide solution and water and evaporated to dryness. Chromatography on silica gel (dichloromethane/methanol=9:1) yields the product.

Yield: 3.9 g (32% of theory), $C_{11}H_{14}N_2O_3S$ (254.31).

Mass spectrum: $M^+=254$.

b) 4-(4-aminophenylmethyl)-thiomorpholine-1-oxide 1.2 g of Raney nickel are added to a solution of 3.9 g (15 mmol) of 4-(4-nitrophenylmethyl)-thiomorpholine-1-oxide in 10 ml of dichloromethane and 40 ml of methanol. The mixture is hydrogenated under a hydrogen atmosphere. The product is obtained by chromatography on silica gel (dichloromethane/methanol=9:1).

Yield: 1.8 g (51% of theory).

c) (Z)-3-{1-[4-((1-oxo-thiomorpholino)-methyl)-phenylamino]-1-phenyl-methylidene}-5-nitro-2-indolinone Prepared analogously to Example 89.

Melting point: 289–290° C.

$C_{26}H_{24}N_4O_4S$ (488.57).

Mass spectrum: $M^+=488$.

Calc.: C, 63.92; H, 4.95; N, 11.47. Found: 63.90; 5.09; 11.41.

EXAMPLE 231

(Z)-3-{1-[4-((1,1-dioxothiomorpholino)-methyl)-phenylamino]-1-phenyl-methylidene}-5-nitro-2-indolinone a) 4-(4-nitrophenylmethyl)-thiomorpholine-1,1-dioxide 8.6 g (40 mmol) of 4-nitrobenzylbromide are dissolved in 100 ml of acetone. 6.9 g (50 mmol) of potassium carbonate and 5.4 g (40 mmol) of thiomorpholine-1,1-dioxide are added. The reaction solution is stirred for 7 hours at ambient temperature. After the undissolved solids have been filtered off, the solution is concentrated by evaporation. The residue is divided between ethyl acetate and water. The organic phases are freed from solvent in vacuo. The product is triturated with ether and dried.

Yield: 7.2 g (67% of theory),

Melting point: 181–182° C.

b) 4-(4-aminophenylmethyl)-thiomorpholine-1,1-dioxide

Prepared analogously to Example 230b.

Melting point: 171–172° C.

c) (Z)-3-{1-[4-((1,1-dioxothiomorpholino)-methyl)-phenylamino]-1-phenyl-methylidene}-5-nitro-2-indolinone Prepared analogously to Example 89.

Melting point: 328–329° C. (decomposition).

$C_{26}H_{24}N_4O_5S$ (504.57).

Mass spectrum: $M^+=504$.

Calc.: C, 61.89; H, 4.79; N, 11.10. Found: 61.90; 5.03; 11.10.

EXAMPLE 232

(Z)-3-{1-[4-(N-cyclohexyl-N-methyl-aminomethyl)-phenylamino]-1-phenyl-methylidene}-5-nitro-2-indolinone Prepared analogously to Example 231.

Yield: 44% of theory,

Melting point: 215° C.

$C_{29}H_{30}N_4O_3$ (482.59).

Mass spectrum: $M^+=482$.

EXAMPLE 233

(Z)-3-{1-[4-(phenylaminomethyl)-phenylamino]-1-phenyl-methylidene}-5-nitro-2-indolinone Prepared analogously to Example 231.

Melting point: 274–277° C.

$C_{28}H_{22}N_4O_3$ (462.51).

Mass spectrum: $M^+=462$.

Calc.: C, 72.71; H, 4.79; N, 12.11. Found: 72.61; 4.91; 12.09.

EXAMPLE 234

(Z)-3-{1-[4-(N-methyl-N-phenyl-aminomethyl)-phenylamino]-1-phenyl-methylidene}-5-nitro-2-indolinone Prepared analogously to Example 231.

Melting point: 228–230° C.

$C_{29}H_{24}N_4O_3$ (476.54).

Mass spectrum: $M^+=476$.

Calc.: C, 73.09; H, 5.08; N, 11.76. Found: 72.79; 5.25; 11.56.

EXAMPLE 235

(Z)-3-{1-[4-(N-methyl-N-(2-pyridyl)-aminomethyl)-phenylamino]-1-phenyl-methylidene}-5-nitro-2-indolinone Prepared analogously to Example 231.

Melting point: 213°–216° C.

$C_{28}H_{23}N_5O_3$ (477.53).

Mass spectrum: $M^+=477$.

EXAMPLE 236

(Z)-3-{1-[4-(N-benzyl-N-tert.butoxycarbonyl-aminomethyl)-phenylamino]-1-phenyl-methylidene}-5-nitro-2-indolinone Prepared analogously to Example 231.

Melting point: 202–203° C. (decomposition).

$C_{34}H_{32}N_4O_5$ (576.66).

Mass spectrum: $M^+=576$.

Calc.: C, 70.82; H, 5.59; N, 9.72. Found: 70.81; H, 5.74; N, 9.65.

EXAMPLE 237

(Z)-3-{1-[4-(benzylaminomethyl)-phenylamino]-1-phenyl-methylidene}-5-nitro-2-indolinone-hydrochloride Prepared analogously to Examples 236 and 29a.

Melting point: 298–300° C.

$C_{29}H_{24}N_4O_3$ (476.534).

Mass spectrum: $M^+=476$.

$C_{29}H_{24}N_4O_3 \times HCl \times 1.5H_2O$ (540.02).

Calc.: C, 64.50; H, 5.23; N, 10.37. Found: 64.79; 5.08; 10.38.

EXAMPLE 238

(Z)-3-{1-[4-(N-benzyl-N-methyl-aminomethyl)-phenylamino]-1-phenyl-methylidene}-5-nitro-2-indolinone Prepared analogously to Example 231.

Melting point: 200–201° C.

$C_{30}H_{26}N_4O_3$ (490.57).

Mass spectrum: $M^+=490$.

Calc.: C, 73.45; H, 5.34; N, 11.42. Found: 73.25; 5.50; 11.32.

EXAMPLE 239

(Z)-3-{1-[4-(2-hydroxy-ethylaminomethyl)-phenylamino]-1-phenyl-methylidene}-5-nitro-2-indolinone Prepared analogously to Example 231.

Melting point: 196–198° C.

$C_{24}H_{22}N_4O_4$ (430.47).

Mass spectrum: $M^+$ 430.

Calc.: C, 66.97; H, 5.15; N, 13.02. Found: 66.67; 5.35; 12.80.

EXAMPLE 240

(Z)-3-{1-[4-(Bis-(2-hydroxyethyl)-aminomethyl)-phenylamino]-1-phenyl-methylidene}-5-nitro-2-indolinone Prepared analogously to Example 231.

Melting point: 196–198° C.

$C_{26}H_{26}N_4O_5$ (474.52).

Mass spectrum: $M^+=474$.

Calc.: C, 65.81; H, 5.52; N, 11.81. Found: 65.53; 5.53; 11.69.

EXAMPLE 241

(Z)-3-{1-[4-(2-ethoxycarbonyl-ethylaminomethyl)-phenylamino]-1-phenyl-methylidene}-5-nitro-2-indolinone Prepared analogously to Example 231.

Melting point: 129–131° C.

$C_{27}H_{26}N_4O_5$ (486.53).

Mass spectrum: $M^+=486$.

Calc.: C, 66.66; H, 5.39; N, 11.52. Found: 66.68; 5.42; 11.50.

EXAMPLE 242

(Z)-3-{1-[4-(2-carboxy-ethylaminomethyl)-phenylamino]-1-phenyl-methylidene}-5-nitro-2-indolinone Prepared analogously to Example 241 and 8.

Melting point: 220–222° C.

$C_{25}H_{22}N_4O_5$ (458.47).

Mass spectrum: $M^+=458$.

EXAMPLE 243

(Z)-3-{1-[4-(2-dimethylaminocarbonyl-ethylaminomethyl)-phenylamino]-1-phenyl-methylidene}-5-nitro-2-indolinone Prepared analogously to Example 242 and 18.

Melting point: 215–217° C.

$C_{27}H_{27}N_5O_4$ (485.54).

Mass spectrum: $M^+=485$.

EXAMPLE 244

(Z)-3-{1-[4-(4-tert.butoxycarbonyl-piperazin-1-ylmethyl)-phenylamino]-1-phenyl-methylidene}-5-nitro-2-indolinone Prepared analogously to Example 231.

Melting point: 236–237° C. (decomposition).

$C_{31}H_{33}N_5O_5$ (555.64).

Mass spectrum: $M^+=555$.

Calc.: C, 67.01; H, 5.99; N, 12.60. Found: 66.89; 6.08; 12.65.

EXAMPLE 245

(Z)-3-{1-[4-(piperazin-1-ylmethyl)-phenylamino]-1-phenyl-methylidene}-5-nitro-2-indolinone-dihydrochloride Prepared analogously to Example 244 and 29a.

Melting point: >370° C.; sintering from 240° C.

$C_{26}H_{25}N_5O_3$ (455.52).

Mass spectrum: $M^+=455$.

$C_{26}H_{25}N_5O_3 \times 2HCl \times 2H_2O$ (564.47).

Calc.: C, 55.32; H, 5.54; N, 12.41. Found: 54.96; 5.66; 12.26.

EXAMPLE 246

(Z)-3-{1-[4-(4-acetylpiperazin-1-ylmethyl)-phenylamino]-1-phenyl-methylidene}-5-nitro-2-indolinone Prepared analogously to Example 245 and 1a.

Melting point: 275–277° C.

$C_{28}H_{27}N_5O_4$ (497.56).

Mass spectrum: $M^+=497$.

$C_{28}H_{27}N_5O_4 \times 0.5H_2O$ (506.56).

Calc.: C, 66.39; H, 5.57; N, 13.83. Found: 66.51; 5.66; 13.70.

EXAMPLE 247

(Z)-3-{1-[4-(4-aminocarbonyl-piperidinomethyl)-phenylamino]-1-phenyl-methylidene}-5-nitro-2-indolinone Prepared analogously to Example 177 and 20.

Melting point: 296–297° C.

$C_{28}H_{27}N_5O_4$ (497.56).

Mass spectrum: $M^+=497$.

$C_{28}H_{27}N_5O_4 \times 1.5H_2O$ (524.58).

Calc.: C, 64.11; H, 5.76; N, 13.35. Found: 64.33; 5.32; 13.19.

EXAMPLE 248

(Z)-3-{1-[4-(4-methylaminocarbonyl-piperidinomethyl)-phenylamino]-1-phenyl-methylidene}-5-nitro-2-indolinone Prepared analogously to Example 177 and 18.

Melting point: 263–265° C.

$C_{29}H_{29}N_5O_4$ (511.59).

Mass spectrum: $M^+=511$.

Calc.: C, 68.09; H, 5.71; N, 13.69. Found: 67.94; 5.78; 13.53.

EXAMPLE 249

(Z)-3-{1-[4-(4-dimethylaminocarbonyl-piperidinomethyl)-phenylamino]-1-phenyl-methylidene}-5-nitro-2-indolinone Prepared analogously to Example 177 and 18.

Melting point: 272–273° C.

$C_{30}H_{31}N_5O_4$ (525.61).

Mass spectrum: $M^+=525$.

$C_{30}H_{31}N_5O_4 \times 0.5H_2O$ (534.61).

Calc.: C, 67.40; H, 6.03; N, 13.10. Found: 67.52; 6.00; 13.15.

EXAMPLE 250

(Z)-3-{1-[4-(4-hydroxymethyl-piperidinomethyl)-phenylamino]-1-phenyl-methylidene}-5-nitro-2-indolinone Prepared analogously to Example 231.

Melting point: 227–228° C.

$C_{28}H_{28}N_4O_4$ (484.56).

Mass spectrum: $M^+=484$.

$C_{28}H_{28}N_4O_4 \times 0.5H_2O$ (493.56).

Calc.: C, 68.14; H, 5.92; N, 11.35. Found: 68.25; 5.94; 11.18.

EXAMPLE 251

(Z)-3-{1-[4-(4-hydroxy-4-methyl-piperidinomethyl)-phenylamino]-1-phenyl-methylidene}-5-nitro-2-indolinone Prepared analogously to Example 231.

Melting point: 186–187° C.

$C_{28}H_{28}N_4O_4$ (484.56).

Mass spectrum: $M^+=484$.

$C_{28}H_{28}N_4O_4 \times 0.5H_2O$ (493.56).

Calc.: C, 68.14; H, 5.92; N, 11.35. Found: 67.87; 6.00; 11.27.

EXAMPLE 252

(Z)-3-{1-[3-(2-carboxyethylaminomethyl)-phenylamino]-1-phenyl-methylidene}-5-nitro-2-indolinone Prepared analogously to Example 112 and 8.

Melting point: 247–249° C.

$C_{25}H_{22}N_4O_5$ (458.47).

Mass spectrum: $M^+=458$.

$C_{25}H_{22}N_4O_5 \times 1.5H_2O$ (485.50).

Calc.: C, 61.85; H, 5.19; N, 11.54. Found: 61.80; 5.16; 11.46.

EXAMPLE 253

(Z)-3-{1-[3-(2-dimethylaminocarbonyl-ethylaminomethyl)-phenylamino]-1-phenyl-methylidene}-5-nitro-2-indolinone Prepared analogously to Example 253 and 18.

Melting point: 177–179° C.

$C_{27}H_{27}N_5O_4$ (485.54).

Mass spectrum: $M^+=485$.

$C_{27}H_{27}N_5O_4 \times 0.5H_2O$ (494.55).

Calc.: C, 65.57; H, 5.71; N, 14.16. Found: 65.43; 5.61; 13.83.

EXAMPLE 254

(Z)-3-{1-[4-(2-methylamino-ethyl)-phenylamino]-1-phenyl-methylidene}-5-nitro-2-indolinone a) 4-(2-methylamino-ethyl)-nitrobenzene 2.7 g (86 mmol) of methylamine are dissolved in 120 ml of dichloromethane while cooling with ice. 4.9 g (21 mmol) of 4-(2-bromoethyl)-nitrobenzene are added and the mixture is allowed to come up slowly to ambient temperature. After 15 hours stirring the solvent is eliminated in vacuo and the residue taken up in water. An acid pH is created using 2 N hydrochloric acid and the mixture is washed with dichloromethane. The aqueous phase is then adjusted to a basic pH using 4 N sodium hydroxide solution and the product is extracted with dichloromethane.

Yield: 3.1 g (82% of theory).

b) 4-(2-methylamino-ethyl)-aniline

Prepared by catalytic hydrogenation of 4-(2-methylamino-ethyl)-nitrobenzene over palladium-charcoal in methanol analogously to Example 39c.

Yield: 96% of theory.

c) (Z)-3-{1-[4-(2-methylamino-ethyl)-phenylamino]-1-phenyl-methylidene}-5-nitro-2-indolinone Prepared analogously to Example 89 by reacting 3-(1-ethoxy-1-phenyl-methylidene)-5-nitro-2-indolinone and 4-(2-methylamino-ethyl)-aniline.

Yield: 12% of theory.
Melting point: 250–252° C.
$C_{24}H_{22}N_4O_3$ (414.46).
Mass spectrum: $M^+$=414.

EXAMPLE 255

(Z)-3-{1-[4-(2-ethylamino-ethyl)-phenylamino]-1-phenyl-methylidene}-5-nitro-2-indolinone Prepared analogously to Example 254.
Melting point: 235–237° C.
$C_{25}H_{24}N_4O_3$ (428.49).
Mass spectrum: $M^+$=428.
Calc.: C, 70.08; H, 5.65; N, 13.07. Found: 69.73; 5.72; 12.92.

EXAMPLE 256

(Z)-3-{1-[4-(2-(2-hydroxyethylamino)-ethyl)-phenylamino]-1-phenyl-methylidene}-5-nitro-2-indolinone Prepared analogously to Example 254.
Melting point: 236–238° C.
$C_{25}H_{24}N_4O_4$ (444.49).
Mass spectrum: $M^+$=444.
$C_{25}H_{24}N_4O_4 \times 1.5H_2O$ (471.51).
Calc.: C, 63.68; H, 5.77; N, 11.88. Found: 63.77; 5.82; 11.60.

EXAMPLE 257

(Z)-3-{1-[4-(2-(2-methoxyethylamino)-ethyl)-phenylamino]-1-phenyl-methylidene}-5-nitro-2-indolinone-hydrobromide Prepared analogously to Example 254.
Melting point: 297–299° C.
$C_{26}H_{26}N_4O_4$ (458.52).
Mass spectrum: $M^+$=458.

EXAMPLE 258

(Z)-3-{1-[4-(2-carboxymethylamino-ethyl)-phenylamino]-1-phenyl-methylidene}-5-nitro-2-indolinone Prepared analogously to Example 178 and 8.
Melting point: 242–243° C. (decomposition).
$C_{25}H_{22}N_4O_5$ (458.48).
Mass spectrum: $(M+H)^+$=459.
$C_{25}H_{22}N_4O_5 \times 0.5H_2O$ (467.48).
Calc.: C, 64.23; H, 4.96; N, 11.98. Found: 64.09; 5.00; 11.87.

EXAMPLE 259

(Z)-3-{1-[4-(2-(4-methylpiperidino)-ethyl)-phenylamino]-1-phenyl-methylidene}-5-nitro-2-indolinone Prepared analogously to Example 254.
Melting point: 252–253° C.
$C_{29}H_{30}N_4O_3$ (482.58).
Mass spectrum: $M^+$=483.

EXAMPLE 260

(Z)-3-{1-[4-(2-(4-hydroxypiperidino)-ethyl)-phenylamino]-1-phenyl-methylidene}-5-nitro-2-indolinone Prepared analogously to Example 254.
Melting point: 274–276° C.
$C_{28}H_{28}N_4O_4$ (484.55).
Mass spectrum: $[M+H]^+$=485.

EXAMPLE 261

(Z)-3-{1-[4-(2-(4-methoxypiperidino)-ethyl)-phenylamino]-1-phenyl-methylidene}-5-nitro-2-indolinone Prepared analogously to Example 254.
Melting point: 212–214° C.
$C_{29}H_{30}N_4O_4$ (498.58).
Mass spectrum: $[M+H]^+$=499.

EXAMPLE 262

(Z)-3-{1-[4-(2-(4-ethoxycarbonyl-piperidino)-ethyl)-phenylamino]-1-phenyl-methylidene}-5-nitro-2-indolinone Prepared analogously to Example 254.
Melting point: 208–213° C.
$C_{31}H_{32}N_4O_5$ (540.62).
Mass spectrum: $[M+H]^+$=541.

EXAMPLE 263

(Z)-3-{1-[4-(2-(4-carboxypiperidino)-ethyl)-phenylamino]-1-phenyl-methylidene}-5-nitro-2-indolinone Prepared analogously to Example 262 and 8.
Melting point: 287–288° C.
$C_{29}H_{28}N_4O_5$ (512.56).
Mass spectrum: $[M+H]^+$=513.

EXAMPLE 264

(Z)-3-{1-[4-(2-(4-dimethylaminocarbonyl-piperidino)-ethyl)-phenylamino]-1-phenyl-methylidene}-5-nitro-2-indolinone Prepared analogously to Example 263 and 18.
Melting point: 288° C. (decomposition).
$C_{31}H_{33}N_5O_4$ (539.63).
Mass spectrum: $[M+H]^+$=540.

EXAMPLE 265

(Z)-3-{1-[4-(2-hexamethyleneimino-ethyl)-phenylamino]-1-phenyl-methylidene}-5-nitro-2-indolinone Prepared analogously to Example 254.
Melting point: 217–222° C.

$C_{29}H_{30}N_4O_3$ (482.58).

Mass spectrum: $[M+H]^+$=483.

EXAMPLE 266

(Z)-3-{1-[4-(dimethylaminomethyl)-phenylamino]-1-phenyl-methylidene}-2-indolinone Prepared analogously to Example 1.

Melting point: 237–240° C.

$C_{24}H_{23}N_3O$ (369.47).

Mass spectrum: $[M+H]^+$=370.

EXAMPLE 267

(Z)-3-{1-[4-(piperidinomethyl)-phenylamino]-1-phenyl-methylidene}-2-indolinone

Prepared analogously to Example 1.

Melting point: 235–240° C.

$C_{27}H_{27}N_3O$ (409.53).

Mass spectrum: $[M+H]^+$=410.

EXAMPLE 268

(Z)-3-{1-[4-(2-dimethylamino-ethyl)-phenylamino]-1-phenyl-methylidene}-2-indolinone Prepared analogously to Example 1 and 254.

Melting point: 244–246° C.

$C_{25}H_{25}N_3O$ (383.49).

Mass spectrum: $[M+H]^+$=384.

EXAMPLE 269

(Z)-3-{1-[4-(2-(3,6-Dihydro-2H-pyridin-1-yl)-ethyl)-phenylamino]-1-phenyl-methylidene}-5-nitro-2-indolinone a) 4-[2-(3,6-Dihydro-2H-pyridin-1-yl)-ethyl]-aniline 2.5 g (11.1 mmol) of tin dichloride dihydrate are added at ambient temperature to a solution of 1.5 g (6.46 mmol) of 4-[2-(3,6-dihydro-2H-pyridin-1-yl)-ethyl]-nitrobenzene, prepared analogously to Example 254, in 7 ml of glacial acetic acid and 2.5 ml of concentrated hydrochloric acid. The mixture is heated for 4 hours to 100° C., then another 2.5 g (11.1 mmol) of tin dichloride dihydrate are added and the mixture is heated for 12 hours to 100° C. After cooling the solvent is eliminated in vacuo and the residue taken up in water. The mixture is made alkaline with 4N sodium hydroxide solution and extracted with dichloromethane. After removal of the solvent in vacuo the product is obtained as an oil.

Yield: 1.14 g (88% of theory).

$C_{13}H_{18}N_2$ (202.3).

Mass spectrum: $[M+H]^+$=203.

b) (Z)-3-{1-[4-(2-(3,6-Dihydro-2H-pyridin-1-yl)-ethyl)-phenylamino]-1-phenyl-methylidene}-5-nitro-2-indolinone Prepared analogously to Example 89 by reacting 3-(1-ethoxy-1-phenyl-methylidene)-5-nitro-2-indolinone and 4-[2-(3,6-dihydro-2H-pyridin-1-yl)-ethyl]-aniline.

Yield: 88% of theory.

Melting point: 249–254° C. (decomposition).

$C_{28}H_{26}N_4O_3$ (466.54).

Mass spectrum: $[M+H]^+$=467.

EXAMPLE 270

(Z)-3-{1-[4-(3,6-Dihydro-2H-pyridin-1-ylmethyl)-phenylamino]-1-phenyl-methylidene}-5-nitro-2-indolinone Prepared analogously to Example 269.

Melting point: 222–225° C.

$C_{27}H_{24}N_4O_3$ (452.51).

Mass spectrum: $M^+$=452.

EXAMPLE 271

(Z)-3-{1-[4-(pyrimidin-2-ylaminomethyl)-phenylamino]-1-phenyl-methylidene}-5-nitro-2-indolinone a) 4-(pyrimidin-2-ylaminomethyl)-nitrobenzene 9.4 g (50 mmol) of 4-nitrobenzylamine-hydrochloride, 11.7 g (110 mmol) of sodium carbonate and 7.5 g (50 mmol) of sodium iodide are added to a solution of 5.7 g (50 mmol) of 2-chloropyrimidine in 250 ml of ethanol. The mixture is refluxed for 20 hours. Then the salts are removed by suction filtering, the filtrate is evaporated down and taken up in 300 ml of ethyl acetate. It is washed with water, the solvent is eliminated in vacuo and the residue is chromatographed on silica gel (dichloromethane/methanol=97:3).

Yield: 2.4 g (21% of theory),

Melting point: 157–158° C.

$C_{11}H_{10}N_4O_2$ (230.23).

Mass spectrum: $[M+H]^+$=231.

b) 4-(pyrimidin-2-ylaminomethyl)-aniline

Prepared analogously to Example 55 by catalytic hydrogenation of 4-(pyrimidin-2-ylaminomethyl)-nitrobenzene with Raney nickel.

Yield: 89% of theory,

Melting point: 145–146° C.

$C_{11}H_{12}N_4$ (200.25).

Mass spectrum: $[M+H]^+$=201.

c) (Z)-3-{1-[4-(pyrimidin-2-ylaminomethyl)-phenylamino]-1-phenyl-methylidene}-5-nitro-2-indolinone Prepared analogously to Example 89 by reacting 3-(1-ethoxy-1-phenyl-methylidene)-5-nitro-2-indolinone with 4-(pyrimidin-2-ylaminomethyl)-aniline.

Yield: 80% of theory,

Melting point: 284°–286° C.

$C_{26}H_{20}N_6O_3$ (464.49).

Mass spectrum: $M^+$=464.

Calc.: C, 67.23; H, 4.34; N, 18.09. Found: 66.86; 4.42; 17.85.

EXAMPLE 272

(Z)-3-{1-[4-((N-methyl-N-pyrimidin-2-yl-amino)-methyl)-phenylamino]-1-phenyl-methylidene}-5-nitro-2-indolinone Prepared analogously to Example 271.

Melting point: 236°–239° C.

$C_{27}H_{22}N_6O_3$ (478.51).

Mass spectrum: $M^+$=478.

EXAMPLE 273

(Z)-3-{1-[4-(Azetidin-1-yl-methyl)-phenylamino]-1-phenyl-methylidene}-5-nitro-2-indolinone a) 4-(Azetidin-1-yl-methyl)-nitrobenzene 6.2 g (41 mmol) of 4-nitrobenzaldehyde and 3.8 g (40.6 mmol) of azetidine-hydrochloride are dissolved in 120 ml of ethanol. 2.6 g (41 mmol) of sodium cyanoborohydride are added at 0° C. The mixture is slowly heated to ambient temperature and then stirred for 18 hours. Then the solvent is eliminated in vacuo, the residue is taken up in ethyl acetate and washed with water. The solvent is eliminated in vacuo and after chromatography of the residue on silica gel (ethyl acetate/methanol/$NH_4OH$=95:5:0.5) a light brown oil is obtained.

Yield: 0.9 g (11% of theory),
$C_{10}H_{12}N_2O_2$ (192.22).
Mass spectrum: [M+H]$^+$=193.

b) 4-(Azetidin-1-yl-methyl)-aniline

Prepared analogously to Example 55 by catalytic hydrogenation of 4-(azetidin-1-yl-methyl)-nitrobenzene with Raney nickel as a light brown oil.
Yield: 94% of theory,
$C_{10}H_{14}N_2$ (162.24).
Mass spectrum: [M+H]$^+$=163.

c) (Z)-3-{1-[4-(Azetidin-1-yl-methyl)-phenylamino]-1-phenyl-methylidene}-5-nitro-2-indolinone Prepared analogously to Example 89 by reacting 3-(1-ethoxy-1-phenyl-methylidene)-5-nitro-2-indolinone with 4-(azetidin-1-yl-methyl)-aniline.
Yield: 84% of theory,
Melting point: 228–229° C.
$C_{25}H_{22}N_4O_3$ (426.48).
Mass spectrum: M$^+$=426.

EXAMPLE 274

(Z)-3-{1-[4-(cyclopropylaminomethyl)-phenylamino]-1-phenyl-methylidene}-5-nitro-2-indolinone Prepared analogously to Example 273.
Melting point: 220–221° C. (decomposition).
$C_{25}H_{22}N_4O_3$ (426.48).
Mass spectrum: M$^+$=426.

EXAMPLE 275

(Z)-3-{1-[4-((N-cyclopropyl-N-methyl-amino)-methyl)-phenylamino]-1-phenyl-methylidene}-5-nitro-2-indolinone Prepared analogously to Example 273.
Melting point: 216–217° C.
$C_{26}H_{24}N_4O_3$ (440.51).
Mass spectrum: M$^+$=440.
Calc.: C, 70.89; H, 5.49; N, 12.72. Found: 70.42; 5.52; 12.48.

EXAMPLE 276

(Z)-3-{1-[4-(cyclopentylaminomethyl)-phenylamino]-1-phenyl-methylidene}-5-nitro-2-indolinone Prepared analogously to Example 273.
Melting point: 231° C.
$C_{27}H_{26}N_4O_3$ (454.53).
Mass spectrum: M$^+$=454.
$C_{27}H_{26}N_4O_3 \times H_2O$ (472.55).
Calc.: C, 68.63; H, 5.97; N, 11.86. Found: 68.93; 6.12; 11.62.

EXAMPLE 277

(Z)-3-{1-[4-(N-cyclopentyl-N-methyl-aminomethyl)-phenylamino]-1-phenyl-methylidene}-5-nitro-2-indolinone Prepared analogously to Example 273.
Melting point: 228° C.
$C_{28}H_{28}N_4O_3$ (468.56).
Mass spectrum: M$^+$=468.
$C_{28}H_{28}N_4O_3 \times 1.5H_2O$ (495.58).
Calc.: C, 67.86; H, 6.30; N, 11.31. Found: 68.35; 6.42; 11.16.

EXAMPLE 278

(Z)-3-{1-[4-(cyclohexylaminomethyl)-phenylamino]-1-phenyl-methylidene}-5-nitro-2-indolinone Prepared analogously to Example 273.
Melting point: 245° C.
$C_{28}H_{28}N_4O_3$ (468.55).
Mass spectrum: M$^+$=468.
$C_{28}H_{28}N_4O_3 \times 0.5H_2O$ (477.56).
Calc.: C, 70.42; H, 16.12; N, 11.73. Found: 70.60; 6.20; 11.83.

EXAMPLE 279

(Z)-3-{1-[4-(pyridine-2-ylaminomethyl)-phenylamino]-1-phenyl-methylidene}-5-nitro-2-indolinone Prepared analogously to Example 273.
Melting point: 266–268° C.
$C_{27}H_{21}N_5O_3$ (463.49).
Mass spectrum: M$^+$=463.
Calc.: C, 69.97; H, 4.57; N, 15.11. Found: 69.76; 4.62; 14.87.

EXAMPLE 280

(Z)-3-{1-[4-(3-dimethylaminoprop-1-ynyl)-phenylamino]-1-phenyl-methylidene}-5-nitro-2-indolinone a) 4-(3-hydroxyprop-1-ynyl)-nitrobenzene 8.55 g (0.15 mol) of propargyl alcohol and 152 ml (110 g, 1.09 mol) of triethylamine are added to a solution of 20.2 g (0.1 mol) of 4-bromonitrobenzene in 285 ml of acetonitrile. The reaction solution is heated to 100° C. 11.9 g (10 mmol) of Pd(Pph$_3$)$_4$ and 3.94 g (20 mmol) of copper (I) iodide are added. After 10 minutes the solvent is eliminated in vacuo and the residue taken up in ethyl acetate. It is washed with water and ammonia water, filtered through Celite and the solvent is eliminated in vacuo. The product is obtained by chromatography on silica gel (dichloromethane/methanol= 10:1).
Yield: 5.95 g (34% of theory).
Melting point: 98–105° C.
$C_9H_7NO_3$ (177.2).
Mass spectrum: [M–H]$^-$=176.

b) 4-[3-(p-Tolylsulphonyloxy)-prop-1-ynyl]-nitrobenzene 4.4 ml (54 mmol) of pyridine are added dropwise to a solution of 5.8 g (33 mmol) of 4-(3-hydroxyprop-1-ynyl)-nitrobenzene and 5.2 g (27 mmol) of p-toluenesulphonic acid chloride in 50 ml of dichloromethane at 0° C. After 2 hours at 0° C. about 25 g of ice and 8 ml of conc. hydrochloric acid are added. The organic phase is separated off and washed with water. After removal of the solvent in vacuo and chromatography of the residue on silica gel (dichloromethane/methanol=1:1) the product is obtained as an oil.
Yield: 0.7 g (8% of theory).
$C_{16}H_{13}NO_5S$ (331.3).
Mass spectrum: M$^+$=331.

c) 4-(3-dimethylaminoprop-1-ynyl)-nitrobenzene 190 ml (4.2 mmol) of dimethylamine dissolved in 2.5 ml of dichloromethane are added dropwise at 0° C. to a solution of 0.7 g (2.1 mmol) of 4-[3-(p-tolylsulphonyloxy)-prop-1-ynyl]-nitrobenzene in 10 ml of dichloromethane. The cooling is stopped and the mixture is stirred for 18 hours at ambient temperature. Then the reaction solution is washed with water and freed from solvent. The residue is chromatographed on silica gel (dichloromethane/methanol=10:1). The product is obtained as an oil.

Yield: 278 mg (65% of theory).
$C_{11}H_{12}N_2O_2$ (204.2).
Mass spectrum: $[M+H]^+=205$.

d) 4-(3-dimethylaminoprop-1-ynyl)-aniline

The reaction of 4-(3-dimethylaminoprop-1-ynyl)-nitrobenzene with tin dichloride analogously to Example 269 yields the following three products:

4-(3-dimethylaminoprop-1-ynyl)-aniline
$C_{11}H_{14}N_2$ (174.2).
Mass spectrum: $M^+=174$.
(Z)-4-(3-dimethylamino-2-chloroprop-1-enyl)-aniline
$C_{11}H_{15}ClN_2$ (210.7).
Mass spectrum: $M^+=212/210$.
(E)-4-(3-dimethylaminoprop-1-enyl)-aniline
$C_{11}H_{16}N_2$ (176.2).
Mass spectrum: $M^+=176$.

e) (Z)-3-{1-[4-(3-dimethylaminoprop-1-ynyl)-phenylamino]-1-phenyl-methylidene}-5-nitro-2-indolinone Prepared analogously to Example 89 by reacting 3-(1-ethoxy-1-phenyl-methylidene)-5-nitro-2-indolinone with 4-(3-dimethylaminoprop-1-ynyl)-aniline.

Yield: 22% of theory.
$C_{26}H_{22}N_4O_3$ (438.48).
Mass spectrum: $[M+H]^+=439.5$.
$R_f$ value: 0.54 (silica gel; dichloromethane/methanol= 5:1).

EXAMPLE 281

(Z)-3-{1-[(Z)-4-(3-dimethylamino-2-chloroprop-1-enyl)-phenylamino]-1-phenyl-methylidene}-5-nitro-2-indolinone Prepared analogously to Example 280.
$C_{26}H_{23}ClN_4O_3$ (474.95).
Mass spectrum: $[M+H]^+=477/475$.
$R_f$ value: 0.48 (silica gel; dichloromethane/methanol= 5:1).

EXAMPLE 282

(Z)-3-{1-[(E)-4-(3-dimethylaminoprop-1-enyl)-phenylamino]-1-phenyl-methylidene}-5-nitro-2-indolinone Prepared analogously to Example 280.
$C_{26}H_{24}N_4O_3$ (440.50).
Mass spectrum: $M^+=440$.
$R_f$ value: 0.51 (silica gel; dichloromethane/methanol 5:1).

EXAMPLE 283

(Z)-3-{1-[4-(3-dimethylamino-propyl)-phenylamino]-1-phenyl-methylidene}-5-nitro-2-indolinone a) 4-(3-dimethylaminopropyl)-aniline Prepared by catalytic hydrogenation of 4-(3-dimethylaminoprop-1-ynyl)-nitrobenzene (Example 280) analogously to Example 39c.

$C_{11}H_{18}N_2$ (178.3).
Mass spectrum: $M^+=178$.

b) (Z)-3-{1-[4-(3-dimethylaminopropyl)-phenylamino]-1-phenyl-methylidene}-5-nitro-2-indolinone Prepared analogously to Example 89 by reacting 3-(1-ethoxy-1-phenyl-methylidene)-5-nitro-2-indolinone with 4-(3-dimethylaminopropyl)-aniline.

Yield: 35% of theory.
Melting point: 269° C. (decomposition).
$C_{26}H_{26}N_4O_3$ (442.52).
Mass spectrum: $M^+=442$.

EXAMPLE 284

(Z)-3-{1-[4-(2-dimethylaminoethyloxy)-phenylamino]-1-phenyl-methylidene}-2-indolinone a) 4-(2-Bromoethyloxy)-nitrobenzene 18 g (161 mmol) of potassium tert.butoxide are added to a solution of 20.8 g (150 mmol) of 4-nitrophenol in 100 ml of dimethylformamide. The temperature of the reaction solution meanwhile is maintained at <50° C. After 30 minutes the reaction solution is added dropwise to a solution of 113 g (602 mmol) of 1,2-dibromoethane in 50 ml of dimethylformamide. Then it is heated to 80° C. for 18 hours. The solvent is then eliminated in vacuo, the residue taken up in dichloromethane, washed with dilute sodium hydroxide solution, dried and evaporated to dryness. The oily residue is chromatographed on silica gel (dichloromethane/cyclohexane=6:4)

Yield: 13 g (35% of theory).
Melting point: 66° C.
$R_f$ value: 0.53 (silica gel; dichloromethane/cyclohexane= 6:4).

b) 4-(2-dimethylaminoethyloxy)-nitrobenzene 4.9 g (20 mmol) of 4-(2-bromoethyloxy)-nitrobenzene and 2.7 g (60 mmol) of dimethylamine in 50 ml of dimethylformamide are heated to 100° C. for 24 hours in a bomb tube. After removal of the solvent in vacuo the residue is taken up in water and extracted with dichloromethane. The organic phase is dried and concentrated by evaporation.

Yield: 2.9 g (69% of theory).
$C_{10}H_{14}N_2O_3$ (210.224).
Mass spectrum: $[M+H]^+=211$.
$R_f$ value: 0.45 (silica gel; dichloromethane/ethanol=9:1).

c) 4-(2-dimethylaminoethyloxy)-aniline

Prepared by catalytic hydrogenation of 4-(2-dimethylaminoethyloxy)-nitrobenzene analogously to Example 39

Yield: 93% of theory.
$C_{10}H_{16}N_2O$ (180.25).
Mass spectrum: $[M+H]^+=181$.

d) (Z)-3-{1-[4-(2-dimethylaminoethyloxy)-phenylamino]-1-phenyl-methylidene}-2-indolinone Prepared analogously to Example 11 by reacting 3-(1-ethoxy-1-phenyl-methylidene)-2-indolinone with 4-(2-dimethylaminoethyloxy)-aniline.

Yield: 35% of theory.
Melting point: 258–260° C.
$C_{25}H_{25}N_3O_2$ (399.49).
Mass spectrum: $M^+=399$.
Calc.: C, 76.79; H, 6.89; N, 9.26. Found: 76.43; 6.83; 9.20.

EXAMPLE 285

(Z)-3-{1-[4-(2-piperidinoethyloxy)-phenylamino]-1-phenyl-methylidene}-2-indolinone Prepared analogously to Example 284.
Melting point: 198–200° C.

$C_{28}H_{29}N_3O_2$ (439.56).
Mass spectrum: M⁺=439.

EXAMPLE 286

(Z)-3-{1-[4-(3-dimethylaminopropyloxy)-phenylamino]-1-phenyl-methylidene}-2-indolinone Prepared analogously to Example 284.
Melting point: 215–217° C.
$C_{26}H_{27}N_3O_2$ (413.52).
Mass spectrum: M⁺=413.

EXAMPLE 287

(Z)-3-{1-[4-(3-piperidinopropyloxy)-phenylamino]-1-phenyl-methylidene}-2-indolinone Prepared analogously to Example 284.
Melting point: 223–225° C.
$C_{29}H_{31}N_3O_2$ (453.58).
Mass spectrum: M⁺=453.

EXAMPLE 288

(Z)-3-{1-[4-(3-(N-benzyl-N-methyl-amino)-propyloxy)-phenylamino]-1-phenyl-methylidene}-2-indolinone Prepared analogously to Example 284.
Melting point: 187–189° C.
$C_{32}H_{31}N_3O_2$ (489.62).
Mass spectrum: M⁺=489.

EXAMPLE 289

(Z)-3-{1-[4-(ethyloxycarbonylmethyloxy)-phenylamino]-1-phenyl-methylidene}-2-indolinone Prepared analogously to Example 284.
Melting point: 175–177° C.
$C_{25}H_{22}N_2O_4$ (414.46).
Mass spectrum: M⁺=414.

EXAMPLE 290

(Z)-3-{1-[4-(carboxymethyloxy)-phenylamino]-1-phenyl-methylidene}-2-indolinone

Prepared analogously to Example 289 and 8.
Melting point: 238–240° C.
$C_{23}H_{18}N_2O_4$ (386.41).
Mass spectrum: M⁺=386.

EXAMPLE 291

(Z)-3-{1-[4-(dimethylaminocarbonylmethyloxy)-phenylamino]-1-phenyl-methylidene}-2-indolinone Prepared analogously to Example 290 and 18.
Melting point: 224–226° C.
$C_{25}H_{23}N_3O_3$ (413.47).
Mass spectrum: M⁺=413.

EXAMPLE 292

(Z)-3-1-[4-(N-(2-dimethylamino-ethylaminocarbonylmethyl)-N-methylsulphonyl-amino)-phenylamino]-1-phenyl-methylidene}-5-nitro-2-indolinone Prepared analogously to Example 192.
Melting point: 145° C.
$C_{28}H_{30}N_6O_6S$ (578.65).
Mass spectrum: M⁺=578.
$C_{28}H_{30}N_6O_6S \times 1.5 H_2O$ (605.67).
Calc.: C, 55.53; H, 5.49; N, 13.88. Found: 55.54; 5.59; 13.68.

EXAMPLE 293

(Z)-3-{1-[4-(N—((N-(2-dimethylaminoethyl)-N-methyl-amino)-carbonylmethyl)-N-methylsulphonyl-amino)-phenylamino]-1-phenyl-methylidene}-2-indolinone Prepared analogously to Example 192.
Melting point: 170° C.
$C_{29}H_{33}N_5O_4S$ (547.68).
Mass spectrum: M⁺=547.
Calc: C, 63.60; H, 6.07; N, 12.79. Found: 63.38; 6.12; 12.67.

EXAMPLE 294

(Z)-3-{1-[4-(N—((N-(2-dimethylaminoethyl)-N-methyl-amino)-carbonylmethyl)-N-methylsulphonyl-amino)-phenylamino]-1-phenyl-methylidene}-5-nitro-2-indolinone Prepared analogously to Example 192.
Melting point: 138–140° C.
$C_{29}H_{32}N_6O_6S$ (592.67).
Mass spectrum: M⁺=592.
$C_{29}H_{32}N_6O_6S \times H_2O$ (601.68).
Calc: C, 57.89; H, 5.53; N, 13.97. Found: 57.58; 5.57; 13.84.

EXAMPLE 295

(Z)-3-{1-[4-(N-(2-dimethylamino-ethylaminocarbonylmethyl)-N-ethylsulphonyl-amino)-phenylamino]-1-phenyl-methylidene}-5-nitro-2-indolinone Prepared analogously to Example 192.
Melting point: 155° C.
$C_{29}H_{32}N_6O_6S$ (592.67).
Mass spectrum: M⁺=592.
$C_{29}H_{32}N_6O_6S \times H_2O$ (610.69).
Calc: C, 57.04; H, 5.61; N, 13.76. Found: 56.96; 5.63; 13.73.

EXAMPLE 296

(Z)-3-{1-[4-(N—((N-(2-dimethylaminoethyl)-N-methyl-amino)-carbonylmethyl)-N-ethylsulphonyl-amino)-phenylamino]-1-phenyl-methylidene}-5-nitro-2-indolinone Prepared analogously to Example 192.
Melting point: 117° C.
$C_{30}H_{34}N_6O_6S$ (606.70).
Mass spectrum: M⁺=606.
Calc: C, 59.39; H, 5.65; N, 13.85. Found: 59.29; 5.78; 13.65.

EXAMPLE 297

(Z)-3-{1-[4-(N-ethoxycarbonylmethyl-N-ethylsulphonyl-amino)-phenylamino]-1-phenyl-methylidene}-2-indolinone Prepared analogously to Example 198.
Melting point: 228–230° C.

$C_{27}H_{27}N_3O_5S$ (505.59).
Mass spectrum: $M^+=505$.
$C_{27}H_{27}N_3O_5S \times 0.5H_2O$ (514.60).
Calc.: C, 63.02; H, 5.48; N, 8.17. Found: 62.70; 5.37; 8.29.

EXAMPLE 298

(Z)-3-{1-[4-(N-carboxymethyl-N-ethylsulphonyl-amino)-phenylamino]-1-phenyl-methylidene}-2-indolinone Prepared analogously to Example 297 and 8.
Melting point: 240–242° C.
$C_{25}H_{23}N_3O_5S$ (477.54).
Mass spectrum: $M^+=477$.
$R_f$ value: 0.3 (silica gel; dichloromethane/methanol=9:1).

EXAMPLE 299

(Z)-3-{1-[4-(N-aminocarbonylmethyl-N-ethylsulphonyl-amino)-phenylamino]-1-phenyl-methylidene}-2-indolinone Prepared analogously to Example 298 and 20.
Melting point: 259° C.
$C_{25}H_{24}N_4O_4S$ (476.55).
Mass spectrum: $M^+=476$.
$C_{25}H_{24}N_4O_4S \times 0.3H_2O$ (481.96).
Calc: C, 62.30; H, 15.14; N, 11.62. Found: 62.50; 5.31; 11.55.

EXAMPLE 300

(Z)-3-{1-[4-(N-methylaminocarbonylmethyl-N-ethylsulphonyl-amino-phenylamino]-1-phenyl-methylidene}-2-indolinone Prepared analogously to Example 298 and 18.
Melting point: 242° C.
$C_{26}H_{26}N_4O_4S$ (490.58).
Mass spectrum: $M^+=490$.

EXAMPLE 301

(Z)-3-{1-[4-(N-(2-dimethylamino-ethylaminocarbonylmethyl)-N-ethylsulphonyl-amino)-phenylamino]-1-phenyl-methylidene}-2-indolinone Prepared analogously to Example 298 and 18.
Melting point: 203° C.
$C_{29}H_{33}N_5O_4S$ (547.68).
Mass spectrum: $M^+=547$.

EXAMPLE 302

(Z)-3-{1-[4-(N—((N-(2-dimethylaminoethyl)-N-methyl-amino)-carbonylmethyl)-N-ethylsulphonyl-amino)-phenylamino]-1-phenyl-methylidene}-2-indolinone Prepared analogously to Example 298 and 18.
Melting point: 170–172° C.
$C_{30}H_{35}N_5O_4S$ (561.70).
Mass spectrum: $M^+=561$.

EXAMPLE 303

(Z)-3-{1-[4-(N-(dimethylaminocarbonylmethyl)-N-benzylsulphonyl-amino)-phenylamino]-1-phenyl-methylidene}-5-nitro-2-indolinone Prepared analogously to Example 187.
Melting point: 159–161° C.
$C_{32}H_{29}N_5O_6S$ (611.68).
Mass spectrum: $M^+=611$.

EXAMPLE 304

(Z)-3-{1-[4-(N-(dimethylaminocarbonylmethyl)-N-isopropylsulphonyl-amino)-phenylamino]-1-phenyl-methylidene}-2-indolinone Prepared analogously to Example 187.
Melting point: 146–148° C.
$C_{28}H_{30}N_4O_4S$ (518.63).
Mass spectrum: $M^+=518$.
Calc.: C, 64.84; H, 5.83; N, 10.80. Found: 65.11; 5.82; 10.67.

EXAMPLE 305

(Z)-3-{1-[4-(N-(dimethylaminocarbonylmethyl)-N-propylsulphonyl-amino)-phenylamino]-1-phenyl-methylidene}-2-indolinone Prepared analogously to Example 187.
Melting point: 178–180° C.
$C_{28}H_{30}N_4O_4S$ (518.63).
Mass spectrum: $M^+=518$.

EXAMPLE 306

(Z)-3-{1-[4-(N-(dimethylaminocarbonylmethyl)-N-butylsulphonyl-amino)-phenylamino]-1-phenyl-methylidene}-2-indolinone Prepared analogously to Example 187.
Melting point: 121–123° C.
$C_{29}H_{32}N_4O_4S$ (532.66).
Mass spectrum: $M^+=532$.
$C_{29}H_{32}N_4O_4S \times 2H_2O$ (568.69).
Calc.: C, 61.25; H, 6.38; N, 9.85. Found: 61.59; 6.49; 10.00.

EXAMPLE 307

(Z)-3-{1-[4-(N-(2-dimethylaminoethyl)-N-ethylsulphonyl-amino)-phenylamino]-1-phenyl-methylidene}-2-indolinone Prepared analogously to Example 187.
Melting point: 245° C.
$C_{27}H_{30}N_4O_3S$ (490.63).
Mass spectrum: $M^+=490$.
$C_{27}H_{30}N_4O_3S \times 0.2H_2O$ (494.22).
Calc: C, 65.62; H, 6.20; N, 11.34. Found: 65.72; 6.33; 11.27.

EXAMPLE 308

(Z)-3-{1-[4-(N-(2-morpholinoethyl)-N-ethylsulphonyl-amino)-phenylamino]-1-phenyl-methylidene}-2-indolinone Prepared analogously to Example 187.
Melting point: 222–224° C.

$C_{29}H_{32}N_4O_4S$ (532.66).
Mass spectrum: $M^+=532$.

EXAMPLE 309

(Z)-3-{1-[4-(N-(2-dimethylaminoethyl)-N-isopropylsulphonyl-amino)-phenylamino]-1-phenyl-methylidene}-2-indolinone a) isopropylsulphonic acid-(4-tert.butoxycarbonylamino-phenyl)-amide 1.2 g (10 mmol) of isopropylsulphonic acid chloride are added dropwise to a solution of 1.0 g (4.8 mmol) of 4-tert.butoxycarbonylamino-aniline in 10 ml of pyridine. The mixture is stirred for 18 hours at ambient temperature. Then the reaction solution is poured onto 150 ml of ice water and then extracted with ethyl acetate. The organic phases are washed with water and freed from solvent. The residue is chromatographed on silica gel (dichloromethane/methanol/ $NH_4OH=19:1:0.1$).

Yield: 0.8 g (53% of theory).
$C_{14}H_{22}N_2O_4S$ (314.41).
Mass spectrum: $[M-H]^-=313$.

b) 4-isopropylsulphonylamino-aniline

Prepared analogously to Example 29a from isopropylsulphonic acid-(4-tert.butoxycarbonylamino-phenyl)-amide.
$C_9H_{14}N_2O_2S$ (214.28).
Mass spectrum: $M^+=214$.

c) (Z)-1-acetyl-3-[1-(4-isopropylsulphonylamino-phenylamino)-1-phenyl-methylidene]-2-indolinone Prepared analogously to Example 1c from 1-acetyl-3-(1-ethoxy-1-phenyl-methylidene)-2-indolinone and 4-isopropylsulphonylamino-aniline.

Yield: 27% of theory.
Melting point: 258° C.
$C_{26}H_{25}N_3O_4S$ (475.57).
Mass spectrum: $[M-H]^-=474$.

d) (Z)-3-{1-[4-(N-(2-dimethylaminoethyl)-N-isopropylsulphonyl-amino]-phenylamino]-1-phenyl-methylidene}-2-indolinone Prepared analogously to Example 36 from (Z)-3-{1-[4-(isopropylsulphonylamino)-phenylamino]-1-phenyl-methylidene}-2-indolinone, 1-chloro-2-dimethylamino-ethane, potassium carbonate and sodium iodide in acetone.

Yield: 14% of theory.
Melting point: 247° C.
$C_{28}H_{32}N_4O_3S$ (504.65).
Mass spectrum: $[M+H]^+=505$.
$C_{28}H_{32}N_4O_3S \times 0.2H_2O$ (508.25).
Calc.: C, 66.17; H, 6.43; N, 11.02. Found: 66.19; 6.40; 10.78.

EXAMPLE 310

(Z)-3-{1-[4-(N-(2-dimethylaminoethyl)-N-propylsulphonyl-amino)-phenylamino]-1-phenyl-methylidene}-5-nitro-2-indolinone Prepared analogously to Example 187.
Melting point: 212° C.
$C_{28}H_{31}N_5O_5S$ (549.65).
Mass spectrum: $M^+=549$.

EXAMPLE 311

(Z)-3-{1-[4-(N-(2-dimethylaminoethyl)-N-propylsulphonyl-amino)-phenylamino]-1-phenyl-methylidene}-2-indolinone Prepared analogously to Example 187.
Melting point: 245° C.
$C_{28}H_{32}N_4O_3S$ (504.65).
Mass spectrum: $M^+=504$.
Calc: C, 66.64; H, 6.39; N, 11.10. Found: 66.40; 6.44; 11.00.

EXAMPLE 312

(Z)-3-{1-[4-(N-(2-dimethylaminoethyl)-N-phenylsulphonyl-amino)-phenylamino]-1-phenyl-methylidene}-2-indolinone Prepared analogously to Example 187.
Melting point: 241–243° C.
$C_{31}H_{30}N_4O_3S$ (538.67).
Mass spectrum: $M^+=538$.

EXAMPLE 313

(Z)-3-{1-[4-(N-(2-dimethylaminoethyl)-N-benzylsulphonyl-amino)-phenylamino]-1-phenyl-methylidene}-5-nitro-2-indolinone Prepared analogously to Example 187.
Melting point: 248° C.
$C_{32}H_{31}N_5O_5S$ (597.69).
Mass spectrum: $M^+=597$.

EXAMPLE 314

(Z)-3-{1-[4-(N-(2-dimethylaminoethyl)-N-benzylsulphonyl-amino)-phenylamino]-1-phenyl-methylidene}-2-indolinone Prepared analogously to Example 187.
Melting point: 244° C.
$C_{32}H_{32}N_4O_3S$ (552.70).
Mass spectrum: $M^+=552$.
$C_{32}H_{32}N_4O_3S \times 0.5H_2O$ (560.69).
Calc: C, 68.55; H, 5.75; N, 9.99. Found: 68.99; 5.99; 9.83.

EXAMPLE 315

(Z)-3-{1-[4-(N-(3-dimethylaminopropyl)-N-methylsulphonyl-amino-phenylamino]-1-phenyl-methylidene}-2-indolinone Prepared analogously to Example 187.
Melting point: 227° C.
$C_{27}H_{30}N_4O_3S$ (490.63).
Mass spectrum: $[M+H]^+=491$.
Calc.: C, 66.10; H, 6.16; N, 11.42. Found: 66.04; 6.14; 11.43.

EXAMPLE 316

(Z)-3-{1-[4-(N-(3-dimethylaminopropyl)-N-ethylsulphonyl-amino)-phenylamino]-1-phenyl-methylidene}-2-indolinone Prepared analogously to Example 187.
Melting point: 194° C.
$C_{28}H_{32}N_4O_3S$ (504.65).
Mass spectrum: $[M+H]^+=505$.
Calc.: C, 66.64; H, 6.39; N, 11.10. Found: 66.43; 6.37; 10.88.

EXAMPLE 317

(Z)-3-{1-[3-(N-ethoxycarbonylmethyl-N-methylsulphonyl-amino)-phenylamino]-1-phenyl-methylidene}-2-indolinone Prepared analogously to Example 187.
Melting point: 188–190° C.

$C_{26}H_{25}N_3O_5S$ (491.57).
Mass spectrum: $M^+$=491.
Calc.: C, 63.53; H, 5.13; N, 8.55. Found: 63.67; 5.20; 8.59.

EXAMPLE 318

(Z)-3-{1-[3-(N-carboxymethyl-N-methylsulphonyl-amino)-phenylamino]-1-phenyl-methylidene}-2-indolinone Prepared analogously to Example 317 and 8.
Melting point: 270° C. (decomposition).
$C_{24}H_{21}N_3O_5S$ (463.51).
Mass spectrum: $[M-H]^-$=462.

EXAMPLE 319

(Z)-3-{1-[3-(N-aminocarbonylmethyl-N-methylsulphonyl-amino)-phenylamino]-1-phenyl-methylidene}-2-indolinone Prepared analogously to Example 318 and 20.
Melting point: 227–230° C.
$C_{24}H_{22}N_4O_4S$ (462.53).
Mass spectrum: $M^+$=462.

EXAMPLE 320

(Z)-3-{1-[3-(N-methylaminocarbonylmethyl-N-methylsulphonyl-amino)-phenylamino]-1-phenyl-methylidene}-2-indolinone Prepared analogously to Example 318 and 20.
Melting point: 163° C.
$C_{25}H_{24}N_4O_4S$ (476.55).
Mass spectrum: $M^+$=476.

EXAMPLE 321

(Z)-3-{1-[3-(N-dimethylaminocarbonylmethyl-N-methylsulphonyl-amino)-phenylamino]-1-phenyl-methylidene}-2-indolinone Prepared analogously to Example 318 and 20.
Melting point: 213–216° C.
$C_{26}H_{26}N_4O_4S$ (490.58).
Mass spectrum: $M^+$=490.

EXAMPLE 322

(Z)-3-{1-[3-(N-(2-dimethylamino-ethylaminocarbonylmethyl)-N-methylsulphonyl-amino)-phenylamino]-1-phenyl-methylidene}-2-indolinone Prepared analogously to Example 318 and 18.
Melting point: 179–181° C.
$C_{28}H_{31}N_5O_4S$ (533.65).
Mass spectrum: $M^+$=533.

EXAMPLE 323

(Z)-3-{1-[3-(N—((N-(2-dimethylaminoethyl)-N-methyl-amino)-carbonylmethyl)-N-methylsulphonyl-amino)-phenylamino]-1-phenyl-methylidene}-2-indolinone Prepared analogously to Example 318 and 18.
Melting point: 197–199° C.
$C_{29}H_{33}N_5O_4S$ (547.68).
Mass spectrum: $M^+$=547.
Calc.: C, 63.60; H, 6.07; N, 12.79; S, 5.85. Found: 63.52; 6.14; 12.72; 5.85.

EXAMPLE 324

(Z)-3-{1-[3-(N-(2-dimethylaminoethyl)-N-methylsulphonyl-amino)-phenylamino]-1-phenyl-methylidene}-2-indolinone Prepared analogously to Example 187.
Melting point: 208–211° C.
$C_{26}H_{28}N_4O_3S$ (476.60).
Mass spectrum: $M^+$=476.
Calc.: C, 65.52; H, 5.92; N, 11.76. Found: 65.22; 5.84; 11.64.

EXAMPLE 325

(Z)-3-{1-[3-(N-(2-morpholinoethyl)-N-methylsulphonyl-amino)-phenylamino]-1-phenyl-methylidene}-2-indolinone Prepared analogously to Example 187.
Melting point: 177–179° C.
$C_{28}H_{30}N_4O_4S$ (518.63).
Mass spectrum: $M^+$=518.

EXAMPLE 326

(Z)-3-{1-[4-(2-dimethylamino-ethylamino)-phenylamino]-1-phenyl-methylidene}-5-nitro-2-indolinone a) 4-(2-dimethylamino-ethylamino)-nitrobenzene 2.2 ml of (20 mmol) of 4-fluoronitrobenzene and 2.6 ml (24 mmol) of N,N-dimethylethylene-diamine are heated in 10 ml of ethanol at 120° C. in a microwave oven for 1.5 hours. Then 50 ml of 1 N hydrochloric acid are added. The reaction solution is washed with ethyl acetate. Then the aqueous phase is combined with 4 N sodium hydroxide solution until an alkaline reaction is obtained and extracted with ethyl acetate.

The combined organic phases are washed with water, dried over magnesium sulphate and freed from solvent. The product is obtained as a yellow oil.
Yield: 11.7 g (61% of theory).
$C_{10}H_{15}N_3O_2$ (209.25).
Mass spectrum: $[M+H]^+$=210.

b) 4-(2-dimethylamino-ethylamino)-aniline

Prepared analogously to Example 39c by catalytic hydrogenation of 4-(2-dimethylamino-ethylamino)-nitrobenzene.
Yield: 94% of theory.
$C_{10}H_{17}N_3$ (179.27).
Mass spectrum: $[M+H]^+$=180.

c) (Z)-3-{1-[4-(2-dimethylamino-ethylamino)-phenylamino]-1-phenyl-methylidene}-5-nitro-2-indolinone Prepared analogously to Example 89 from 3-(1-ethoxy-1-phenyl-methylidene)-5-nitro-2-indolinone and 4-(2-dimethylamino-ethylamino)-aniline.
Yield: 25% of theory.
Melting point: 227–229° C.
$C_{25}H_{25}N_5O_3$ (443.50).
Mass spectrum: $M^+$=443.
$C_{25}H_{25}N_5O_3 \times 0.5H_2O$ (452.51).
Calc.: C, 66.36; H, 5.79; N, 15.48. Found: 66.25; 5.60; 15.52.

EXAMPLE 327

(Z)-3-{1-[4-(N-(2-dimethylaminoethyl)-N-formyl-amino)-phenylamino]-1-phenyl-methylidene}-5-nitro-2-indolinone a) 4-(N-(2-dimethylaminoethyl)-N-formyl-amino)-nitrobenzene 1.4 g (6.7 mmol) of 4-(2-dimethylamino-ethylamino)-nitrobenzene (Example 326a) are refluxed for 4 hours in 20 ml of formic acid. Then the solvent is eliminated in vacuo, the residue taken up in water and combined with 2 N sodium hydroxide solution until an alkaline reaction is obtained. The mixture is extracted with ethyl acetate, the combined organic phases are dried over magnesium sulphate and the solvent is eliminated in vacuo. The product is obtained as an oil.

Yield: 1.3 g (78% of theory).
$C_{11}H_{15}N_3O_3$ (237.26).
Mass spectrum: $[M+H]^+=238$.

b) 4-(N-(2-dimethylaminoethyl)-N-formyl-amino)-aniline

Prepared analogously to Example 39c by catalytic hydrogenation of 4-(N-(2-dimethylaminoethyl)-N-formyl-amino)-nitrobenzene.

Yield: 82% of theory.
$C_{11}H_{17}N_3O$ (207.28).
Mass spectrum: $M^+=207$.

c) (Z)-3-{1-[4-(N-(2-dimethylaminoethyl)-N-formyl-amino)-phenylamino]-1-phenyl-methylidene}-5-nitro-2-indolinone Prepared analogously to Example 89 from 3-(1-ethoxy-1-phenyl-methylidene)-5-nitro-2-indolinone and 4-(N-(2-dimethylaminoethyl)-N-formyl-amino)-aniline.

Yield: 47% of theory.
Melting point: 215–218° C.
$C_{26}H_{25}N_5O_4$ (471.51).
Mass spectrum: $M^+=471$.

EXAMPLE 328

(Z)-3-{1-[4-(N-(2-dimethylaminoethyl)-N-acetyl-amino)-phenylamino]-1-phenyl-methylidene}-5-nitro-2-indolinone Prepared analogously to Example 327.
Melting point: 228–230° C.
$C_{27}H_{27}N_5O_4$ (485.54).
Mass spectrum: $[M+H]^+=486$.

EXAMPLE 329

(Z)-3-{1-[4-(N-(2-dimethylaminoethyl)-N-propionyl-amino)-phenylamino]-1-phenyl-methylidene}-5-nitro-2-indolinone Prepared analogously to Example 327.
Melting point: 263–265° C.
$C_{28}H_{29}N_5O_4$ (499.57).
Mass spectrum: $M^+=499$.
Calc.: C, 67.32; H, 5.85; N, 14.02. Found: 67.16; 6.00; 13.81.

EXAMPLE 330

(Z)-3-{1-[4-(N-(2-dimethylaminoethyl)-N-isopropylcarbonyl-amino)-phenylamino]-1-phenyl-methylidene}-5-nitro-2-indolinone Prepared analogously to Example 327.
Melting point: 296–298° C.
$C_{29}H_{31}N_5O_4$ (513.59).
Mass spectrum: $M^+=513$.
Calc.: C, 67.82; H, 6.08; N, 13.64. Found: 67.53; 6.29; 13.51.

EXAMPLE 331

(Z)-3-{1-[4-(N-(2-dimethylaminoethyl)-N-propylcarbonyl-amino)-phenylamino]-1-phenyl-methylidene}-5-nitro-2-indolinone Prepared analogously to Example 327.
Melting point: 275–277° C.
$C_{29}H_{31}N_5O_4$ (513.59).
Mass spectrum: $M^+=513$.
Calc.: C, 67.82; H, 6.08; N, 13.64. Found: 67.71; 6.31; 13.54.

EXAMPLE 332

(Z)-3-{1-[4-(2-morpholinoethylamino)-phenylamino]-1-phenyl-methylidene}-5-nitro-2-indolinone Prepared analogously to Example 326.
Melting point: 253° C.
$C_{27}H_{27}N_5O_4$ (485.54).
Mass spectrum: $M^+=485$.
$C_{27}H_{27}N_5O_4 \times 0.5H_2O$ (494.54).
Calc.: C, 65.57; H, 5.71; N, 14.16. Found: 65.58; 5.70; 14.08.

EXAMPLE 333

(Z)-3-{1-[4-(N-(2-morpholinoethyl)-N-formyl-amino)-phenylamino]-1-phenyl-methylidene}-5-nitro-2-indolinone Prepared analogously to Example 327.
Melting point: 207° C.
$C_{28}H_{27}N_5O_5$ (513.55).
Mass spectrum: $M^+=513$.
Calc: C, 65.49; H, 5.30; N, 13.64. Found: 65.19; 5.30; 13.51.

EXAMPLE 334

(Z)-3-{1-[4-(N-(2-morpholinoethyl)-N-acetyl-amino)-phenylamino]-1-phenyl-methylidene}-5-nitro-2-indolinone 486 mg (1.0 mmol) of (Z)-3-{1-[4-(2-morpholinoethylamino)-phenylamino]-1-phenyl-methylidene}-5-nitro-2-indolinone (Example 332) are dissolved in 30 ml of dichloromethane and combined with 1.2 ml (16 mmol) of acetylchloride. The mixture is stirred for 1 hour at ambient temperature. The precipitate is removed by suction filtering and the reaction solution is washed with water. Then the solvent is eliminated in vacuo, the residue is dissolved in 20 ml of methanol and combined with 4 ml of 1 N sodium hydroxide solution. The mixture is stirred for 30 minutes at ambient temperature and then the solvent is eliminated in vacuo. The residue is suspended in water and a little ether. Then the product is suction filtered and dried.

Yield: 35% of theory.
Melting point: 229° C.

$C_{29}H_{29}N_5O_5$ (527.58).

Mass spectrum: $M^+=527$.

$C_{29}H_{29}N_5O_5 \times 0.5H_2O$ (536.59).

Calc: C, 64.91; H, 5.64; N, 13.05. Found: 65.29; 5.62; 12.98.

EXAMPLE 335

(Z)-3-{1-[4-(N-(2-morpholinoethyl)-N-propionyl-amino)-phenylamino]-1-phenyl-methylidene}-5-nitro-2-indolinone Prepared analogously to Example 327.

Melting point: 232° C.

$C_{30}H_{31}N_5O_5$ (541.60).

Calc: C, 66.53; H, 5.77; N, 12.93. Found: 66.60; 5.99; 12.65.

EXAMPLE 336

(Z)-3-{1-[4-(N-(2-morpholinoethyl)-N-isopropylcarbonyl-amino)-phenylamino]-1-phenyl-methylidene}-5-nitro-2-indolinone Prepared analogously to Example 327.

Melting point: 254° C.

$C_{31}H_{33}N_5O_5$ (555.63).

Mass spectrum: $M^+=555$.

Calc: C, 67.01; H, 5.99; N, 12.60. Found: 66.80; 6.01; 12.54.

EXAMPLE 337

(Z)-3-{1-[4-(N-(2-morpholinoethyl)-N-propylcarbonyl-amino)-phenylamino]-1-phenyl-methylidene}-5-nitro-2-indolinone Prepared analogously to Example 327.

Melting point: 228° C.

$C_{31}H_{33}N_5O_5$ (555.63).

Mass spectrum: $M^+=555$.

Calc: C, 67.01; H, 5.99; N, 12.60. Found: 66.85; 6.00; 12.52.

EXAMPLE 338

(Z)-3-{1-[4-(2-dimethylamino-ethylamino)-phenylamino]-1-phenyl-methylidene}-2-indolinone Prepared analogously to Example 326.

Melting point: 258–260° C.

$C_{25}H_{26}N_4O$ (398.51).

Mass spectrum: $M^+=398$.

EXAMPLE 339

(Z)-3-{1-[4-(N-(2-dimethylaminoethyl)-N-formyl-amino)-phenylamino]-1-phenyl-methylidene}-2-indolinone Prepared analogously to Example 327.

Melting point: 246–248° C.

$C_{26}H_{26}N_4O_2$ (426.52).

Mass spectrum: $M^+=426$.

EXAMPLE 340

(Z)-3-{1-[4-(N-(2-dimethylaminoethyl)-N-acetyl-amino)-phenylamino]-1-phenyl-methylidene}-2-indolinone Prepared analogously to Example 327.

Melting point: 197–199° C.

$C_{27}H_{28}N_4O_2$ (440.54).

Mass spectrum: $M^+=440$.

EXAMPLE 341

(Z)-3-{1-[4-(N-(2-dimethylaminoethyl)-N-propionyl-amino)-phenylamino]-1-phenyl-methylidene}-2-indolinone Prepared analogously to Example 327.

Melting point: 272–274° C.

$C_{28}H_{30}N_4O_2$ (454.57).

Mass spectrum: $M^+=454$.

Calc.: C, 73.98; H, 6.65; N, 12.33. Found: 73.71; 6.79; 12.32.

EXAMPLE 342

(Z)-3-{1-[4-(N-(2-dimethylaminoethyl)-N-isopropylcarbonyl-amino)-phenylamino]-1-phenyl-methylidene}-2-indolinone Prepared analogously to Example 327.

Melting point: 280–282° C.

$C_{29}H_{32}N_4O_2$ (468.60).

Mass spectrum: $M^+=468$.

$C_{29}H_{32}N_4O_2 \times 0.5H_2O$ (477.61).

Calc.: C, 72.93; H, 6.96; N, 11.73. Found: 72.71; 6.86; 11.87.

EXAMPLE 343

(Z)-3-{1-[4-(N-(2-dimethylaminoethyl)-N-propylcarbonyl-amino)-phenylamino]-1-phenyl-methylidene}-2-indolinone Prepared analogously to Example 327.

Melting point: 268–270° C.

$C_{29}H_{32}N_4O_2$ (468.60).

Mass spectrum: $M^+=468$.

Calc.: C, 74.33; H, 6.88; N, 11.96. Found: 74.27; 6.95; 11.97.

EXAMPLE 344

(Z)-3-{1-[4-(N-(3-dimethylaminopropyl)-N-acetyl-amino)-phenylamino]-1-phenyl-methylidene}-2-indolinone Prepared analogously to Example 327.

Melting point: 227° C.

$C_{28}H_{30}N_4O_2$ (454.57).

Mass spectrum: $M^+=454$.

Calc.: C, 73.98; H, 6.65; N, 12.33. Found: 73.62; 6.61; 12.13.

EXAMPLE 345

(Z)-3-{1-[4-(N-(3-dimethylaminopropyl)-N-propionyl-amino)-phenylamino]-1-phenyl-methylidene}-2-indolinone Prepared analogously to Example 327.

Melting point: 224° C.

$C_{29}H_{32}N_4O_2$ (468.60).

Mass spectrum: $M^+=468$.

$C_{29}H_{32}N_4O_2 \times 0.5H_2O$ (477.61).

Calc.: C, 72.93; H, 6.96; N, 11.73. Found: 72.99; 6.85; 11.63.

EXAMPLE 346

(Z)-3-{1-[4-(2-morpholinoethylamino)-phenylamino]-1-phenyl-methylidene}-2-indolinone Prepared analogously to Example 326.
Melting point: 257° C.
$C_{27}H_{28}N_4O_2$ (440.54).
Mass spectrum: $M^+$=440.
Calc: C, 73.61; H, 6.41; N, 12.72. Found: 73.57; 6.48; 12.62.

EXAMPLE 347

(Z)-3-{1-[4-(N-(2-morpholinoethyl)-N-formyl-amino)-phenylamino]-1-phenyl-methylidene}-2-indolinone Prepared analogously to Example 327.
Melting point: 218° C.
$C_{28}H_{28}N_4O_3$ (468.55).
Mass spectrum: $M^+$=468.

EXAMPLE 348

(Z)-3-{1-[4-(N-(2-morpholinoethyl)-N-acetyl-amino)-phenylamino]-1-phenyl-methylidene}-2-indolinone Prepared analogously to Example 334.
Melting point: from 90° C. (sintering).
$C_{29}H_{30}N_4O_3$ (482.58).
Mass spectrum: $M^+$=482.

EXAMPLE 349

(Z)-3-{1-[4-(N-(2-morpholinoethyl)-N-propionyl-amino)-phenylamino]-1-phenyl-methylidene}-2-indolinone Prepared analogously to Example 334.
Melting point: 228° C.
$C_{30}H_{32}N_4O_3$ (496.61).
Mass spectrum: $M^+$=496.
$C_{30}H_{32}N_4O_3 \times 0.3H_2O$ (502.01).
Calc.: C, 71.78; H, 16.55; N, 11.16. Found: 71.70; 6.56; 11.13.

EXAMPLE 350

(Z)-3-{1-[4-(N-(2-morpholinoethyl)-N-isopropylcarbonyl-amino)-phenylamino]-1-phenyl-methylidene}-2-indolinone Prepared analogously to Example 327.
Melting point: 239° C.
$C_{31}H_{34}N_4O_3$ (510.63).
Mass spectrum: $M^+$=510.

EXAMPLE 351

(Z)-3-{1-[4-(N-(2-morpholinoethyl)-N-propylcarbonyl-amino)-phenylamino]-1-phenyl-methylidene}-2-indolinone Prepared analogously to Example 327.
Melting point: 219° C.
$C_{31}H_{34}N_4O_3$ (510.63).
Mass spectrum: $M^+$=510.
$C_{31}H_{34}N_4O_3 \times 0.3H_2O$ (516.04).
Calc.: C, 72.15; H, 6.76; N, 10.86. Found: 72.10; 6.66; 10.79.

EXAMPLE 352

(Z)-3-{1-[4-(N-ethoxycarbonylmethyl-N-acetyl-amino)-phenylamino]-1-phenyl-methylidene}-2-indolinone Prepared analogously to Example 187.
Melting point: 244–247° C.
$C_{27}H_{25}N_3O_4$ (455.51).
Mass spectrum: $M^+$=455.
Calc.: C, 71.19; H, 5.53; N, 9.22. Found: 71.01; 5.59; 9.36.

EXAMPLE 353

(Z)-3-{1-[4-(N-carboxymethyl-N-acetyl-amino)-phenylamino]-1-phenyl-methylidene}-2-indolinone Prepared analogously to Example 352 and 8.
Melting point: 276° C. (decomposition).
$C_{25}H_{21}N_3O_4$ (427.46).
Mass spectrum: $M^+$=427.
$C_{25}H_{21}N_3O_4 \times 0.3H_2O$ (432.86).
Calc.: C, 69.37; H, 5.03; N, 9.71. Found: 69.41; 5.16; 9.70.

EXAMPLE 354

(Z)-3-{1-[4-(N-methylaminocarbonylmethyl-N-acetyl-amino)-phenylamino]-1-phenyl-methylidene}-2-indolinone Prepared analogously to Example 353 and 18.
Melting point: 270° C. (decomposition).
$C_{26}H_{24}N_4O_3$ (440.50).
Mass spectrum: $M^+$=440.

EXAMPLE 355

(Z)-3-{1-[4-(N-dimethylaminocarbonylmethyl-N-acetyl-amino)-phenylamino]-1-phenyl-methylidene}-2-indolinone Prepared analogously to Example 353 and 18.
Melting point: 264–268° C.
$C_{27}H_{26}N_4O_3$ (454.53).
Mass spectrum: $M^+$=454.
$C_{27}H_{26}N_4O_3 \times 0.3H_2O$ (459.93).
Calc.: C, 70.51; H, 5.83; N, 12.18. Found: 70.52; 5.86; 12.10.

EXAMPLE 356

(Z)-3-{1-[4-(N-ethoxycarbonylmethyl-N-propionyl-amino)-phenylamino]-1-phenyl-methylidene}-2-indolinone Prepared analogously to Example 187.
Melting point: 229–232° C.
$C_{28}H_{27}N_3O_4$ (469.54).

Mass spectrum: M$^+$=469.
Calc.: C, 71.63; H, 5.80; N, 8.95. Found: 71.49; 5.85; 8.92.

EXAMPLE 357

(Z)-3-{1-[4-(N-carboxymethyl-N-propionyl-amino)-phenylamino]-1-phenyl-methylidene}-2-indolinone Prepared analogously to Example 356 and 8.
Melting point: 270° C. (decomposition).
$C_{26}H_{23}N_3O_4$ (441.48).
Mass spectrum: M$^+$=441.
Calc.: C, 70.74; H, 5.25; N, 9.52. Found: 70.46; 5.44; 9.39.

EXAMPLE 358

(Z)-3-{1-[4-(N-methylaminocarbonylmethyl-N-propionyl-amino)-phenylamino]-1-phenyl-methylidene}-2-indolinone Prepared analogously to Example 357 and 18.
Melting point: 268° C.
$C_{27}H_{26}N_4O_3$ (454.53).
Mass spectrum: M$^+$=454.
$C_{27}H_{26}N_4O_3 \times 0.5H_2O$ (463.54).
Calc.: C, 69.96; H, 5.87; N, 12.09. Found: 69.53; 6.01; 12.17.

EXAMPLE 359

(Z)-3-{1-[4-(N-dimethylaminocarbonylmethyl-N-propionyl-amino)-phenylamino]-1-phenyl-methylidene}-2-indolinone Prepared analogously to Example 357 and 18.
Melting point: 274–277° C.
$C_{28}H_{28}N_4O_3$ (468.55).
Mass spectrum: M$^+$=468.
Calc.: C, 71.78; H, 6.02; N, 11.96. Found: 71.70; 6.21; 11.94.

EXAMPLE 360

(Z)-3-{1-[4-(N-ethoxycarbonylmethyl-N-benzoyl-amino)-phenylamino]-1-phenyl-methylidene}-2-indolinone Prepared analogously to Example 187.
Melting point: 209–211° C.
$C_{32}H_{27}N_3O_4$ (517.58).
Mass spectrum: M$^+$=517.

EXAMPLE 361

(Z)-3-{1-[4-(N-carboxymethyl-N-benzoyl-amino)-phenylamino]-1-phenyl-methylidene}-2-indolinone Prepared analogously to Example 360 and 8.
Melting point: 277° C. (decomposition).
$C_{30}H_{23}N_3O_4$ (489.53).
Mass spectrum: M$^+$=489.

EXAMPLE 362

(Z)-3-{1-[4-(N-methylaminocarbonylmethyl-N-benzoyl-amino)-phenylamino]-1-phenyl-methylidene}-2-indolinone Prepared analogously to Example 361 and 18.
Melting point: 260–262° C.
$C_{31}H_{26}N_4O_3$ (502.57).
Mass spectrum: M$^+$=502.
Calc.: C, 74.09; H, 5.21; N, 11.15. Found: 74.01; 5.36; 11.09.

EXAMPLE 363

(Z)-3-{1-[4-(N-dimethylaminocarbonylmethyl-N-benzoyl-amino)-phenylamino]-1-phenyl-methylidene}-2-indolinone Prepared analogously to Example 361 and 18.
Melting point: 284–287° C.
$C_{32}H_{28}N_4O_3$ (516.60).
Mass spectrum: M$^+$=516.
$C_{32}H_{28}N_4O_3 \times 0.25H_2O$ (521.10).
Calc.: C, 73.76; H, 5.51; N, 10.75. Found: 73.71; 5.67; 10.89.

EXAMPLE 364

(Z)-3-{1-[4-(N-(pyrrolidin-1-ylmethylcarbonyl)-N-methyl-amino)-phenylamino]-1-phenyl-methylidene}-5-nitro-2-indolinone Prepared analogously to Example 43.
Melting point: 246–247° C.
$C_{28}H_{27}N_5O_4$ (497.55).
Mass spectrum: M$^+$=497.
Calc.: C, 67.59; H, 5.47; N, 14.08. Found: 67.34; 5.53; 14.00.

EXAMPLE 365

(Z)-3-{1-[4-(N-phthalimidomethylcarbonyl-N-methyl-amino)-phenylamino]-1-phenyl-methylidene}-2-indolinone Prepared analogously to Example 43.
Melting point: 278–280° C.
$C_{32}H_{24}N_4O_4$ (528.57).
Mass spectrum: M$^+$=528.

EXAMPLE 366

(Z)-3-{1-[4-(N-aminomethylcarbonyl-N-methyl-amino)-phenylamino]-1-phenyl-methylidene}-2-indolinone Prepared analogously to Example 365 and 139b.
Melting point: 238–239° C.
$C_{24}H_{22}N_4O_2$ (398.46).
Mass spectrum: M$^+$=398.
$C_{24}H_{22}N_4O_2 \times 0.5H_2O$ (407.47).
Calc.: C, 70.74; H, 5.69; N, 13.75. Found: 70.91; 5.76; 13.73.

EXAMPLE 367

(Z)-3-{1-[4-(N-acetylaminomethylcarbonyl-N-methyl-amino)-phenylamino]-1-phenyl-methylidene}-2-indolinone Prepared analogously to Example 366 and 140.
Melting point: 255–256° C.

$C_{26}H_{24}N_4O_3$ (440.50).
Mass spectrum: $[M-H]^-$=439.

EXAMPLE 368

(Z)-3-{1-[4-(acetylaminomethylcarbonylamino)-phenylamino]-1-phenyl-methylidene}-2-indolinone Prepared analogously to Example 43.
Melting point: 245–247° C.
$C_{25}H_{22}N_4O_3$ (426.47).
Mass spectrum: $M^+$=426.

EXAMPLE 369

(Z)-3-{1-[4-(N-(pyrrolidin-1-ylmethylcarbonyl)-N-methyl-amino)-phenylamino]-1-phenyl-methylidene}-2-indolinone Prepared analogously to Example 43.
Melting point: 253–255° C.
$C_{28}H_{28}N_4O_2$ (452.56).
Mass spectrum: $M^+$=452.

EXAMPLE 370

(Z)-3-{1-[4-(N—(N-benzyl-N-methyl-aminomethylcarbonyl)-N-methyl-amino)-phenylamino]-1-phenyl-methylidene}-2-indolinone Prepared analogously to Example 43.
Melting point: 195–197° C.
$C_{32}H_{30}N_4O_2$ (502.62).
Mass spectrum: $[M+H]^+$=503.
$C_{32}H_{30}N_4O_2 \times 0.5H_2O$ (511.62).
Calc.: C, 75.12; H, 6.11; N, 10.95. Found: 75.41; 6.00; 10.92.

EXAMPLE 371

(Z)-3-{1-[4-(N-(2-methoxyethylaminomethylcarbonyl)-N-methyl-amino)-phenylamino]-1-phenyl-methylidene}-2-indolinone Prepared analogously to Example 43.
Melting point: 186–188° C.
$C_{27}H_{28}N_4O_3$ (456.54).
Mass spectrum: $M^+$=456.

EXAMPLE 372

(Z)-3-{1-[4-(N—(N-(2-methoxyethyl)-N-methyl-aminomethylcarbonyl)-N-methyl-amino)-phenylamino]-1-phenyl-methylidene}-2-indolinone Prepared analogously to Example 43.
Melting point: 197–199° C.
$C_{28}H_{30}N_4O_3$ (470.57).
Mass spectrum: $M^+$=470.

EXAMPLE 373

(Z)-3-{1-[4-(N-(2-morpholinoethylaminomethylcarbonyl)-N-methyl-amino)-phenylamino]-1-phenyl-methylidene}-2-indolinone Prepared analogously to Example 43.
Melting point: 117–119° C.
$C_{30}H_{33}N_5O_3$ (511.62).
Mass spectrum: $M^+$=511.

EXAMPLE 374

(Z)-3-{1-[4-(N—(N-(2-morpholinoethyl)-N-methyl-aminomethyl-carbonyl)-N-methylamino)-phenylamino]-1-phenyl-methylidene}-2-indolinone Prepared analogously to Example 43.
Melting point: 116–118° C.
$C_{31}H_{35}N_5O_3$ (525.65).
Mass spectrum: $M^+$=525.

EXAMPLE 375

(Z)-3-{1-[4-(N—(N-(2-dimethylaminoethyl)-N-methyl-aminomethylcarbonyl)-N-methylamino)-phenylamino]-1-phenyl-methylidene}-2-indolinone Prepared analogously to Example 43.
Melting point: 167–169° C.
$C_{29}H_{33}N_5O_2$ (483.61).
Mass spectrum: $M^+$=483.

EXAMPLE 376

(Z)-3-{1-[4-(N-(2-tert.butoxycarbonylamino-ethylcarbonyl)-N-methyl-amino)-phenylamino]-1-phenyl-methylidene}-2-indolinone Prepared analogously to Example 39.
Melting point: 246–248° C.
$C_{30}H_{32}N_4O_4$ (512.61).
Mass spectrum: $M^+$=512.
Calc.: C, 70.29; H, 6.29; N, 10.93. Found: 70.43; 6.15; 11.12.

EXAMPLE 377

(Z)-3-{1-[4-(N-(2-aminoethylcarbonyl)-N-methyl-amino)-phenylamino]-1-phenyl-methylidene}-2-indolinone-hydrochloride Prepared analogously to Example 376 and 29a.
Melting point: 97–99° C.
$C_{25}H_{24}N_4O_2$ (412.49).
Mass spectrum: $M^+$=412.

EXAMPLE 378

(Z)-3-{1-[4-(N-(2-acetylamino-ethylcarbonyl)-N-methyl-amino)-phenylamino]-1-phenyl-methylidene}-2-indolinone Prepared analogously to Example 376 and 31.
Melting point: 187–189° C.
$C_{27}H_{26}N_4O_3$ (454.53).
Mass spectrum: $M^+$=454.

EXAMPLE 379

(Z)-3-{1-[4-(2-dimethylamino-ethylsulphonylamino)-phenylamino]-1-phenyl-methylidene}-2-indolinone a) 4-(2-dimethylamino-ethylsulphonylamino)-nitrobenzene
2.45 g (15 mmol) of 2-chloroethanesulphonic acid chloride are slowly added dropwise at 0° C. to a solution of 1.4 g (10 mmol) of nitroaniline in 25 ml of pyridine. The mixture is then stirred for 2 hours at ambient temperature. After removal of the solvent in vacuo the residue is combined with water. The precipitate is suction filtered and washed with water. 3.0 g of 1-[2-(4-nitrophenylsulphamoyl)-ethyl]-pyridinium-chloride are obtained as a crude product. 2.6 g of this crude product are dissolved in 25 ml of DMF and combined with 2 g (20 mmol) of triethylamine and 1.2 g (15 mmol) of dimethylamine-hydrochloride. The mixture is stirred for 1.5 hours at 100° C., then the reaction solution is poured into water and extracted with ethyl acetate. The organic extracts are dried over magnesium sulphate and evaporated to dryness.

Yield: 1.6 g (59% of theory).
$R_f$ value: 0.26 (silica gel; dichloromethane/methanol/$NH_4OH$=7:3:0.1).

b) 4-(2-dimethylamino-ethylsulphonylamino)-aniline

Prepared analogously to Example 39c by catalytic hydrogenation of 4-(2-dimethylamino-ethylsulphonylamino)-nitrobenzene.

Yield: 88% of theory.
$R_f$ value: 0.34 (silica gel; dichloromethane/methanol=7:3).

c) (Z)-3-{1-[4-(2-dimethylamino-ethylsulphonylamino)-phenylamino]-1-phenyl-methylidene}-2-indolinone Prepared analogously to Example 39 from 3-(1-ethoxy-1-phenyl-methylidene)-2-indolinone and 4-(2-dimethylamino-ethylsulphonylamino)-aniline.

Yield: 50% of theory.
Melting point: 214–216° C.
$C_{25}H_{26}N_4O_3S$ (462.57).
Mass spectrum: $M^+$=462.
Calc.: C, 64.92; H, 5.67; N, 12.11. Found: 64.88; 5.71; 11.98.

EXAMPLE 380

(Z)-3-{1-[4-(2-piperidinoethylsulphonylamino)-phenylamino]-1-phenyl-methylidene}-2-indolinone Prepared analogously to Example 379.
Melting point: 225–227° C.
$C_{28}H_{30}N_4O_3S$ (502.64).
Mass spectrum: $M^+$=502.
Calc.: C, 66.91; H, 6.02; N, 11.15. Found: 67.09; 5.95; 11.10.

EXAMPLE 381

(Z)-3-{1-[4-(2-morpholinoethylsulphonylamino)-phenylamino]-1-phenyl-methylidene}-2-indolinone Prepared analogously to Example 379.
Melting point: 240–242° C.
$C_{27}H_{28}N_4O_4S$ (504.61).
Mass spectrum: $M^+$=504.

EXAMPLE 382

(Z)-3-{1-[4-(N-(2-dimethylamino-ethylsulphonyl)-N-methyl-amino)-phenylamino]-1-phenyl-methylidene}-2-indolinone a) 4-[N-(2-dimethylamino-ethylsulphonyl)-N-methyl-amino]-nitrobenzene 0.49 g (4.4 mmol) of potassium tert.butoxide are added at ambient temperature to a solution of 1.1 g (4 mmol) of 4-(2-dimethylamino-ethylsulphonylamino)-nitrobenzene (Example 379a) in 20 ml of DMSO. After 1.5 hours stirring 0.85 g (6 mmol) of methyl iodide are added. The mixture is stirred for 18 hours, then the reaction solution is poured into water and extracted with ethyl acetate. The combined organic phases are dried over magnesium sulphate and the solvent is eliminated in vacuo. 0.9 g of ethenesulphonic acid-N-(4-nitrophenyl)-N-methyl-amide are obtained as a crude product. 0.75 g of this crude product are dissolved in ethanol and combined with an excess of dimethylamine. After 18 hours stirring the mixture is evaporated to dryness.

Yield: 81% of theory.
$R_f$ value: 0.35 (silica gel; dichloromethane/methanol 19:1).

b) 4-[N-(2-dimethylamino-ethylsulphonyl)-N-methyl-amino]-aniline

Prepared analogously to Example 39c by catalytic hydrogenation of 4-[N-(2 -dimethylamino-ethylsulphonyl)-N-methyl-amino]-nitrobenzene.

Yield: 89% of theory.
$R_f$ value: 0.29 (silica gel; dichloromethane/methanol=9:1).

c) (Z)-3-{1-[4-(N-(2-dimethylamino-ethylsulphonyl)-N-methyl-amino)-phenylamino]-1-phenyl-methylidene}-2-indolinone Prepared analogously to Example 39 from 3-(1-ethoxy-1-phenyl-methylidene)-2-indolinone and 4-[N-(2-dimethylamino-ethylsulphonyl)-N-methyl-amino]-aniline.

Yield: 42% of theory.
Melting point: 165–168° C.
$C_{26}H_{28}N_4O_3S$ (476.60).
Mass spectrum: $[M+H]^+$=476.

EXAMPLE 383

(Z)-3-{1-[4-(N-(2-piperidinoethylsulphonyl)-N-methyl-amino)-phenylamino]-1-phenyl-methylidene}-2-indolinone Prepared analogously to Example 382.
Melting point: 121–123° C.
$C_{29}H_{32}N_4O_3S$ (516.66).
Mass spectrum: $M^+$=516.

EXAMPLE 384

(Z)-3-{1-[4-(N-(2-morpholinoethylsulphonyl)-N-methyl-amino)-phenylamino]-1-phenyl-methylidene}-2-indolinone Prepared analogously to Example 382.
Melting point: 115–117° C.
$C_{28}H_{30}N_4O_4S$ (518.63).
Mass spectrum: $M^+$=518.

EXAMPLE 385

(Z)-3-{1-[4-(diethylaminocarbonyl)-phenylamino]-1-phenyl-methylidene}-2-indolinone Prepared analogously to Example 18.
Melting point: 202–204° C.
$C_{26}H_{25}N_3O_2$ (411.50).
Mass spectrum: $M^+$=411.

EXAMPLE 386

(Z)-3-{1-[4-(pyrrolidin-1-ylcarbonyl)-phenylamino]-1-phenyl-methylidene}-2-indolinone Prepared analogously to Example 18.
Melting point: 127–129° C.

$C_{26}H_{23}N_3O_2$ (409.49).
Mass spectrum: $M^+=409$.

EXAMPLE 387

(Z)-3-{1-[4-(piperidinocarbonyl)-phenylamino]-1-phenyl-methylidene}-2-indolinone Prepared analogously to Example 18.
Melting point: 212–214° C.
$C_{27}H_{25}N_3O_2$ (423.51).
Mass spectrum: $M^+=423$.

EXAMPLE 388

(Z)-3-{1-[4-(2-methoxyethylaminocarbonyl)-phenylamino]-1-phenyl-methylidene}-2-indolinone Prepared analogously to Example 18.
Melting point: 277–279° C.
$C_{25}H_{23}N_3O_3$ (413.47).
Mass spectrum: $M^+=413$.

EXAMPLE 389

(Z)-3-{1-[4-(N-(2-methoxyethyl)-N-methyl-aminocarbonyl)-phenylamino]-1-phenyl-methylidene}-2-indolinone Prepared analogously to Example 18.
Melting point: 198–200° C.
$C_{26}H_{25}N_3O_3$ (427.50).
Mass spectrum: $M^+=427$.
Calc.: C, 73.05; H, 5.89; N, 9.83. Found: 72.75; 6.04; 9.75.

EXAMPLE 390

(Z)-3-{1-[4-(2-dimethylamino-ethylaminocarbonyl)-phenylamino]-1-phenyl-methylidene}-2-indolinone Prepared analogously to Example 18.
Melting point: 145–147° C.
$C_{26}H_{26}N_4O_2$ (426.52).
Mass spectrum: $M^+=426$.

EXAMPLE 391

(Z)-3-{1-[4-(N-(2-dimethylaminoethyl)-N-methyl-aminocarbonyl)-phenylamino]-1-phenyl-methylidene}-2-indolinone Prepared analogously to Example 18.
Melting point: 181–183° C.
$C_{27}H_{28}N_4O_2$ (440.54).
Mass spectrum: $M^+=440$.
Calc.: C, 73.61; H, 6.41; N, 12.72. Found: 73.51; 6.59; 12.75.

EXAMPLE 392

(Z)-3-{1-[4-(ethoxycarbonylmethylaminocarbonyl)-phenylamino]-1-phenyl-methylidene}-2-indolinone Prepared analogously to Example 18.
Melting point: 235–237° C.
$C_{26}H_{23}N_3O_4$ (441.48).
Mass spectrum: $M^+=441$.

EXAMPLE 393

(Z)-3-{1-[4-(carboxymethylaminocarbonyl)-phenylamino]-1-phenyl-methylidene}-2-indolinone Prepared analogously to Example 392 and 8.
Melting point: 245–247° C.
$C_{24}H_{19}N_3O_4$ (413.43).
Mass spectrum: $M^+=413$.

EXAMPLE 394

(Z)-3-{1-[4-(N-ethoxycarbonylmethyl-N-methyl-aminocarbonyl)-phenylamino]-1-phenyl-methylidene}-2-indolinone Prepared analogously to Example 18.
Melting point: 95–98° C.
$C_{27}H_{25}N_3O_4$ (455.51).
Mass spectrum: $M^+=455$.

EXAMPLE 395

(Z)-3-{1-[4-(N-carboxymethyl-N-methyl-aminocarbonyl)-phenylamino]-1-phenyl-methylidene}-2-indolinone Prepared analogously to Example 394 and 8.
Melting point: 168–170° C.
$C_{25}H_{21}N_3O_4$ (427.46).
Mass spectrum: $M^+=427$.

EXAMPLE 396

(Z)-3-{1-[4-(aminosulphonyl)-phenylamino]-1-phenyl-methylidene}-2-indolinone

Prepared analogously to Example 39d.
Melting point: 254° C.
$C_{21}H_{17}N_3O_3S$ (391.45).
Mass spectrum: $M^+=391$.
$C_{21}H_{17}N_3O_3S \times H_2O$ (409.35).
Calc.: C, 61.60; H, 4.68; N, 10.26. Found: 61.86; 4.72; 10.27.

EXAMPLE 397

(Z)-3-{1-[4-(pyrrolidin-1-ylsulphonyl)-phenylamino]-1-phenyl-methylidene}-2-indolinone a) 4-(pyrrolidin-1-ylsulphonyl)-aniline 525 mg (3 mmol) of sulphanilic acid fluoride and 1.07 g (15 mmol) of pyrrolidine are heated together to 80° C. for 15 minutes. Then water is added to the reaction mixture. The precipitate formed is filtered off and recrystallised from methanol.
Yield: 375 mg (55% of theory).
Melting point: 170–172° C.
$R_f$ value: 0.44 (silica gel; dichloromethane/ethyl acetate= 9:1).

b) (Z)-3-{1-[4-(pyrrolidin-1-ylsulphonyl)-phenylamino]-1-phenyl-methylidene}-2-indolinone Prepared analogously to Example 1c from 1-acetyl-3-(1-ethoxy-1-phenyl-methylidene)-2-indolinone and 4-(pyrrolidin-1-ylsulphonyl)-aniline.

Yield: 45% of theory.
Melting point: 293–294° C.
$C_{25}H_{23}N_3O_3S$ (445.54).
Mass spectrum: $M^+$=445.
$C_{25}H_{23}N_3O_3S \times 0.25H_2O$ (450.04).
Calc.: C, 66.72; H, 5.26; N, 9.34. Found: 66.62; 5.29; 9.12.

EXAMPLE 398

(Z)-3-{1-[4-(diethylaminosulphonyl)-phenylamino]-1-phenyl-methylidene}-2-indolinone Prepared analogously to Example 397.
Melting point: 252–254° C.
$C_{25}H_{25}N_3O_3S$ (447.56).
Mass spectrum: $M^+$=447.
Calc.: C, 67.09; H, 5.63; N, 9.39. Found: 66.96; 5.68; 9.25.

EXAMPLE 399

(Z)-3-{1-[4-(2-dimethylamino-ethylaminosulphonyl)-phenylamino]-1-phenyl-methylidene}-2-indolinone Prepared analogously to Example 397.
Melting point: 233–235° C.
$C_{25}H_{26}N_4O_3S$ (462.57).
Mass spectrum: $M^+$=462.
$C_{25}H_{26}N_4O_3S \times 0.25H_2O$ (467.07).
Calc.: C, 64.29; H, 5.72; N, 12.00. Found: 64.15; 5.64; 12.00.

EXAMPLE 400

(Z)-3-{1-[4-(N-(2-dimethylaminoethyl)-N-methyl-aminosulphonyl)-phenylamino]-1-phenyl-methylidene}-2-indolinone Prepared analogously to Example 397.
Melting point: 200–203° C.
$C_{26}H_{28}N_4O_3S$ (476.60).
Mass spectrum: $M^+$=476.

EXAMPLE 401

(Z)-3-{1-[4-(2-dimethylamino-ethylaminosulphonyl)-phenylamino]-1-phenyl-methylidene}-5-nitro-2-indolinone Prepared analogously to Example 397.
Melting point: 260–261° C.
$C_{25}H_{25}N_5O_5S$ (507.57).
Mass spectrum: $M^+$=507.

EXAMPLE 402

(Z)-3-{1-[4-(N-(2-dimethylaminoethyl)-N-methyl-aminosulphonyl)-phenylamino]-1-phenyl-methylidene}-5-nitro-2-indolinone Prepared analogously to Example 397.
Melting point: 215–218° C.
$C_{26}H_{27}N_5O_5S$ (521.60).
Mass spectrum: $[M+H]^+$=522.
$C_{26}H_{27}N_5O_5S \times 0.3H2O$ (527.00).
Calc.: C, 59.26; H, 5.28; N, 13.29. Found: 59.25; 5.19; 13.17.

EXAMPLE 403

(Z)-3-{1-[4-(3-dimethylamino-propylaminosulphonyl)-phenylamino]-1-phenyl-methylidene}-5-nitro-2-indolinone Prepared analogously to Example 397.
Melting point: 268–269° C.
$C_{26}H_{27}N_5O_5S$ (521.60).
Mass spectrum: $M^+$=521.
Calc.: C, 59.87; H, 5.22; N, 13.43. Found: 59.65; 5.32; 13.26.

EXAMPLE 404

(Z)-3-{1-[4-(N-(3-dimethylaminopropyl)-N-methyl-aminosulphonyl)-phenylamino]-1-phenyl-methylidene}-5-nitro-2-indolinone Prepared analogously to Example 397.
Melting point: 269–270° C. (decomposition).
$C_{27}H_{29}N_5O_5S$ (535.62).
Mass spectrum: $M^+$=535.
Calc.: C, 60.55; H, 5.46; N, 13.08. Found: 60.28; 5.56; 12.90.

EXAMPLE 405

(Z)-3-{1-[4-(dimethylaminosulphonyl)-phenylamino]-1-phenyl-methylidene}-2-indolinone a) 4-nitrobenzenesulphonic acid-dimethylamide 4.43 g (20 mmol) of 4-nitrobenzenesulphonic acid chloride are added dropwise at 0° C. to a solution of 2.45 g (30 mmol) of dimethylamine-hydrochloride and 6.46 g (50 mmol) of N,N-diisopropyl-N-methylamine in 30 ml of dichloromethane. The mixture is stirred for 18 hours at ambient temperature. Then the reaction solution is washed with water and dilute hydrochloric acid, dried over magnesium sulphate and evaporated to dryness.
Yield: 4.4 g (90% of theory).

b) 4-aminobenzenesulphonic acid-dimethylamide

Prepared analogously to Example 39c by catalytic hydrogenation of 4-nitrobenzenesulphonic acid-dimethylamide.
Yield: 78% of theory.
Melting point: 172–173° C.

c) (Z)-3-{1-[4-(dimethylaminosulphonyl)-phenylamino]-1-phenyl-methylidene}-2-indolinone Prepared analogously to Example 1c from 1-acetyl-3-(1-ethoxy-1-phenyl-methylidene)-2-indolinone and 4-aminobenzenesulphonic acid-dimethylamide.
Yield: 78% of theory.
Melting point: 280° C.
$C_{23}H_{21}N_3O_3S$ (419.50).
Mass spectrum: $M^+$=419.
Calc.: C, 65.85; H, 5.05; N, 10.02. Found: 65.54; 5.24; 9.96.

EXAMPLE 406

(Z)-3-{1-[4-(ethoxycarbonylmethylaminosulphonyl)-phenylamino]-1-phenyl-methylidene}-2-indolinone Prepared analogously to Example 405.
Melting point: 196–199° C.

$C_{25}H_{23}N_3O_5S$ (477.54).

Mass spectrum: $M^+$=477.

Calc.: C, 62.88; H, 4.85; N, 8.80. Found: 62.79; 5.04; 8.68.

EXAMPLE 407

(Z)-3-{1-[4-(carboxymethylaminosulphonyl)-phenylamino]-1-phenyl-methylidene}-2-indolinone Prepared analogously to Example 406 and 8.

Melting point: 236° C. (decomposition).

$C_{23}H_{19}N_3O_5S$ (449.49).

Mass spectrum: $M^+$=449.

EXAMPLE 408

(Z)-3-{1-[4-(N-ethoxycarbonylmethyl-N-methyl-aminosulphonyl)-phenylamino]-1-phenyl-methylidene}-2-indolinone Prepared analogously to Example 405.

Melting point: 178–180° C.

$C_{26}H_{25}N_3O_5S$ (491.57).

Mass spectrum: $M^+$=491.

EXAMPLE 409

(Z)-3-{1-[4-(N-carboxymethyl-N-methyl-aminosulphonyl)-phenylamino]-1-phenyl-methylidene}-2-indolinone Prepared analogously to Example 408 and 8.

Melting point: 237° C. (decomposition).

$C_{24}H_{21}N_3O_5S$ (463.51).

Mass spectrum: $M^+$=463.

EXAMPLE 410

(Z)-3-{1-[4-(ethoxycarbonylmethylaminosulphonyl)-phenylamino]-1-phenyl-methylidene}-5-nitro-2-indolinone Prepared analogously to Example 405.

Melting point: 247–249° C.

$C_{25}H_{22}N_4O_7S$ (522.54).

Mass spectrum: $M^+$=522.

Calc.: C, 57.47; H, 4.24; N, 10.72. Found: 57.44; 4.22; 10.66.

EXAMPLE 411

(Z)-3-{1-[4-(carboxymethylaminosulphonyl)-phenylamino]-1-phenyl-methylidene}-5-nitro-2-indolinone Prepared analogously to Example 410 and 8.

Melting point: 177–180° C. (decomposition).

$C_{23}H_{18}N_4O_7S$ (494.48).

Mass spectrum: $M^+$=494.

$C_{23}H_{18}N_4O_7S \times H_2O$ (512.50).

Calc.: C, 53.90; H, 3.93; N, 10.93. Found: 53.98; 3.95; 10.86.

EXAMPLE 412

(Z)-3-{1-[4-(dimethylaminocarbonylmethylaminosulphonyl)-phenylamino]-1-phenyl-methylidene}-5-nitro-2-indolinone Prepared analogously to Example 411 and 18.

Melting point: 281–283° C.

$C_{25}H_{23}N_5O_6S$ (521.55).

Mass spectrum: $M^+$=521.

$C_{25}H_{23}N_5O_6S \times 0.5H_2O$ (530.56).

Calc.: C, 56.60; H, 4.56; N, 13.20. Found: 56.51; 4.56; 13.15.

EXAMPLE 413

(Z)-3-{1-[4-(N-ethoxycarbonylmethyl-N-methyl-aminosulphonyl)-phenylamino]-1-phenyl-methylidene}-5-nitro-2-indolinone Prepared analogously to Example 405.

Melting point: 206–207° C.

$C_{26}H_{24}N_4O_7S$ (536.56).

Mass spectrum: $M^+$=536.

EXAMPLE 414

(Z)-3-{1-[4-(N-carboxymethyl-N-methyl-aminosulphonyl)-phenylamino]-1-phenyl-methylidene}-5-nitro-2-indolinone Prepared analogously to Example 413 and 8.

Melting point: 259–260° C.

$C_{24}H_{20}N_4O_7S$ (508.51).

Mass spectrum: $M^+$=508.

EXAMPLE 415

(Z)-3-{1-[4-(N-dimethylaminocarbonylmethyl-N-methyl-aminosulphonyl)-phenylamino]-1-phenyl-methylidene}-5-nitro-2-indolinone Prepared analogously to Example 414 and 18.

Melting point: 277–278° C.

$C_{26}H_{25}N_5O_6S$ (535.58).

Mass spectrum: $M^+$=535.

Calc.: C, 58.31; H, 4.71; N, 13.08. Found: 58.07; 4.68; 13.03.

EXAMPLE 416

(Z)-3-{1-[3-(N-aminocarbonylmethyl-N-methylsulphonyl-amino)-phenylamino]-1-(4-aminomethyl-phenyl)-methylidene}-2-indolinone Prepared analogously to Examples 146, 148 and 191.

Melting point: 167° C.

$C_{25}H_{25}N_5O_4S$ (491.57).

Mass spectrum: $[M+H]^+$=492.

EXAMPLE 417

(Z)-3-{1-[3-(N-aminocarbonylmethyl-N-methylsulphonyl-amino)-phenylamino]-1-(4-acetylaminomethyl-phenyl)-methylidene}-2-indolinone Prepared analogously to Example 416 and 31.

Melting point: 215° C.

$C_{27}H_{27}N_5O_5S$ (533.61).

Mass spectrum: $[M-H]^-$=532.

EXAMPLE 418

(Z)-3-{1-[3-(N-methylaminocarbonylmethyl-N-methylsulphonyl-amino)-phenylamino]-1-(4-aminomethyl-phenyl)-methylidene}-2-indolinone Prepared analogously to Example 146, 148 and 192.

Melting point: 164° C.

$C_{26}H_{27}N_5O_4S$ (505.60).

Mass spectrum: $M^+=505$.

$C_{26}H_{27}N_5O_4S \times 0.7H_2O$ (518.21).

Calc.: C, 60.26; H, 5.52; N, 13.51. Found: 60.28; 5.51; 13.78.

EXAMPLE 419

(Z)-3-{1-[3-(N-methylaminocarbonylmethyl-N-methylsulphonyl-amino)-phenylamino]-1-(4-acetylaminomethyl-phenyl)-methylidene}-2-indolinone Prepared analogously to Example 418 and 31.

Melting point: 242° C.

$C_{28}H_{29}N_5O_5S$ (547.63).

Mass spectrum: $M^+=547$.

$C_{28}H_{29}N_5O_5S \times 0.5H_2O$ (556.64).

Calc.: C, 60.42; H, 5.43; N, 12.58. Found: 60.67; 5.67; 12.30.

EXAMPLE 420

(Z)-3-{1-[3-(N-dimethylaminocarbonylmethyl-N-methylsulphonyl-amino)-phenylamino]-1-(4-aminomethyl-phenyl)-methylidene}-2-indolinone Prepared analogously to Example 146, 148 and 192.

Melting point: 220° C.

$C_{27}H_{29}N_5O_4S$ (519.62).

Mass spectrum: $[M+H]^+=520$.

$C_{27}H_{29}N_5O_4S$ $0.2H_2O$ (523.23).

Calc.: C, 61.98; H, 5.66; N, 13.38. Found: 61.95; 5.73; 13.27.

EXAMPLE 421

(Z)-3-{1-[3-(N-dimethylaminocarbonylmethyl-N-methylsulphonyl-amino)-phenylamino]-1-(4-acetylaminomethyl-phenyl)-methylidene}-2-indolinone Prepared analogously to Example 420 and 31.

Melting point: 194° C. (sintering).

$C_{29}H_{31}N_5O_5S$ (561.66).

Mass spectrum: $[M-H]^-=560$.

EXAMPLE 422

(Z)-3-{1-[3-(N-(2-dimethylaminoethyl)-N-methylsulphonyl-amino)-phenylamino]-1-(4-aminomethyl-phenyl)-methylidene}-2-indolinone Prepared analogously to Example 146, 148 and 324.

Melting point: 161° C.

$C_{27}H_{31}N_5O_3S$ (505.64).

Mass spectrum: $M^+=505$.

EXAMPLE 423

(Z)-3-{1-[3-(N-(2-dimethylaminoethyl)-N-methylsulphonyl-amino)-phenylamino]-1-(4-acetylaminomethyl-phenyl)-methylidene}-2-indolinone Prepared analogously to Example 422 and 31.

Melting point: 180° C.

$C_{29}H_{33}N_5O_4S$ (547.68).

Mass spectrum: $M^+=547$.

EXAMPLE 424

(Z)-3-{1-[3-(N-(3-dimethylaminopropyl)-N-methylsulphonyl-amino)-phenylamino]-1-(4-aminomethyl-phenyl)-methylidene}-2-indolinone Prepared analogously to Example 146, 148 and 324.

Melting point: 197° C.

$C_{28}H_{33}N_5O_3S$ (519.67).

Mass spectrum: $M^+=519$.

$C_{28}H_{33}N_5O_3S$ $0.5H_2O$ (528.67).

Calc.: C, 63.61; H, 6.48; N, 13.25. Found: 63.64; 6.47; 13.39.

EXAMPLE 425

(Z)-3-{1-[3-(N-(3-dimethylaminopropyl)-N-methylsulphonyl-amino)-phenylamino]-1-(4-acetylaminomethyl-phenyl)-methylidene}-2-indolinone Prepared analogously to Example 424 and 31.

Melting point: 208° C.

$C_{30}H_{35}N_5O_4S$ (561.70).

Mass spectrum: $M^+=561$.

$C_{30}H_{35}N_5O_4S$ $0.8H2O$ (576.12).

Calc.: C, 62.54; H, 6.40; N, 12.16. Found: 62.51; 6.37; 12.13.

EXAMPLE 426

(Z)-3-{1-[4-(N-(2-dimethylaminoethyl)-N-methylsulphonyl-amino)-phenylamino]-1-(4-aminomethyl-phenyl)-methylidene}-2-indolinone Prepared analogously to Example 146, 148 and 188.

Melting point: 203–205° C.

$C_{27}H_{31}N_5O_3S$ (505.64).

Mass spectrum: $M^+=505$.

EXAMPLE 427

(Z)-3-{1-[4-(N-(2-dimethylaminoethyl)-N-methylsulphonyl-amino)-phenylamino]-1-(4-acetylaminomethyl-phenyl)-methylidene}-2-indolinone Prepared analogously to Example 426 and 31.

Melting point: 225–227° C.

$C_{29}H_{33}N_5O_4S$ (547.68).

Mass spectrum: $M^+=547$.

EXAMPLE 428

(Z)-3-{1-[4-(N-dimethylaminocarbonylmethyl)-N-methylsulphonyl-amino)-phenylamino]-1-(4-aminomethyl-phenyl)-methylidene}-2-indolinone Prepared analogously to Example 146, 148 and 193.

Melting point: 118–120° C.

$C_{27}H_{29}N_5O_4S$ (519.62).

Mass spectrum: $[M+H]^+=520$.

EXAMPLE 429

(Z)-3-{1-[4-(N-dimethylaminocarbonylmethyl)-N-methylsulphonyl-amino)-phenylamino]-1-(4-acetylaminomethyl-phenyl)-methylidene}-2-indolinone Prepared analogously to Example 428 and 31.

Melting point: 147–149° C.

$C_{29}H_{31}N_5O_5S$ (561.66).
Mass spectrum: $[M-H]^-=560$.

EXAMPLE 430

(Z)-3-{1-[4-(N-dimethylaminomethylcarbonyl-N-methyl-amino)-phenylamino]-1-(4-aminomethyl-phenyl)-methylidene}-2-indolinone Prepared analogously to Example 146, 148 and 48.
Melting point: 188–190° C.
$C_{27}H_{29}N_5O_2$ (455.56).
Mass spectrum: $M^+=455$.

EXAMPLE 431

(Z)-3-{1-[4-(N-dimethylaminomethylcarbonyl-N-methyl-amino)-phenylamino]-1-(4-acetylaminomethyl-phenyl)-methylidene}-2-indolinone Prepared analogously to Example 430 and 31.
Melting point: 123–125° C.
$C_{29}H_{31}N_5O_3$ (497.60).
Mass spectrum: $M^+=497$.

EXAMPLE 432

(Z)-3-[1-(4-piperdinomethyl-phenylamino)-1-(4-bromophenyl)-methylidene]-5-nitro-2-indolinone Prepared analogously to Example 146.
Melting point: 295–297° C.
$C_{27}H_{25}BrN_4O_3$ (533.42).
Mass spectrum: $M^+=534/532$.

EXAMPLE 433

(Z)-3-[1-(4-piperdinomethyl-phenylamino)-1-(4-iodophenyl)-methylidene]-5-nitro-2-indolinone Prepared analogously to Example 146.
Melting point: 280–283° C.
$C_{27}H_{25}IN_4O_3$ (580.42).
Mass spectrum: $[M+H]^+=581$.

EXAMPLE 434

(Z)-3-[1-(4-methoxyphenylamino)-1-(4-iodphenyl)-methylidene]-5-nitro-2-indolinone Prepared analogously to Example 146.
Melting point: 280–283° C.
$C_{22}H_{16}IN_3O_4$ (513.29).
Mass spectrum: $M^+=513$.

EXAMPLE 435

(Z)-3-{1-(4-methoxyphenylamino)-1-[(E)-4-(2-methoxycarbonylethenyl)-phenyl]-methylidene}-5-nitro-2-indolinone 257 mg (0.5 mmol) of (Z)-3-[1-(4-methoxyphenylamino)-1-(4-iodophenyl)-methylidene]-5-nitro-2-indolinone (Example 434), 0.06 ml (0.75 mmol) of methyl acrylate, 4.5 mg (0.02 mmol) of palladium-II-acetate and 1 ml of (7.2 mmol) of triethylamine are dissolved in 20 ml of acetonitrile under a nitrogen atmosphere. The solution is heated for 10 hours to 80° C. Then the reaction solution is filtered through Celite and the solvent is eliminated in vacuo. The residue is chromatographed on silica gel (dichloromethane/methanol=20:1).

Yield: 0.2 g (85% of theory).
Melting point: 266–270° C.
$C_{26}H_{21}N_3O_6$ (471.47).
Mass spectrum: $M^+=471$.

EXAMPLE 436

(Z)-3-{1-[4-(N-(2-dimethylaminoethyl)-N-methylsulphonyl-phenylamino]-1-[4-methoxyphenyl]-methylidene}-2-indolinone Prepared analogously to Example 146 and 188.
Melting point: 219° C.
$C_{27}H_{30}N_4O_4S$ (506.62).
Mass spectrum: $M^+=506$.
$C_{27}H_{30}N_4O_4S \times 0.2H_2O$ (510.23).
Calc.: C, 63.56; H, 6.01; N, 10.98. Found: 63.61; 6.11; 10.97.

EXAMPLE 437

(Z)-3-{1-[4-(N-(2-dimethylaminoethyl)-N-methylsulphonyl-phenylamino]-1-[4-chlorophenyl]-methylidene}-2-indolinone Prepared analogously to Example 146 and 188.
Melting point: 263° C.
$C_{26}H_{27}ClN_4O_3S$ (511.04).
Mass spectrum: $M^+=512/510$.

EXAMPLE 438

(Z)-3-{1-[4-Bromophenylamino]-1-[4-(imidazol-1-ylmethyl)-phenyl]-methylidene}-5-nitro-2-indolinone Prepared analogously to Example 146.
Melting point: 260–265° C.
$C_{25}H_{18}BrN_5O_3$ (516.35).
Mass spectrum: $M^+=517/515$.

EXAMPLE 439

(Z)-3-{1-[4-piperidinomethyl-phenylamino]-1-[4-(imidazol-1-yl-methyl)-phenyl]-methylidene}-5-nitro-2-indolinone Prepared analogously to Example 146.
Melting point: 226–228° C.
$C_{31}H_{30}N_6O_3$ (534.62).
Mass spectrum: $M^+=535$.

EXAMPLE 440

(Z)-3-{1-[4-(N-benzyl-N-methyl-aminomethyl)-phenylamino]-1-[4-(imidazol-1-ylmethyl)-phenyl]-methylidene}-5-nitro-2-indolinone Prepared analogously to Example 146.
Melting point: 195–198° C.
$C_{34}H_{30}N_6O_3$ (570.65).
Mass spectrum: $[M+H]^+=571$.

EXAMPLE 441

(Z)-3-[1-(4-piperidinomethyl-phenylamino)-1-(4-methoxyphenyl)-methylidene]-5-nitro-2-indolinone a) diethyl [methoxy-(4-methoxyphenyl)-methyl]-phosphonate 4.3 ml (35 mmol) of boron trifluoride-etherate are added dropwise at −20° C. to a solution of 5.6 ml (33 mmol) of anisaldehyde dimethylacetal and 5.7 ml (33 mmol) of triethylphosphite in 60 ml of dichloromethane under a nitrogen atmosphere. The mixture is stirred for 18 hours at ambient temperature and then water is added. After 1 hour's stirring the phases are separated. The organic phase is dried over magnesium sulphate and the solvent is eliminated in vacuo. The residue is on silica gel chromatographed (dichloromethane/ethyl acetate, 10:1).

Yield: 7.5 g (79% of theory).
$R_f$ value: 0.5 (silica gel; dichloromethane/ethyl acetate=10:1).

b) 3-[1-methoxy-1-(4-methoxyphenyl)-methylidene]-5-nitro-2-indolinone 6.3 g (22 mmol) of diethyl [methoxy-(4-methoxyphenyl)-methyl]-phosphonate are dissolved in 40 ml of DMF under a nitrogen atmosphere. 5.1 g (45 mmol) of potassium tert.butoxide are added batchwise at −40° C. and the mixture is then stirred for another 30 minutes at −10° C. Then 3.84 g (20 mmol) of 5-nitroisatine are added. The mixture is stirred for 1 hour at ambient temperature and then poured onto ice water containing 20 ml of saturated potassium hydrogen sulphate solution. The precipitate is suction filtered and chromatographed over silica gel (dichloromethane/methanol=10:1).

Yield: 4.4 g (67% of theory).
Melting point: 220–225° C.
$C_{17}H_{14}N_2O_5$ (326.31).
Mass spectrum: $[M-H]^-$=325.

c) (Z)-3-[1-(4-piperidinomethyl-phenylamino)-1-(4-methoxyphenyl)-methylidene]-5-nitro-2-indolinone Prepared analogously to Example 39d from 3-[1-methoxy-1-(4-methoxyphenyl)-methylidene]-5-nitro-2-indolinone and 4-piperidinomethyl-aniline.

Yield: 90% of theory.
Melting point: 230–233° C.
$C_{28}H_{28}N_4O_4$ (484.55).
Mass spectrum: $[M+H]^+$=484.

EXAMPLE 442

(Z)-3-[1-(4-piperidinomethyl-phenylamino)-1-(4-trifluoromethyl-phenyl)-methylidene]-5-nitro-2-indolinone Prepared analogously to Example 441.
Melting point: 300–302° C.
$C_{28}H_{25}F_3N_4O_3$ (522.52).
Mass spectrum: $M^+$=522.

EXAMPLE 443

(Z)-3-[1-(4-piperidinomethyl-phenylamino)-1-(4-chlorophenyl)-methylidene]-5-nitro-2-indolinone Prepared analogously to Example 441.
Melting point: 309–311° C.
$C_{27}H_{25}ClN_4O_3$ (488.97).
Mass spectrum: $[M+H]^+$=491/489.

EXAMPLE 444

(Z)-3-[1-(4-piperidinomethyl-phenylamino)-1-(4-methoxycarbonyl-phenyl)-methylidene]-5-nitro-2-indolinone Prepared analogously to Example 441.
Melting point: 178–83° C.
$C_{29}H_{28}N_4O_5$ (512.56).
Mass spectrum: $M^+$=512.

EXAMPLE 445

(Z)-3-[1-(4-piperidinomethyl-phenylamino)-1-(4-carboxyphenyl)-methylidene]-5-nitro-2-indolinone Prepared analogously to Example 444 and 8.
Melting point: 230° C.
$C_{28}H_{26}N_4O_5$ (498.54).
Mass spectrum: $[M-H]^-$=497.

EXAMPLE 446

(Z)-3-[1-(4-piperidinomethyl-phenylamino)-1-(4-methoxycarbonylmethylaminocarbonyl-phenyl)-methylidene]-5-nitro-2-indolinone Prepared analogously to Example 445 and 18.
Melting point: 230–235° C.
$C_{31}H_{31}N_5O_6$ (569.61).
Mass spectrum: $[M+H]^+$=570.

EXAMPLE 447

(Z)-3-[1-(4-piperidinomethyl-phenylamino)-1-(4-(2-methoxycarbonyl-ethylaminocarbonyl)-phenyl)-methylidene]-5-nitro-2-indolinone Prepared analogously to Example 445 and 18.
Melting point: 130° C.
$C_{32}H_{33}N_5O_6$ (583.64).
Mass spectrum: $M^+$=583.

EXAMPLE 448

(Z)-3-[1-(4-piperidinomethyl-phenylamino)-1-phenyl-methylidene]-6-nitro-2-indolinone a) 1-hydroxy-6-nitro-2-indolinone 31 g (137 mmol) of 2,4-dinitrophenylacetic acid are dissolved in 400 ml of ethyl acetate and hydrogenated over Pd-charcoal analogously to Example 39c.

Yield: 13.2 g (50% of theory).
$R_f$ value: 0.6 (silica gel; dichloromethane/methanol 9:1).
$C_8H_6N_2O_4$ (194.15).
Mass spectrum: $[M-H]^-$=193.

b) 1-acetoxy-3-(1-ethoxy-1-phenyl-methylidene)-6-nitro-2-indolinone

Prepared analogously to Example 1b from 1-hydroxy-6-nitro-2-indolinone and triethyl orthobenzoate in acetic anhydride.

Yield: 62% of theory.
$R_f$ value: 0.3 (silica gel; dichloromethane).
$C_{19}H_{16}N_2O_6$ (368.35).
Mass spectrum: $[M+Na]^+$=391.

c) (Z)-3-[1-(4-piperidinomethyl-phenylamino)-1-phenyl-methylidene]-1-hydroxy-6-nitro-2-indolinone Prepared analogously to Example 1c from 1-acetoxy-3-(1-ethoxy-1-phenyl-methylidene)-6-nitro-2-indolinone and 4-piperidino-methyl-aniline.

Yield: 88% of theory.
$R_f$ value: 0.48 (silica gel; dichloromethane/methanol=9:1).
$C_{27}H_{26}N_4O_4$ (470.53).
Mass spectrum: $[M+H]^+$=471.

d) (Z)-3-[1-(4-piperidinomethyl-phenylamino)-1-phenyl-methylidene]-6-nitro-2-indolinone Prepared analogously to Example 39c by catalytic hydrogenation of (Z)-3-[1-(4-piperidinomethyl-phenylamino)-1-phenyl-methylidene]-1-hydroxy-6-nitro-2-indolinone.
Yield: 4% of theory.
$R_f$ value: 0.4 (silica gel; dichloromethane/methanol=9:1).
$C_{27}H_{26}N_4O_3$ (454.53).
Mass spectrum: [M⁺]=454.

EXAMPLE 449

(Z)-3-[1-(4-piperidinomethyl-phenylamino)-1-phenyl-methylidene]-6-bromo-2-indolinone Prepared analogously to Example 1.
$R_f$ value: 0.24 (silica gel; dichloromethane/ethanol=9:1).
$C_{27}H_{26}BrN_3O$ (488.43).
Mass spectrum: M⁺=489/487.

EXAMPLE 450

(Z)-3-[1-(4-piperidinomethyl-phenylamino)-1-phenyl-methylidene]-5-bromo-2-indolinone Prepared analogously to Example 1.
Melting point: 170° C.
$C_{27}H_{26}BrN_3O$ (488.43).
Mass spectrum: M⁺=489/487.

EXAMPLE 451

(Z)-3-[1-(4-(N-(2-dimethylaminoethyl)-N-methoxymethylcarbonyl-amino)-phenylamino)-1-phenyl-methylidene]-2-indolinone Prepared analogously to Example 327.
Melting point: 246–249° C.
$C_{28}H_{30}N_4O_3$ (470.48).
Mass spectrum: [M+H]⁺=471.

EXAMPLE 452

(Z)-3-[1-(4-(N-(2-dimethylaminoethyl)-N-benzoyl-amino)-phenylamino)-1-phenyl-methylidene]-2-indolinone Prepared analogously to Example 327.
Melting point: 272–274° C.
$C_{32}H_{30}N_4O_2$ (505.62).
Mass spectrum: M⁺=502.

EXAMPLE 453

(Z)-3-[1-(4-(N-(2-dimethylaminoethyl)-N-butylsulphonyl-amino)-phenylamino)-1-phenyl-methylidene]-2-indolinone Prepared analogously to Example 188.
Melting point: 225–227° C.
$C_{29}H_{34}N_4O_3S$ (518.68).
Mass spectrum: [M+H]⁺=519.

EXAMPLE 454

(Z)-3-[1-(4-(N-(2-dimethylaminoethyl)-N-(p-tolylsulphonyl)-amino)-phenylamino)-1-phenyl-methylidene]-2-indolinone Prepared analogously to Example 188.
Melting point: 213–215° C.
$C_{32}H_{32}N_4O_3S$ (552.70).
Mass spectrum: M⁺=552.

EXAMPLE 455

(Z)-3-{1-[4-((2,6-dimethylpiperidino)-methyl)-1-phenyl-methylidene]-2-indolinone Prepared analogously to Example 231.
Melting point: 215–17° C.
$C_{29}H_{31}N_3O$ (437.58).
Mass spectrum: (M+H)⁺=438.

The following compounds may be prepared analogously to the preceding Examples:

(1) (Z)-3-[1-(4-piperidinomethyl-phenylamino)-1-phenyl-methylidene]-5-methyl-2-indolinone
(2) (Z)-3-[1-(4-piperidinomethyl-phenylamino)-1-phenyl-methylidene]-5-chloro-2-indolinone
(3) (Z)-3-[1-(4-piperidinomethyl-phenylamino)-1-phenyl-methylidene]-6-methyl-2-indolinone
(4) (Z)-3-[1-(4-piperidinomethyl-phenylamino)-1-phenyl-methylidene]-6-chloro-2-indolinone
(5) (Z)-3-{1-[4-(N-(2-dimethylaminoethyl)-N-methylsulphonyl-amino)-phenylamino]-1-(4-methylphenyl)-methylidene}-2-indolinone
(6) (Z)-3-{1-[4-(N-(2-dimethylaminoethyl)-N-methylsulphonyl-amino)-phenylamino]-1-(3-methylphenyl)-methylidene}-2-indolinone
(7) (Z)-3-{1-[4-(N-(2-dimethylaminoethyl)-N-methylsulphonyl-amino)-phenylamino]-1-(3-methoxyphenyl)-methylidene}-2-indolinone
(8) (Z)-3-{1-[4-(N-(2-dimethylaminoethyl)-N-methylsulphonyl-amino)-phenylamino]-1-(3-chlorophenyl)-methylidene}-2-indolinone
(9) (Z)-3-{1-[4-(N-(2-dimethylaminoethyl)-N-methylsulphonyl-amino)-phenylamino]-1-(4-nitrophenyl)-methylidene}-2-indolinone
(10) (Z)-3-{1-[4-(N-(2-dimethylaminoethyl)-N-methylsulphonyl-amino)-phenylamino]-1-(3-nitrophenyl)-methylidene}-2-indolinone
(11) (Z)-3-{1-[4-(N-(2-aminoethyl)-N-methylsulphonyl-amino)-phenylamino]-1-phenyl-methylidene}-2-indolinone
(12) (Z)-3-{1-[4-(N-(2-acetylaminoethyl)-N-methylsulphonyl-amino)-phenylamino]-1-phenyl-methylidene}-2-indolinone
(13) (Z)-3-{1-[4-(N-(2-methylaminoethyl)-N-methylsulphonyl-amino)-phenylamino]-1-phenyl-methylidene}-2-indolinone
(14) (Z)-3-{1-[4-(N-(2-(N-acetyl-N-methyl-amino)-ethyl)-N-methylsulphonyl-amino)-phenylamino]-1-phenyl-methylidene}-2-indolinone
(15) (Z)-3-{1-[4-(N-(2-ethylamino-ethyl)-N-methylsulphonyl-amino)-phenylamino]-1-phenyl-methylidene}-2-indolinone
(16) (Z)-3-{1-[4-(N-(2-(N-acetyl-N-ethyl-amino)-ethyl)-N-methylsulphonyl-amino)-phenylamino]-1-phenyl-methylidene}-2-indolinone
(17) (Z)-3-{1-[4-(N-diethylaminoethyl-N-methylsulphonyl-amino)-phenylamino]-1-phenyl-methylidene}-2-indolinone
(18) (Z)-3-{1-[4-(N-(3-aminopropyl)-N-methylsulphonyl-amino)-phenylamino]-1-phenyl-methylidene}-2-indolinone
(19) (Z)-3-{1-[4-(N-(3-aminopropyl)-N-ethylsulphonyl-amino)-phenylamino]-1-phenyl-methylidene}-2-indolinone

(20) (Z)-3-{1-[4-(N-(3-methylaminopropyl)-N-methylsulphonyl-amino)-phenylamino]-1-phenyl-methylidene}-2-indolinone
(21) (Z)-3-{1-[4-(N-(3-methylaminopropyl)-N-ethylsulphonyl-amino)-phenylamino]-1-phenyl-methylidene}-2-indolinone
(22) (Z)-3-{1-[4-(N-(3-aminopropyl)-N-acetyl-amino)-phenylamino]-1-phenyl-methylidene}-2-indolinone
(23) (Z)-3-{1-[4-(N-(3-aminopropyl)-N-propionyl-amino)-phenylamino]-1-phenyl-methylidene}-2-indolinone
(24) (Z)-3-{1-[4-(N-(3-methylaminopropyl)-N-acetyl-amino)-phenylamino]-1-phenyl-methylidene}-2-indolinone
(25) (Z)-3-{1-[4-(N-(3-methylaminopropyl)-N-propionyl-amino)-phenylamino]-1-phenyl-methylidene}-2-indolinone
(26) (Z)-3-{1-[4-(N-methylaminomethylcarbonyl-N-methyl-amino)-phenylamino]-1-phenyl-methylidene}-2-indolinone
(27) (Z)-3-{1-[4-(N—(N-acetyl-N-methyl-aminomethylcarbonyl)-N-methyl-amino)-phenylamino]-1-phenyl-methylidene}-2-indolinone
(28) (Z)-3-{1-[4-(N-ethylaminomethylcarbonyl-N-methyl-amino)-phenylamino]-1-phenyl-methylidene}-2-indolinone
(29) (Z)-3-{1-[4-(N—(N-acetyl-N-ethyl-aminomethylcarbonyl)-N-methyl-amino)-phenylamino]-1-phenyl-methylidene}-2-indolinone
(30) (Z)-3-{1-[4-(N-(2-hydroxyethyl-aminomethylcarbonyl)-N-methyl-amino)-phenylamino]-1-phenyl-methylidene}-2-indolinone
(31) (Z)-3-{1-[4-(N—(N-(2-hydroxyethyl)-N-methyl-aminomethylcarbonyl)-N-methyl-amino)-phenylamino]-1-phenyl-methylidene}-2-indolinone
(32) (Z)-3-{1-[4-(N—(N-(2-hydroxyethyl)-N-methyl-aminomethylcarbonyl)-N-methyl-amino)-phenylamino]-1-phenyl-methylidene}-2-indolinone
(33) (Z)-3-{1-[4-(N-(2-dimethylamino-ethylcarbonyl)-N-methyl-amino)-phenylamino]-1-phenyl-methylidene}-2-indolinone

EXAMPLE 456

Dry Ampoule Containing 75 mg of Active Substance per 10 ml

Composition:

| Active substance | 75.0 mg |
|---|---|
| Mannito | 150.0 mg |
| water for injections | ad 10.0 ml |

Preparation:

Active substance and mannitol are dissolved in water. After packaging the solution is freeze-dried. To produce the solution ready for use, the product is dissolved in water for injections.

EXAMPLE 457

Dry Ampoule Containing 35 mg of Active Substance per 2 ml

Composition:

| Active substance | 35.0 mg |
|---|---|
| Mannitol | 100.0 mg |
| water for injections | ad 2.0 ml |

Preparation:

Active substance and mannitol are dissolved in water. After packaging, the solution is freeze-dried.

To produce the solution ready for use, the product is dissolved in water for injections.

EXAMPLE 458

Tablet Containing 50 mg of Active Substance

Composition:

| (1) Active substance | 50.0 mg |
|---|---|
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 9 mm.

EXAMPLE 459

Tablet Containing 350 mg of Active Substance

Composition:

| (1) Active substance | 350.0 mg |
|---|---|
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 12 mm.

EXAMPLE 460

Capsules Containing 50 mg of Active Substance

Composition:

| (1) Active substance | 50.0 mg |
|---|---|
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into size 3 hard gelatin capsules in a capsule filling machine.

EXAMPLE 461
Capsules Containing 350 mg of Active Substance
Composition:

| | |
|---|---|
| (1) Active substance | 350.0 mg |
| (2) Dried maize starch | 46.0 mg |
| (3) Powdered lactose | 30.0 mg |
| (4) Magnesium stearate | 4.0 mg |
| | 430.0 mg |

Preparation:
(1) is triturated with (3). This trituration is added to the mixture of (2) and (4) with vigorous mixing.
This powder mixture is packed into size 0 hard gelatin capsules in a capsule filling machine.

EXAMPLE 462
Suppositories Containing 100 mg of Active Substance
1 Suppository Contains:

| | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Preparation:
The polyethyleneglycol is melted together with polyethylene sorbitan monostearate. At 40° C. the ground active substance is homogeneously dispersed in the melt. It is cooled to 38° C. and poured into slightly chilled suppository moulds.

What is claimed is:
1. A compound of formula

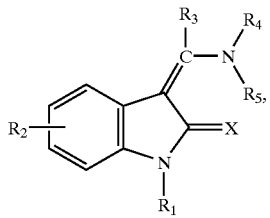

(I)

X denotes an oxygen or sulphur atom, $R_1$ denotes a hydrogen atom, $C_{1-3}$-alkyl, hydroxy, $C_{1-4}$-alkoxycarbonyl, or $C_{2-4}$-alkanoyl group, $R_2$ denotes a hydrogen, fluorine, chlorine, bromine or iodine atom, a $C_{1-3}$-alkyl or nitro group, $R_3$ denotes a phenyl or naphthyl group, each of which may be mono- or disubstituted by fluorine, chlorine, bromine or iodine atoms, by $C_{1-3}$-alkyl, $C_{1-3}$-alkoxy, carboxy, cyano, trifluoromethyl, nitro, amino, $C_{1-3}$-alkylamino, di-($C_{1-3}$-alkyl)-amino, $C_{1-3}$-alkylsulphonylamino, amino-$C_{1-3}$-alkyl, 2-carboxyphenylcarbonylaminomethyl, $C_{1-3}$-alkylamino-$C_{1-3}$-alkyl, $C_{2-4}$-alkanoylamino-$C_{1-3}$-alkyl, N—($C_{2-4}$-alkanoyl)-$C_{1-3}$-alkylamino-$C_{1-3}$-alkyl, di-($C_{1-3}$-alkyl)-amino-$C_{1-3}$-alkyl, carboxy-$C_{2-3}$-alkenyl, N-(carboxy-$C_{1-3}$-alkyl)-aminocarbonyl, N-(carboxy-$C_{1-3}$-alkyl)-N—($C_{1-3}$-alkyl)-aminocarbonyl or imidazolyl-$C_{1-3}$-alkyl groups, while the substituents may be identical or different, $R_4$ denotes a hydrogen atom or a $C_{1-3}$-alkyl group and $R_5$ denotes a substituted phenyl or naphthyl group, which is optionally, additionally substituted by a $C_{1-3}$-alkyl group, the substituted phenyl or naphthyl group being substituted in the aromatic moiety by a fluorine, chlorine, bromine or iodine atom, by a $C_{1-3}$-alkyl, $C_{1-3}$-alkoxy, cyano, nitro or trifluoromethyl group, by a $C_{1-3}$-alkoxy group which is substituted by a carboxy, aminocarbonyl, $C_{1-3}$-alkylaminocarbonyl or di-($C_{1-3}$-alkyl)-aminocarbonyl group or in the 2 or 3 position by an amino, $C_{1-3}$-alkylamino, di-($C_{1-3}$-alkyl)-amino, phenyl-$C_{1-3}$-alkylamino, N-(phenyl-$C_{1-3}$-alkyl)-N—($C_{1-3}$-alkyl)-amino, pyrrolidino, piperidino or hexamethyleneimino group, by a $C_{2-3}$-alkenyl group optionally substituted by a di-($C_{1-3}$-alkyl)-amino group, which may additionally be substituted in the alkenyl moiety by a chlorine or bromine atom, by a $C_{2-3}$-alkynyl group optionally substituted by a di-($C_{1-3}$-alkyl)-amino group, by a $C_{1-3}$-alkyl group which is substituted by a 3- to 7-membered cycloalkyleneimino group, by a dehydropiperidino, morpholino, thiomorpholino, 1-oxido-thiomorpholino, 1,1-dioxido-thiomorpholino, piperazino, N—($C_{1-3}$-alkyl)-piperazino, N—($C_{1-3}$-alkanoyl)-piperazino or N—($C_{1-5}$-alkoxycarbonyl)-piperazino group, whilst the abovementioned substituents may be substituted by a $C_{1-3}$-alkyl, phenyl or phenyl-$C_{1-3}$-alkyl group and the abovementioned piperidino or hexamethyleneimino groups may additionally be substituted by a $C_{1-3}$-alkyl group or in the 3 or 4 position by a hydroxy, $C_{1-3}$-alkoxy, hydroxy-$C_{1-3}$-alkyl, carboxy, aminocarbonyl, N—($C_{1-3}$-alkyl)-aminocarbonyl or N,N-di-($C_{1-3}$-alkyl)-aminocarbonyl group, by a $C_{1-3}$-alkyl group substituted by a hydroxy, $C_{1-3}$-alkoxy, carboxy or cyano group, whilst a $C_{1-3}$-alkyl group substituted by a carboxy group may additionally be substituted in the alkyl moiety by an amino or $C_{1-5}$-alkoxycarbonylamino group, by an aminocarbonylamino, amidino or guanidino group optionally substituted by one or two $C_{1-3}$-alkyl groups, by a piperidino, hexamethyleneimino, morpholino, piperazino or N—($C_{1-3}$-alkyl)-piperazino group, by a formyl, carboxy or trifluoroacetyl group, by a carbonyl group which
is substituted by a $C_{1-3}$-alkyl, $C_{1-3}$-alkoxy-$C_{1-3}$-alkyl, amino, $C_{1-5}$-alkylamino or di-($C_{1-3}$-alkyl)-amino group, while the abovementioned amino and $C_{1-3}$-alkylamino groups may additionally be substituted at the nitrogen atom by a carboxy-$C_{1-3}$-alkyl group or by a $C_{2-3}$-alkyl group which may be substituted in the 2 or 3 position by a hydroxy, $C_{1-3}$-alkoxy, amino, $C_{1-3}$-alkylamino or di-($C_{1-3}$-alkyl)-amino group, by a pyrrolidinocarbonyl, piperidinocarbonyl, hexamethyleneiminocarbonyl, morpholinocarbonyl, piperazinocarbonyl, N—($C_{1-3}$-alkyl)-piperazinocarbonyl or N-(phenyl-$C_{1-3}$-alkyl)-piperazinocarbonyl group, by an amidosulphonyl, pyrrolidinosulphonyl, piperidinosulphonyl or hexamethyleneiminosulphonyl group, by a $C_{1-3}$-alkylamidosulphonyl or di-($C_{1-3}$-alkyl)-amidosulphonyl group, wherein an alkyl moiety may be substituted in each case by a carboxy, aminocarbonyl, N—($C_{1-3}$-alkyl)-aminocarbonyl or N,N-di-($C_{1-3}$-alkyl)-aminocarbonyl group or, in the 2 or 3 position, by a $C_{1-3}$-alkylamino or di-($C_{1-3}$-alkyl)-amino group, by an amino, $C_{1-5}$-alkylamino, $C_{3-7}$-cycloalkylamino, phenyl-$C_{1-3}$-alkylamino, phenylamino, 6-membered heteroarylamino, amino-$C_{1-3}$-alkyl, N—($C_{1-5}$-alkyl)-amino-$C_{1-3}$-alkyl, di-($C_{1-5}$-alkyl)-amino-$C_{1-3}$-alkyl, $C_{3-7}$-cycloalkylamino-$C_{1-3}$-alkyl, N—($C_{1-5}$-alkyl)-$C_{3-7}$-cycloalkylamino-$C_{1-3}$-alkyl, phenylamino-$C_{1-3}$-alkyl, N—($C_{1-3}$-alkyl)-phenylamino-$C_{1-3}$-alkyl, phenyl-$C_{1-3}$-alkylamino-$C_{1-3}$-alkyl or N—($C_{1-5}$-alkyl)-phenyl-$C_{1-3}$-alkylamino-$C_{1-3}$-alkyl group or by a 6-membered heteroarylamino-$C_{1-3}$-alkyl group optionally substituted at the nitrogen atom by a $C_{1-5}$-alkyl group, while the N-alkyl moiety of the abovementioned groups may be substituted in each case by a cyano, carboxy, aminocarbonyl, $C_{1-3}$-alkylaminocarbonyl, di-($C_{1-3}$-alkyl)-aminocarbonyl, 2-[di-($C_{1-3}$-alkyl)-amino]-ethylaminolocarbonyl, 3-[di-($C_{1-3}$-alkyl)-amino]-propylamincarbonyl, N-{2-[di-($C_{1-3}$-alkyl)-amino]-ethyl}-N—($C_{1-3}$-alkyl)-aminocarbonyl or N-{3-[di-($C_{1-3}$-alkyl)-amino]-propyl}-N—($C_{1-3}$-alkyl)-aminocarbonyl group or in the 2 or 3 position by a hydroxy, $C_{1-3}$-alkoxy, amino, $C_{1-3}$-alkylamino, di-($C_{1-3}$-alkyl)-amino, pyrrolidino, piperidino, hexamethyleneimino, morpholino, piperazino or N—($C_{1-3}$-alkyl)-piperazino group and the nitrogen atom of the abovementioned amino, N—($C_{1-5}$-alkyl)-amino, $C_{3-7}$-cycloalkylamino, phenyl-$C_{1-3}$-alkylamino, phenylamino, 6-membered heteroarylamino, amino-$C_{1-3}$-alkyl- and N—($C_{1-5}$-alkylamino)-$C_{1-3}$-alkyl groups may additionally be substituted by a $C_{1-5}$-alkoxycarbonyl group, by a formyl, trifluoroacetyl or benzoyl group, by a carboxy-$C_{1-3}$-alkyl, aminocarbonyl-$C_{1-3}$-alkyl, N—($C_{1-3}$-alkyl)-aminocarbonyl-$C_{1-3}$-alkyl or N,N-di-($C_{1-3}$-alkyl)-aminocarbonyl-$C_{1-3}$-alkyl group, by a $C_{1-5}$-alkyl group which may be substituted, except in the 1 position, by a hydroxy, $C_{1-3}$-alkoxy, amino, $C_{1-3}$-alkylamino or di-($C_{1-3}$-alkyl)-amino group, by a $C_{2-4}$-alkanoyl group which may be substituted in the alkanoyl moiety by a carboxy, hydroxy, $C_{1-3}$-alkoxy, phenyl, amino, phthalimido, $C_{1-3}$-alkylamino, di-($C_{1-3}$-alkyl)-amino, pyrrolidino, piperidino, hexamethyleneimino or morpholino group or by a piperazino group optionally substituted at the nitrogen atom by a $C_{1-3}$-alkyl or phenyl-$C_{1-3}$-alkyl group, while the alkyl moiety of the abovementioned $C_{1-3}$-alkylamino- and di-($C_{1-3}$-alkyl)-amino substituents may be substituted in the 2 or 3 position by a hydroxy, $C_{1-3}$-alkoxy, amino, $C_{1-5}$-alkoxycarbonylamino, $C_{1-3}$-alkylamino, di-($C_{1-3}$-alkyl)-amino, phenyl, pyrrolidino, piperidino, hexamethyleneimino or morpholino group, by a $C_{1-5}$-alkylsulphonyl group in which the alkyl moiety may be substituted except in the 1 position by a di-($C_{1-3}$-alkyl)-amino, pyrrolidino, piperidino, hexamethyleneimino or morpholino group, by a phenyl-($C_{1-3}$)-alkylsulphonyl or phenylsulphonyl group optionally substituted in the phenyl moiety by a fluorine, chlorine or bromine atom or by a $C_{1-3}$-alkyl or $C_{1-3}$-alkoxy group, while additionally any carboxy, amino or imino group present may be substituted by a group which can be cleaved in vivo, the stereoisomers and the salts thereof.

2. The compound of formula I according to claim 1, wherein

X denotes an oxygen or sulphur atom, $R_1$ denotes a hydrogen atom, a $C_{1-3}$-alkyl, hydroxy, $C_{1-4}$-alkoxycarbonyl or $C_{2-4}$-alkanoyl group, $R_2$ denotes a hydrogen, fluorine, chlorine, bromine or iodine atom, a $C_{1-3}$-alkyl or nitro group, $R_3$ denotes a phenyl or naphthyl group, each of which may be mono- or disubstituted by fluorine, chlorine, bromine or iodine atoms, by $C_{1-3}$-alkyl, imidazolylmethyl, 2-carboxy-ethenyl, 2-($C_{1-3}$-alkoxycarbonyl)-ethenyl, $C_{1-3}$-alkoxy, cyano, carboxy, $C_{1-3}$-alkoxycarbonyl, trifluoromethyl, nitro, amino, phthalimidomethyl, 2-carboxy-phenylcarbonyl-aminomethyl, $C_{1-3}$-alkylamino, di-($C_{1-3}$-alkyl)-amino, $C_{1-3}$-alkylsulphonylamino, amino-$C_{1-3}$-alkyl, $C_{1-3}$-alkylamino-$C_{1-3}$-alkyl, $C_{2-4}$-alkanoyl-amino-$C_{1-3}$-alkyl, N—($C_{2-4}$-alkanoyl)-$C_{1-3}$-alkylamino-$C_{1-3}$-alkyl, di-($C_{1-3}$-alkyl)-amino-$C_{1-3}$-alkyl, carboxy-$C_{1-3}$-alkylaminocarbonyl or $C_{1-3}$-alkoxycarbonyl-$C_{1-3}$-alkylaminocarbonyl groups, while the substituents may be identical or different, $R_4$ denotes a hydrogen atom or a $C_{1-3}$-alkyl group and $R_5$ denotes a substituted phenyl or naphthyl group, which is optionally, additionally substituted by a $C_{1-3}$-alkyl group, the substituted phenyl or naphthyl group being substituted in the aromatic moiety by a fluorine, chlorine, bromine or iodine atom, by a $C_{1-3}$-alkyl, $C_{1-3}$-alkoxy, cyano, nitro or trifluoromethyl group, while the abovementioned alkyl group may simultaneously be substituted by a carboxy or $C_{1-3}$-alkoxycarbonyl group and an amino or $C_{1-4}$-alkoxycarbonylamino group, a $C_{1-3}$-alkyl group which is substituted by a 4- to 7-membered cycloalkyleneimino group, by a dehydropiperidino, morpholino, thiomorpholino, 1-oxido-thiomorpholino, 1,1-dioxido-thiomorpholino, piperazino or N—($C_{1-4}$-alkoxycarbonyl)-piperazino group, while the abovementioned piperidino, hexamethyleneimino, morpholino, thio-morpholino, 1-oxido-thiomorpholino, 1,1-dioxido-thiomorpholino- and piperazino groups may be substituted by a $C_{1-3}$-alkyl, phenyl or phenyl-$C_{1-3}$-alkyl group and the abovementioned piperidino groups may additionally be substituted by a $C_{1-3}$-alkyl group or in the 3 or 4 position by a hydroxy, $C_{1-3}$-alkoxy, hydroxy-$C_{1-3}$-alkyl, carboxy, aminocarbonyl, N—($C_{1-3}$-alkyl)-aminocarbonyl or N,N-di-($C_{1-3}$-alkyl)-aminocarbonyl group, by a $C_{1-3}$-alkyl group optionally substituted by a hydroxy, $C_{1-3}$-alkoxy, carboxy, $C_{1-3}$-alkoxycarbonyl or cyano group, by an aminocarbonylamino, amidino or guanidino group optionally substituted by one or two $C_{1-3}$-alkyl groups, by a piperidino, hexamethyleneimino, morpholino, piperazino or N—($C_{1-3}$-alkyl)-piperazino group, by a formyl, carboxy, $C_{1-3}$-alkoxycarbonyl or trifluoroacetyl group, by a carbonyl group which
is substituted by a $C_{1-3}$-alkyl, $C_{1-3}$-alkoxy-$C_{1-3}$-alkyl, amino, $C_{1-5}$-alkylamino or di-($C_{1-3}$-alkyl)-amino group, while the abovementioned amino- and $C_{1-3}$-alkylamino groups may additionally be substituted at the nitrogen atom by a carboxy-$C_{1-3}$-alkyl or $C_{1-3}$-alkoxycarbonyl-$C_{1-3}$-alkyl group or by a $C_{2-3}$-alkyl group which may be substituted in the 2 or 3 position by a hydroxy, $C_{1-3}$-alkoxy, amino, $C_{1-3}$-alkylamino or di-($C_{1-3}$-alkyl)-amino group,
by a pyrrolidinocarbonyl, pyrrolidinosulphonyl, piperidinocarbonyl, hexamethyleneiminocarbonyl, morpholinocarbonyl, piperazinocarbonyl, N—($C_{1-3}$-alkyl)-piperazinocarbonyl or N-(phenyl-$C_{1-3}$-alkyl)-piperazinocarbonyl group,
by an amidosulphonyl, $C_{1-3}$-alkylamidosulphonyl or di-($C_{1-3}$-alkyl)-amidosulphonyl group, wherein an alkyl moiety may be substituted by a carboxy, $C_{1-3}$-alkoxycarbonyl, aminocarbonyl, $C_{1-3}$-alkylaminocarbonyl or di-($C_{1-3}$-alkyl)-aminocarbonyl group or in the 2 or 3 position may be substituted by an amino, $C_{1-3}$-alkylamino or di-($C_{1-3}$-alkyl)-amino group,
by an amino, $C_{1-5}$-alkylamino, amino-$C_{1-3}$-alkyl, N—($C_{1-3}$-alkyl)-amino-$C_{1-3}$-alkyl, N-(2-hydroxyethyl)-amino-$C_{1-3}$-alkyl, N-(3-hydroxypropyl)-amino-$C_{1-3}$-alkyl, di-($C_{1-5}$-alkyl)-amino-$C_{1-3}$-alkyl, N—($C_{3-7}$-cycloalkyl)-amino-$C_{1-3}$-alkyl, N—($C_{3-7}$-cycloalkyl)-N—($C_{1-3}$-alkyl)-amino-$C_{1-3}$-alkyl or N-(phenyl-$C_{1-3}$-alkyl)-amino-$C_{1-3}$-alkyl group, while the N-alkyl moiety of the abovementioned groups may be substituted by a cyano, carboxy, $C_{1-3}$-alkylcarbonyl, aminocarbonyl, $C_{1-3}$-alkylaminocarbonyl, di-($C_{1-3}$-alkyl)-aminocarbonyl, 2-[di-($C_{1-3}$-alkyl)-amino]-ethylaminocarbonyl, 3-[di-($C_{1-3}$-alkyl)-amino]-propylaminocarbonyl, N-{2-[di-($C_{1-3}$-alkyl)-amino]-ethyl}-N—($C_{1-3}$-alkyl)-aminocarbonyl or N-{3-[di-($C_{1-3}$-alkyl)-amino]-propyl}-N—($C_{1-3}$-alkyl)-aminocarbonyl group or may be substituted in the 2 or 3 position by a hydroxy, $C_{1-3}$-alkoxy, amino, $C_{1-3}$-alkylamino, di-($C_{1-3}$-alkyl)-amino or morpholino group, while the nitrogen atom of the abovementioned amino, $C_{1-3}$-alkylamino, amino-$C_{1-3}$-alkyl or N—($C_{1-5}$-alkylamino)-$C_{1-3}$-alkyl moieties may additionally be substituted
by a $C_{1-5}$-alkoxycarbonyl group,
by a formyl, trifluoroacetyl or benzoyl group,
by a $C_{1-5}$-alkyl group which may be substituted, except in the 1 position, by a hydroxy, $C_{1-3}$-alkoxy, amino, $C_{1-3}$-alkylamino or di-($C_{1-3}$)-alkylamino group,
by a $C_{2-4}$-alkanoyl group which may be substituted in the alkanoyl moiety by a hydroxy, $C_{1-3}$-alkoxy, amino, $C_{2-4}$-alkanoylamino, $C_{1-5}$-alkoxycarbonylamino, phthalimido, $C_{1-3}$-alkylamino, di-($C_{1-3}$-alkyl)-amino, N—($C_{1-3}$-alkyl)-phenylamino, pyrrolidino, piperidino or morpholino group or by a piperazino group optionally substituted at the nitrogen atom by a $C_{1-3}$-alkyl or phenyl-$C_{1-3}$-alkyl group, while the N-alkyl moiety of the abovementioned groups may be substituted in the 2 or 3 position by a methoxy, di-($C_{1-3}$-alkyl)-amino or morpholino group,
by a $C_{1-5}$-alkylsulphonyl group in which the alkyl moiety may be substituted, except in the 1 position, by a di-($C_{1-3}$-alkyl)-amino, pyrrolidino, piperidino, hexamethyleneimino or morpholino group,
by a pyridinyl or pyrimidinyl group,
by a phenyl, phenyl-($C_{1-3}$)-alkylsulphonyl or phenylsulphonyl group optionally substituted in the phenyl moiety by a $C_{1-3}$-alkyl group,
by a $C_{1-3}$-alkoxy group which is substituted by a carboxy, $C_{1-3}$-alkoxycarbonyl, aminocarbonyl, $C_{1-3}$-alkylaminocarbonyl or di-($C_{1-3}$-alkyl)-aminocarbonyl group or is substituted in the 2 or 3 position by an amino, $C_{1-3}$-alkylamino, di-($C_{1-3}$-alkyl)-amino, N—($C_{1-3}$-alkyl)-N-(phenyl-$C_{1-3}$-alkyl)-amino, piperidino or hexamethyleneimino group,
by a prop-1-enyl, 2-chloro-prop-1-enyl or prop-1-ynyl group which is substituted in the 3 position by a di-($C_{1-3}$-alkyl)-amino group,
the stereoisomers and the salts thereof.

3. The compound of formula I according to claim 1, wherein
X denotes an oxygen atom,
$R_1$ denotes a hydrogen atom, a $C_{1-3}$-alkyl, $C_{1-4}$-alkoxycarbonyl or $C_{2-4}$-alkanoyl group,
$R_2$ denotes a hydrogen, fluorine, chlorine, bromine or iodine atom, a $C_{1-3}$-alkyl or nitro group,
$R_3$ denotes a phenyl group which may be mono- or disubstituted by fluorine, chlorine, bromine or iodine atoms, by $C_{1-3}$-alkyl, trifluoromethyl, imidazolylmethyl, 2-carboxy-ethenyl, 2-$C_{1-3}$-alkoxycarbonyl-ethenyl, $C_{1-3}$-alkoxy, cyano, carboxy, $C_{1-3}$-alkoxycarbonyl, nitro, amino, phthalimidomethyl, 2-carboxy-benzoylamineomethyl, $C_{1-3}$-alkylamino, di-($C_{1-3}$-alkyl)-amino, $C_{1-3}$-alkylsulphonylamino, amino-$C_{1-3}$-alkyl, $C_{1-3}$-alkylamino-$C_{1-3}$-alkyl, $C_{2-4}$-alkanoylamino-$C_{1-3}$-alkyl, N—($C_{2-4}$-alkanoyl)-$C_{1-3}$-alkylamino-$C_{1-3}$-alkyl, di-($C_{1-3}$-alkyl)-amino-$C_{1-3}$-alkyl, carboxy-$C_{1-3}$-alkylaminocarbonyl or $C_{1-3}$-alkoxycarbonyl-$C_{1-3}$-alkylaminocarbonyl groups, while the substituents may be identical or different,
$R_4$ denotes a hydrogen atom or a $C_{1-3}$-alkyl group and
$R_5$ denotes a substituted phenyl or naphthyl group, which is optionally, additionally substituted by a $C_{1-3}$-alkyl group, the substituted phenyl or naphthyl group being substituted in the aromatic moiety
by a fluorine, chlorine, bromine or iodine atom, by a $C_{1-3}$-alkoxy, cyano, nitro or trifluoromethyl group,
a $C_{1-3}$-alkyl group which is substituted by a 4- to 7-membered cycloalkyleneimino group, by a dehydropiperidino, morpholino, thiomorpholino, 1-oxido-thiomorpholino, 1,1-dioxido-thiomorpholino, piperazino or N—($C_{1-4}$-alkoxycarbonyl)-piperazino group, while the abovementioned piperidino, hexamethyleneimino, morpholino and piperazino groups may be substituted by a $C_{1-3}$-alkyl, phenyl or phenyl-$C_{1-3}$-alkyl group and the abovementioned piperidino groups may additionally be substituted by a $C_{1-3}$-alkyl group or may be substituted in the 3 or 4 position by a hydroxy, $C_{1-3}$-alkoxy, hydroxy-$C_{1-3}$-alkyl, carboxy, aminocarbonyl, N—($C_{1-3}$-alkyl)-aminocarbonyl or N,N-di-($C_{1-3}$-alkyl)-aminocarbonyl group,
by a $C_{1-3}$-alkyl group optionally substituted by a hydroxy, $C_{1-3}$-alkoxy, carboxy, $C_{1-3}$-alkoxycarbonyl or cyano group,
by an aminocarbonylamino, amidino or guanidino group optionally substituted by one or two $C_{1-3}$-alkyl groups, by a piperidino, hexamethyleneimino, morpholino, piperazino or N—($C_{1-3}$-alkyl)-piperazino group, by a formyl, carboxy, $C_{1-3}$-alkoxycarbonyl or trifluoroacetyl group, by a carbonyl group which
is substituted by a $C_{1-3}$-alkyl, $C_{1-3}$-alkoxy-$C_{1-3}$-alkyl, amino, $C_{1-5}$-alkylamino or di-($C_{1-3}$-alkyl)-amino group, while the abovementioned amino and $C_{1-3}$-alkylamino groups may additionally be substituted at the nitrogen atom by a carboxy-$C_{1-3}$-alkyl, $C_{1-3}$-alkoxycarbonyl-$C_{1-3}$-alkyl or $C_{1-3}$-alkoxycarbonyl-$C_{1-3}$-alkyl group or by a $C_{2-3}$-alkyl group which may be substituted in the 2 or 3 position by a hydroxy, $C_{1-3}$-alkoxy, amino, $C_{1-3}$-alkylamino or di-($C_{1-3}$-alkyl)-amino group, by a pyrrolidinocarbonyl, pyrrolidinosulphonyl, piperidinocarbonyl or hexamethyleneiminocarbonyl group, by an amidosulphonyl, $C_{1-3}$-alkylamidosulphonyl or di-($C_{1-3}$-alkyl)-amidosulphonyl group, wherein an alkyl moiety may be substituted by a carboxy, $C_{1-3}$-alkoxycarbonyl or dimethylaminocarbonyl group or in the 2 or 3 position by a dimethylamino group, by a straight-chain $C_{1-2}$-alkyl group which is terminally substituted by an amino, benzylamino, pyridylamino or pyrimidylamino group, by a $C_{1-4}$-alkylamino group in which the alkyl moiety may be substituted in position 2, 3 or 4 by a hydroxy or methoxy group, or by a $C_{1-2}$-alkylamino group substituted in the $C_{1-2}$-alkyl moiety by a carboxy, $C_{1-3}$-alkoxycarbonyl or di-($C_{1-3}$-alkyl)-aminocarbonyl group, while in the abovementioned groups any hydrogen atom present at the amino nitrogen atom may additionally be replaced
by a $C_{3-6}$-cycloalkyl group, by a $C_{1-4}$-alkyl group in which the alkyl moiety may be substituted in position 2, 3 or 4 by a hydroxy group, by a $C_{1-2}$-alkylcarbonyl group optionally substituted by a methoxy, carboxy, $C_{1-3}$-alkoxycarbonyl, amino, methylamino, dimethylamino, acetylamino, $C_{1-5}$-alkoxycarbonylamino, N-methyl-$C_{1-5}$-alkoxycarbonylamino or morpholinocarbonylamino group, by a $C_{1-5}$-alkoxycarbonyl, $C_{1-4}$-alkylsulphonyl, phenylsulphonyl or tolylsulphonyl group, by a 3-dimethylaminopropyl or 3-dimethylamino-prop-1-enyl group, by an ethyl group which is substituted in the 1 position by an amino or $C_{1-5}$-alkoxycarbonylamino group, by an ethyl group which is substituted in the 2 position by an amino or $C_{1-5}$-alkoxycarbonylamino group and by a carboxy or $C_{1-3}$-alkoxycarbonyl group, by an amino or $C_{1-3}$-alkylamino group in which the alkyl moiety may be substituted by a cyano, carboxy, $C_{1-3}$-alkoxycarbonyl, aminocarbonyl, methylaminocarbonyl or dimethylaminocarbonyl group or may be substituted in the 2 or 3 position by an amino, methylamino, dimethylamino, acetylamino, N-methyl-acetylamino or morpholino group, by an N—($C_{1-3}$-alkyl)-aminocarbonyl or N—($C_{1-3}$-alkyl)-methylaminocarbonyl group optionally substituted in the 2 or 3 position of the $C_{1-3}$-alkyl moiety by a dimethylamino group, while any hydrogen atom present at the amino nitrogen atom in the abovementioned groups may additionally be replaced
by a formyl, trifluoroacetyl, benzoyl, $C_{1-4}$-alkoxycarbonyl or $C_{1-4}$-alkylaminocarbonyl group, by a $C_{2-4}$-alkanoyl group which may be terminally substituted by an amino, acetylamino, $C_{1-4}$-alkoxycarbonylamino, pyrrolidino, piperidino, morpholino, piperazino, 4-methylpiperazino, 4-benzylpiperazino or phthalimido group or by a $C_{1-3}$-alkylamino, N-acetyl-$C_{1-3}$-alkyl-amino or di-($C_{1-3}$-alkyl)-amino group, while in the abovementioned $C_{1-3}$-alkylamino, N-acetyl-$C_{1-3}$-alkyl-amino- and di-($C_{1-3}$-alkyl)-amino groups any $C_{1-3}$-alkyl moiety may additionally be substituted by a phenyl group or in the 2 or 3 position by a methoxy, dimethylamino or morpholino group, by a $C_{1-4}$-alkylsulphonyl group in which the alkyl moiety may additionally be substituted in the 2 or 3 position by a dimethylamino, piperidino or morpholino group, by a phenylsulphonyl or toluenesulphonyl group, by a $C_{1-3}$-alkoxy group which is substituted by a carboxy, $C_{1-3}$-alkoxycarbonyl, aminocarbonyl, methylaminocarbonyl or dimethylaminocarbonyl group or is substituted in the 2 or 3 position by an amino, methylamino, dimethylamino, N-methyl-benzylamino, piperidino or hexamethyleneimino group, by a $C_{1-3}$-alkylaminocarbonyl or di-($C_{1-3}$-alkyl)-aminocarbonyl group wherein a $C_{1-3}$-alkyl moiety may be substituted in the 2 or 3 position by a methoxy or dimethylamino group, the stereoisomers and the salts thereof.

4. The compound of formula I according to claim 1, wherein

X denotes an oxygen atom $R_1$ denotes a hydrogen atom, $R_2$ denotes a hydrogen, chlorine or bromine atom, a methyl or nitro group, $R_3$ denotes a phenyl group which may be substituted by a fluorine, chlorine or bromine atom, by a methyl, methoxy, aminomethyl, acetylaminomethyl, carboxy, methoxycarbonyl or imidazolylmethyl group, $R_4$ denotes a hydrogen atom, $R_5$ denotes a phenyl group which is substituted
by a fluorine, chlorine or bromine atom, by a methyl, methoxy, nitro, cyano or trifluoromethyl group,
by a methyl or ethyl group, each of which is substituted by a carboxy, $C_{1-3}$-alkoxycarbonyl, cyano, azetidin-1-yl, pyrrolidino, piperidino, 4-phenylpiperidino, 3,6-dihydro-2H-pyridin-1-yl, hexamethyleneimino, morpholino, thiomorpholino, 1-oxido-thiomorpholino, piperazino, 4-methylpiperazino or 4-acetylpiperazino group, while the abovementioned piperidino groups may additionally be substituted by one or two methyl groups or may be substituted in the 3 or 4 position by a hydroxy, methoxy, carboxy, hydroxymethyl, $C_{1-3}$-alkoxycarbonyl, aminocarbonyl, methylaminocarbonyl or dimethylaminocarbonyl group,
by a straight-chain $C_{1-2}$-alkyl group which is terminally substituted by an amino or benzylamino group, by a $C_{1-4}$-alkylamino group in which the alkyl moiety in positions 2, 3 or 4 may be substituted by a hydroxy or methoxy group, by a $C_{1-2}$-alkylamino group substituted in the $C_{1-2}$-alkyl moiety by a carboxy, $C_{1-3}$-alkoxycarbonyl or dimethylaminocarbonyl group, while in the abovementioned groups a hydrogen atom present at the amino nitrogen may additionally be replaced by a $C_{3-6}$-cycloalkyl group, by a $C_{1-4}$-alkyl group in which the alkyl moiety may be substituted in positions 2, 3 or 4 by a hydroxy group, or by a $C_{1-2}$-alkylcarbonyl group optionally substituted by an amino, methylamino or dimethylamino group, by a 3-dimethylamino-prop-1-enyl group, by an ethyl group which is substituted in the 1-position by an amino or $C_{1-4}$-alkoxycarbonylamino group, by an amino or $C_{1-3}$-alkylamino group in which the alkyl moiety may be terminally substituted by a carboxy, aminocarbonyl, methylaminocarbonyl or dimethylaminocarbonyl group or in the 2 or 3 position by an amino, methylamino, dimethylamino, acetylamino, N-acetyl-methylamino or morpholino group or by an N—($C_{1-3}$-alkyl)-aminocarbonyl or N—($C_{1-3}$-alkyl)-methylaminocarbonyl group optionally substituted in the 2 or 3 position by a dimethylamino group, while a hydrogen atom present at the amino nitrogen in the abovementioned groups may additionally be substituted by a formyl or benzoyl group, by a $C_{2-4}$-alkanoyl group which may be terminally substituted by an amino, acetylamino, pyrrolidino, piperidino, morpholino, piperazino or 4-methylpiperazino group or by a $C_{1-3}$-alkylamino, N-acetyl-$C_{1-3}$-alkylamino or di-($C_{1-3}$-alkyl)-amino group, while in the abovementioned $C_{1-3}$-alkylamino, N-acetyl-$C_{1-3}$-alkylamino or di-($C_{1-3}$-alkyl)-amino groups a $C_{1-3}$-alkyl moiety may additionally be substituted in the 2 or 3 position by a methoxy, dimethylamino or morpholino group, by a $C_{1-4}$-alkylsulphonyl group which may be substituted in the 2 or 3 position by a dimethylamino group, by a pyrrolidinosulphonyl group, an aminosulphonyl, $C_{1-3}$-alkylaminosulphonyl or di-($C_{1-3}$-alkyl)-aminosulphonyl group, wherein in each case a $C_{1-3}$-alkyl moiety may be substituted by a carboxy, $C_{1-3}$-alkoxycarbonyl, aminocarbonyl, methylaminocarbonyl or dimethylaminocarbonyl group or, except in the 1 position, by a dimethylamino group, by a $C_{2-3}$-alkoxy group which is substituted in the 2 or 3 position by a dimethylamino or piperidino group, by an aminocarbonyl, $C_{1-3}$-alkylaminocarbonyl or di-($C_{1-3}$-alkyl)-aminocarbonyl group, wherein in each case the $C_{1-3}$-alkyl moieties may be substituted by a methoxy or dimethylamino group, except in the 1 position, the stereoisomers and the salts thereof.

5. The compound of formula I according to claim 1, wherein

X and $R_2$ to $R_4$ are as hereinbefore defined, $R_1$ denotes a hydrogen atom and $R_5$ denotes a phenyl group which is substituted by a methyl or ethyl group, each of which is substituted by an azetidin-1-yl, pyrrolidino, piperidino, hexamethyleneimino, morpholino, 1-oxido-thiomorpholino, piperazino, 4-methylpiperazino or 4-acetylpiperazino group, while the abovementioned piperidino groups may additionally be substituted by one or two methyl groups or in the 4 position may be substituted by a hydroxy, methoxy, hydroxymethyl, aminocarbonyl, methylaminocarbonyl or dimethylaminocarbonyl group, by a straight-chain $C_{1-2}$-alkyl group which is terminally substituted by an amino group or by a $C_{1-3}$-alkylamino group, while the alkyl moiety of the $C_{1-3}$-alkylamino group may be substituted in positions 2 or 3 by a hydroxy or methoxy group and in the abovementioned groups the hydrogen atom present at the amino nitrogen may additionally be replaced by a $C_{3-6}$-cycloalkyl group, by a $C_{1-3}$-alkyl group in which the alkyl moiety in positions 2 or 3 may be substituted by a hydroxy group, or by a $C_{1-2}$-alkylcarbonyl group substituted by an amino, methylamino or dimethylamino group, by an ethyl group substituted in the 1 position by an amino group, by an amino or $C_{1-3}$-alkylamino group in which the alkyl moiety may be terminally substituted by a carboxy, aminocarbonyl, methylaminocarbonyl, dimethylaminocarbonyl, N-(2-dimethylamino-ethyl)-aminocarbonyl or N-(2-dimethylamino-ethyl)-N-methyl-aminocarbonyl group or may be substituted in the 2 or 3 position by an amino, methylamino, dimethylamino, acetylamino, N-acetyl-methylamino or morpholino group, while the hydrogen atom present at the amino nitrogen of the abovementioned groups may additionally be replaced by a $C_{2-4}$-alkanoyl group which may be terminally substituted by an amino, acetylamino, pyrrolidino, piperidino, morpholino, piperazino or 4-methylpiperazino group or by a $C_{1-3}$-alkylamino, N-acetyl-$C_{1-3}$-alkylamino or di-($C_{1-3}$-alkyl)-amino group, while in the abovementioned $C_{1-3}$-alkylamino, N-acetyl-$C_{1-3}$-alkylamino or di-($C_{1-3}$-alkyl)-amino groups a $C_{1-3}$-alkyl moiety may additionally be substituted in the 2 or 3 position by a methoxy, dimethylamino or morpholino group, by a $C_{1-4}$-alkylsulphonyl group which may be substituted in the 2 or 3 position by a dimethylamino group, by a pyrrolidinosulphonyl group, an aminosulphonyl, $C_{1-3}$-alkylaminosulphonyl or di-($C_{1-3}$-alkyl)-aminosulphonyl group, wherein in each case a $C_{1-3}$-alkyl moiety may be substituted by a carboxy, methoxycarbonyl, aminocarbonyl, methylaminocarbonyl or dimethylaminocarbonyl group or, except in the 1 position, by a dimethylamino group, by a $C_{1-3}$-alkoxy group substituted in the 2 or 3 position by a dimethylamino or piperidino group, by an aminocarbonyl, $C_{1-3}$-alkylaminocarbonyl or di-($C_{1-3}$-alkyl)-aminocarbonyl group, wherein in each case a $C_{1-3}$-alkyl moiety may be substituted by a methoxy or dimethylamino group, except in the 1 position, the stereoisomers and the salts thereof.

6. A pharmaceutical composition of matter comprising a compound of formula I as recited in claim 1 wherein R1 denotes a hydrogen atom, a $C_{1-3}$-alkyl group or a prodrug group or a physiologically acceptable salt thereof, together with one or more inert carriers or diluents.

7. A method for protecting proliferating cells in a warm-blooded animal from DNA damage caused by radiation, UV treatment or cytostatic treatment which comprises administering to said animal a therapeutically effective amount of a compound as recited in claim 1.

8. A compound selected from the group consisting of:
(a) (Z)-3-[1-(4-dimethylaminomethyl-phenylamino)-1-phenyl-methylidene]5-nitro-2-indolinone,
(b) (Z)-3-[1-(4-piperidinomethyl-phenylamino)-1-phenyl-methylidene]-5-nitro-2-indolinone,
(c) (Z)-3-{1-[4-(2-morpholinoethyl)-phenylamino]-1-phenyl-methylidene}-5-nitro-2-indolinone,
(d) (Z)-3-{1-[4-(2-dimethylamino-ethyl)-phenylamino]-1-phenyl-methylidene}-5-nitro-2-indolinone and
(e) (Z)-3-{1-[4-(N-(2-dimethylamino-ethyl)-N-methylsulphonyl-amino)-phenylamino]-1-phenyl-methylidene}-2-indolinone;

or a salt thereof.

9. The physiologically acceptable salt of a compound as recited in claim 8.

* * * * *